(12) United States Patent
Stockley et al.

(10) Patent No.: US 10,654,846 B2
(45) Date of Patent: May 19, 2020

(54) AUTOTAXIN INHIBITORY COMPOUNDS

(71) Applicant: CANCER RESEARCH TECHNOLOGY LIMITED, London (GB)

(72) Inventors: Martin Lee Stockley, Cambridge (GB); Ellen Catherine MacDonald, Cambridge (GB); Pritom Shah, Cambridge (GB); Allan Jordan, Manchester (GB); James Hitchin, Manchester (GB); Niall Hamilton, Manchester (GB)

(73) Assignee: Cancer Research Technology Limited, London (GB)

( * ) Notice: Subject to any disclaimer, the term of this patent is extended or adjusted under 35 U.S.C. 154(b) by 0 days.

(21) Appl. No.: 15/548,079

(22) PCT Filed: Feb. 4, 2016

(86) PCT No.: PCT/GB2016/050268
§ 371 (c)(1),
(2) Date: Aug. 1, 2017

(87) PCT Pub. No.: WO2016/124939
PCT Pub. Date: Aug. 11, 2016

(65) Prior Publication Data
US 2018/0016274 A1    Jan. 18, 2018

(30) Foreign Application Priority Data

Feb. 6, 2015 (GB) .................................. 1502020.9

(51) Int. Cl.
| | |
|---|---|
| *A61K 31/496* | (2006.01) |
| *A61K 31/551* | (2006.01) |
| *A61K 31/404* | (2006.01) |
| *A61K 31/55* | (2006.01) |
| *A61K 31/444* | (2006.01) |
| *A61K 31/437* | (2006.01) |
| *A61K 31/4184* | (2006.01) |
| *A61K 31/4545* | (2006.01) |
| *A61K 31/5025* | (2006.01) |
| *A61K 31/5377* | (2006.01) |
| *A61K 45/06* | (2006.01) |
| *C07D 471/04* | (2006.01) |
| *C07D 235/02* | (2006.01) |

(52) U.S. Cl.
CPC .......... *C07D 471/04* (2013.01); *A61K 31/404* (2013.01); *A61K 31/4184* (2013.01); *A61K 31/437* (2013.01); *A61K 31/444* (2013.01); *A61K 31/4545* (2013.01); *A61K 31/496* (2013.01); *A61K 31/5025* (2013.01); *A61K 31/5377* (2013.01); *A61K 31/55* (2013.01); *A61K 31/551* (2013.01); *A61K 45/06* (2013.01); *C07D 235/02* (2013.01)

(58) Field of Classification Search
CPC .. A61K 31/404; A61K 31/496; A61K 31/551; A61K 31/55; A61K 31/444; A61K 31/437; A61K 31/4184; A61K 31/4545; A61K 31/5025; A61K 31/5377; A61K 45/06; C07D 471/04; C07D 235/02
See application file for complete search history.

(56) References Cited

U.S. PATENT DOCUMENTS

| | | | |
|---|---|---|---|
| 6,184,225 | B1 | 2/2001 | Thomas et al. |
| 6,291,455 | B1 | 9/2001 | Thomas et al. |
| 6,362,336 | B1 | 3/2002 | Lohmann et al. |

(Continued)

FOREIGN PATENT DOCUMENTS

| | | |
|---|---|---|
| JP | H09-124609 | 5/1997 |
| WO | WO-0208213 A1 | 1/2002 |

(Continued)

OTHER PUBLICATIONS

Pharmaceutical excipients, 2014, https://web.archive.org/web/20141126115509/https://www.slideshare.net/nahidhasan7921/pharmaceutical-excipients.*
Grimble, 1994, https://www.ncbi.nlm.nih.gov/pubmed/7922442.*
RN 902436-55-9, entry date Aug. 17, 2006.*
RN 902436-70-8, entry date Aug. 17, 2006.*
Aurora-Fine-Chemicals, 2018, http://online.aurorafinechemicals.com/index.htm.*
Goldfarb-RN603094-05-9, 2009, caplus an 2009:846113.*
Goldfarb-RN902298-97-9, 2009, caplus an 2009:846114.*

(Continued)

*Primary Examiner* — Sun Jae Yoo
(74) *Attorney, Agent, or Firm* — Mintz Levin Cohn Ferris Glovsky and Popeo P.C.

(57) ABSTRACT

The present invention relates to compounds of formula I, wherein $A_1$, $A_2$, $A_3$, $R_1$, $R_2$, $R_3$, $R_4$, $R_5$, $R_6$, L, Ar and Q are each as defined herein. The compounds of the present invention are inhibitors of autotaxin (ATX) enzyme activity. The present invention also relates to processes for the preparation of these compounds, to pharmaceutical compositions comprising them, and to their use in the treatment of proliferative disorders, such as cancer, as well as other diseases or conditions (e.g. fibrosis) in which ATX activity is implicated.

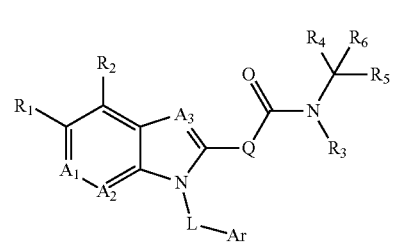

I

2 Claims, 3 Drawing Sheets

(56) References Cited

U.S. PATENT DOCUMENTS

| | | | |
|---|---|---|---|
| 6,423,753 | B1 | 7/2002 | Dougherty |
| 6,897,210 | B2 | 5/2005 | Thomas et al. |
| 7,030,123 | B2 | 4/2006 | Arnould et al. |
| 7,135,502 | B1 | 11/2006 | Davis et al. |
| 7,696,214 | B2 | 4/2010 | Hennequin et al. |
| 7,875,727 | B2 | 1/2011 | Davis |
| 8,022,239 | B2 | 9/2011 | Parrill-Baker et al. |
| 8,268,891 | B1 | 9/2012 | Parrill-Baker et al. |
| 8,343,934 | B2 | 1/2013 | Parrill-Baker et al. |
| 8,492,560 | B2 | 7/2013 | Stokes et al. |
| 8,497,283 | B2 | 7/2013 | Schultz et al. |
| 8,530,650 | B2 | 9/2013 | Schiemann et al. |
| 8,552,001 | B2 | 10/2013 | Schiemann et al. |
| 8,557,824 | B2 | 10/2013 | Schiemann et al. |
| 8,642,660 | B2 * | 2/2014 | Goldfarb .............. A61K 31/122 514/641 |
| 8,673,882 | B2 | 3/2014 | Gupte et al. |
| 8,791,111 | B2 | 7/2014 | Schiemann et al. |
| 8,841,324 | B2 | 9/2014 | Staehle et al. |
| 8,969,555 | B2 | 3/2015 | Beauchamp et al. |
| 9,029,387 | B2 | 5/2015 | Staehle et al. |
| 9,260,416 | B2 | 2/2016 | Roppe et al. |
| 9,273,011 | B2 | 3/2016 | Gibson et al. |
| 9,394,317 | B2 | 7/2016 | Jones et al. |
| 9,452,997 | B2 | 9/2016 | Schiemann et al. |
| 9,499,485 | B2 | 11/2016 | Guckian et al. |
| 9,522,889 | B2 | 12/2016 | Guckian et al. |
| 9,549,911 | B2 | 1/2017 | Sang et al. |
| 9,550,774 | B2 | 1/2017 | Bleisch et al. |
| 9,550,798 | B2 | 1/2017 | Guckian et al. |
| 9,555,050 | B2 | 1/2017 | Guckian et al. |
| 9,630,945 | B2 | 4/2017 | Furminger et al. |
| 9,636,330 | B2 | 5/2017 | Ohata et al. |
| 9,670,204 | B2 | 6/2017 | Desroy et al. |
| 9,771,326 | B2 | 9/2017 | Peng et al. |
| 9,850,206 | B2 | 12/2017 | Peng et al. |
| 9,862,721 | B2 | 1/2018 | Ohata et al. |
| 2005/0277627 | A1 | 12/2005 | Arnould et al. |
| 2010/0016258 | A1 | 1/2010 | Lynch et al. |
| 2010/0249132 | A1 | 9/2010 | Schultz et al. |
| 2011/0230471 | A1 | 9/2011 | Staehle et al. |
| 2012/0115852 | A1 | 5/2012 | Schultz et al. |
| 2015/0203493 | A1 | 7/2015 | Guckian et al. |
| 2015/0376194 | A1 | 12/2015 | Hert et al. |
| 2016/0002247 | A1 | 1/2016 | Nagano et al. |
| 2017/0050960 | A1 | 2/2017 | Hert et al. |

FOREIGN PATENT DOCUMENTS

| | | |
|---|---|---|
| WO | WO-2011053597 A1 | 5/2011 |
| WO | WO 2012/135296 | 10/2012 |
| WO | WO-2013054185 A1 | 4/2013 |
| WO | WO 2013/190320 | 12/2013 |
| WO | WO-2015193669 A1 | 12/2015 |

OTHER PUBLICATIONS

RN902297-99-8-pubchem, pubchem record for compound RN 902297-99-8, 2006.*
RN902297-99-8-pubchem-biological-test-results, pubchem record for compound RN 902297-99-8 for biological test results, 2006.*
RN902436-80-0, registry database, 2006.*
RN931935-18-1, registry database, 2006.*
RN902484-98-4, registry database compound, entry date Aug. 17, 2006.*
RN902570-67-6, registry database compound, entry date Aug. 18, 2006.*
RN931719-21-0, registry database compound, Apr. 22, 2007.*
Goldfarb, 2009, caplus an 2009:846114.*
PCT International Search Report and Written Opinion for Application No. PCT/GB2016/050268 dated May 9, 2016. (15 pages).

XP-002756980; Ambinter Stock Screening Collection, "Amb16693806", Database Chemcats, Database accession No. 0715145974 Chemcats, Sep. 15, 2014. (1 page).
XP-002756981; Ambinter Stock Screening Collection, "Amb16693782", Database Chemcats, Database accession No. 0189282133, Sep. 15, 2014. (1 page).
XP-002756982; ChemDiv Screening Collection, "C614-0971", Database Chemcats, Database accession No. 2058888426, May 13, 2015. (1 page).
XP-002756983; ChemDiv Screening Collection, "C614-0943", Database Chemcats, Database accession No. 1904759099, May 13, 2015. (1 page).
XP-002756984; Ambinter Stock Screening Collection, "Amb16693756", Database Chemcats, Database accession No. 0901256646, Sep. 15, 2014. (1 page).
XP-002756985; Ambinter Stock Screening Collection, "Amb16693812", Database Chemcats, Database accession No. 1678771737, Sep. 15, 2014. (1 page).
XP-002756986; AKos Out of Stock Catalog, "AKOS001836265", Database Chemcats, Database accession No. 1667788084, May 4, 2015. (1 page).
XP-002756987; Ambinter Stock Screening Collection, "Amb16693825", Database Chemcats, Database accession No. 0196105010, Sep. 15, 2014. (1 page).
XP-002756988; ChemDiv Screening Collection, "C614-0930", Database Chemcats, Database accession No. 0674250759, May 13, 2015. (1 page).
XP-002756989; AKos Screening Library, "AKOS001840275", Database Chemcats, Database accession No. 0181431037, May 4, 2015. (1 page).
Aznavoorian, Sadie, et al. "Signal transduction for chemotaxis and haptotaxis by matrix molecules in tumor cells." *The Journal of cell biology* 110.4 (1990): 1427-1438.
Baumforth, Karl RN, et al. "Induction of autotaxin by the Epstein-Barr virus promotes the growth and survival of Hodgkin lymphoma cells." *Blood* 106.6 (2005): 2138-2146.
Boucharaba, Ahmed, et al. "Platelet-derived lysophosphatidic acid supports the progression of osteolytic bone metastases in breast cancer." *The Journal of clinical investigation* 114.12 (2004): 1714-1725.
Boucher, Jérémie, et al. "Potential involvement of adipocyte insulin resistance in obesity-associated up-regulation of adipocyte lysophospholipase D/autotaxin expression." *Diabetologia* 48.3 (2005): 569-577.
Choi, Ji Woong, et al. "LPA receptors: subtypes and biological actions." *Annual review of pharmacology and toxicology* 50 (2010): 157-186.
Cui, Peng, et al. "α-and β-substituted phosphonate analogs of LPA as autotaxin inhibitors." *Bioorganic & medicinal chemistry* 16.5 (2008): 2212-2225.
Cui, Peng, et al. "Synthesis and biological evaluation of phosphonate derivatives as autotaxin (ATX) inhibitors." *Bioorganic & medicinal chemistry letters* 17.6 (2007): 1634-1640.
Ferry, Gilles, et al. "S32826, a nanomolar inhibitor of autotaxin: discovery, synthesis and applications as a pharmacological tool." *Journal of Pharmacology and Experimental Therapeutics* 327.3 (2008): 809-819.
Gajewiak, Joanna, et al. "Synthesis, pharmacology, and cell biology of sn-2-aminooxy analogues of lysophosphatidic acid." *Organic letters* 10.6 (2008): 1111-1114.
Hausman, D. B., et al. "The biology of white adipocyte proliferation." *Obesity reviews* 2.4 (2001): 239-254.
Houben, Anna JS, et al. "Autotaxin and LPA receptor signaling in cancer." *Cancer and Metastasis Reviews* 30.3-4 (2011): 557-565.
Inoue, Makoto, et al. "Autotaxin, a synthetic enzyme of lysophosphatidic acid (LPA), mediates the induction of nerve-injured neuropathic pain." *Molecular pain* 4.1 (2008): 6.
Inoue, Makoto, et al. "Initiation of neuropathic pain requires lysophosphatidic acid receptor signaling." *Nature medicine* 10.7 (2004): 712.
Jiang, Guowei, et al. "α-Substituted Phosphonate Analogues of Lysophosphatidic Acid (LPA) Selectively Inhibit Production and Action of LPA." *ChemMedChem* 2.5 (2007): 679-690.

(56) References Cited

OTHER PUBLICATIONS

Kanda, Hidenobu, et al. "Autotaxin, an ectoenzyme that produces lysophosphatidic acid, promotes the entry of lymphocytes into secondary lymphoid organs." *Nature immunology* 9.4 (2008): 415.
Knowlden, Sara, et al. "The autotaxin-LPA axis emerges as a novel regulator of lymphocyte homing and inflammation." *The Journal of Immunology* 192.3 (2014): 851-857.
Kremer, Andreas E., et al. "Serum autotaxin is increased in pruritus of cholestasis, but not of other origin, and responds to therapeutic interventions." *Hepatology* 56.4 (2012): 1391-1400.
Leblanc, Raphaël, et al. "New insights into the autotaxin/LPA axis in cancer development and metastasis." *Experimental cell research* 333.2 (2015): 183-189.
Lin, Songbai, et al. "The absence of LPA2 attenuates tumor formation in an experimental model of colitis-associated cancer." *Gastroenterology* 136.5 (2009): 1711-1720.
Liu, Shuying, et al. "Expression of autotaxin and lysophosphatidic acid receptors increases mammary tumorigenesis, invasion, and metastases." *Cancer cell* 15.6 (2009): 539-550.
Marshall, Jean-Claude A., et al. "Effect of inhibition of the lysophosphatidic acid receptor 1 on metastasis and metastatic dormancy in breast cancer." *Journal of the National Cancer Institute* 104.17 (2012): 1306-1319.
Masuda, Akiko, et al. "Serum autotaxin measurement in haematological malignancies: a promising marker for follicular lymphoma." *British journal of haematology* 143.1 (2008): 60-70.
Moolenaar, Wouter H., et al. "Autotaxin in embryonic development." *Biochimica et Biophysica Acta (BBA)-Molecular and Cell Biology of Lipids* 1831.1 (2013): 13-19.
Murakami, Masanori, et al. "Identification of the orphan GPCR, P2Y10 receptor as the sphingosine-1-phosphate and lysophosphatidic acid receptor." *Biochemical and biophysical research communications* 371.4 (2008): 707-712.
Nakamura, Kazuhiro, et al. "Serum lysophospholipase D/autotaxin may be a new nutritional assessment marker: study on prostate cancer patients." *Annals of clinical biochemistry* 44.6 (2007): 549-556.
Nakao, Momoko, et al. "Serum autotaxin levels correlate with pruritus in patients with atopic dermatitis." *The Journal of investigative dermatology* 134.6 (2014): 1745.
Nakasaki, Tae, et al. "Involvement of the lysophosphatidic acid-generating enzyme autotaxin in lymphocyte-endothelial cell interactions." *The American journal of pathology* 173.5 (2008): 1566-1576.
Nishimura, Satoshi, et al. "ENPP2 contributes to adipose tissue expansion and insulin resistance in diet-induced obesity." *Diabetes* 63.12 (2014): 4154-4164.
Pamuklar, Zehra, et al. "Autotaxin/lysopholipase D and lysophosphatidic acid regulate murine hemostasis and thrombosis." *Journal of Biological Chemistry* 284.11 (2009): 7385-7394.
Pradere, Jean-Philippe, et al. "LPA1 receptor activation promotes renal interstitial fibrosis." *Journal of the American Society of Nephrology* 18.12 (2007): 3110-3118.
Reynolds, G., et al. "The autotaxin-lysophosphatidate axis plays a key role in the pathogenesis of Hepatitis C virus-associated Hepatocellular carcinoma." *Virchows Archiv.* vol. 465. 233 Spring St, New York, NY 10013 USA: Springer, 2014.
Saga, Hiroshi, et al. "A novel highly potent autotaxin/ENPP2 inhibitor produces prolonged decreases in plasma lysophosphatidic acid formation in vivo and regulates urethral tension." *PLoS One* 9.4 (2014): e93230.
Siess, Wolfgang, et al. "Lysophosphatidic acid mediates the rapid activation of platelets and endothelial cells by mildly oxidized low density lipoprotein and accumulates in human atherosclerotic lesions." *Proceedings of the National Academy of Sciences* 96.12 (1999): 6931-6936.
Siess, Wolfgang, et al. "Thrombogenic and atherogenic activities of lysophosphatidic acid." *Journal of cellular biochemistry* 92.6 (2004): 1086-1094.
Tabata, Ken-ichi, et al. "The orphan GPCR GPR87 was deorphanized and shown to be a lysophosphatidic acid receptor." *Biochemical and biophysical research communications* 363.3 (2007): 861-866.
Tager, Andrew M., et al. "The lysophosphatidic acid receptor LPA1 links pulmonary fibrosis to lung injury by mediating fibroblast recruitment and vascular leak." *Nature medicine* 14.1 (2008): 45.
Taghavi, P., et al. "In vitro genetic screen identifies a cooperative role for LPA signaling and c-Myc in cell transformation." *Oncogene* 27.54 (2008): 6806.
Tigyi, Gabor. "Physiological responses to lysophosphatidic acid and related glycero-phospholipids." *Prostaglandins & other lipid mediators* 64.1-4 (2001): 47-62.
Van Meeteren, Laurens A., et al. "Inhibition of autotaxin by lysophosphatidic acid and sphingosine 1-phosphate." *Journal of Biological Chemistry* 280.22 (2005): 21155-21161.
Van Meeteren, Laurens A., et al. "Regulation and biological activities of the autotaxin-LPA axis." *Progress in lipid research* 46.2 (2007): 145-160.
Watanabe, Naoko, et al. "Both plasma lysophosphatidic acid and serum autotaxin levels are increased in chronic hepatitis C." *Journal of clinical gastroenterology* 41.6 (2007): 616-623.
Wu, Jian-Min, et al. "Autotaxin expression and its connection with the TNF-alpha-NF-κB axis in human hepatocellular carcinoma." *Molecular cancer* 9.1 (2010): 71.
Zhang, Honglu, et al. "Dual activity lysophosphatidic acid receptor pan-antagonist/autotaxin inhibitor reduces breast cancer cell migration in vitro and causes tumor regression in vivo." *Cancer research* 69.13 (2009): 5441-5449.
Zhang, Yafeng, et al. "Autotaxin through lysophosphatidic acid stimulates polarization, motility, and transendothelial migration of naive T cells." *The Journal of Immunology* 189.8 (2012): 3914-3924.
Zhao, Hongjuan, et al. "Distinctive gene expression of prostatic stromal cells cultured from diseased versus normal tissues." *Journal of cellular physiology* 210.1 (2007): 111-121.
Zu Heringdorf, Dagmar Meyer, et al. "Lysophospholipid receptors: signalling, pharmacology and regulation by lysophospholipid metabolism." *Biochimica et Biophysica Acta (BBA)-Biomembranes* 1768.4 (2007): 923-940.
Monforte, et al., Design and synthesis of N1-aryl-benzimidazoles 2-substituted as novel HIV-1 non-nucleoside reverse transcriptase inhibitors, Bioorganic & Medicinal Chemistry, 2014, pp. 1459-1467, vol. 22.

\* cited by examiner

AUTOTAXIN INHIBITORY COMPOUNDS

CROSS-REFERENCE TO RELATED APPLICATIONS

This application is a U.S. national stage application of International Patent Application No. PCT/GB2016/050268, filed on Feb. 4, 2016, which claims priority to GB Application No. 1502020.9, filed on Feb. 6, 2015, the content of each of these applications is incorporated herein in its entirety by reference.

FIELD OF THE INVENTION

The present invention relates to certain compounds that function as inhibitors of autotaxin (ATX) enzyme activity. The present invention also relates to processes for the preparation of these compounds, to pharmaceutical compositions comprising them, and to their use in the treatment of proliferative disorders, such as cancer, as well as other diseases or conditions (e.g. fibrosis) in which ATX activity is implicated.

BACKGROUND OF THE INVENTION

Autotaxin (ATX), also known as ectonucleotide pyrophosphatase/phosphodiesterase family member 2 (ENPP2), is a secreted lysophospholipase D (lysoPLD) that cleaves choline from lysophosphatidylcholine (LPC) forming lysophosphatidic acid (LPA), a potent mitogen and motily factor that has been implicated in the pathophysiology of cancer (Liu et al., 2009) (Houben and Moolenaar, 2011) (Leblanc and Peyruchaud, 2014) and many other biological processes such as vascular development lymphocyte homing and inflammation (see, e.g., Van Meeteren et al., 2007) (Moolenaar et al., 2013) (Knowlden and Georas, 2014). LPA consists of a single fatty acyl chain, a glycerol backbone and a free phosphate group. The great variety of cellular and biological actions of LPA is explained by the fact that the six known LPA receptors show broad tissue expression and can couple to at least six distinct G proteins, which, in turn, feed into multiple effector systems (Choi et al., 2010).

ATX is processed along the classical export pathway and secreted as a catalytically active glycoprotein. ATX's major lipid substrate, LPC, is secreted by the liver and is abundantly present in plasma and interstitial fluids.

As previously indicated, ATX is implicated in cancer and numerous other disease states. The role of ATX in cancer and various other disease states is summarised below.

ATX and Cancer

ATX is widely expressed, with highest mRNA levels detected in lymph nodes, brain, kidney, testis, pancreas, lung and liver. ATX is found overexpressed in several common human cancers, while many established tumour cell lines express ATX to varying levels (see references above). Expression is also detected in stromal cells, including macrophages, fibroblasts and endothelial cells.

ATX is an attractive target for the treatment of cancer because it acts extracellularly and stimulates the metastatic cascade at multiple levels. In addition, ATX has been implicated in inflammatory processes by regulating lymphocyte homing (Kanda et al, 2008; Zhang et al, 2012; Knowlden and Georas, 2014).

ATX is thought to act in an autocrine/paracrine manner to promote tumour progression, i.e., by providing an invasive and angiogenic microenvironment for malignant cells. A causal link between the ATX-LPA axis and cancer is supported by a growing number of studies (for a review, see Van Meeteren et al., 2007; Houben A J, Moolenaar W H (2011). Cancer Metastasis Rev. 30:557-65.) (Leblanc and Peyruchaud, 2015).

Overexpressed ATX promotes tumour aggressiveness, metastasis and angiogenesis in mice (Liu et al., 2009).

ATX is overexpressed in various human cancers, including glioblastoma, lung and breast cancer, renal cell carcinoma and Hodgkin lymphoma. Furthermore, ATX is upregulated in stromal cells from cancer patients. (See, e.g., Zhao et al., 2007).

ATX mediates the EBV-induced growth and survival of Hodgkin lymphoma cells, while ATX knockdown reduces lymphoma cell growth and viability. (See, e.g., Baumforth et al., 2005).

Inducible overexpression of LPA1 receptors in breast carcinoma cells promotes tumour growth and bone metastasis, while LPA1 knockdown reduces tumour progression (Bouchabara et al. 2006).

ATX and LPA receptors have transforming potential both in vitro and in mice. (See, e.g., Taghavi et al., 2008. Liu et al. (2009) Cancer Cell. 15:539-50).

Inhibition of the LPA1 receptor reduces metastasis and metastatic dormancy in breast cancer. (Marshall et al., 2012).

Serum ATX levels in patients with B-cell neoplasms, especially follicular lymphoma (FL), are higher than those in healthy subjects (see, e.g., Masuda et al., 2008). Serum ATX in FL patients was associated with tumour burden and changed in parallel with the patients' clinical courses. Plasma LPA levels in FL patients correlated well with ATX levels. Since tumour cells from FL patients expressed ATX, secreted ATX from lymphoma cells probably underlies the increase in serum ATX. Thus, serum ATX is a promising marker for FL.

ATX/lysoPLD activity is also significantly elevated in malignant effusions from ovarian cancer patients. Furthermore, serum ATX activity decreases after prostate cancer surgery and may reflect postoperative damage or nutritional status. See, e.g., Nakamura et al., 2007.

Dual ATX and pan-LPA receptor inhibitors inhibit breast cancer cell migration and invasion and cause tumour regression in breast cancer xenograft model. (See, e.g., Zhang et al., 2009).

Overexpression of ATX or LPA receptors in breast cancer epithelium causes high frequency of late-onset mammary carcinomas. (See, e.g., Liu et al., 2009).

LPA2 knockout mice have reduced incidence of chemically induced colon carcinoma. (See, e.g., Lin et al., 2009).

ATX and Inflammation

High ATX expression is found in the high endothelial venules (HEVs) of lymphoid organs and in venules at sites of chronic inflammation, where it may play a role in T cell trafficking across the endothelial walls during inflammation. (See, e.g., Kanda et al., 2008). Intravenous injection of enzymatically inactive ATX attenuated the homing of T cells to lymphoid tissues, probably through competition with endogenous ATX. These results suggest that ATX is a potential target for anti-inflammatory therapy.

Along similar lines, Japanese investigators recently showed that injection of neutralizing monoclonal antibodies against ATX into mice reduced plasma LPA levels to zero. (See, e.g., Nakasaki et al., 2008). It thus appears that plasma LPA can be depleted by targeting ATX. These results suggest that ATX is a potential target for anti-inflammatory therapy.

ATX and Diabetes Melitus

ATX expression is significantly up-regulated in adipose tissue from patients exhibiting both insulin resistance and impaired glucose tolerance (see, for example, Boucher et al., 2005). This suggests that ATX may serve as a therapeutic target in obesity-associated type 2 diabetes (Nishimura S, et al. (2014). ENPP2 Contributes to Adipose Tissue Expansion and Insulin Resistance in Diet-Induced Obesity. Diabetes 63:4154-64).

ATX and Hypertension, Atherosclerosis and Thrombosis

LPA accumulates in the lipid core of human atherosclerotic plaques and is the primary platelet-activating lipid constituent of the plaques (see, for example, Siess et al., 1999). Furthermore, due to its ability to stimulate the proliferation of vascular smooth muscle cells, LPA may play an important role in the development of both hypertension and atherosclerosis (see, for example, Siess et al., 2004). Recent evidence shows that plasma ATX associates with platelets during aggregation and concentrates in arterial thrombus (see, for example, Pamuklar et al., 2009). Thus, unbalanced LPA homeostasis is a potential risk factor for thrombosis. Therefore, LPA-lowering ATX inhibitors may prove useful in the treatment of both hypertension and atherosclerosis.

ATX and Fibrosis

Mice lacking the LPA1 receptor are markedly protected from pulmonary fibrosis and mortality (see, e.g., Tager et al., 2008). The absence of LPA1 leads to reduced fibroblast recruitment and vascular leak, two responses that are excessive when injury leads to fibrosis rather than to repair. Thus, the ATX-LPA axis represents a therapeutic target for diseases in which aberrant responses to injury contribute to fibrosis, such as idiopathic pulmonary fibrosis, as well as renal interstitial fibrosis (see, e.g., Pradere et al., 2007), hepatic fibrosis and skin fibrosis.

ATX and Pain

Mice lacking the LPA1 receptor are also protected against injury-induced neuropathic pain and related behaviour (see, e.g., Inoue et al., 2004). Heterozygous Enpp2(+/−) mice, which have 50% ATX protein compared to wild-type mice, show approx. 50% recovery of nerve injury-induced neuropathic pain (see, e.g., Inoue et al., 2008). Therefore, targeting ATX (and its downstream LPA signaling pathways) represents a novel way to prevent nerve injury-induced neuropathic pain.

ATX and Urethral Obstructive Disease

Smooth muscle contraction is known to be promoted by lysophosphatidic acid and inhibition of ATX has been shown to decrease intraurethral pressure accompanied by urethral relaxation (see e.g. Saga et al., 2014). Therefore, targeting ATX (and its downstream LPA signaling pathways) represents a useful method for the treatment of urethral obstructive disease such as benign prostatic hyperplasia.

ATX and Pruritus

Serum ATX levels have been reported to correlate with pruritus of cholestasis (Kremer et al., 2012). Serum ATX levels have also been shown to correlate with pruritus in patients with atopic dermatitis (Nakao et al., 2014). This suggests that targeting ATX (and its downstream LPA signaling pathways) represents a useful method for the treatment of pruritus.

ATX and Hepatitis C and B/Human Hepatocellular Carcinoma

Serum ATX activity and plasma LPA levels are increased in chronic hepatitis C (HCV) in association with liver fibrosis (Watanabe et al, 2007). ATX and genes related to ATX signalling pathway were up regulated in human hepatocellular carcinoma (HCC) patients co-infected with HCV (Wu et al, 2010). It has recently been reported that ATX expression in tumour cells is specifically associated with HCV and that ATX plays a key role in HCV replication. (Reynolds et al, 2014). Recent studies have also reported the ATX-LPA signalling axis to play an essential role in the lifecycle of both chronic hepatitis B (HBV) and chronic hepatitis C (HCV) (WO2015193669). Thus, ATX-LPA is also a potential therapeutic target for the treatment of hepatitis B and hepatitis C.

ATX Inhibitors

Potent and selective ATX inhibitors are now needed as a starting point for the development of targeted anti-ATX therapy. Direct targeting of LPA receptors seems to be a less attractive strategy, since there are at least six distinct LPA receptors that show overlapping activities (see Choi et al. (2010). Since it was reported that ATX is subject to product inhibition by LPA and sphingosine-1-phosphate (S1P) (see, e.g., van Meeteren et al., 2005), various synthetic phospho- and phosphonate lipids have been explored as ATX inhibitors (see, e.g., Gajewiak et al., 2008; Cui et al, 2007; Jiang et al., 2007; Ferry et al., 2008; Zhang et al., 2009; Cui et al., 2008). However, these inhibitors have the inherent danger of inadvertently activating downstream LPA/S1P receptors, thereby inducing the opposite of the intended effect. Furthermore, lipids offer relatively few avenues for chemical diversification and usually have poor pharmacokinetic properties.

Non-lipid inhibitors of ATX have recently been identified and some of which are described in the following patents: WO2009046841; WO2009046804; WO2009046842; WO 2010115491; WO2010060532; WO2010063352; WO2010112116; WO2010112124; US2010/0016258; WO201040080; WO2011006569; WO2011044978; WO2011116867; WO2011053597; WO2011002918; WO2012166415; WO2012005227; WO2012127885; U.S. Pat. No. 8,268,891; WO2012100018; WO2013061297; WO2013054185; WO2014018881; WO2014018887; WO2014081756; WO2014152725; WO2014110000; WO2014168824; WO2014018891; WO2014025708; WO2014025709; WO2014081752; WO2014139882; WO2014143583; WO2014097151; WO 2014048865; WO2014139978; WO 2014133112.

SUMMARY OF THE INVENTION

In one aspect, the present invention provides a compound as defined herein, or a pharmaceutically acceptable salt or solvate thereof.

In another aspect, the present invention provides a pharmaceutical composition as defined herein which comprises a compound as defined herein, or a pharmaceutically acceptable salt or solvate thereof, and one or more pharmaceutically acceptable excipients.

In another aspect, the present invention provides a compound as defined herein, or a pharmaceutically acceptable salt or solvate thereof, or a pharmaceutical composition as defined herein, for use in therapy.

In another aspect, the present invention provides a compound as defined herein, or a pharmaceutically acceptable salt or solvate thereof, or a pharmaceutical composition as defined herein, for use in the treatment of a proliferative condition.

In another aspect, the present invention provides a compound as defined herein, or a pharmaceutically acceptable salt or solvate thereof, or a pharmaceutical composition as defined herein, for use in the treatment of cancer. In a particular embodiment, the cancer is a human cancer.

In another aspect, the present invention provides a compound as defined herein, or a pharmaceutically acceptable salt or solvate thereof, or a pharmaceutical composition as defined herein, for use in the treatment of inflammation.

In another aspect, the present invention provides a compound as defined herein, or a pharmaceutically acceptable salt or solvate thereof, or a pharmaceutical composition as defined herein, for use in the treatment of diabetes mellitus.

In another aspect, the present invention provides a compound as defined herein, or a pharmaceutically acceptable salt or solvate thereof, or a pharmaceutical composition as defined herein, for use in the treatment of hypertension, Atherosclerosis or Thrombosis.

In another aspect, the present invention provides a compound as defined herein, or a pharmaceutically acceptable salt or solvate thereof, or a pharmaceutical composition as defined herein, for use in the treatment of pain. In a particular embodiment, the pain is neuropathic pain.

In another aspect, the present invention provides a compound as defined herein, or a pharmaceutically acceptable salt or solvate thereof, or a pharmaceutical composition as defined herein, for use in the treatment of urethral obstructive disease. In a particular embodiment, the urethral obstructive disease is benign prostatic hyperplasia.

In another aspect, the present invention provides a compound as defined herein, or a pharmaceutically acceptable salt or solvate thereof, or a pharmaceutical composition as defined herein, for use in the treatment of pruritus.

In another aspect, the present invention provides a compound as defined herein, or a pharmaceutically acceptable salt or solvate thereof, or a pharmaceutical composition as defined herein, for use in the treatment of hepatitis B and/or C.

In another aspect, the present invention provides a compound as defined herein, or a pharmaceutically acceptable salt or solvate thereof, or a pharmaceutical composition as defined herein, for use in the treatment of fibrosis, including lung, renal, hepatic and skin fibrosis.

In another aspect, the present invention provides a compound as defined herein, or a pharmaceutically acceptable salt or solvate thereof, or a pharmaceutical composition as defined herein, for use in the production of an ATX inhibitory effect.

In another aspect, the present invention provides the use of a compound as defined herein, or a pharmaceutically acceptable salt or solvate thereof, in the manufacture of a medicament for use in the treatment of a proliferative condition.

In another aspect, the present invention provides the use of a compound as defined herein, or a pharmaceutically acceptable salt or solvate thereof, in the manufacture of a medicament for use in the treatment of cancer. Suitably, the medicament is for use in the treatment of human cancers.

In another aspect, the present invention provides the use of a compound as defined herein, or a pharmaceutically acceptable salt or solvate thereof, in the manufacture of a medicament for use in the production of an ATX inhibitory effect.

In another aspect, the present invention provides a method of inhibiting ATX in vitro or in vivo, said method comprising contacting a cell with an effective amount of a compound as defined herein, or a pharmaceutically acceptable salt or solvate thereof.

In another aspect, the present invention provides a method of inhibiting cell proliferation in vitro or in vivo, said method comprising contacting a cell with an effective amount of a compound as defined herein, or a pharmaceutically acceptable salt or solvate thereof.

In another aspect, the present invention provides a method of treating a proliferative disorder in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a method of treating cancer in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a method of treating fibrosis in a patient in need of such treatment, said method comprising administering to said patient a therapeutically effective amount of a compound as defined herein, or a pharmaceutically acceptable salt or solvate thereof, or a pharmaceutical composition as defined herein. Suitably, the method is for the treatment of lung, renal, hepatic or skin fibrosis.

The present invention further provides a method of synthesising a compound, or a pharmaceutically acceptable salt or solvate thereof, as defined herein.

In another aspect, the present invention provides a compound as defined herein, or a pharmaceutically acceptable salt or solvate thereof, obtainable by, or obtained by, or directly obtained by a method of synthesis as defined herein.

In another aspect, the present invention provides novel intermediates as defined herein which are suitable for use in any one of the synthetic methods as set out herein.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

An "alkylene," "alkenylene," or "alkynylene" group is an alkyl, alkenyl, or alkynyl group that is positioned between and serves to connect two other chemical groups. Thus, "(1-6C)alkylene" means a linear saturated divalent hydrocarbon radical of one to six carbon atoms or a branched saturated divalent hydrocarbon radical of three to six carbon atoms, for example, methylene, ethylene, propylene, 2-methylpropylene, pentylene, and the like.

"(2-6C)alkenylene" means a linear divalent hydrocarbon radical of two to six carbon atoms or a branched divalent hydrocarbon radical of three to six carbon atoms, containing at least one double bond, for example, as in ethenylene, 2,4-pentadienylene, and the like.

"(2-6C)alkynylene" means a linear divalent hydrocarbon radical of two to six carbon atoms or a branched divalent hydrocarbon radical of three to six carbon atoms, containing at least one triple bond, for example, as in ethynylene, propynylene, and butynylene and the like.

"(3-8C)cycloalkyl" means a hydrocarbon ring containing from 3 to 8 carbon atoms, for example, cyclopropyl, cyclobutyl, cyclopentyl, cyclohexyl, cycloheptyl or bicyclo[2.2.1]heptyl.

"(3-8C)cycloalkenyl" means a hydrocarbon ring containing at least one double bond, for example, cyclobutenyl, cyclopentenyl, cyclohexenyl or cycloheptenyl, such as 3-cyclohexen-1-yl, or cyclooctenyl.

"(3-8C)cycloalkyl-(1-6C)alkylene" means a (3-8C)cycloalkyl group covalently attached to a (1-6C)alkylene group, both of which are defined herein.

The term "halo" or "halogeno" refers to fluoro, chloro, bromo and iodo.

The term "heterocyclyl", "heterocyclic" or "heterocycle" means a non-aromatic saturated or partially saturated monocyclic, fused, bridged, or Spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example *Advanced Organic Chemistry*, by Jerry March, 4th Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

By "spiro bi-cyclic ring systems" we mean that the two ring systems share one common spiro carbon atom, i.e. the heterocyclic ring is linked to a further carbocyclic or heterocyclic ring through a single common Spiro carbon atom. Examples of Spiro ring systems include 6-azaspiro[3.4]octane, 2-oxa-6-azaspiro[3.4]octane, 2-azaspiro[3.3]heptanes, 2-oxa-6-azaspiro[3.3]heptanes, 7-oxa-2-azaspiro[3.5]nonane, 6-oxa-2-azaspiro[3.4]octane, 2-oxa-7-azaspiro[3.5]nonane and 2-oxa-6-azaspiro[3.5]nonane.

"Heterocyclyl(1-6C)alkyl" means a heterocyclyl group covalently attached to a (1-6C)alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur.

Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:
a benzene ring fused to a 5- or 6-membered ring containing 1, 2 or 3 ring heteroatoms;
a pyridine ring fused to a 5- or 6-membered ring containing 1, 2 or 3 ring heteroatoms;
a pyrimidine ring fused to a 5- or 6-membered ring containing 1 or 2 ring heteroatoms;
a pyrrole ring fused to a 5- or 6-membered ring containing 1, 2 or 3 ring heteroatoms;
a pyrazole ring fused to a 5- or 6-membered ring containing 1 or 2 ring heteroatoms;
a pyrazine ring fused to a 5- or 6-membered ring containing 1 or 2 ring heteroatoms;
an imidazole ring fused to a 5- or 6-membered ring containing 1 or 2 ring heteroatoms;
an oxazole ring fused to a 5- or 6-membered ring containing 1 or 2 ring heteroatoms;
an isoxazole ring fused to a 5- or 6-membered ring containing 1 or 2 ring heteroatoms;
a thiazole ring fused to a 5- or 6-membered ring containing 1 or 2 ring heteroatoms;
an isothiazole ring fused to a 5- or 6-membered ring containing 1 or 2 ring heteroatoms;
a thiophene ring fused to a 5- or 6-membered ring containing 1, 2 or 3 ring heteroatoms;
a furan ring fused to a 5- or 6-membered ring containing 1, 2 or 3 ring heteroatoms;
a cyclohexyl ring fused to a 5- or 6-membered heteroaromatic ring containing 1, 2 or 3 ring heteroatoms; and
a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzfuranyl, benzthiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl(1-6C)alkyl" means a heteroaryl group covalently attached to a (1-6C)alkylene group, both of which are defined herein. Examples of heteroaralkyl groups include pyridin-3-ylmethyl, 3-(benzofuran-2-yl)propyl, and the like.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The term "aryl(1-6C)alkyl" means an aryl group covalently attached to a (1-6C)alkylene group, both of which are defined herein. Examples of aryl-(1-6C)alkyl groups include benzyl, phenylethyl, and the like.

This specification also makes use of several composite terms to describe groups comprising more than one functionality. Such terms will be understood by a person skilled in the art. For example heterocyclyl(m-nC)alkyl comprises (m-nC)alkyl substituted by heterocyclyl.

The term "optionally substituted" refers to either groups, structures, or molecules that are substituted and those that are not substituted. The term "wherein a/any $CH$, $CH_2$, $CH_3$ group or heteroatom (i.e. NH) within a $R^1$ group is optionally substituted" suitably means that (any) one of the hydrogen radicals of the $R^1$ group is substituted by a relevant stipulated group.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Compounds of the Invention

In one aspect, the present invention relates compounds, or a pharmaceutically acceptable salts or solvates thereof, having the structural formula I shown below:

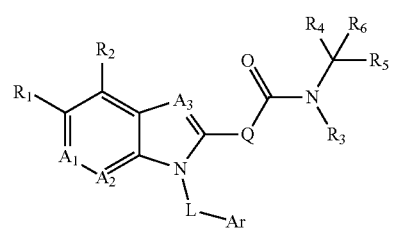

wherein:
$R_1$ and $R_2$ are independently selected from H, (1-2C)alkyl, halo, cyano, nitro, hydroxyl, amino, mercapto, (1-2C)haloalkyl, (1-2C)alkoxy or (1-2C)fluoroalkoxy;

$A_1$ is N or C—$R_d$, wherein $R_d$ is selected from H, halo, (1-2C)alkyl, cyano, nitro, hydroxyl, amino, (1-2C)haloalkyl, (1-2C)alkoxy, or (1-2C)haloalkoxy;

$A_2$ is N or C—$R_e$ wherein $R_e$ is selected form H, F, Cl or (1-2C)alkyl;

$A_3$ is N or $CR_f$, wherein $R_f$ is selected from H, halo, (1-2C)alkyl, cyano, nitro, hydroxyl, amino, (1-2C)haloalkyl, (1-2C)alkoxy, (1-2C)haloalkoxy, $NR_gR_g$, $OR_g$, $C(O)R_g$, $C(O)OR_g$, $OC(O)R_g$, $C(O)N(R_h)R_g$, $N(R_h)C(O)R_g$, $S(O)_yR_g$ (where y is 0, 1 or 2), $SO_2N(R_h)R_g$, $N(R_h)SO_2R_g$ or $(CH_2)_zNR_hR_g$ (where z is 1, 2 or 3), wherein $R_g$ and $R_h$ are each independently selected from H or (1-2C)alkyl;

L is a methylene optionally substituted by (1-2C)alkyl or oxo;

Ar is either a 5 or 6 membered heteroaryl optionally substituted by H, halo, (1-4C)alkyl, (1-4C)haloalkyl, $OCF_3$, (1-4C)alkoxy, (2-4C)alkenyl, (2-4C)alkynyl, (3-6C)cycloalkyl, (3-6C)cycloalkyl(1-2C)alkyl or a group of the formula:

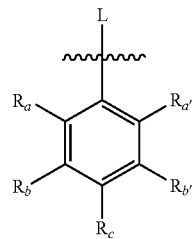

wherein:
$R_a$ and $R_{a'}$ are independently selected from H, fluoro, (1-2C)alkyl (1-2C)alkoxy or (1-2C)fluoroalkoxy;

$R_b$ and $R_{b'}$ are independently selected from H, fluoro, chloro, (1-2C)alkyl, (1-2Cfluoroalkoxy or (1-2C)alkoxy;

$R_c$ is selected from is H, (1-4C)alkyl, halo, hydroxyl, (1-4C)haloalkyl, (1-4C)alkoxy, (1-4C)haloalkoxy, (2-4C)alkenyl, (2-4C)alkynyl, (3-6C)cycloalkyl, (3-6C)cycloalkyl(1-2C)alkyl, $NR_iR_j$, $OR_i$, $C(O)R_i$, $C(O)OR_i$, $OC(O)R_i$, $C(O)N(R_j)R_i$, $N(R_j)C(O)R_i$, $S(O)_yR_i$ (where y is 0, 1 or 2), $SO_2N(R_j)R_i$, $N(R_j)SO_2R_i$ or $(CH_2)_zNR_jR_i$ (where z is 1, 2 or 3), wherein $R_i$ and $R_j$ are each independently selected from H or (1-2C)alkyl; or $R_c$ is a group of the formula:

-$L_1$-B wherein:
$L_1$ is (1-2C)alkylene or —O-(1-2C)alkylene, each of which is optionally substituted by (1-2C)alkyl or oxo; and B is phenyl or 5 or 6 membered heteroaryl optionally substituted with halo or (1-2C)alkyl;

Q is either a group of the formula:

—$CHR_x$—$R_k$— wherein:
$R_k$ is $CH_2$, NR, or O, wherein $R_i$ is selected from H or (1-2C)alkyl; and
$R_x$ is H or (1-2C)alkyl;

or Q is a group of the formula:

—$R_m$—$CHR_y$— wherein:
$R_m$ is O, S, SO, $SO_2$ or SO(NH); and
$R_y$ is H or (1-2C)alkyl;

$R_3$ is selected from H or (1-6C)alkyl optionally substituted by one or more substituents selected from halo, trifluoromethyl, trifluoromethoxy, amino, cyano, hydroxyl, mercapto, carboxyl, carbamoyl, sulphamoyl, (1-4C)alkyl, $NR_nR_o$, $OR_n$, $C(O)R_n$, $C(O)OR_n$, $OC(O)R_n$, $C(O)N(R_o)R_n$, $N(R_o)C(O)R_n$, $S(O)_yR_n$ (where y is 0, 1 or 2), $SO_2N(R_o)R_n$, $N(R_o)SO_2R_n$ or $(CH_2)_zNR_oR_n$ (where z is 1, 2 or 3), wherein $R_n$ and $R_o$ are each independently selected from H or (1-4C)alkyl;

$R_4$ is H, (1-4C)alkyl, carboxyl, carbamoyl, sulphamoyl, amido, ureido, (3-4C)cycloalkyl, (3-4C)cycloalkyl(1-4C)alkyl, wherein said (1-4C)alkyl, (3-4C)cycloalkyl or (3-4C)cycloalkyl(1-4C)alkyl is optionally substituted with one or more substituents selected from halo, amino, mercapto, cyano, hydroxyl, carboxyl, carbamoyl, sulphamoyl, (1-4C)alkyl, (1-4C)haloalkyl, (1-4C)alkoxy, (1-4C)haloalkoxy, $NR_pR_q$, $OR_i$, $C(O)R_p$, $C(O)OR_p$, $OC(O)R_p$, $C(O)N(R_q)R_p$, $N(R_q)C(O)R_p$, $S(O)_yR_p$ (where y is 0, 1 or 2), $SO_2N(R_q)R_p$, $N(R_q)SO_2R_p$ or $(CH_2)_zNR_qR_p$ (where z is 1, 2 or 3), wherein $R_p$ and $R_q$ are each independently selected from H or (1-4C)alkyl;

$R_5$ is selected from hydrogen or a group of formula:

-$L_5$W—Z wherein:
$L_5$ is absent or (1-2C)alkylene optionally substituted by (1-2C)alkyl or oxo;

W is absent or selected from C(O), C(O)O, C(O)N($R_r$), wherein $R_r$ is selected from hydrogen or (1-2C)alkyl; and Z is phenyl, heteroaryl, heterocycyl or (3-6C)carbocyclyl, optionally substituted with one or more substituents selected from halo, (1-4C)haloalkyl, (1-4C)alkoxy, (1-4C)haloalkoxy, (2-4C)alkenyl, (2-4C)alkynyl, amino, mercapto, cyano, hydroxyl, carboxyl, carbamoyl, sulphamoyl, (1-4C)alkyl, $NR_sR_t$, $OR_s$, $C(O)R_s$, $C(O)OR_s$, $OC(O)R_s$, $C(O)N(R_t)R_s$, $N(R_t)C(O)R_s$, $S(O)_y R_s$ (where y is 0, 1 or 2), $SO_2N(R_t)R_s$, $N(R_t)SO_2R_s$ or $(CH_2)_zNR_sR_t$ (where z is 1, 2 or 3), wherein $R_s$ and $R_t$ are each independently selected from H or (1-4C)alkyl; or Z is optionally substituted by a group of formula:

—V-$L_6$-Y wherein
V is absent or selected from O, S, SO, $SO_2$, N($R_u$), C(O), C(O)O or OC(O), wherein $R_u$ is hydrogen or (1-2C)alkyl;

$L_6$ is absent or a (1-4C)alkylene optionally substituted by (1-2C)alkyl or oxo;

Y is selected from amino, (1-6C)alkyl, phenyl, 5 or 6 membered heteroaryl, (3-7C)heterocycyl or amino, optionally substituted with one or more substituents selected from halo, (1-2C)alkyl, cyano, nitro, hydroxyl, (1-2C)hydroxyalkyl, amino, (1-2C)haloalkyl, $NR_{aa}R_{bb}$, $OCF_3$ or (1-2C)alkoxy, wherein $R_{aa}$ and $R_{bb}$ are each independently selected from H or (1-2C)alkyl;

or $R_4$ and $R_5$ are linked such that, together with the carbon atom to which they are attached, they form: (i) a mono or bicyclic heteroaryl ring; (ii) a mono or bicyclic heterocyclyl ring; (iii) a mono or bicyclic aryl ring; or (iv) a 5 or 6 membered cycloalkyl ring which is fused with a phenyl, 5 or 6 membered heteroaryl, 5 or 6 membered heterocyclyl or (3-6C)carbocyclyl ring;

each of which is optionally substituted with one or more substituents selected from halo, amino, mercapto, cyano, hydroxyl, carboxyl, carbamoyl, sulphamoyl, (1-4C)alkyl, (1-4C)haloalkyl, (1-4C)alkoxy, (1-4C)haloalkoxy, (2-4C)alkenyl, (2-4C)alkynyl, $NR_vR_w$, $C(O)R_v$, $C(O)OR_v$, $OC(O)R_v$, $C(O)N(R_w)R_v$, $N(R_w)C(O)R_v$, $S(O)_yR_v$ (where y is 0, 1 or 2), $SO_2N(R_w)R_v$, $N(R_w)SO_2R_v$ or $(CH_2)_zNR_vR_w$ (where z is 1, 2 or 3), wherein $R_v$ and $R_w$ are each independently selected from H or (1-4C)alkyl;

$R_6$ is selected from H or (1-2C)alkyl;

with the proviso that:
(i) only one or two of $A_1$, $A_2$ and $A_3$ can be N;
(ii) $A_1$ and $A_2$ cannot both be CH;
(iii) when $R_1$ and $R_2$ are H, $A_1$ is CH, $A_2$ is N, $A_3$ is N, Q is ethylene, $R_3$ is H, $R_4$ is H, $R_6$ is H, L is methylene, $R_5$ is: phenyl, 2-chlorophenyl, 3-chlorophenyl, 4-chlorophenyl, 4-methylphenyl, 2-methoxyphenyl, 4-methoxyphenyl, 4-ethoxyphenyl, 4-ethoxybenzyl, 2,5-dimethoxyphenyl, 4-methylsulfanyl-phenyl, 4-fluorophenyl, 2-furanyl, 5-(4-morpholinylmethyl)-2-furanyl, benzyl, 3-methylbenzyl, 4-methylsulfanylbenzyl, 2-pyridyl, 3-pyridyl, 1,3-benzodioxyl-5-yl, or 1-[(3-chlorophenyl)methyl]-4-piperidinyl;
then Ar is not phenyl, furanyl, thiophenyl or paramethoxyphenyl; and
(iv) when $R_4$ and $R_6$ are H, $R_5$ is furanyl and Ar is phenyl, $R_m$ is not S.

In an embodiment of the invention, the compounds of formula I defined herein are as defined above with the proviso that (proviso (iii)) when $R_1$ and $R_2$ are H, $A_1$ is CH, $A_2$ is N, $A_3$ is N, Q is ethylene, $R_3$ is H, $R_4$ is H, $R_6$ is H, L is methylene, then Ar is not phenyl, furanyl, thiophenyl or paramethoxyphenyl.

In a further embodiment of the invention, the compounds of formula I defined herein are as defined above with the proviso that (proviso (iii)) when $R_4$ and $R_6$ are H, then Ar is not phenyl, furanyl, thiophenyl or paramethoxyphenyl.

In a further embodiment of the invention, the compounds of formula I defined herein are as defined above with the proviso that (proviso (iii)) when $R_4$ is H, then Ar is not phenyl, furanyl, thiophenyl or paramethoxyphenyl.

Particular compounds of the invention include, for example, compounds of the Formula I, or pharmaceutically acceptable salts and/or solvates thereof, wherein, unless otherwise stated, each of $A_1$, $A_2$, $A_3$, L, Ar, Q, $R_1$, $R_2$, $R_3$, $R_4$, $R_5$, $R_6$, $R_a$, $R_{a'}$, $R_b$, $R_{b'}$, $R_c$ and any associated substituent groups has any of the meanings defined hereinbefore or in any of paragraphs (1) to (72) hereinafter:

(1) $A_1$ is N or C—$R_d$, wherein $R_d$ is selected from H, halo, (1-2C)alkyl, cyano, nitro, hydroxyl, amino, (1-2C)fluoroalkyl, (1-2C)alkoxy, or (1-2C)fluoroalkoxy;
(2) $A_1$ is N or C—$R_d$, wherein $R_d$ is selected from H, halo, (1-2C)alkyl, cyano, nitro, hydroxyl, amino, $CF_3$, (1-2C)alkoxy or $OCF_3$;
(3) $A_1$ is N or C—$R_d$, wherein $R_d$ is selected from H, halo, (1-2C)alkyl, $CF_3$, OMe or $OCF_3$;
(4) $A_1$ is N or C—$R_d$, wherein $R_d$ is selected from H, fluoro or methyl;
(5) $A_1$ is N or C—$R_d$, wherein $R_d$ is selected from H or methyl;
(6) $A_1$ is N or CH;
(7) $A_1$ is CH;
(8) $A_2$ is N or C—$R_c$, wherein $R_c$ is selected form H, F or methyl;
(9) $A_2$ is N or C—$R_c$, wherein $R_c$ is selected form H or F;
(10) $A_2$ is N or CH;
(11) $A_2$ is N;
(12) $A_3$ is N or $CR_f$, wherein $R_f$ is selected from H, halo, (1-2C)alkyl, cyano, nitro, hydroxyl, amino, (1-2C)haloalkyl, (1-2C)alkoxy, (1-2C)haloalkoxy, $NR_gR_h$, $OR_g$, $C(O)R_g$, $C(O)OR_g$, $OC(O)R_g$, $C(O)N(R_h)R_g$, $N(R_h)C(O)R_g$, $S(O)_yR_g$ (where y is 0, 1 or 2), wherein $R_g$ and $R_h$ are each independently selected from H or (1-2C)alkyl;
(13) $A_3$ is N or $CR_f$, wherein $R_f$ is selected from H, halo, (1-2C)alkyl, cyano, nitro, hydroxyl, amino, (1-2C)haloalkyl, (1-2C)alkoxy, (1-2C)haloalkoxy, $NR_gR_h$, $C(O)R_g$, wherein $R_g$ and $R_h$ are each independently selected from H or (1-2C)alkyl;
(14) $A_3$ is N or $CR_f$, wherein $R_f$ is selected from H, halo, (1-2C)alkyl, cyano, nitro, hydroxyl, amino, (1-2C)fluoroalkyl, (1-2C)alkoxy, (1-2C)fluoroalkoxy;
(15) $A_3$ is N or $CR_f$, wherein $R_f$ is selected from H, halo, methyl, $CF_3$, OMe, $OCF_3$;
(16) $A_3$ is N or $CR_f$, wherein $R_f$ is selected from H, fluoro, methyl, $CF_3$;
(17) $A_3$ is N or CH;
(18) $A_3$ is N;
(19) L is a methylene optionally substituted by methyl or oxo;
(20) L is a methylene optionally substituted by methyl;
(21) L is a methylene;
(22) Ar is either a 5 or 6 membered heteroaryl optionally substituted by H, halo, (1-4C)alkyl, (1-4C)fluoroalkyl, $OCF_3$, (1-4C)alkoxy, (2-4C)alkenyl, (2-4C)alkynyl, (3-6C)cycloalkyl, (3-6C)cycloalkyl(1-2C)alkyl or a group of the formula:

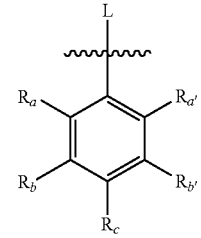

wherein:
$R_a$, $R_{a'}$, $R_b$, $R_{b'}$ and $R_c$ are as described hereinabove or as described in paragraphs (28) to (36);
(23) Ar is either a 5 or 6 membered heteroaryl optionally substituted by H, halo, (1-4C)alkyl, (1-4C)fluoroalkyl, $OCF_3$, (1-4C)alkoxy, (2-4C)alkenyl, (2-4C)alkynyl, cyclopropyl, cyclobutyl or a group of the formula:

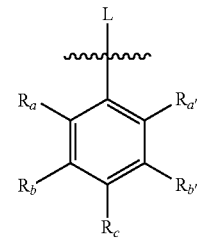

wherein:
$R_a$, $R_{a'}$, $R_b$, $R_{b'}$ and $R_c$ are as described hereinabove or as described in paragraphs (28) to (36);
(24) Ar is either a 5 or 6 membered heteroaryl optionally substituted by H, halo, (1-4C)alkyl, $CF_3$, $OCF_3$, (1-2C)alkoxy, cyclopropyl, cyclobutyl or a group of the formula:

15

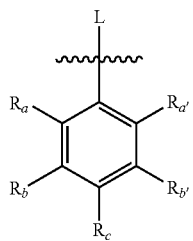

wherein:
$R_a$, $R_{a'}$, $R_b$, $R_{b'}$ and $R_c$ are as described hereinabove or as described in paragraphs (28) to (36);
(25) Ar is either a 5 or 6 membered heteroaryl optionally substituted by H, halo, methyl, $CF_3$, $OCF_3$, OMe or a group of the formula:

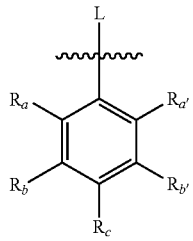

wherein:
$R_a$, $R_{a'}$, $R_b$, $R_{b'}$ and $R_c$ are as described hereinabove or as described in paragraphs (28) to (36);
(26) Ar is either a 5 membered heteroaryl optionally substituted by H, fluoro, methyl, $CF_3$, $OCF_3$, OMe or a group of the formula:

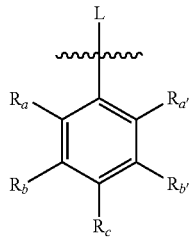

wherein:
$R_a$, $R_{a'}$, $R_b$, $R_{b'}$ and $R_c$ are as described hereinabove or as described in paragraphs (28) to (36);
(27) Ar is either a 5 membered heteroaryl or a group of the formula:

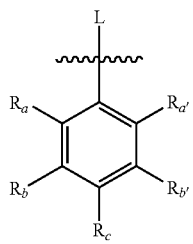

16 wherein:
$R_a$, $R_{a'}$, $R_b$, $R_{b'}$ and $R_c$ are as described hereinabove or as described in paragraphs (28) to (36);
(28) Ar is group of the formula:

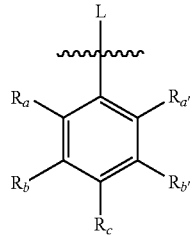

wherein:
$R_a$, $R_{a'}$, $R_b$, $R_{b'}$ and $R_c$ are as described hereinabove or as described in paragraphs (28) to (36);
(29) $R_a$ and $R_{a'}$ are independently selected from H, fluoro, methyl, methoxy, or $OCF_3$;
(30) $R_a$ and $R_{a'}$ are independently selected from H, methyl, methoxy, or $OCF_3$;
(31) $R_a$ and $R_{a'}$ are H;
(32) $R_b$ and $R_{b'}$ are independently selected from H, fluoro, methyl, $OCF_3$ or methoxy;
(33) $R_b$ and $R_{b'}$ are H;
(34) $R_c$ is selected from H, (1-4C)alkyl, halo, hydroxyl, (1-4C)haloalkyl, (1-4C)alkoxy, (1-4C)haloalkoxy, (2-4C)alkenyl, (2-4C)alkynyl, (3-6C)cycloalkyl, (3-6C)cycloalkyl(1-2C)alkyl, $NR_iR_j$, $C(O)R_i$, $C(O)OR_j$, $OC(O)R_j$, wherein $R_i$ and $R_j$ are each independently selected from H or (1-2C)alkyl; or
$R_c$ is a group of the formula:

-$L_1$-B wherein:
$L_1$ is (1-2C)alkylene or —O-(1-2C)alkylene optionally substituted by (1-2C)alkyl or oxo; and
B is phenyl or 5 or 6 membered heteroaryl optionally substituted with halo or (1-2C)alkyl;
(35) $R_c$ is selected from H, (1-4C)alkyl, halo, hydroxyl, (1-4C)fluoroalkyl, (1-4C)alkoxy, (1-4C)fluoroalkoxy, (2-4C)alkenyl, (2-4C)alkynyl, cyclopropyl, cyclobutyl, $NR_iR_j$, $C(O)R_i$, $C(O)OR_j$, $OC(O)R_i$, wherein $R_i$ and $R_j$ are each independently selected from H or (1-2C)alkyl; or
$R_c$ is a group of the formula:

-$L_1$-B wherein:
$L_1$ is (1-2C)alkylene or —O-(1-2C)alkylene, each of which is optionally substituted by (1-2C)alkyl or oxo; and
B is phenyl or 5 or 6 membered heteroaryl optionally substituted with halo or (1-2C)alkyl;
(36) $R_c$ is selected from H, (1-2C)alkyl, halo, hydroxyl, (1-4C)fluoroalkyl, (1-4C)alkoxy, (1-4C)fluoroalkoxy, or
$R_c$ is a group of the formula:

-$L_1$-B wherein:
$L_1$ is (1-2C)alkylene or optionally substituted by methyl or oxo or —O-(1-2C)alkylene; and
B is phenyl or 5 or 6 membered heteroaryl optionally substituted with fluoro or methyl;

(37) $R_c$ is selected from H, halo, hydroxyl, (1-2C)fluoroalkyl, (1-2C)alkoxy, (1-2C)fluoroalkoxy, or
$R_c$ is a group of the formula:

-L$_1$-B wherein:
$L_1$ is (1-2C)alkylene optionally substituted by methyl or oxo or —O-(1-2C)alkylene; and
B is phenyl optionally substituted with fluoro or methyl;
(38) $R_c$ is selected from is H, F, Cl, Br, OMe, (1-2C)fluoroalkyl, (1-2C)fluoroalkoxy or $R_c$ is a group of the formula:

-L$_1$-B wherein:
$L_1$ is (1-2C)alkylene optionally substituted by oxo or —O-(1C)alkylene; and
B is phenyl;
(39) $R_c$ is selected from H, F, Cl, Br, OMe, (1-2C)fluoroalkyl, (1-2C)fluoroalkoxy;
(40) $R_c$ is selected from (1-2C)fluoroalkyl or (1-2C)fluoroalkoxy;
(41) $R_c$ is (1-2C)fluoroalkoxy;
(42) Q is either a group of the formula:

—CHR$_k$—R$_k$— wherein:
$R_k$ is CH$_2$, NR$_i$ or O, wherein $R_i$ is selected from H or methyl; and
$R_k$ is H or methyl;
or Q is a group of the formula:

—R$_m$—CHR$_y$— wherein:
$R_m$ is O, S, SO, SO$_2$ or SO(NH); and
$R_y$ is H or methyl;
(43) Q is either a group of the formula:

—CH$_2$—R$_k$— wherein:
$R_k$ is CH$_2$, NR$_i$ or O, wherein $R_i$ is selected from H or methyl;
or Q is a group of the formula:

—R$_m$—CHR$_y$— wherein:
$R_m$ is O, S, SO or SO$_2$; and
$R_y$ is H or methyl;
(44) Q is either a group of the formula:

—CH$_2$—R$_k$— wherein:
$R_k$ is CH$_2$, NR$_i$ or O, wherein $R_i$ is selected from H or methyl;
or Q is a group of the formula:

—R$_m$—CHR$_y$— wherein:
$R_m$ is O, SO or SO$_2$; and
$R_y$ is H or methyl;
(45) Q is —CH$_2$CH$_2$—;
(46) $R_1$ and $R_2$ are independently selected from H, (1-2C)alkyl, halo, cyano, nitro, hydroxyl, amino, mercapto, (1-2C)fluoroalkyl, (1-2C)alkoxy or (1-2C)fluoroalkoxy;
(47) $R_1$ and $R_2$ are independently selected from H, (1-2C)alkyl, halo, (1-2C)fluoroalkyl, (1-2C)alkoxy or (1-2C)fluoroalkoxy;
(48) $R_1$ and $R_2$ are independently selected from H, (1-2C)alkyl, halo, CF$_3$, OMe or OCF$_3$;
(49) $R_1$ and $R_2$ are independently selected from H, (1-2C)alkyl or halo;
(50) $R_1$ and $R_2$ are independently selected from H, methyl or fluoro;
(51) $R_3$ is selected from H or (1-6C)alkyl optionally substituted by one or more substituents selected from halo, trifluoromethyl, trifluoromethoxy, amino, cyano, hydroxyl, mercapto, carboxyl, carbamoyl, sulphamoyl, (1-4C)alkyl or NR$_n$R$_o$, wherein R$_n$ and R$_o$ are each independently selected from H or (1-4C)alkyl;
(52) $R_3$ is selected from H or (1-6C)alkyl optionally substituted by one or more substituents selected from halo, trifluoromethyl, trifluoromethoxy, amino, cyano, hydroxyl, mercapto, carboxyl, carbamoyl, sulphamoyl or (1-2C)alkyl;
(53) $R_3$ is selected from H or (1-6C)alkyl optionally substituted by one or more substituents selected from halo, trifluoromethyl, trifluoromethoxy, amino, cyano, hydroxyl or methyl;
(54) $R_3$ is selected from H or (1-4C)alkyl optionally substituted by one or more substituents selected from fluoro, trifluoromethyl, trifluoromethoxy or methyl;
(55) $R_3$ is selected from H or (1-4C)alkyl;
(56) $R_3$ is H;
(57) $R_4$ is H, (1-4C)alkyl, carboxyl, carbamoyl, sulphamoyl, amido, ureido, (3-4C)cycloalkyl, (3-4C)cycloalkyl(1-4C)alkyl, wherein said (1-4C)alkyl, (3-4C)cycloalkyl or (3-4C)cycloalkyl(1-4C)alkyl is optionally substituted with one or more substituents selected from halo, amino, mercapto, cyano, hydroxyl, carboxyl, carbamoyl, sulphamoyl, (1-4C)alkyl, (1-4C)haloalkyl, (1-4C)alkoxy, (1-4C)haloalkoxy or NR$_p$R$_q$, wherein R$_p$ and R$_q$ are each independently selected from H or (1-2C)alkyl;
(58) $R_4$ is H, (1-4C)alkyl, carboxyl, carbamoyl, sulphamoyl, amido, ureido, cyclopropyl or cyclobutyl, wherein said (1-4C)alkyl, cyclopropyl or cyclobutyl, is optionally substituted with one or more substituents selected from halo, amino, mercapto, cyano, hydroxyl, carboxyl, carbamoyl, sulphamoyl, (1-4C)alkyl, (1-4C)fluoroalkyl, (1-4C)alkoxy, (1-4C)fluoroalkoxy or NR$_p$R$_q$, wherein R$_p$ and R$_q$ are each independently selected from H or methyl;
(59) $R_4$ is H, (1-4C)alkyl, carboxyl, carbamoyl, sulphamoyl, amido, ureido, cyclopropyl or cyclobutyl, wherein said (1-4C)alkyl, cyclopropyl or cyclobutyl, is optionally substituted with one or more substituents selected from halo, amino, mercapto, hydroxyl, (1-4C)alkyl, (1-4C)fluoroalkyl, (1-4C)alkoxy or (1-4C)fluoroalkoxy;
(60) $R_4$ is H, (1-4C)alkyl, carboxyl, wherein said (1-4C)alkyl, is optionally substituted with one or more substituents selected from halo, amino, mercapto, hydroxyl, (1-4C)alkyl, (1-4C)fluoroalkyl, (1-4C)alkoxy or (1-4C)fluoroalkoxy;
(61) $R_4$ is H, (1-4C)alkyl, carboxyl, wherein said (1-4C)alkyl, is optionally substituted with one or more substituents selected from fluoro, amino, mercapto, hydroxyl, methyl, CF$_3$, or OCF$_3$;
(62) $R_4$ is H, (1-4C)alkyl or carboxyl, wherein said (1-4C)alkyl, is optionally substituted with one or more substituents selected from amino, mercapto or hydroxyl;
(63) $R_4$ is (1-4C)alkyl optionally substituted with one or more substituents selected from amino, mercapto or hydroxyl;

(64) $R_4$ is (1-4C)alkyl;
(65) $R_5$ is selected from hydrogen or a group of formula:

-$L_5$-W—Z wherein:
  $L_5$ is absent or (1-2C)alkylene optionally substituted by (1-2C)alkyl or oxo;
  W is absent or selected from C(O), C(O)O, C(O)N($R_r$), wherein $R_r$ is selected from hydrogen or (1-2C)alkyl; and
  Z is phenyl, heteroaryl, heterocycyl or (3-6C)carbocyclyl, optionally substituted with one or more substituents selected from halo, (1-4C)haloalkyl, (1-4C)alkoxy, (1-4C)haloalkoxy, (2-4C)alkenyl, (2-4C)alkynyl, amino, mercapto, cyano, hydroxyl, carboxyl, carbamoyl, sulphamoyl, (1-4C)alkyl, $NR_sR_t$, $C(O)R_s$, $C(O)OR_s$, $OC(O)R_s$, $C(O)N(R_t)R_s$, $N(R_t)C(O)R_s$, $S(O)_yR_s$ (where y is 0, 1 or 2), wherein $R_s$ and $R_t$ are each independently selected from H or (1-4C)alkyl; or
  Z is optionally substituted by a group of formula:

—V-$L_6$-Y wherein
  V is absent or selected from O, S, SO, $SO_2$, N($R_o$), C(O), C(O)O or OC(O), wherein $R_o$ is hydrogen or (1-2C)alkyl;
  $L_6$ is absent or a (1-4C)alkylene optionally substituted by (1-2C)alkyl or oxo;
  Y is selected from amino, (1-6C)alkyl, phenyl, 5 or 6 membered heteroaryl, (3-7C)heterocycyl or amino, optionally substituted with one or more substituents selected from halo, (1-2C)alkyl, hydroxyl, (1-2C)hydroxyalkyl, amino, (1-2C)haloalkyl, $NR_{aa}R_{bb}$, $OCF_3$ or (1-2C)alkoxy, wherein $R_{aa}$ and $R_{bb}$ are each independently selected from H or (1-2C)alkyl;
  or $R_4$ and $R_5$ are linked such that, together with the carbon atom to which they are attached, they form: (i) a mono or bicyclic heteroaryl ring; (ii) a mono or bicyclic heterocyclyl ring; (iii) a mono or bicyclic aryl ring; or (iv) a 5 or 6 membered cycloalkyl ring which is fused with a phenyl, 5 or 6 membered heteroaryl, 5 or 6 membered heterocycyl or (3-6C)carbocyclyl ring;
  each of which is optionally substituted with one or more substituents selected from halo, amino, mercapto, cyano, hydroxyl, carboxyl, carbamoyl, sulphamoyl, (1-4C)alkyl, (1-4C)fluoroalkyl, (1-4C)alkoxy or (1-4C)fluoroalkoxy;
(66) $R_5$ is selected from hydrogen or a group of formula:

-$L_5$-Z wherein:
  $L_5$ is absent or (1-2C)alkylene optionally substituted by (1-2C)alkyl or oxo;
  Z is phenyl, heteroaryl, heterocycyl or (3-6C)carbocyclyl, optionally substituted with one or more substituents selected from halo, (1-4C)haloalkyl, (1-4C)alkoxy, (1-4C)haloalkoxy, (2-4C)alkenyl, (2-4C)alkynyl, amino, mercapto, cyano, hydroxyl, carboxyl, carbamoyl, sulphamoyl, (1-4C)alkyl, $NR_sR_t$, $C(O)R_s$, $C(O)OR_s$, $S(O)_yR_s$ (where y is 0, 1 or 2), wherein $R_s$ and $R_t$ are each independently selected from H or (1-4C)alkyl; or
  Z is optionally substituted by a group of formula:

—V-$L_6$-Y wherein
  V is absent or selected from O, S, SO, $SO_2$, N($R_o$) or C(O), wherein $R_o$ is hydrogen or (1-2C)alkyl;
  $L_6$ is absent or a (1-4C)alkylene optionally substituted by methyl or oxo;
  Y is selected from phenyl, 5 or 6 membered heteroaryl, (3-7C)heterocycyl or amino, optionally substituted with one or more substituents selected from halo, (1-2C)alkyl, hydroxyl, (1-2C)hydroxyalkyl, amino, (1-2C)haloalkyl, $NR_{aa}R_{bb}$, $OCF_3$ or (1-2C)alkoxy, wherein $R_{aa}$ and $R_{bb}$ are each independently selected from H or (1-2C)alkyl;
  or $R_4$ and $R_5$ are linked such that, together with the carbon atom to which they are attached, they form: (i) a mono or bicyclic heteroaryl ring; (ii) a mono or bicyclic heterocyclyl ring; (iii) a mono or bicyclic aryl ring; or (iv) a 5 or 6 membered cycloalkyl ring which is fused with a phenyl, 5 or 6 membered heteroaryl, 5 or 6 membered heterocycyl or (3-6C)carbocyclyl ring;
  each of which is optionally substituted with one or more substituents selected from halo, amino, mercapto, hydroxyl, carboxyl, carbamoyl, sulphamoyl, (1-4C)alkyl, $CF_3$, OMe or $OCF_3$;
(67) $R_5$ is selected from hydrogen or a group of formula:
  -$L_5$-Z wherein:
  $L_5$ is absent or (1-2C)alkylene optionally substituted by methyl or oxo;
  Z is phenyl, heteroaryl, heterocycyl or (3-6C)carbocyclyl, optionally substituted with one or more substituents selected from halo, (1-4C)fluoroalkyl, (1-4C)alkoxy, (1-4C)fluoroalkoxy, amino, mercapto, cyano, hydroxyl, carboxyl, carbamoyl, sulphamoyl, (1-4C)alkyl, $NR_sR_t$, $C(O)R_s$, $C(O)OR_s$, $S(O)_yR_s$ (where y is 0, 1 or 2), wherein $R_s$ and $R_t$ are each independently selected from H or (1-4C)alkyl; or
  Z is optionally substituted by a group of formula:
  —V-$L_6$-Y wherein
  V is absent or selected from O or N($R_o$) wherein $R_o$ is hydrogen or methyl;
  $L_6$ is absent or a (1-4C)alkylene optionally substituted by methyl or oxo;
  Y is selected from phenyl, 5 membered heteroaryl, (3-7C)heterocycyl or amino, optionally substituted with one or more substituents selected from halo, (1-2C)alkyl, hydroxyl, (1-2C)hydroxyalkyl, $NR_{aa}R_{bb}$, amino, (1-2C)haloalkyl, $OCF_3$ or (1-2C)alkoxy, wherein $R_{aa}$ and $R_{bb}$ are each independently selected from H or methyl;
  or $R_4$ and $R_5$ are linked such that, together with the carbon atom to which they are attached, they form: (i) a mono or bicyclic heteroaryl ring; (ii) a mono or bicyclic heterocyclyl ring; (iii) a mono or bicyclic aryl ring; or (iv) a 5 or 6 membered cycloalkyl ring which is fused with a phenyl;
  each of which is optionally substituted with one or more substituents selected from fluoro, amino, mercapto, hydroxyl, (1-2C)alkyl, $CF_3$, OMe or $OCF_3$;
(68) $R_5$ is selected from hydrogen or a group of formula:
  wherein:
  $L_5$ is absent or (1-2C)alkylene optionally substituted by methyl or oxo;
  Z is phenyl, heteroaryl, heterocycyl or (3-6C)carbocyclyl, optionally substituted with one or more substituents selected from halo, $CF_3$, (1-2C)alkoxy, OCF$_3$ amino, mercapto, hydroxyl, (1-2C)alkyl, NR$_s$R$_t$, C(O)R$_s$, C(O)OR$_s$, S(O)$_y$R$_s$ (where y is 0, 1 or 2), wherein R$_s$ and R$_t$ are each independently selected from H or (1-4C)alkyl; or Z is optionally substituted by a group of formula:

—V-L$_6$-Y wherein

V is absent or selected from O or N(R$_o$) wherein R$_o$ is hydrogen or methyl;

L$_6$ is absent or a (1-4C)alkylene optionally substituted by methyl or oxo;

Y is selected from (3-7C)heterocycyl or amino, optionally substituted with one or more substituents selected from halo, (1-2C)alkyl, hydroxyl, (1-2C)hydroxyalkyl, NR$_{aa}$R$_{bb}$, CF$_3$, OCF$_3$ or OMe, wherein R$_{aa}$ and R$_{bb}$ are each independently selected from H or methyl;

or R$_4$ and R$_5$ are linked such that, together with the carbon atom to which they are attached, they form: (i) a monocyclic heteroaryl ring; (ii) a monocyclic heterocyclyl ring; or (iii) a 5 or 6 membered cycloalkyl ring which is fused with a phenyl;

each of which is optionally substituted with one or more substituents selected from hydroxyl, methyl, CF$_3$, or OCF$_3$;

(69) R$_5$ is selected from hydrogen or a group of formula:

-L$_5$-Z wherein:

L$_5$ is absent or (1-2C)alkylene optionally substituted by methyl or oxo;

Z is phenyl, 5- or 6-membered heteroaryl, 5- or 6-membered heterocycyl or (3-6C)carbocyclyl, optionally substituted with one or more substituents selected from halo, CF$_3$, (1-2C)alkoxy, OCF$_3$ amino, mercapto, hydroxyl, (1-2C)alkyl, NR$_s$R$_t$, C(O)R$_s$, C(O)OR$_s$, S(O)$_y$R$_s$ (where y is 0, 1 or 2), wherein R$_s$ and R$_t$ are each independently selected from H or (1-4C)alkyl; or Z is optionally substituted by a group of formula:

—V-L$_6$-Y wherein

V is absent or selected from O or N(R$_o$) wherein R$_o$ is hydrogen or methyl;

L$_6$ is absent or a (1-4C);

Y is selected from (3-7C)heterocycyl or amino, optionally substituted with one or more substituents selected from halo, (1-2C)alkyl, hydroxyl, (1-2C)hydroxyalkyl, NR$_{aa}$R$_{bb}$, CF$_3$, OCF$_3$ or OMe, wherein R$_{aa}$ and R$_{bb}$ are each independently selected from H or methyl;

or R$_4$ and R$_5$ are linked such that, together with the carbon atom to which they are attached, they form: (i) a monocyclic 5- or 6-membered heteroaryl ring; (ii) a monocyclic 5- or 6-membered heterocyclyl ring; or (iii) a 5 or 6 membered cycloalkyl ring which is fused with a phenyl;

each of which is optionally substituted with one or more substituents selected from hydroxyl, methyl, CF$_3$, or OCF$_3$;

(70) R$_5$ is selected from hydrogen or a group of formula:

-L$_5$-Z wherein:

L$_5$ is absent or (1-2C)alkylene optionally substituted by methyl or oxo;

Z is phenyl, 5- or 6-membered heteroaryl, 5- or 6-membered heterocycyl or (3-6C)carbocyclyl, optionally substituted with one or more substituents selected from halo, CF$_3$, (1-2C)alkoxy, OCF$_3$ amino, mercapto, hydroxyl, (1-2C)alkyl, NR$_s$R$_t$, C(O)R$_s$, C(O)OR$_s$, S(O)$_y$R$_s$ (where y is 0, 1 or 2), wherein R$_s$ and R$_t$ are each independently selected from H or (1-4C) alkyl; or Z is optionally substituted by a group of formula:

—V-L$_6$-Y wherein

V is absent or selected from O or N(R$_o$) wherein R$_o$ is hydrogen or methyl;

L$_6$ is absent or a (1-4C);

Y is selected from (3-7C)heterocycyl or amino, optionally substituted with one or more substituents selected from halo, (1-2C)alkyl, hydroxyl, (1-2C)hydroxyalkyl, NR$_{aa}$R$_{bb}$, CF$_3$, OCF$_3$ or OMe, wherein R$_{aa}$ and R$_{bb}$ are each independently selected from H or methyl;

(71) R$_6$ is selected from H or methyl;

(72) R$_6$ is H.

Suitably, a heteroaryl or heterocyclyl group as defined herein is a monocyclic heteroaryl or heterocyclyl group comprising one, two or three heteroatoms selected from N, O or S.

Suitably, a heteroaryl is a 5- or 6-membered heteroaryl ring comprising one, two or three heteroatoms selected from N, O or S.

Suitably, a heterocyclyl group is a 4-, 5- or 6-membered heterocyclyl ring comprising one, two or three heteroatoms selected from N, O or S. Most suitably, a heterocyclyl group is a 5- or 6-membered ring comprising one, two or three heteroatoms selected from N, O or S [e.g. morpholinyl (e.g. 4-morpholinyl), oxetane, methyloxetane (e.g. 3-methyloxetane), pyrrolidinone (e.g. pyrrolidin-2-one)].

Suitably an aryl group is phenyl.

Suitably, A$_1$ is as defined in any one of paragraphs (1) to (7) above. Most suitably, A$_1$ is N or CH.

Suitably, A$_2$ is as defined in any one of paragraphs (8) to (11) above. Most suitably, A$_2$ is N or CH.

Suitably, A$_3$ is as defined in any one of paragraphs (12) to (18) above. Most suitably, A$_3$ is N or CH.

Suitably, L is as defined in any one of paragraphs (19) to (21) above. Most suitably, L is methylene.

Suitably, Ar is as defined in any one of paragraphs (22) to (28) above. Most preferably, Ar is as defined in paragraph (28). In a particular embodiment, Ar is a para-halophenyl, e.g. p-fluorophenyl or p-chlorophenyl.

Suitably, R$_a$ and R$_{a'}$ are as defined in any one of paragraphs (29) to (31) above. Most preferably, R$_a$ and R$_{a'}$ are as defined in paragraph (31).

Suitably, R$_b$ and R$_{b'}$ are as defined in any one of paragraphs (32) to (33) above. In an embodiment, R$_a$ and R$_{a'}$ are as defined in paragraph (33).

Suitably, R$_c$ is as defined in any one of paragraphs (34) to (41) above. Most preferably, R$_c$ is as defined in paragraph (41).

Suitably, Q is as defined in any one of paragraphs (42) to (45) above. Most preferably, Q is as defined in paragraph (45).

Suitably, $R_1$ and $R_2$ are as defined in any one of paragraphs (46) to (50) above. Most preferably, $R_1$ and $R_2$ are as defined in paragraph (50). In a particular embodiment, $R_1$ and $R_2$ are hydrogen.

Suitably, $R_3$ is as defined in any one of paragraphs (51) to (56) above. Most preferably, $R_3$ is as defined in paragraph (56).

Suitably, $R_4$ is as defined in any one of paragraphs (57) to (64) above. Most preferably, $R_4$ is as defined in paragraph (64). In a particular embodiment, $R_4$ is methyl.

Suitably, $R_5$ is as defined in any one of paragraphs (65) to (70) above. Most preferably, $R_5$ is as defined in paragraph (70).

Suitably, $R_6$ is as defined in any one of paragraphs (71) to (72) above. Most preferably, $R_6$ is as defined in paragraph (71).

In a particular group of compounds of the invention, L is methylene and Ar is a substituted phenyl as defined herein, i.e. the compounds have the structural formula Ia (a sub-definition of formula I) shown below:

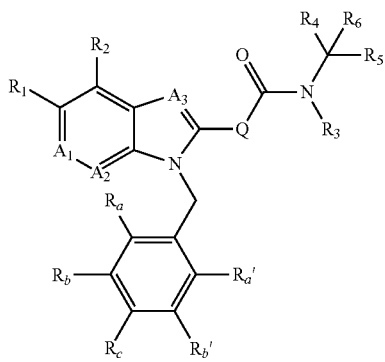

Ia wherein $A_1$, $A_2$, $A_3$, Q, $R_1$, $R_2$, $R_3$, $R_4$, $R_5$, $R_6$, $R_a$, $R_{a'}$, $R_b$, $R_{b'}$, and $R_c$ each have any one of the meanings defined herein; or a pharmaceutically acceptable salt, hydrate and/or solvate thereof.

In an embodiment of the compounds of formula Ia:
$A_1$ is as defined in any one of paragraphs (1) to (7) above;
$A_2$ is as defined in any one of paragraphs (8) to (11) above;
$A_3$ is as defined in any one of paragraphs (12) to (18) above;
$R_a$ and $R_{a'}$ are as defined in any one of paragraphs (29) to (31) above;
$R_b$ and $R_{b'}$ are as defined in any one of paragraphs (32) to (33) above;
$R_c$ is as defined in any one of paragraphs (34) to (41) above;
Q is as defined in any one of paragraphs (42) to (45) above;
$R_1$ and $R_2$ are as defined in any one of paragraphs (46) to (50) above;
$R_3$ is as defined in any one of paragraphs (51) to (56) above;
$R_4$ is as defined in any one of paragraphs (57) to (64) above;
$R_5$ is as defined in any one of paragraphs (65) to (70) above; and
$R_6$ is as defined in any one of paragraphs (71) to (72) above.

In an embodiment of the compounds of formula Ia:
$A_1$ is as defined in paragraph (7) above;
$A_2$ is as defined in paragraph (10) above;
$A_3$ is as defined in paragraph (17) above;
$R_a$ and $R_{a'}$ are as defined in paragraph (31) above;
$R_b$ and $R_{b'}$ are as defined in paragraph (33) above;
$R_c$ is as defined in paragraph (41) above;
Q is as defined in paragraph (45) above;
$R_1$ and $R_2$ are as defined in paragraph (50) above;
$R_3$ is as defined in paragraph (56) above;
$R_4$ is as defined in paragraph (64) above;
$R_5$ is as defined in paragraph (70) above; and
$R_6$ is as defined in paragraph (71) above.

In a particular group of compounds of the invention, L is methylene, Ar is a substituted phenyl shown below and $R_a$ and $R_{a'}$ are H, i.e. the compounds have the structural formula Ib (a sub-definition of formula I) shown below:

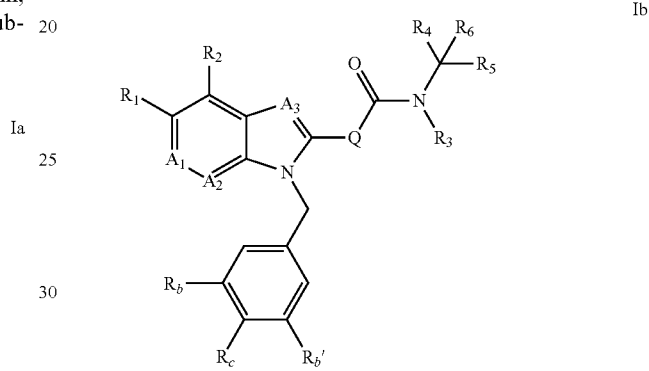

Ib wherein $A_1$, $A_2$, $A_3$, Q, $R_1$, $R_2$, $R_3$, $R_4$, $R_5$, $R_6$, $R_b$, $R_{b'}$ and $R_c$ each have any one of the meanings defined herein; or a pharmaceutically acceptable salt, hydrate and/or solvate thereof.

In an embodiment of the compounds of formula Ib:
$A_1$ is as defined in any one of paragraphs (1) to (7) above;
$A_2$ is as defined in any one of paragraphs (8) to (11) above;
$A_3$ is as defined in any one of paragraphs (12) to (18) above;
$R_b$ and $R_{b'}$ are as defined in any one of paragraphs (32) to (33) above;
$R_c$ is as defined in any one of paragraphs (34) to (41) above;
Q is as defined in any one of paragraphs (42) to (45) above;
$R_1$ and $R_2$ are as defined in any one of paragraphs (46) to (50) above;
$R_3$ is as defined in any one of paragraphs (51) to (56) above;
$R_4$ is as defined in any one of paragraphs (57) to (64) above;
$R_5$ is as defined in any one of paragraphs (65) to (70) above; and
$R_6$ is as defined in any one of paragraphs (71) to (72) above.

In an embodiment of the compounds of formula Ib:
$A_1$ is as defined in paragraph (7) above;
$A_2$ is as defined in paragraph (10) above;
$A_3$ is as defined in paragraph (17) above;
$R_b$ and $R_{b'}$ are as defined in paragraph (33) above;
$R_c$ is as defined in paragraph (41) above;
Q is as defined in paragraph (45) above;

$R_1$ and $R_2$ are as defined in paragraph (50) above;
$R_3$ is as defined in paragraph (56) above;
$R_4$ is as defined in paragraph (64) above;
$R_5$ is as defined in paragraph (70) above; and
$R_6$ is as defined in paragraph (71) above.

In a further group of compounds of the invention, $R_6$ is hydrogen, i.e. the compounds have the structural formula Ic shown below:

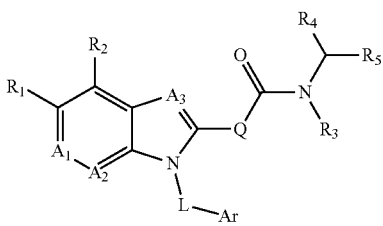

Ic wherein $A_1$, $A_2$, $A_3$, Q, $R_1$, $R_2$, $R_3$, $R_4$, $R_5$, L and Ar each have any one of the meanings defined herein; or a pharmaceutically acceptable salt, hydrate and/or solvate thereof.

In an embodiment of the compounds of formula Ic:
$A_1$ is as defined in any one of paragraphs (1) to (7) above;
$A_2$ is as defined in any one of paragraphs (8) to (11) above;
$A_3$ is as defined in any one of paragraphs (12) to (18) above; and
L is as defined in any one of paragraphs (19) to (21) above;
Ar is as defined in any one of paragraphs (22) to (28) above and $R_a$ and $R_{a'}$ are as defined in any one of paragraphs (29) to (31) above, $R_b$ and $R_{b'}$ are as defined in any one of paragraphs (32) to (33) above and $R_c$ is as defined in any one of paragraphs (34) to (41) above;
Q is as defined in any one of paragraphs (42) to (45) above;
$R_1$ and $R_2$ are as defined in any one of paragraphs (46) to (50) above;
$R_3$ is as defined in any one of paragraphs (51) to (56) above;
$R_4$ is as defined in any one of paragraphs (57) to (64) above;
$R_5$ is as defined in any one of paragraphs (65) to (70) above; and
$R_6$ is as defined in any one of paragraphs (71) to (72) above.

In an embodiment of the compounds of formula Ic:
$A_1$ is as defined in paragraph (7) above;
$A_2$ is as defined in paragraph (10) above;
$A_3$ is as defined in paragraph (17) above;
L is as defined in paragraphs (21) above;
Ar is as defined in any one of paragraphs (28), and $R_a$ and $R_{a'}$ are as defined in paragraph (31) above, $R_b$ and $R_{b'}$ are as defined in paragraph (33) above and $R_c$ is as defined in paragraph (41) above;
Q is as defined in paragraph (45) above;
$R_1$ and $R_2$ are as defined in paragraph (50) above;
$R_3$ is as defined in paragraph (56) above;
$R_4$ is as defined in paragraph (64) above;
$R_5$ is as defined in paragraph (70) above; and
$R_6$ is as defined in paragraph (71) above.

In a particular group of compounds of the invention, L is methylene, Ar is a substituted phenyl shown below, $R_6$ and $R_3$ are H, and $R_a$ and $R_{a'}$ are H, i.e. the compounds have the structural formula Id (a sub-definition of formula I) shown below:

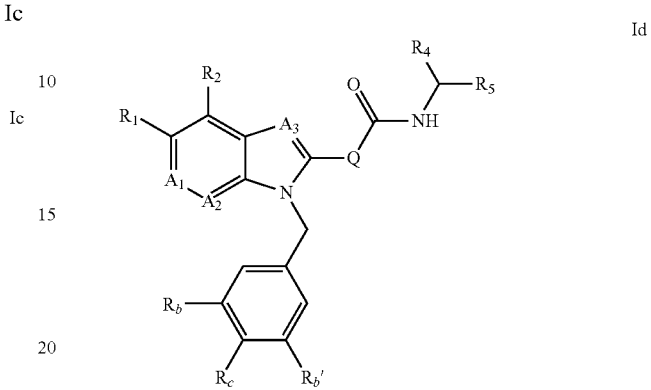

Id wherein $A_1$, $A_2$, $A_3$, Q, $R_1$, $R_2$, $R_4$, $R_5$, $R_b$, $R_{b'}$ and $R_c$ each have any one of the meanings defined herein; or a pharmaceutically acceptable salt, hydrate and/or solvate thereof.

In an embodiment of the compounds of formula Id:
$A_1$ is as defined in any one of paragraphs (1) to (7) above;
$A_2$ is as defined in any one of paragraphs (8) to (11) above;
$A_3$ is as defined in any one of paragraphs (12) to (18) above;
$R_b$ and $R_{b'}$ are as defined in any one of paragraphs (32) to (33) above;
$R_c$ is as defined in any one of paragraphs (34) to (41) above;
Q is as defined in any one of paragraphs (42) to (45) above;
$R_1$ and $R_2$ are as defined in any one of paragraphs (46) to (50) above;
$R_4$ is as defined in any one of paragraphs (57) to (64) above; and
$R_5$ is as defined in any one of paragraphs (65) to (70) above.

In an embodiment of the compounds of formula Id:
$A_1$ is as defined in paragraph (7) above;
$A_2$ is as defined in paragraph (10) above;
$A_3$ is as defined in paragraph (17) above;
$R_b$ and $R_{b'}$ are as defined in paragraph (33) above;
$R_c$ is as defined in paragraph (41) above;
Q is as defined in paragraph (45) above;
$R_1$ and $R_2$ are as defined in paragraph (50) above;
$R_4$ is as defined in paragraph (64) above; and
$R_5$ is as defined in paragraph (70) above.

In a particular group of compounds of the invention, L is methylene, Ar is a substituted phenyl shown below, $R_6$ and $R_3$ are H, Q is —$CH_2CH_2$—, $A_2$ is N and $R_a$ and $R_{a'}$ are H, i.e. the compounds have the structural formula Ie (a sub-definition of formula I) shown below:

27

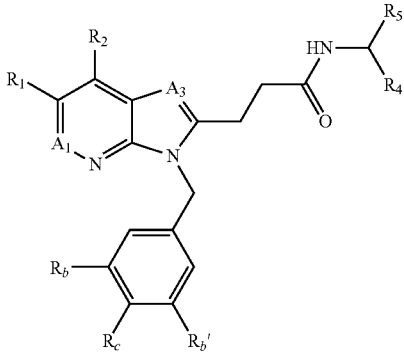

Ie wherein $A_1$, $A_3$, $R_1$, $R_2$, $R_4$, $R_5$, $R_b$, $R_{b'}$ and $R_c$ each have any one of the meanings defined herein; or a pharmaceutically acceptable salt, hydrate and/or solvate thereof.

In an embodiment of the compounds of formula Ie:
$A_1$ is as defined in any one of paragraphs (1) to (7) above;
$A_3$ is as defined in any one of paragraphs (12) to (18) above;
$R_b$ and $R_{b'}$ are as defined in any one of paragraphs (32) to (33) above;
$R_c$ is as defined in any one of paragraphs (34) to (41) above;
$R_1$ and $R_2$ are as defined in any one of paragraphs (45) to (50) above;
$R_4$ is as defined in any one of paragraphs (57) to (64) above; and
$R_5$ is as defined in any one of paragraphs (65) to (70) above.

In an embodiment of the compounds of formula Ie:
$A_1$ is as defined in paragraph (7) above;
$A_3$ is as defined in paragraph (17) above;
$R_b$ and $R_{b'}$ are as defined in paragraph (33) above;
$R_c$ is as defined in paragraph (41) above;
$R_1$ and $R_2$ are as defined in paragraph (50) above;
$R_4$ is as defined in paragraph (64) above; and
$R_5$ is as defined in paragraph (70) above.

In a particular group of compounds of the invention, L is methylene, Ar is a substituted phenyl shown below, $R_1$, $R_2$, $R_6$ and $R_3$ are H, Q is —$CH_2CH_2$—, $A_2$ and $A_3$ are N, $A_2$ is CH and $R_a$ and $R_{a'}$ are H, i.e. the compounds have the structural formula If (a sub-definition of formula I) shown below:

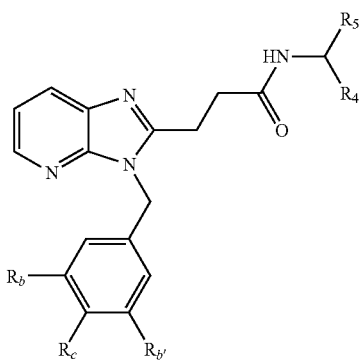

If

28 wherein $R_4$, $R_5$, $R_b$, $R_{b'}$ and $R_c$ each have any one of the meanings defined herein; or a pharmaceutically acceptable salt, hydrate and/or solvate thereof.

In an embodiment of the compounds of formula If:
$R_b$ and $R_{b'}$ are as defined in any one of paragraphs (32) to (33) above;
$R_c$ is as defined in any one of paragraphs (34) to (41) above;
$R_4$ is as defined in any one of paragraphs (57) to (64) above; and
$R_5$ is as defined in any one of paragraphs (65) to (70) above.

In an embodiment of the compounds of formula If:
$R_b$ and $R_{b'}$ are as defined in paragraph (33) above;
$R_c$ is as defined in paragraph (41) above;
$R_4$ is as defined in paragraph (64) above; and
$R_5$ is as defined in paragraph (70) above.

In a particular group of compounds of the invention, $R_4$, $R_5$ and $R_6$ are different groups and the compound of formula I has the following stereochemistry shown in formula Ig below:

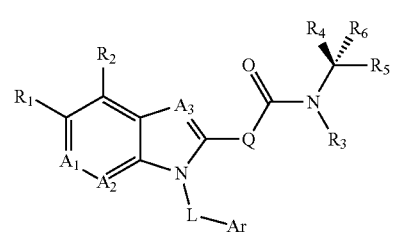

Ig wherein $A_1$, $A_2$, $A_3$, Q, $R_1$, $R_2$, $R_3$, $R_4$, $R_5$, $R_6$, L and Ar each have any one of the meanings defined herein; or a pharmaceutically acceptable salt, hydrate and/or solvate thereof.

In an embodiment of the compounds of formula Ig:
$A_1$ is as defined in any one of paragraphs (1) to (7) above;
$A_2$ is as defined in any one of paragraphs (8) to (10) above;
$A_3$ is as defined in any one of paragraphs (12) to (18) above; and
L is as defined in any one of paragraphs (19) to (21) above;
Ar is as defined in any one of paragraphs (22) to (28) above and $R_a$ and $R_{a'}$ are as defined in any one of paragraphs (29) to (31) above, $R_b$ and $R_{b'}$ are as defined in any one of paragraphs (32) to (33) above and $R_c$ is as defined in any one of paragraphs (34) to (41) above;
Q is as defined in any one of paragraphs (42) to (45) above;
$R_1$ and $R_2$ are as defined in any one of paragraphs (46) to (50) above;
$R_3$ is as defined in any one of paragraphs (51) to (56) above;
$R_4$ is as defined in any one of paragraphs (57) to (64) above;
$R_5$ is as defined in any one of paragraphs (65) to (70) above; and
$R_6$ is as defined in any one of paragraphs (71) to (72) above.

In an embodiment of the compounds of formula Ig:
$A_1$ is as defined in paragraph (7) above;
$A_2$ is as defined in paragraph (10) above;
$A_3$ is as defined in paragraph (17) above;
L is as defined in paragraphs (21) above;

Ar is as defined in any one of paragraphs (28), and $R_a$ and $R_{a'}$ are as defined in paragraph (31) above, $R_b$ and $R_{b'}$ are as defined in paragraph (33) above and $R_c$ is as defined in paragraph (41) above;

Q is as defined in paragraph (45) above;

$R_1$ and $R_2$ are as defined in paragraph (50) above;

$R_3$ is as defined in paragraph (56) above;

$R_4$ is as defined in paragraph (64) above;

$R_5$ is as defined in paragraph (70) above; and $R_6$ is as defined in paragraph (71) above.

Particular compounds of the present invention include any of the compounds exemplified in the present application, or a pharmaceutically acceptable salt or solvate thereof, and, in particular, any of the following:

3-(3-Benzyl-3H-imidazo[4,5-b]pyridin-2-yl)-N—((S)-1-phenyl-ethyl)-propionamide;

3-(3-Benzyl-3H-imidazo[4,5-b]pyridin-2-yl)-N-thiophen-2-ylmethyl-propionamide;

3-(3-Benzyl-3H-imidazo[4,5-b]pyridin-2-yl)-N—((R)-1-phenyl-ethyl)-propionamide;

3-(3-Benzyl-3H-imidazo[4,5-b]pyridin-2-yl)-N-(2-methyl-benzyl)-propionamide;

N-(3-Trifluoromethyl-benzyl)-3-[3-(3-trifluoromethoxy-benzyl)-3H-imidazo[4,5-b]pyridin-2-yl]-propionamide;

N—((R)-2-Hydroxy-1-phenyl-ethyl)-3-[3-(4-trifluoromethoxy-benzyl)-3H-imidazo[4,5-b]pyridin-2-yl]-propionamide;

N-((1R,2S)-2-Hydroxy-indan-1-yl)-3-[3-(4-trifluoromethoxy-benzyl)-3H-imidazo[4,5-b]pyridin-2-yl]-propionamide;

N-((1R,2R)-2-Hydroxy-indan-1-yl)-3-[3-(4-trifluoromethoxy-benzyl)-3H-imidazo[4,5-b]pyridin-2-yl]-propionamide;

N-[4-(3-Dimethylamino-propoxy)-benzyl]-3-[3-(4-trifluoromethoxy-benzyl)-3H-imidazo[4,5-b]pyridin-2-yl]-propionamide;

N—[(S)-1-(4-Chloro-phenyl)-ethyl]-3-[3-(4-difluoromethoxy-benzyl)-3H-imidazo[4,5-b]pyridin-2-yl]-propionamide;

N—[(S)-1-(4-Chloro-phenyl)-ethyl]-3-[3-(4-trifluoromethyl-benzyl)-3H-imidazo[4,5-b]pyridin-2-yl]-propionamide;

N—[(S)-1-(4-Fluoro-phenyl)-ethyl]-3-[3-(4-trifluoromethoxy-benzyl)-3H-imidazo[4,5-b]pyridin-2-yl]-propionamide;

N-(4-Methoxy-benzyl)-3-[3-(4-trifluoromethoxy-benzyl)-3H-imidazo[4,5-b]pyridin-2-yl]-propionamide;

N-[1-(4-Fluoro-phenyl)-2-hydroxy-ethyl]-3-[3-(4-trifluoromethoxy-benzyl)-3H-imidazo[4,5-b]pyridin-2-yl]-propionamide;

3-[3-(4-Bromo-benzyl)-3H-imidazo[4,5-b]pyridin-2-yl]-N—[(S)-1-(4-fluoro-phenyl)-ethyl]-propionamide;

N—[(S)-1-(4-Bromo-phenyl)-ethyl]-3-[3-(3,4-difluoro-benzyl)-3H-imidazo[4,5-b]pyridin-2-yl]-propionamide;

N-(4-Chloro-benzyl)-3-[3-(4-trifluoromethoxy-benzyl)-3H-imidazo[4,5-b]pyridin-2-yl]-propionamide;

N-[4-(2-Dimethylamino-ethoxy)-benzyl]-3-[3-(4-trifluoromethoxy-benzyl)-3H-imidazo[4,5-b]pyridin-2-yl]-propionamide;

N-[2-Hydroxy-1-(4-trifluoromethoxy-phenyl)-ethyl]-3-[3-(4-trifluoromethoxy-benzyl)-3H-imidazo[4,5-b]pyridin-2-yl]-propionamide;

3-[3-(4-Bromo-benzyl)-3H-imidazo[4,5-b]pyridin-2-yl]-N—[(S)-1-(4-chloro-phenyl)-ethyl]-propionamide;

N-(4-Trifluoromethoxy-benzyl)-3-[3-(4-trifluoromethoxy-benzyl)-3H-imidazo[4,5-b]pyridin-2-yl]-propionamide;

N-[2-Hydroxy-1-(4-trifluoromethyl-phenyl)-ethyl]-3-[3-(4-trifluoromethoxy-benzyl)-3H-imidazo[4,5-b]pyridin-2-yl]-propionamide;

N—[(S)-1-(4-Chloro-phenyl)-ethyl]-3-[3-(3-fluoro-4-methoxy-benzyl)-3H-imidazo[4,5-b]pyridin-2-yl]-propionamide;

N—(S)-Indan-1-yl-3-[3-(4-trifluoromethoxy-benzyl)-3H-imidazo[4,5-b]pyridin-2-yl]-propionamide;

N-[4-(3-Dimethylamino-propoxy)-benzyl]-3-[6-methyl-3-(4-trifluoromethoxy-benzyl)-3H-imidazo[4,5-b]pyridin-2-yl]-propionamide;

N-(3-Fluoro-4-methoxy-benzyl)-3-[3-(4-trifluoromethoxy-benzyl)-3H-imidazo[4,5-b]pyridin-2-yl]-propionamide;

3-[3-(4-Fluoro-benzyl)-3H-imidazo[4,5-b]pyridin-2-yl]-N—((R)-2-hydroxy-1-phenyl-ethyl)-propionamide;

N—((S)-1-Pyridin-2-yl-ethyl)-3-[3-(4-trifluoromethoxy-benzyl)-3H-imidazo[4,5-b]pyridin-2-yl]-propionamide;

N-(4-Fluoro-benzyl)-3-[3-(4-trifluoromethoxy-benzyl)-3H-imidazo[4,5-b]pyridin-2-yl]-propionamide;

N-(4-Dimethylamino-benzyl)-3-[3-(4-trifluoromethoxy-benzyl)-3H-imidazo[4,5-b]pyridin-2-yl]-propionamide;

N-[2-Hydroxy-1-(4-trifluoromethoxy-phenyl)-ethyl]-3-[3-(4-trifluoromethyl-benzyl)-3H-imidazo[4,5-b]pyridin-2-yl]-propionamide;

3-[3-(4-Fluoro-benzyl)-3H-imidazo[4,5-b]pyridin-2-yl]-N-[2-hydroxy-1-(4-trifluoromethoxy-phenyl)-ethyl]-propionamide;

N-(1-Pyridin-4-yl-ethyl)-3-[3-(4-trifluoromethoxy-benzyl)-3H-imidazo[4,5-b]pyridin-2-yl]-propionamide;

N-[1-(4-Chloro-phenyl)-2-hydroxy-ethyl]-3-[3-(3,4-difluoro-benzyl)-3H-imidazo[4,5-b]pyridin-2-yl]-propionamide;

N—((S)-2-Hydroxy-2-phenyl-ethyl)-3-[3-(4-trifluoromethoxy-benzyl)-3H-imidazo[4,5-b]pyridin-2-yl]-propionamide;

N—((R)-2-Hydroxy-2-phenyl-ethyl)-3-[3-(4-trifluoromethoxy-benzyl)-3H-imidazo[4,5-b]pyridin-2-yl]-propionamide;

N—(S)-1,2,3,4-Tetrahydro-naphthalen-1-yl-3-[3-(4-trifluoromethoxy-benzyl)-3H-imidazo[4,5-b]pyridin-2-yl]-propionamide;

3-[3-(3,4-Difluoro-benzyl)-3H-imidazo[4,5-b]pyridin-2-yl]-N-[2-hydroxy-1-(4-trifluoromethoxy-phenyl)-ethyl]-propionamide;

N—[(S)-1-(4-Chloro-phenyl)-ethyl]-3-[3-(4-trifluoromethoxy-benzyl)-3H-imidazo[4,5-b]pyridin-2-yl]-propionamide;

N-((1S,2R)-2-Hydroxy-1-methyl-2-phenyl-ethyl)-3-[3-(4-trifluoromethoxy-benzyl)-3H-imidazo[4,5-b]pyridin-2-yl]-propionamide;

N-Cyclohexylmethyl-3-[3-(4-trifluoromethoxy-benzyl)-3H-imidazo[4,5-b]pyridin-2-yl]-propionamide;

4-(1-{3-[3-(4-Trifluoromethoxy-benzyl)-3H-imidazo[4,5-b]pyridin-2-yl]-propionylamino}-ethyl)-piperidine-1-carboxylic acid tert-butyl ester;

N—[(S)-1-(4-Chloro-phenyl)-ethyl]-3-(3-thiophen-2-ylmethyl-3H-imidazo[4,5-b]pyridin-2-yl)-propionamide;

3-[3-(3,4-Difluoro-benzyl)-3H-imidazo[4,5-b]pyridin-2-yl]-N—[(S)-1-(4-morpholin-4-yl-phenyl)-ethyl]-propionamide;

3-[3-(3,4-Difluoro-benzyl)-3H-imidazo[4,5-b]pyridin-2-yl]-N-((1R,2S)-2-hydroxy-indan-1-yl)-propionamide;

3-[3-(4-Fluoro-benzyl)-3H-imidazo[4,5-b]pyridin-2-yl]-N-[1-(4-fluoro-phenyl)-2-hydroxy-ethyl]-propionamide;

3-[3-(3,4-Difluoro-benzyl)-3H-imidazo[4,5-b]pyridin-2-yl]-N-[1-(4-fluoro-phenyl)-3-hydroxy-propyl]-propionamide;

N—[(R)-1-(4-Chloro-phenyl)-ethyl]-3-[3-(4-trifluoromethoxy-benzyl)-3H-imidazo[4,5-b]pyridin-2-yl]-propionamide;

3-[3-(3,4-Difluoro-benzyl)-3H-imidazo[4,5-b]pyridin-2-yl]-N-[1-(4-fluoro-phenyl)-2-hydroxy-ethyl]-propionamide;

4-({3-[3-(4-Trifluoromethoxy-benzyl)-3H-imidazo[4,5-b]pyridin-2-yl]-propionylamino}-methyl)-piperidine-1-carboxylic acid tert-butyl ester;

N-(3-Fluoro-4-methoxy-benzyl)-3-[6-methyl-3-(4-trifluoromethoxy-benzyl)-3H-imidazo[4,5-b]pyridin-2-yl]-propionamide;

N-(4-Methoxy-benzyl)-3-[6-methyl-3-(4-trifluoromethoxy-benzyl)-3H-imidazo[4,5-b]pyridin-2-yl]-propionamide;

(S)-3-({3-[3-(4-Trifluoromethoxy-benzyl)-3H-imidazo[4,5-b]pyridin-2-yl]-propionylamino}-methyl)-piperidine-1-carboxylic acid tert-butyl ester;

3-[3-(3,4-Difluoro-benzyl)-3H-imidazo[4,5-b]pyridin-2-yl]-N—(S)-indan-1-yl-propionamide;

N-[1-(Tetrahydro-pyran-4-yl)-ethyl]-3-[3-(4-trifluoromethoxy-benzyl)-3H-imidazo[4,5-b]pyridin-2-yl]-propionamide;

3-[3-(3,4-Difluoro-benzyl)-3H-imidazo[4,5-b]pyridin-2-yl]-N-(4-trifluoromethoxy-benzyl)-propionamide;

N-(4-Dimethylamino-benzyl)-3-[3-(4-fluoro-benzyl)-3H-imidazo[4,5-b]pyridin-2-yl]-propionamide;

3-[3-(3,4-Difluoro-benzyl)-3H-imidazo[4,5-b]pyridin-2-yl]-N-((1R,2R)-2-hydroxy-indan-1-yl)-propionamide;

N—((S)-1-Cyclopropyl-ethyl)-3-[3-(4-trifluoromethoxy-benzyl)-3H-imidazo[4,5-b]pyridin-2-yl]-propionamide;

3-[6-Bromo-3-(4-fluoro-benzyl)-3H-imidazo[4,5-b]pyridin-2-yl]-N—[(S)-1-(4-chloro-propionimide)];

N-(Tetrahydro-pyran-4-ylmethyl)-3-[3-(4-trifluoromethoxy-benzyl)-3H-imidazo[4,5-b]pyridin-2-yl]-propionamide;

3-[3-(3,4-Difluoro-benzyl)-3H-imidazo[4,5-b]pyridin-2-yl]-N-(4-dimethylamino-benzyl)-propionamide;

3-[3-(4-Fluoro-benzyl)-3H-imidazo[4,5-b]pyridin-2-yl]-N—((S)-2-hydroxy-1-phenyl-ethyl)-propionamide;

3-[3-(3,4-Difluoro-benzyl)-3H-imidazo[4,5-b]pyridin-2-yl]-N—((S)-2-hydroxy-2-phenyl-ethyl)-propionamide;

(R)-3-({3-[3-(4-Trifluoromethoxy-benzyl)-3H-imidazo[4,5-b]pyridin-2-yl]-propionylamino}-methyl)-piperidine-1-carboxylic acid tert-butyl ester;

3-[3-(3,4-Difluoro-benzyl)-3H-imidazo[4,5-b]pyridin-2-yl]-N—((R)-2-hydroxy-2-phenyl-ethyl)-propionamide;

3-[3-(4-Fluoro-benzyl)-3H-imidazo[4,5-b]pyridin-2-yl]-N—((S)-1-pyridin-2-yl-ethyl)-propionamide;

N-Thiazol-2-yl-3-[3-(4-trifluoromethoxy-benzyl)-3H-imidazo[4,5-b]pyridin-2-yl]-propionamide;

3-[6-Bromo-3-(4-fluoro-benzyl)-3H-imidazo[4,5-b]pyridin-2-yl]-N—[(S)-1-(4-chloro-propionimide)];

N-Cyclohexylmethyl-3-[3-(3,4-difluoro-benzyl)-3H-imidazo[4,5-b]pyridin-2-yl]-propionamide;

3-[3-(3,4-Difluoro-benzyl)-3H-imidazo[4,5-b]pyridin-2-yl]-N—((S)-1-pyridin-2-yl-ethyl)-propionamide;

M-[1,3,4]Thiadiazol-2-yl-3-[3-(4-trifluoromethoxy-benzyl)-3H-imidazo[4,5-b]pyridin-2-yl]-propionamide;

3-[3-(3,4-Difluoro-benzyl)-3H-imidazo[4,5-b]pyridin-2-yl]-N-(2-methoxy-4-trifluoromethoxy-benzyl)-propionamide;

3-[3-(3,4-Difluoro-benzyl)-3H-imidazo[4,5-b]pyridin-2-yl]-N-pyridin-2-ylmethyl-propionamide;

3-[3-(4-Benzyloxy-benzyl)-3H-imidazo[4,5-b]pyridin-2-yl]-N—[(S)-1-(4-chloro-phenyl)-ethyl]-propionamide;

N-(4-Methyl-thiazol-2-yl)-3-[3-(4-trifluoromethoxy-benzyl)-3H-imidazo[4,5-b]pyridin-2-yl]-propionamide;

N-Oxazol-2-yl-3-[3-(4-trifluoromethoxy-benzyl)-3H-imidazo[4,5-b]pyridin-2-yl]-propionamide;

N—[(S)-1-(4-Chloro-phenyl)-ethyl]-3-[3-(4-fluoro-benzyl)-5-methyl-3H-imidazo[4,5-b]pyridin-2-yl]-propionamide;

3-[3-(4-Benzyloxy-benzyl)-3H-imidazo[4,5-b]pyridin-2-yl]-N—[(S)-1-(4-fluoro-phenyl)-ethyl]-propionamide;

N-(5-Methyl-thiazol-2-yl)-3-[3-(4-trifluoromethoxy-benzyl)-3H-imidazo[4,5-b]pyridin-2-yl]-propionamide;

3-[3-(3,4-Difluoro-benzyl)-3H-imidazo[4,5-b]pyridin-2-yl]-N-pyridin-4-ylmethyl-propionamide;

N—[(S)-1-(4-Bromo-phenyl)-ethyl]-3-[3-(4-fluoro-benzyl)-3H-imidazo[4,5-b]pyridin-2-yl]-propionamide;

N—[(S)-1-(4-Chloro-phenyl)-ethyl]-3-[3-(4-methoxy-benzyl)-3H-imidazo[4,5-b]pyridin-2-yl]-propionamide;

3-[3-(3,4-Difluoro-benzyl)-3H-imidazo[4,5-b]pyridin-2-yl]-N—((S)-1-p-tolyl-ethyl)-propionamide;

3-[3-(3,4-Difluoro-benzyl)-3H-imidazo[4,5-b]pyridin-2-yl]-N—((S)-1-phenyl-ethyl)-propionamide;

3-[3-(4-Fluoro-benzyl)-3H-imidazo[4,5-b]pyridin-2-yl]-N—((S)-1-phenyl-ethyl)-propionamide;

3-[3-(4-Fluoro-benzyl)-3H-imidazo[4,5-b]pyridin-2-yl]-N—((S)-1-(4-fluoro-phenyl)-ethyl]-propionamide;

3-[3-(3,4-Difluoro-benzyl)-3H-imidazo[4,5-b]pyridin-2-yl]-N—((S)-1-phenyl-propyl)-propionamide;

3-[3-(4-Methoxy-benzyl)-3H-imidazo[4,5-b]pyridin-2-yl]-N—((S)-1-p-tolyl-ethyl)-propionamide;

3-[7-Fluoro-1-(4-methoxy-benzyl)-1H-benzoimidazol-2-yl]-N-(4-methoxy-benzyl)-propionamide;

3-[3-(4-Methoxy-benzyl)-3H-imidazo[4,5-b]pyridin-2-yl]-N—((S)-1-phenyl-ethyl)-propionamide;

3-[3-(4-Methoxy-benzyl)-3H-imidazo[4,5-b]pyridin-2-yl]-N—((S)-1-phenyl-propyl)-propionamide;

N-(4-Fluoro-benzyl)-3-[3-(4-fluoro-benzyl)-3H-imidazo[4,5-b]pyridin-2-yl]-propionamide;

3-[3-(3,4-Difluoro-benzyl)-3H-imidazo[4,5-b]pyridin-2-yl]-N—[(S)-1-(4-fluoro-phenyl)-ethyl]-propionamide;

N—[(S)-1-(4-Fluoro-phenyl)-ethyl]-3-[3-(4-methoxy-benzyl)-3H-imidazo[4,5-b]pyridin-2-yl]-propionamide;

3-[3-(4-Fluoro-benzyl)-3H-imidazo[4,5-b]pyridin-2-yl]-N-(4-methoxy-benzyl)-propionamide;

N-(4-Methoxy-benzyl)-3-[3-(3-trifluoromethoxy-benzyl)-3H-imidazo[4,5-b]pyridin-2-yl]-propionamide;

3-[3-(4-Methoxy-benzyl)-3H-imidazo[4,5-b]pyridin-2-yl]-N—((S)-1-methyl-1-phenyl-butyl)-propionamide;

3-[3-(3,4-Difluoro-benzyl)-3H-imidazo[4,5-b]pyridin-2-yl]-N-(4-methoxy-benzyl)-propionamide;

3-[6-Fluoro-3-(2-methoxy-benzyl)-3H-imidazo[4,5-b]pyridin-2-yl]-N-(4-methoxy-benzyl)-propionamide;

3-[3-(4-Methoxy-benzyl)-3H-imidazo[4,5-b]pyridin-2-yl]-N-(3-methyl-benzyl)-propionamide;

N-(4-Methoxy-benzyl)-3-[3-(4-methyl-benzyl)-3H-imidazo[4,5-b]pyridin-2-yl]-propionamide;

3-[3-(4-Methoxy-benzyl)-3H-imidazo[4,5-b]pyridin-2-yl]-N-methyl-N—((S)-1-phenyl-ethyl)-propionamide;

3-[3-(4-Methoxy-benzyl)-3H-imidazo[4,5-b]pyridin-2-yl]-N-(1-methyl-1H-indol-5-ylmethyl)-propionamide;

3-[3-(4-Methoxy-benzyl)-3H-imidazo[4,5-b]pyridin-2-yl]-N-(2-methyl-benzyl)-propionamide;

N-(3,4-Difluoro-benzyl)-3-[3-(4-methoxy-benzyl)-3H-imidazo[4,5-b]pyridin-2-yl]-propionamide;

3-[3-(4-Methoxy-benzyl)-3H-imidazo[4,5-b]pyridin-2-yl]-N-(2-p-tolyl-ethyl)-propionamide;

3-[3-(4-Fluoro-benzyl)-6-methyl-3H-imidazo[4,5-b]pyridin-2-yl]-N-(4-methoxy-benzyl)-propionamide;

3-[3-(3-Fluoro-benzyl)-3H-imidazo[4,5-b]pyridin-2-yl]-N-(4-methoxy-benzyl)-propionamide;

3-(3-Benzyl-3H-imidazo[4,5-b]pyridin-2-yl)-N-cyclohexylmethyl-propionamide;
3-[3-(4-Methoxy-benzyl)-3H-imidazo[4,5-b]pyridin-2-yl]-N-((R)-1-phenyl-ethyl)-propionamide;
N-Isopropyl-3-[3-(4-methoxy-benzyl)-3H-imidazo[4,5-b]pyridin-2-yl]-propionamide;
N-(2-Fluoro-benzyl)-3-[3-(4-methoxy-benzyl)-3H-imidazo[4,5-b]pyridin-2-yl]-propionamide;
3-[3-(4-Methoxy-benzyl)-3H-imidazo[4,5-b]pyridin-2-yl]-N-(3-methyl-benzyl)-propionamide;
3-[3-(4-Methoxy-benzyl)-3H-imidazo[4,5-b]pyridin-2-yl]-N-[2-(4-methoxy-phenyl)-ethyl]-propionamide;
N-(3-Fluoro-benzyl)-3-[3-(4-methoxy-benzyl)-3H-imidazo[4,5-b]pyridin-2-yl]-propionamide;
N-(4-Methoxy-benzyl)-3-[3-(3-methyl-benzyl)-3H-imidazo[4,5-b]pyridin-2-yl]-propionamide;
N-(4-Fluoro-benzyl)-3-[3-(4-methoxy-benzyl)-3H-imidazo[4,5-b]pyridin-2-yl]-N-methyl-propionamide;
N-(4-Trifluoromethoxy-benzyl)-3-[3-(2-trifluoromethoxy-benzyl)-3H-imidazo[4,5-b]pyridin-2-yl]-propionamide;
3-[3-(4-Fluoro-benzyl)-5-methyl-3H-imidazo[4,5-b]pyridin-2-yl]-N—[(S)-1-(4-fluoro-phenyl)-ethyl]-propionamide;
N—[(S)-1-(4-Chloro-phenyl)-ethyl]-3-[3-(4-trifluoromethoxy-benzyl)-3H-imidazo[4,5-c]pyridin-2-yl]-propionamide;
N—((R)-2-Hydroxy-1-phenyl-ethyl)-3-[3-(4-trifluoromethoxy-benzyl)-3H-imidazo[4,5-c]pyridin-2-yl]-propionamide;
N—[(S)-1-(4-Fluoro-phenyl)-ethyl]-3-[3-(4-trifluoromethoxy-benzyl)-3H-imidazo[4,5-c]pyridin-2-yl]-propionamide;
N—{(S)-1-[4-(4-Methyl-piperazin-1-yl)-phenyl]-ethyl}-3-[3-(4-trifluoromethoxy-benzyl)-3H-imidazo[4,5-c]pyridin-2-yl]-propionamide;
N-[2-Hydroxy-1-(4-trifluoromethoxy-phenyl)-ethyl]-3-[3-(4-trifluoromethoxy-benzyl)-3H-imidazo[4,5-c]pyridin-2-yl]-propionamide;
3-[3-(4-Fluoro-benzyl)-3H-imidazo[4,5-c]pyridin-2-yl]-N—((S)-1-phenyl-propyl)-propionamide;
N-[4-(3-Dimethylamino-propoxy)-benzyl]-3-[3-(4-trifluoromethoxy-benzyl)-3H-imidazo[4,5-c]pyridin-2-yl]-propionamide;
N-(4-Chloro-benzyl)-3-[3-(4-trifluoromethoxy-benzyl)-3H-imidazo[4,5-c]pyridin-2-yl]-propionamide;
3-[3-(4-Fluoro-benzyl)-3H-imidazo[4,5-c]pyridin-2-yl]-N—((S)-1-phenyl-ethyl)-propionamide;
3-[3-(4-Fluoro-benzyl)-3H-imidazo[4,5-c]pyridin-2-yl]-N—((S)-1-p-tolyl-ethyl)-propionamide;
3-[3-(4-Fluoro-benzyl)-3H-imidazo[4,5-c]pyridin-2-yl]-N—[(S)-1-(4-fluoro-phenyl)-ethyl]-propionamide;
N-(4-Fluoro-benzyl)-3-[3-(4-trifluoromethoxy-benzyl)-3H-imidazo[4,5-c]pyridin-2-yl]-propionamide;
3-[3-(4-Fluoro-benzyl)-3H-imidazo[4,5-c]pyridin-2-yl]-N—((S)-1-phenyl-butyl)-propionamide;
4-({3-[3-(4-Trifluoromethoxy-benzyl)-3H-imidazo[4,5-c]pyridin-2-yl]-propionylamino}-methyl)-piperidine-1-carboxylic acid tert-butyl ester;
3-[3-(4-Fluoro-benzyl)-3H-imidazo[4,5-c]pyridin-2-yl]-N-(1-methyl-1-phenyl-ethyl)-propionamide;
N—[(S)-1-(4-Fluoro-phenyl)-ethyl]-3-[1-(4-trifluoromethoxy-benzyl)-1H-pyrrolo[2,3-b]pyridin-2-yl]-propionamide;
3-[1-(4-Chloro-benzyl)-1H-pyrrolo[2,3-b]pyridin-2-yl]-N—[(S)-1-(4-fluoro-phenyl)-ethyl]-propionamide;
N—[(S)-1-(4-Fluoro-phenyl)-ethyl]-3-[5-fluoro-1-(4-trifluoromethoxy-benzyl)-1H-pyrrolo[2,3-b]pyridin-2-yl]-propionamide
3-[1-(4-Fluoro-benzyl)-1H-pyrrolo[2,3-b]pyridin-2-yl]-N—[(S)-1-(4-fluoro-phenyl)-ethyl]-propionamide;
3-[1-(4-Chloro-benzyl)-5-fluoro-1H-pyrrolo[2,3-b]pyridin-2-yl]-N—[(S)-1-(4-fluoro-phenyl)-ethyl]-propionamide;
N—((R)-2-Hydroxy-1-phenyl-ethyl)-2-[3-(4-trifluoromethoxy-benzyl)-3H-imidazo[4,5-b]pyridin-2-ylsulfanyl]acetamide;
2-[3-(4-Fluoro-benzyl)-3H-imidazo[4,5-b]pyridin-2-ylsulfanyl]-N—((R)-2-hydroxy-1-phenyl-ethyl)-acetamide;
N—[(S)-1-(4-Chloro-phenyl)-ethyl]-2-[3-(4-trifluoromethoxy-benzyl)-3H-imidazo[4,5-b]pyridin-2-ylsulfanyl]acetamide;
N—[(S)-1-(4-Fluoro-phenyl)-ethyl]-2-[3-(4-trifluoromethoxy-benzyl)-3H-imidazo[4,5-b]pyridin-2-ylsulfanyl]-acetamide;
2-[3-(4-Fluoro-benzyl)-3H-imidazo[4,5-b]pyridin-2-ylsulfanyl]-N—[(S)-1-(4-fluoro-phenyl)-ethyl]acetamide;
2-[3-(4-Fluoro-benzyl)-3H-imidazo[4,5-b]pyridin-2-ylsulfanyl]-N—[(S)-1-(4-morpholin-4-yl-phenyl)-ethyl]-acetamide;
N—[(S)-1-(4-Fluoro-phenyl)-ethyl]-2-[3-(4-trifluoromethoxy-benzyl)-3H-imidazo[4,5-b]pyridine-2-sulfinyl]-acetamide (diastereomer 1);
N—[(S)-1-(4-Fluoro-phenyl)-ethyl]-2-[3-(4-trifluoromethoxy-benzyl)-3H-imidazo[4,5-b]pyridine-2-sulfinyl]-acetamide (diastereomer 2);
N—[(S)-1-(4-Fluoro-phenyl)-ethyl]-2-[3-(4-trifluoromethoxy-benzyl)-3H-imidazo[4,5-b]pyridine-2-sulfonyl]-acetamide;
N—((R)-2-Hydroxy-1-phenyl-ethyl)-2-[3-(4-trifluoromethoxy-benzyl)-3H-imidazo[4,5-b]pyridin-2-yloxy]-acetamide;
N—[(S)-1-(4-Chloro-phenyl)-ethyl]-2-[3-(4-trifluoromethoxy-benzyl)-3H-imidazo[4,5-b]pyridin-2-yloxy]-acetamide;
2-[3-(4-Fluoro-benzyl)-3H-imidazo[4,5-b]pyridin-2-yloxy]-N—[(S)-1-(4-fluoro-phenyl)-ethyl]-acetamide;
N—((R)-2-Hydroxy-1-phenyl-ethyl)-2-[3-(4-trifluoromethoxy-benzyl)-3H-imidazo[4,5-b]pyridin-2-ylsulfanyl]-propionamide;
N—[(S)-1-(4-Fluoro-phenyl)-ethyl]-3-[3-(4-hydroxy-benzyl)-3H-imidazo[4,5-b]pyridin-2-yl]-propionamide;
N—[(S)-1-(4-Fluoro-phenyl)-ethyl]-3-[3-(4-isobutoxy-benzyl)-3H-imidazo[4,5-b]pyridin-2-yl]propionamide;
1-[(S)-1-(4-Chloro-phenyl)-ethyl]-3-[3-(4-fluoro-benzyl)-3H-imidazo[4,5-b]pyridin-2-ylmethyl]urea;
1-[(S)-1-(4-Bromo-phenyl)-ethyl]-3-[3-(3,4-difluoro-benzyl)-3H-imidazo[4,5-b]pyridin-2-ylmethyl]-urea;
1-[3-(4-Fluoro-benzyl)-3H-imidazo[4,5-b]pyridin-2-ylmethyl]-3-[(S)-1-(4-methoxy-phenyl)-ethyl]-urea;
1-[3-(4-Fluoro-benzyl)-3H-imidazo[4,5-b]pyridin-2-ylmethyl]-3-[(S)-1-(4-fluoro-phenyl)-ethyl]-urea;
1-[3-(4-Fluoro-benzyl)-3H-imidazo[4,5-b]pyridin-2-ylmethyl]-3-((S)-1-phenyl-ethyl)-urea;
1-[3-(3,4-Difluoro-benzyl)-3H-imidazo[4,5-b]pyridin-2-ylmethyl]-3-((R)-2-hydroxy-1-phenyl-ethyl)-urea;
1-[3-(3,4-Difluoro-benzyl)-3H-imidazo[4,5-b]pyridin-2-ylmethyl]-3-[(S)-1-(4-morpholin-4-yl-phenyl)-ethyl]-urea;
[3-(4-Fluoro-benzyl)-3H-imidazo[4,5-b]pyridin-2-ylmethyl]-carbamic acid (S)-1-(4-fluoro-phenyl)-ethyl ester;
1-[3-(4-Fluoro-benzyl)-3H-imidazo[4,5-b]pyridin-2-ylmethyl]-3-[(S)-1-(3-methoxy-phenyl)-ethyl]-urea;
[(S)-1-(4-Fluoro-phenyl)-ethyl]-carbamic acid 3-(4-fluoro-benzyl)-3H-imidazo[4,5-b]pyridin-2-ylmethyl ester;

N—{(S)-1-[4-(4-Methyl-piperazin-1-yl)-phenyl]-ethyl}-3-[3-(4-trifluoromethoxy-benzyl)-3H-imidazo[4,5-b]pyridin-2-yl]-propionamide;

N—{(S)-1-[4-((R)-3-Dimethylamino-pyrrolidin-1-yl)-phenyl]ethyl}-3-[3-(4-trifluoromethoxy-benzyl)-3H-imidazo[4,5-b]pyridin-2-yl]-propionamide;

N—{(S)-1-[4-((S)-3-Dimethylamino-pyrrolidin-1-yl)-phenyl]ethyl}-3-[3-(4-trifluoromethoxy-benzyl)-3H-imidazo[4,5-b]pyridin-2-yl]-propionamide;

N—[(S)-1-(4-[1,4]Diazepan-1-yl-phenyl)-ethyl]-3-[3-(4-trifluoromethoxy-benzyl)-3H-imidazo[4,5-b]pyridin-2-yl]-propionamide;

N—{(S)-1-[4-((cis)-3,5-Dimethyl-piperazin-1-yl)-phenyl]ethyl}-3-[3-(4-trifluoromethoxy-benzyl)-3H-imidazo[4,5-b]pyridin-2-yl]-propionamide;

N—{(S)-1-[4-((S)-3-Ethyl-piperazin-1-yl)-phenyl]ethyl}-3-[3-(4-trifluoromethoxy-benzyl)-3H-imidazo[4,5-b]pyridin-2-yl]-propionamide;

N—{(S)-1-[4-(1-Methyl-piperidin-4-ylamino)-phenyl]ethyl}-3-[3-(4-trifluoromethoxy-benzyl)-3H-imidazo[4,5-b]pyridin-2-yl]-propionamide;

N—{(S)-1-[4-((R)-3-Methyl-piperazin-1-yl)-phenyl]ethyl}-3-[3-(4-trifluoromethoxy-benzyl)-3H-imidazo[4,5-b]pyridin-2-yl]-propionamide;

N—{(S)-1-[4-((S)-Pyrrolidin-3-ylamino)-phenyl]-ethyl}-3-[3-(4-trifluoromethoxy-benzyl)-3H-imidazo[4,5-b]pyridin-2-yl]-propionamide;

N—{(S)-1-[4-((S)-3-Methyl-piperazin-1-yl)-phenyl]ethyl}-3-[3-(4-trifluoromethoxy-benzyl)-3H-imidazo[4,5-b]pyridin-2-yl]-propionamide;

3-[3-(3,4-Difluoro-benzyl)-3H-imidazo[4,5-b]pyridin-2-yl]-N—{(S)-1-[4-(3-dimethylamino-pyrrolidin-1-ylmethyl)-phenyl]-ethyl}-propionamide;

N—[(S)-1-(4-Azepan-1-yl-phenyl)-ethyl]-3-[3-(4-fluoro-benzyl)-3H-imidazo[4,5-b]pyridin-2-yl]-propionamide;

3-[3-(3,4-Difluoro-benzyl)-3H-imidazo[4,5-b]pyridin-2-yl]-N—{(S)-1-[4-(3-trifluoromethyl-piperazin-1-yl)-phenyl]-ethyl}-propionamide;

3-[3-(4-Fluoro-benzyl)-3H-imidazo[4,5-b]pyridin-2-yl]-N—[(S)-1-(4-pyrrolidin-1-yl-phenyl)-ethyl]-propionamide;

3-[3-(4-Fluoro-benzyl)-3H-imidazo[4,5-b]pyridin-2-yl]-N—{(S)-1-[4-(4-hydroxymethyl-piperidin-1-yl)-phenyl]-ethyl}-propionamide;

3-[3-(3,4-Difluoro-benzyl)-3H-imidazo[4,5-b]pyridin-2-yl]-N—{(S)-1-[4-(4-methyl-piperazin-1-ylmethyl)-phenyl]-ethyl}-propionamide;

3-[3-(3,4-Difluoro-benzyl)-3H-imidazo[4,5-b]pyridin-2-yl]-N—[(S)-1-(4-pyrrolidin-1-yl-phenyl)-ethyl]-propionamide;

3-[3-(3,4-Difluoro-benzyl)-3H-imidazo[4,5-b]pyridin-2-yl]-N—{(S)-1-[4-((S)-3-methyl-piperazin-1-yl)-phenyl]-ethyl}-propionamide;

3-[3-(4-Fluoro-benzyl)-3H-imidazo[4,5-b]pyridin-2-yl]-N—[(S)-1-(4-morpholin-4-yl-phenyl)-ethyl]-propionamide;

3-[3-(4-Fluoro-benzyl)-3H-imidazo[4,5-b]pyridin-2-yl]-N—[(S)-1-(4-piperidin-1-yl-phenyl)-ethyl]-propionamide;

3-[3-(3,4-Difluoro-benzyl)-3H-imidazo[4,5-b]pyridin-2-yl]-N—[(S)-1-(4-piperidin-1-yl-phenyl)-ethyl]-propionamide;

3-[3-(3,4-Difluoro-benzyl)-3H-imidazo[4,5-b]pyridin-2-yl]-N—{(S)-1-[4-((R)-3-methyl-piperazin-1-yl)-phenyl]-ethyl}-propionamide;

3-[6-Methyl-3-(4-trifluoromethoxy-benzyl)-3H-imidazo[4,5-b]pyridin-2-yl]-N—{(S)-1-[4-((S)-pyrrolidin-3-ylamino)-phenyl]ethyl}-propionamide;

3-[3-(3,4-Difluoro-benzyl)-3H-imidazo[4,5-b]pyridin-2-yl]-N—{(S)-1-[4-((R)-3-hydroxy-pyrrolidin-1-yl)-phenyl]-ethyl}-propionamide;

N—[(S)-1-(4-[1,4]Diazepan-1-yl-phenyl)-ethyl]-3-[6-methyl-3-(4-trifluoromethoxy-benzyl)-3H-imidazo[4,5-b]pyridin-2-yl]-propionamide;

N—{(S)-1-[4-((S)-3-Methyl-piperazin-1-yl)-phenyl]-ethyl}-3-[6-methyl-3-(4-trifluoromethoxy-benzyl)-3H-imidazo[4,5-b]pyridin-2-yl]-propionamide;

3-[3-(3,4-Difluoro-benzyl)-3H-imidazo[4,5-b]pyridin-2-yl]-N—[(S)-1-(4-piperazin-1-yl-phenyl)-ethyl]-propionamide;

(R)-Cyclohexyl-{3-[3-(4-trifluoromethoxy-benzyl)-3H-imidazo[4,5-b]pyridin-2-yl]-propionylamino}-acetic acid;

(R)-3-Phenyl-2-{3-[3-(4-trifluoromethoxy-benzyl)-3H-imidazo[4,5-b]pyridin-2-yl]-propionylamino}-propionic acid;

(R)-3-Phenyl-2-{3-[3-(4-trifluoromethyl-benzyl)-3H-imidazo[4,5-b]pyridin-2-yl]-propionylamino}-propionic acid;

(R)-2-{3-[3-(4-Difluoromethoxy-benzyl)-3H-imidazo[4,5-b]pyridin-2-yl]-propionylamino}-3-phenyl-propionic acid;

(R)-2-{3-[3-(3,4-Difluoro-benzyl)-3H-imidazo[4,5-b]pyridin-2-yl]-propionylamino}-3-phenyl-propionic acid;

(S)-3-Phenyl-2-{3-[3-(4-trifluoromethoxy-benzyl)-3H-imidazo[4,5-b]pyridin-2-yl]-propionylamino}-propionic acid;

(S)-3-(4-Hydroxy-phenyl)-2-{3-[3-(4-trifluoromethoxy-benzyl)-3H-imidazo[4,5-b]pyridin-2-yl]-propionylamino}-propionic acid;

(R)-2-(3-{3-[(S)-1-(4-Fluoro-phenyl)-ethyl]-3H-imidazo[4,5-b]pyridin-2-yl}-propionylamino)-3-phenyl-propionic acid;

(R)-3-Phenyl-2-[3-(3-thiophen-2-ylmethyl-3H-imidazo[4,5-b]pyridin-2-yl)-propionylamino]-propionic acid;

N—((R)-1-Hydroxymethyl-2-phenyl-ethyl)-3-[3-(4-trifluoromethoxy-benzyl)-3H-imidazo[4,5-b]pyridin-2-yl]-propionamide;

N—((S)-1-Hydroxymethyl-2-phenyl-ethyl)-3-[3-(4-trifluoromethoxy-benzyl)-3H-imidazo[4,5-b]pyridin-2-yl]-propionamide;

N—[(S)-1-Hydroxymethyl-2-(4-hydroxy-phenyl)-ethyl]-3-[3-(4-trifluoromethoxy-benzyl)-3H-imidazo[4,5-b]pyridin-2-yl]-propionamide;

3-[3-(3,4-Difluoro-benzyl)-3H-imidazo[4,5-b]pyridin-2-yl]-N—[(S)-1-(4-morpholin-4-ylmethyl-phenyl)-ethyl]-propionamide;

N—[(S)-1-(4-Diethylaminomethyl-phenyl)-ethyl]-3-[3-(3,4-difluoro-benzyl)-3H-imidazo[4,5-b]pyridin-2-yl]-propionamide;

3-[3-(3,4-Difluoro-benzyl)-3H-imidazo[4,5-b]pyridin-2-yl]-N—[(S)-1-(4-dimethylaminomethyl-phenyl)-ethyl]-propionamide;

N—((R)-2-Mercapto-1-phenyl-ethyl)-3-[3-(4-trifluoromethoxy-benzyl)-3H-imidazo[4,5-b]pyridin-2-yl]-propionamide;

N—((R)-2-Amino-1-phenyl-ethyl)-3-[3-(4-trifluoromethoxy-benzyl)-3H-imidazo[4,5-b]pyridin-2-yl]-propionamide;

N—[(S)-1-(4-Chloro-phenyl)-ethyl]-3-[6-methyl-3-(4-trifluoromethoxy-benzyl)-3H-imidazo[4,5-b]pyridin-2-yl]-propionamide;

N—[(S)-1-(4-Methoxy-phenyl)-ethyl]-3-[6-methyl-3-(4-trifluoromethoxy-benzyl)-3H-imidazo[4,5-b]pyridin-2-yl]-propionamide;

N—[(S)-1-(4-Chloro-phenyl)-ethyl]-3-[3-(4-fluoro-benzyl)-6-methyl-3H-imidazo[4,5-b]pyridin-2-yl]-propionamide;

N-(1-Methanesulfonyl-piperidin-4-ylmethyl)-3-[3-(4-trifluoromethoxy-benzyl)-3H-imidazo[4,5-b]pyridin-2-yl]-propionamide;

N-(1-Cyclopropanecarbonyl-piperidin-4-ylmethyl)-3-[3-(4-trifluoromethoxy-benzyl)-3H-imidazo[4,5-b]pyridin-2-yl]-propionamide;

N-(1-Acetyl-piperidin-4-ylmethyl)-3-[3-(4-trifluoromethoxy-benzyl)-3H-imidazo[4,5-b]pyridin-2-yl]-propionamide.

The various functional groups and substituents making up the compounds of the formula I are typically chosen such that the molecular weight of the compound of the formula I does not exceed 1000. More usually, the molecular weight of the compound will be less than 900, for example less than 800, or less than 750, or less than 700, or less than 650. More preferably, the molecular weight is less than 600 and, for example, is 550 or less.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess antiproliferative activity.

The present invention also encompasses compounds of the invention as defined herein which comprise one or more isotopic substitutions. For example, H may be in any isotopic form, including 1H, 2H(D), and 3H (T); C may be in any isotopic form, including 12C, 13C, and 14C; and O may be in any isotopic form, including 16O and 18O; and the like.

It is also to be understood that certain compounds of the formula I may exist in solvated as well as unsolvated forms such as, for example, hydrated forms. It is to be understood that the invention encompasses all such solvated forms that possess antiproliferative activity.

It is also to be understood that certain compounds of the formula I may exhibit polymorphism, and that the invention encompasses all such forms that possess antiproliferative activity.

Compounds of the formula I may exist in a number of different tautomeric forms and references to compounds of the formula I include all such forms. For the avoidance of doubt, where a compound can exist in one of several tautomeric forms, and only one is specifically described or shown, all others are nevertheless embraced by formula I. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

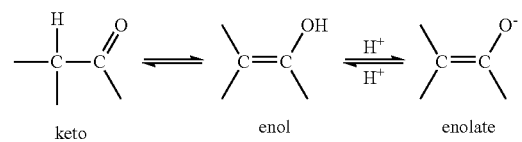

keto    enol    enolate

Compounds of the formula I containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with m-chloroperoxybenzoic acid (mCPBA), for example, in an inert solvent such as dichloromethane.

The compounds of formula I may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the formula I and in-vivo cleavable amide derivatives that may be formed at a carboxy group or an amino group in a compound of the formula I.

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically acceptable pro-drug of a compound of the formula I is one that is based on reasonable medical judgement as being suitable for administration to the human or animal body without undesirable pharmacological activities and without undue toxicity.

Various forms of pro-drug have been described, for example in the following documents:
a) Methods in Enzymology, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, Advanced Drug Delivery Reviews, 8, 1-38 (1992);
e) H. Bundgaard, et al., Journal of Pharmaceutical Sciences, 77, 285 (1988);
f) N. Kakeya, et al., Chem. Pharm. Bull., 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the formula I that possesses a carboxy group is, for example, an in vivo cleavable ester thereof. An in vivo cleavable ester of a compound of the formula I containing a carboxy group is, for example, a pharmaceutically acceptable ester which is cleaved in the human or animal body to produce the parent acid. Suitable pharmaceutically acceptable esters for carboxy include C1-6alkyl esters such as methyl, ethyl and tert-butyl, C1-6alkoxymethyl esters such as methoxymethyl esters, C1-6alkanoyloxymethyl esters such as pivaloyloxymethyl esters, 3-phthalidyl esters, C3-8cycloalkylcarbonyloxy-C1-6alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and C1-6alkoxycarbonyloxy-C1-6alkyl esters such as methoxycarbonyloxymethyl and 1-methoxycarbonyloxyethyl esters.

A suitable pharmaceutically acceptable pro-drug of a compound of the formula I that possesses a hydroxy group is, for example, an in vivo cleavable ester or ether thereof. An in vivo cleavable ester or ether of a compound of the formula I containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include C1-10alkanoyl groups such as acetyl, benzoyl, phenylacetyl and substituted benzoyl and phenylacetyl groups, C1-10alkoxycarbonyl groups such as ethoxycarbonyl, N,N—(C1-6)2carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(C1-4alkyl)piperazin-1-yl methyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the formula I that possesses a carboxy group is, for example, an in vivo cleavable amide thereof, for example an amide formed with an amine such as ammonia, a C1-4alkylamine such as methylamine, a (C1-4alkyl)2amine such as dimethylamine, N-ethyl-N-methylamine or diethylamine, a C1-4alkoxy-C2-4alkylamine such as 2-methoxyethylamine, a phenyl-C1-4alkylamine such as benzylamine and amino acids such as glycine or an ester thereof.

A suitable pharmaceutically acceptable pro-drug of a compound of the formula I that possesses an amino group is, for example, an in vivo cleavable amide derivative thereof.

Suitable pharmaceutically acceptable amides from an amino group include, for example an amide formed with C1-10alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(C1-4alkyl)piperazin-1-ylmethyl.

The in vivo effects of a compound of the formula I may be exerted in part by one or more metabolites that are formed within the human or animal body after administration of a compound of the formula I. As stated hereinbefore, the in vivo effects of a compound of the formula I may also be exerted by way of metabolism of a precursor compound (a pro-drug).

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Suitably, the present invention excludes any individual compounds not possessing the biological activity defined herein.

Synthesis

The compounds of the present invention can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the invention in the processes defined herein, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The methodology employed to synthesise a compound of formula I will vary depending on the nature of $A_1$, $A_2$, $A_3$, L, Ar, Q, $R_1$, $R_2$, $R_3$, $R_4$, $R_5$, $R_6$, $R_a$, $R_{a'}$, $R_b$, $R_{b'}$, $R_c$ and any substituent groups associated therewith. Suitable processes for their preparation are described further in the accompanying Examples.

Once a compound of formula I has been synthesised by any one of the processes defined herein, the processes may then further comprise the additional steps of:

(i) removing any protecting groups present;

(ii) converting the compound formula I into another compound of formula I;

(iii) forming a pharmaceutically acceptable salt, hydrate or solvate thereof; and/or (iv) forming a prodrug thereof.

An example of (ii) above is when a compound of formula I is synthesised and then one or more of the groups of $A_1$, $A_2$, $A_3$, L, Ar, Q, $R_1$, $R_2$, $R_3$, $R_4$, $R_5$, $R_6$, $R_a$, $R_{a'}$, $R_b$, $R_{b'}$ and $R_c$, may be further reacted to change the nature of the group and provide an alternative compound of formula I. For example, the compound can be reacted to covert any R group into a substituent group other than hydrogen.

The resultant compounds of formula I can be isolated and purified using techniques well known in the art.

In one aspect of the present invention, the compounds of formula I, or a pharmaceutically acceptable salt or solvate thereof, may be synthesised by a method comprising either:

a) reacting a compound of formula A:

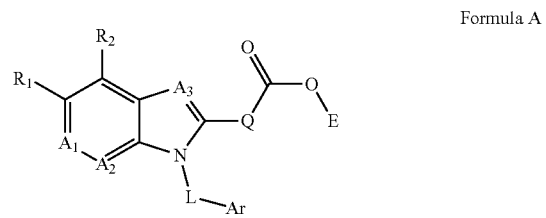

Formula A wherein $A_1$, $A_2$, $A_3$, L, Ar, Q, $R_1$ and $R_2$ are as defined hereinabove, and E is either H or alkyl;

with a compound of formula B, and a suitable amide coupling agent when E is H:

Formula B wherein $R_3$, $R_4$, $R_5$ and $R_6$ are as described hereinabove;

b) reacting a compound of formula C:

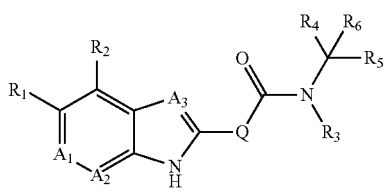
Formula C wherein $A_1$, $A_2$, $A_3$, Q, $R_1$, $R_2$, $R_3$, $R_4$, $R_5$, $R_6$, $R_a$, $R_{a'}$, $R_b$, $R_{b'}$, and $R_c$ are as defined hereinabove;
with a compound of formula D, in the presence of a base:

X-L-Ar          Formula D wherein L and Ar are as defined hereinabove and X is a suitable leaving group (e.g. a halogen);
c) reacting a compound of formula E:

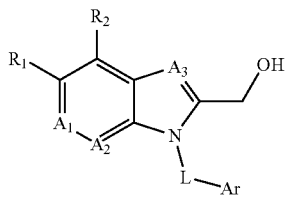
Formula E with a compound of formula F:

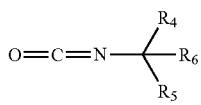
Formula F wherein $R_4$, $R_5$ and $R_6$ are as described hereinabove;
optionally thereafter, and if necessary:
  i) removing any protecting groups present;
  ii) converting the compound formula I into another compound of formula I; and/or
  iii) forming a pharmaceutically acceptable salt or solvate thereof.

Biological Activity

The ATX enzyme assay (Quanta Red assay) described in accompanying Example section may be used to measure the pharmacological effects of the compounds of the present invention.

Although the pharmacological properties of the compounds of formula I vary with structural change, as expected, the compounds of the invention were found to be active in this ATX assay.

In general, the compounds of the invention demonstrate an IC50 of 5 μM or less in the ATX enzyme assay described herein, with preferred compounds of the invention demonstrating an IC50 of 1 μM or less, more preferred compounds demonstrating an IC50 of 500 nM or less, and the most preferred compounds of the invention demonstrating an IC50 of 100 nM or less.

Pharmaceutical Compositions

According to a further aspect of the invention there is provided a pharmaceutical composition which comprises a compound of the invention as defined hereinbefore, or a pharmaceutically acceptable salt, hydrate or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The proviso (iii) recited in the compound definition above excludes certain compounds that are not novel, but the use of these compounds in any of the therapeutic methods or combination therapeies defined herein is still encompassed by the present invention. In other words, compounds of formula I in which $A_1$, $A_2$, $A_3$, Q, $R_1$, $R_2$, $R_3$, $R_4$, $R_5$, $R_6$, L and Ar each have any one of the meanings defined herein; or a pharmaceutically acceptable salt, hydrate and/or solvate thereof, with the proviso that:
(i) only one or two of $A_1$, $A_2$ and $A_3$ can be N; and
(ii) $A_1$ and $A_2$ cannot both be CH
are used in the therapeutic methods, uses and combination therapies defined herein.

The present invention provides compounds that function as inhibitors of ATX.

The present invention therefore provides a method of inhibiting ATX enzyme activity in vitro or in vivo, said method comprising contacting a cell and/or circulating ATX with an effective amount of a compound, or a pharmaceutically acceptable salt, hydrate or solvate thereof, as defined herein.

The present invention also provides a method of treating a disease or disorder in which ATX activity is implicated in a patient in need of such treatment, said method comprising administering to said patient a therapeutically effective amount of a compound, or a pharmaceutically acceptable salt, hydrate or solvate thereof, or a pharmaceutical composition as defined herein.

The present invention further provides a method of inhibiting cell proliferation, in vitro or in vivo, said method comprising contacting a cell and/or circulating ATX with an effective amount of a compound, or a pharmaceutically acceptable salt, hydrate or solvate thereof, as defined herein.

The present invention further provides a method of treating a proliferative disorder in a patient in need of such treatment, said method comprising administering to said patient a therapeutically effective amount of a compound as defined herein, or a pharmaceutically acceptable salt, hydrate or solvate thereof, or a pharmaceutical composition as defined herein.

The present invention further provides a method of treating or preventing cancer in a patient in need of such treatment, said method comprising administering to said patient a therapeutically effective amount of a compound as defined herein, or a pharmaceutically acceptable salt, hydrate or solvate thereof, or a pharmaceutical composition as defined herein.

The present invention further provides a method of treating or preventing invasive and/or metastatic cancer disease in a patient in need of such treatment, said method comprising administering to said patient a therapeutically effective amount of a compound as defined herein, or a pharmaceutically acceptable salt, hydrate or solvate thereof, or a pharmaceutical composition as defined herein.

The present invention further provides a method of treating or preventing fibrosis in a patient in need of such treatment, said method comprising administering to said patient a therapeutically effective amount of a compound as defined herein, or a pharmaceutically acceptable salt, hydrate or solvate thereof, or a pharmaceutical composition as defined herein. Suitably, the present invention provides a method of treating or preventing lung, renal, hepatic or skin fibrosis, most suitably, lung and hepatic fibrosis.

The present invention further provides a compound as defined herein, or a pharmaceutically acceptable salt, hydrate or solvate thereof, or a pharmaceutical composition as defined herein, for use in therapy.

The present invention further provides a compound as defined herein, or a pharmaceutically acceptable salt, hydrate or solvate thereof, or a pharmaceutical composition as defined herein, for use in the treatment of a proliferative condition.

The present invention provides a compound as defined herein, or a pharmaceutically acceptable salt, hydrate or solvate thereof, or a pharmaceutical composition as defined herein, for use in the treatment of cancer. In a particular embodiment, the cancer is human cancer.

The present invention further provides a compound as defined herein, or a pharmaceutically acceptable salt, hydrate or solvate thereof, or a pharmaceutical composition as defined herein, for use in the treatment of invasive and/or metastatic cancer disease. In a particular embodiment, the invasive and/or metastatic cancer is a human invasive and/or metastatic cancer.

The present invention provides a compound, or a pharmaceutically acceptable salt, hydrate or solvate thereof as defined herein, or a pharmaceutical composition as defined herein, for use in the inhibition of ATX enzyme activity.

The present invention provides a compound or a pharmaceutically acceptable salt, hydrate or solvate thereof as defined herein, or a pharmaceutical composition as defined herein, for use in the treatment of a disease or disorder in which ATX activity is implicated.

The present invention provides a use of a compound or a pharmaceutically acceptable salt, hydrate or solvate thereof as defined herein, or a pharmaceutical composition as defined herein, in the manufacture of a medicament for the treatment of a proliferative condition.

The present invention provides a use of a compound, or a pharmaceutically acceptable salt, hydrate or solvate thereof, as defined herein in the manufacture of a medicament for the treatment of cancer. Suitably, the medicament is for use in the treatment of human cancers.

The present invention further provides a use of a compound, or a pharmaceutically acceptable salt, hydrate or solvate thereof, as defined herein in the manufacture of a medicament for the treatment of invasive and/or metastatic cancer. Suitably, the medicament is for use in the treatment of human invasive and/or metastatic cancer disease.

The present invention provides a use of a compound, or a pharmaceutically acceptable salt, hydrate or solvate thereof, as defined herein in the manufacture of a medicament for the inhibition of ATX enzyme activity.

The present invention provides a use of a compound, or a pharmaceutically acceptable salt, hydrate or solvate thereof, as defined herein in the manufacture of a medicament for the treatment of a disease or disorder in which ATX activity is implicated.

The term "proliferative disorder" are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, benign, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, bladder, kidney, bone, nerves and skin.

In an embodiment of the invention, the proliferative disorder is a benign disorder, such as, for example, neuroblastoma or fibrosis.

The anti-proliferative, anti-metastatic and anti-invasive effects of the compounds of the present invention have particular application in the treatment of human cancers (by virtue of their inhibition of ATX enzyme activity).

In an embodiment of the invention, the anti-proliferative, anti-metastatic and anti-invasive effects of the compounds of the present invention have particular application in the treatment and/or prevention of invasive and/or metastatic cancers, such as, for example bladder cancer, invasive breast cancer, kidney cancer, ovarian cancer and glioma (e.g. glioblastoma). Suitably, the anti-proliferative, anti-metastatic and anti-invasive effects of the compounds of the present invention have particular application in the treatment and/or prevention of bladder cancer, invasive breast cancer and/or glioma (e.g. glioblastoma).

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures or within an organ), or the promotion of apoptosis (programmed cell death).

In a particular embodiment of the invention, the proliferative, metastatic and/or invasive condition to be treated is cancer. Suitably, the condition to be treated is highly invasive or metastatic cancer.

In another aspect, the present invention provides a compound as defined herein, or a pharmaceutically acceptable salt or solvate thereof, or a pharmaceutical composition as defined herein, for use in the treatment of inflammation.

In another aspect, the present invention provides a compound as defined herein, or a pharmaceutically acceptable salt or solvate thereof, or a pharmaceutical composition as defined herein, for use in the treatment of diabetes mellitus.

In another aspect, the present invention provides a compound as defined herein, or a pharmaceutically acceptable salt or solvate thereof, or a pharmaceutical composition as defined herein, for use in the treatment of hypertension, Atherosclerosis or Thrombosis.

In another aspect, the present invention provides a compound as defined herein, or a pharmaceutically acceptable salt or solvate thereof, or a pharmaceutical composition as defined herein, for use in the treatment of pain. In a particular embodiment, the pain is neuropathic pain.

In another aspect, the present invention provides a compound as defined herein, or a pharmaceutically acceptable salt or solvate thereof, or a pharmaceutical composition as defined herein, for use in the treatment of urethral obstructive disease. In a particular embodiment, the urethral obstructive disease is benign prostatic hyperplasia.

In another aspect, the present invention provides a compound as defined herein, or a pharmaceutically acceptable salt or solvate thereof, or a pharmaceutical composition as defined herein, for use in the treatment of pruritus.

In another aspect, the present invention provides a compound as defined herein, or a pharmaceutically acceptable salt or solvate thereof, or a pharmaceutical composition as defined herein, for use in the treatment of hepatitis C and B.

In another aspect, the present invention provides a compound as defined herein, or a pharmaceutically acceptable salt or solvate thereof, or a pharmaceutical composition as defined herein, for use in the treatment of fibrosis. In particular, the present invention provides a compound as defined herein, or a pharmaceutically acceptable salt or solvate thereof, or a pharmaceutical composition as defined herein, for use in the treatment of including lung (pulmonary), renal, hepatic and skin fibrosis.

Routes of Administration

The compounds of the invention or pharmaceutical compositions comprising these compounds may be administered to a subject by any convenient route of administration, whether systemically/peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The treatment defined herein may be applied as a sole therapy for the treatment of the specified condition or may involve, in addition to the compound of the invention, one or more additional therapies (including treatment with another therapeutic agent, surgery or other therapeutic interventions such as radiotherapy in the oncology setting).

Typically, the other therapeutic agent used in combination with a compound of the present invention will be one or more therapeutic agents used as the standard of care for the treatment of the disease or condition concerned. The other therapeutic agent may include, for example, another drug used for the treatment of the condition concerned, or an agent that modulates the biological response to the compound of the invention, such as, for example, an immuno-modulatory agent.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

Cancer Therapy

The antiproliferative treatment defined hereinbefore may be applied as a sole therapy or may involve, in addition to the compound of the invention, conventional surgery or radiotherapy or chemotherapy. Such chemotherapy may include one or more of the following categories of anti-tumour agents:

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. (Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA$_2$, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a particular embodiment, the antiproliferative treatment defined hereinbefore may involve, in addition to the compound of the invention, conventional surgery or radiotherapy or chemotherapy.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination for use in the treatment of a cancer (for example a cancer involving a solid tumour) comprising a compound of the invention as defined hereinbefore, or a pharmaceutically acceptable salt, hydrate or solvate thereof, and another anti-tumour agent.

According to this aspect of the invention there is provided a combination for use in the treatment of a proliferative condition, such as cancer (for example a cancer involving a solid tumour), comprising a compound of the invention as defined hereinbefore, or a pharmaceutically acceptable salt, hydrate or solvate thereof, and any one of the anti-tumour agents listed herein above.

In a further aspect of the invention there is provided a compound of the invention or a pharmaceutically acceptable salt, hydrate or solvate thereof, for use in the treatment of cancer in combination with another anti-tumour agent, optionally selected from one listed herein above.

According to a further aspect of the invention there is provided a pharmaceutical composition which comprises a compound of the invention, or a pharmaceutically acceptable salt, hydrate or solvate thereof, in combination with an anti-tumour agent (optionally selected from one listed herein above), in association with a pharmaceutically acceptable diluent or carrier.

Inflammation Therapy

In another aspect of the invention, there is provided a combination for use in the treatment of inflammation, comprising a compound of the invention as defined hereinbefore, or a pharmaceutically acceptable salt, hydrate or solvate thereof, and another anti-inflammatory agent and/or analgesic agent.

In a further aspect of the invention there is provided a compound of the invention or a pharmaceutically acceptable salt, hydrate or solvate thereof, for use in the treatment of inflammation in combination with another anti-inflammatory and/or analgesic agent.

According to a further aspect of the invention there is provided a pharmaceutical composition which comprises a compound of the invention, or a pharmaceutically acceptable salt, hydrate or solvate thereof, and another anti-inflammatory and/or analgesic agent, in association with a pharmaceutically acceptable diluent or carrier.

Diabetes Mellitus Therapy

In another embodiment of the invention, there is provided a combination for use in the treatment of diabetes mellitus (for example type II diabetes), comprising a compound of the invention as defined hereinbefore, or a pharmaceutically acceptable salt, hydrate or solvate thereof, and another anti-diabetic agent.

In a further aspect of the invention there is provided a compound of the invention or a pharmaceutically acceptable salt, hydrate or solvate thereof, for use in the treatment of diabetes mellitus in combination with another anti-diabetic agent.

According to a further aspect of the invention there is provided a pharmaceutical composition which comprises a compound of the invention, or a pharmaceutically acceptable salt, hydrate or solvate thereof, and another anti-diabetic agent, in association with a pharmaceutically acceptable diluent or carrier.

Hypertension, Atherosclerosis and/or Thrombosis Therapy

In another embodiment of the invention, there is provided a combination for use in the treatment of hypertension, atherosclerosis and/or thrombosis, comprising a compound of the invention as defined hereinbefore, or a pharmaceutically acceptable salt, hydrate or solvate thereof, and one or more additional medicaments for the treatment of said conditions.

In a further aspect of the invention there is provided a compound of the invention or a pharmaceutically acceptable salt, hydrate or solvate thereof, for use in the treatment of hypertension, atherosclerosis and/or thrombosis in combination with another agent for the treatment of said conditions.

According to a further aspect of the invention there is provided a pharmaceutical composition which comprises a compound of the invention, or a pharmaceutically acceptable salt, hydrate or solvate thereof, and another agent for the treatment of hypertension, atherosclerosis and/or thrombosis, in association with a pharmaceutically acceptable diluent or carrier.

Urethral Obstructive Disease

In another embodiment of the invention, there is provided a combination for use in the treatment of urethral obstructive disease (for example benign prostatic hyperplasia), comprising a compound of the invention as defined hereinbefore, or a pharmaceutically acceptable salt, hydrate or solvate thereof, and another medicament for the treatment of urethral obstructive disease.

In a further aspect of the invention there is provided a compound of the invention or a pharmaceutically acceptable salt, hydrate or solvate thereof, for use in the treatment of urethral obstructive disease (for example benign prostatic hyperplasia), in combination with another agent for the treatment of said condition.

According to a further aspect of the invention there is provided a pharmaceutical composition which comprises a compound of the invention, or a pharmaceutically acceptable salt, hydrate or solvate thereof, and another agent for the treatment of urethral obstructive disease (for example benign prostatic hyperplasia), in association with a pharmaceutically acceptable diluent or carrier.

Pruritus Therapy

In another embodiment of the invention, there is provided a combination for use in the treatment of pruritus, comprising a compound of the invention as defined hereinbefore, or a pharmaceutically acceptable salt, hydrate or solvate thereof, and another antipruritic agent.

In a further aspect of the invention there is provided a compound of the invention or a pharmaceutically acceptable salt, hydrate or solvate thereof, for use in the treatment of pruritus, in combination with another anti-pruritic agent.

According to a further aspect of the invention there is provided a pharmaceutical composition which comprises a compound of the invention, or a pharmaceutically acceptable salt, hydrate or solvate thereof, and another antipruritic agent, in association with a pharmaceutically acceptable diluent or carrier.

Pain Therapy

In another embodiment of the invention, there is provided a combination for use in the treatment of pain (for example neuropathic pain) comprising a compound of the invention as defined hereinbefore, or a pharmaceutically acceptable salt, hydrate or solvate thereof, and another analgesic and/or anti-inflammatory agent.

In a further aspect of the invention there is provided a compound of the invention or a pharmaceutically acceptable salt, hydrate or solvate thereof, for use in the treatment of pain (for example neuropathic pain) in combination with another analgesic and/or anti-inflammatory agent.

According to a further aspect of the invention there is provided a pharmaceutical composition which comprises a compound of the invention, or a pharmaceutically acceptable salt, hydrate or solvate thereof, and another analgesic agent and/or anti-inflammatory, in association with a pharmaceutically acceptable diluent or carrier.

Hepatitis B and/or C

In another embodiment of the invention, there is provided a combination for use in the treatment of hepatitis B and/or C comprising a compound of the invention as defined hereinbefore, or a pharmaceutically acceptable salt, hydrate or solvate thereof, and another anti-hepatitis B and/or C agent.

In a further aspect of the invention there is provided a compound of the invention or a pharmaceutically acceptable salt, hydrate or solvate thereof, for use in the treatment of hepatitis B and/or C in combination with another anti-hepatitis B and/or C agent.

According to a further aspect of the invention there is provided a pharmaceutical composition which comprises a compound of the invention, or a pharmaceutically acceptable salt, hydrate or solvate thereof, and another anti-hepatitis B and/or C agent, in association with a pharmaceutically acceptable diluent or carrier.

Fibrosis

In another embodiment of the invention, there is provided a combination for use in the treatment of fibrosis (for example lung, renal, hepatic and skin fibrosis) comprising a compound of the invention as defined hereinbefore, or a pharmaceutically acceptable salt, hydrate or solvate thereof, and another anti-fibrotic agent.

In a further aspect of the invention there is provided a compound of the invention or a pharmaceutically acceptable salt, hydrate or solvate thereof, for use in the treatment of fibrosis (for example lung, renal, hepatic and skin fibrosis) in combination with another anti-fibrotic agent.

According to a further aspect of the invention there is provided a pharmaceutical composition which comprises a compound of the invention, or a pharmaceutically acceptable salt, hydrate or solvate thereof, and another anti-fibrotic agent, in association with a pharmaceutically acceptable diluent or carrier.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

DESCRIPTION OF DRAWINGS

Embodiments of the invention will be described, by way of example only, with reference to the accompanying drawings, in which.

EXAMPLES

General Experimental

Figure 1:
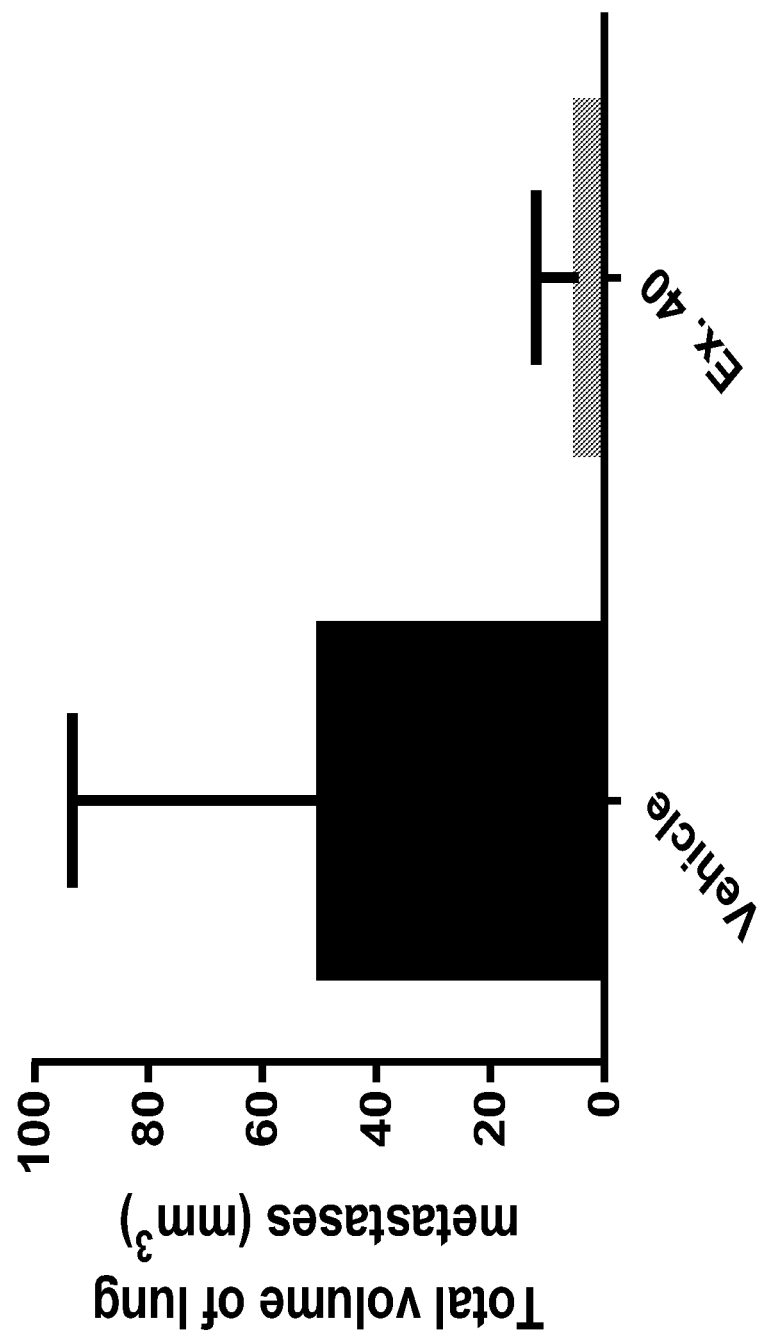
FIG. 1 shows the total volume of lung metastases achieved through administration of Example 40 compared to the administration of the vehicle, using the 4T1 orthotopic metastatic breast cancer model, described hereinbelow.

Analytical Methods
NMR
Method 1:
Proton NMR spectra are recorded using an Oxford Instruments AS400 9.4 Tesla 400 MHz magnet with either a 5 mm BBO or PH SEF 400SB F-H-D-05 probe and an AVANCE/DPX400 console machine at 400 MHz.
Method 2:
Proton NMR spectra are recorded using a 300 MHz Bruker spectrometer.
For both methods, NMR solutions were typically prepared in either deuterated CDCl$_3$ or deuterated DMSO. Shifts are reported in ppm values relative to an internal standard of tetramethylsilane (TMS) or residual protic solvent. The following abbreviations are used to describe the splitting patterns: s (singlet), d (doublet), t (triplet), q (quartet), m (multiplet), dd (doublet-doublet), dt (doublet-triplet), br (broad signal). Deuterated solvents were obtained from the Sigma-Aldrich Chemical Company, Goss or Fluorochem.
LCMS
Method 1 employed Waters 2545 pumps, a Waters SFO mixer and a Waters 2998 UV detector (single wavelength 254 nM). The mass spectrometer was an Acquity SQ which detected masses between 100 and 700 g/mol. A Waters SunFire, 5 micron pore size, C18 of dimensions 50×4.60 mm was used. The injection volume was 10 µl. The mobile phase consisted of a mixture of water and acetonitrile containing 0.1% formic acid. The eluent flow rate was 1.5 ml/min, using 95% water:5% acetonitrile, changed linearly to 5% water:95% acetonitrile over 5.0 minutes and then maintained at this mixture for 0.50 minutes before the eluent level was returned to the starting conditions of 95% water:5% acetonitrile over 6 seconds. These conditions were held for 1.4 minutes to allow equilibration of the column before the next sample was injected. The run lasted 7 minutes in total.

Method 2 employed Waters 2545 pumps, a Waters SFO mixer and a Waters 2998 UV detector (single wavelength 254 nM). The mass spectrometer was an Acquity SQ which detected masses between 100 and 700 g/mol. The detection was done at 254 nm and an array between 210-600 nm. A Waters SunFire, 5 micron pore size, C18 of dimensions 50×4.60 mm was used. The injection volume was 10 µl. The mobile phase consisted of a mixture of water and acetonitrile containing 0.1% formic acid. The eluent flow rate was 1.5 ml/min, using 95% water:5% acetonitrile, changed linearly to 5% water:95% acetonitrile over 10 min and then maintained at this mixture for 0.50 min before the eluent level was returned to the starting conditions of 95% water:5% acetonitrile over 6 seconds. These conditions were held for 1.4 minutes to allow equilibration of the column before the next sample was injected. The run lasted 12 minutes in total.

Method 3 employed Waters 2545 pumps, a Waters SFO mixer and a Waters 2998 UV detector (single wavelength 254 nM). The mass spectrometer was a Waters 3100 which detected masses between 100 and 700 g/mol. The detection was done at 254 nm and an array between 210-600 nm. A SunFire, 5 micron pore size, C18 column of dimensions 50×4.60 mm was used. The injection volume was 10 µl. The mobile phase consisted of a mixture of water and acetonitrile containing 0.1% formic acid. The eluent flow rate was 1.5 ml/min, using 95% water:5% acetonitrile, changed linearly to 5% water:95% acetonitrile over 5.0 min and then maintained at this mixture for 0.50 min before the eluent level was returned to the starting conditions of 95% water:5% acetonitrile over 6 seconds. These conditions were held for 1.4 minutes to allow equilibration of the column before the next sample was injected. The run lasted 7 minutes in total.

Method 4 employed a Waters Acquity UPLC system fitted with a UV diode array detection and a Waters SQD detector. The detection was done at an array between 210-400 nm. A BEH C18 1.7 µM column of dimensions 2.1×50 mm was used. The mobile phase consisted of a mixture of water and 10 mM NH$_4$HCO$_3$ with 0.1% ammonia solution (solvent A) and acetonitrile with 0.1% ammonia solution (solvent B). The eluent flow rate was 0.6 ml/min, using 95% solvent A:5% solvent B, changed linearly to 5% solvent A:95% solvent B over 1.2 min and then maintained at this mixture for 0.5 min.

Method 5 employed Waters 2545 pumps, a Waters SFO mixer with valves directing to the different columns and a Waters 2998 UV detector. The detection was done at 254 nm and an array between 210-600 nm. The mass spectrometer used was a Waters 3100 which detected masses between 100 and 700 g/mol. A SunFire, 5 micron pore size, C18 column of dimensions 50×19 mm was used. The injection volume was chosen by the user and could be up to 500 µl of solution (maximum 50 mg/ml). The mobile phase consisted of a mixture of water and acetonitrile containing 0.1% formic acid. The flow rate was 25 mL/min with elution starting at 95% water:5% acetonitrile and held at this for 0.3 min, changed linearly to 5% water:95% acetonitrile over 5 min. This is then held until 5.8 min. There are 2 purification columns so the second one was equilibrated at 5% water:

95% acetonitrile during the previous run so the next injection could be performed straight away.

Method 6 employed Waters 2545 pumps, a Waters SFO mixer with valves directing to the different columns and a Waters 2998 UV detector. The detection was done at 254 nm and an array between 210-600 nm. The mass spectrometer used was a Waters 3100 which detected masses between 100 and 700 g/mol. A SunFire, 5 micron pore size, C18 column of dimensions 50×19 mm was used. The injection volume was chosen by the user and can be up to 500 µl of solution (maximum 50 mg/mL). The mobile phase consisted of a mixture of water and acetonitrile containing 0.1% formic acid. The eluent flow rate was 25 ml/min with elution starting at 95% water:5% acetonitrile and held at this for 1.5 min, changed linearly to 5% water:95% acetonitrile over 10 min and then held until 12 min. There are 2 purification columns so the second one was equilibrated at 5% water:95% acetonitrile during the previous run so the next injection could be performed straight away.

Method 7 employed Waters 2545 pumps, a Waters SFO mixer with valves directing to the different columns, and a Waters 2998 UV detector. The detection was done at 254 nm and an array between 210-600 nm. The mass spectrometer was a Waters 3100 which detected masses between 100 and 700 g/mol. A SunFire, 5 micron pore size, C18 column of dimensions 30×100 mm was used. The injection volume was chosen by the user and can be up to 2.5 ml of the solution (max 50 mg/ml). The mobile phase consisted of a mixture of water and acetonitrile containing 0.1% formic acid. The eluent flow rate was 30 ml/min, with elution starting at 95% water:5% acetonitrile and held at this for 2 min, changed linearly to 5% water:95% acetonitrile over 13 min and then held for 5 min. This returns to 95% water:5% acetonitrile over 12 seconds then held until 24 min.

Method 8 employed a Waters Fraction Lynx MS autopurification system with UV diode array detection at an array between 210-400 nm and mass-directed collection using both positive and negative mass ion detection. A Waters XBridge 5 micron C18, 100 mm×19 mm column was used. Purifications were performed using buffered acidic or basic solvent systems as appropriate. The mobile phase consisted of a mixture of water and 10 mM $NH_4HCO_3$ with 0.1% ammonia solution (solvent A) and acetonitrile with 5% water and 0.1% formic acid (solvent B). The eluent flow rate was 20 ml/min, with elution starting at 90% solvent A:10% solvent B, changed linearly to 2% solvent A:98% solvent B over 8.5 min and then maintained at this mixture for 3.5 min.

LIST OF ABBREVIATIONS

SM starting material
UV ultraviolet
Pd/C palladium on carbon
$H_2SO_4$ sulphuric acid
EtOH ethanol
K$^t$OBu potassium tert-butoxide
$Cs_2CO_3$ caesium carbonate
EtOAc ethyl acetate
$N_2$ nitrogen
$NaHCO_3$ sodium hydrogen carbonate
$Et_2O$ diethyl ether
$MgSO_4$ magnesium sulphate
DCM dichloromethane
HOAc acetic acid
HBTU O-benzotriazol-1-yl)-N,N,N,N-tetramethyluronium hexafluorophosphate
$Et_3N$ triethylamine
MTBE methyl tert-butyl ether
DMF dimethylformamide
CDI 1,1'-carbonyldiimidazole
Fe iron
EDTA ethylenediaminetetraacetic acid
NaOH sodium hydroxide
IPA isopropanol
$H_2$ hydrogen
r.t. room temperature
SCX propylsulfonic acid bonded sorbent
µl microliters
ml milliliters
HPLC high performance liquid chromatography
NMP N-methyl pyrrolidine
LiOH lithium hydroxide
LiOHx$H_2$O lithium hydroxide monohydrate
DMSO dimethyl sulfoxide
CuI copper (I) iodide
TBAI tetrabutylammonium iodide
$CS_2$ carbon disulfide
$K_2CO_3$ potassium carbonate
TFA trifluoroacetic acid
$KMnO_4$ potassium permanganate
NaH sodium hydride
THF tetrahydrofuran
$POCl_3$ phosphorus oxychloride
$PCl_5$ phosphorus pentachloride
1H-NMR proton nuclear magnetic resonance
ppm parts per million
MHz megahertz
RT retention time
conc. concentrated
MW microwave
$CHCl_3$ chloroform
$Pd(PPh_3)_2Cl_2$ bis(triphenylphosphine)palladium (II) dichloride
$Na_2CO_3$ sodium carbonate
MeI methyl iodide
DABAL-Me$_3$ bis(trimethylaluminium)-1,4-diazabicyclo[2.2.2]octane adduct
$NH_4HCO_3$ ammonium hydrogen carbonate
$PPh_3$ triphenylphosphine
DIAD diisopropyl azodicarboxylate
AcN acetonitrile
$Pd(OH)_2$/C Pearlman's catalyst
$NH_4Cl$ ammonium chloride
° C. degrees Celsius
HCl hydrochloric acid
Na$^t$OBu sodium tert-butoxide
X-Phos 2-dicyclohexylphosphino-2',4',6'-triisopropylbiphenyl
$Pd_2dba_3$ palladium (0) bis (dibenzylideneacetone)
min minutes
nm nanometers
µm micrometers
mm millimeters
mmol millimol
$LiAlH_4$ lithium aluminium hydride
$K_3PO_4$ potassium phosphate
t-BuOH tert-buthanol
$Pd(OAc)_2$ palladium acetate
$PPh_3$ triphenylphosphine
X-Phos 2-dicyclohexylphosphino-2',4',6'-triisopropylbiphenyl
M molar
g gram
mg milligram FBS foetal bovine serum
PBS phosphate buffered saline
RPMI Roswell Park Memorial Institute General Synthesis of 3-(3-aralkyl-3H-imidazo[4,5-b]pyridin-2-M-propionamide of General Formula F-5 (Scheme 001)

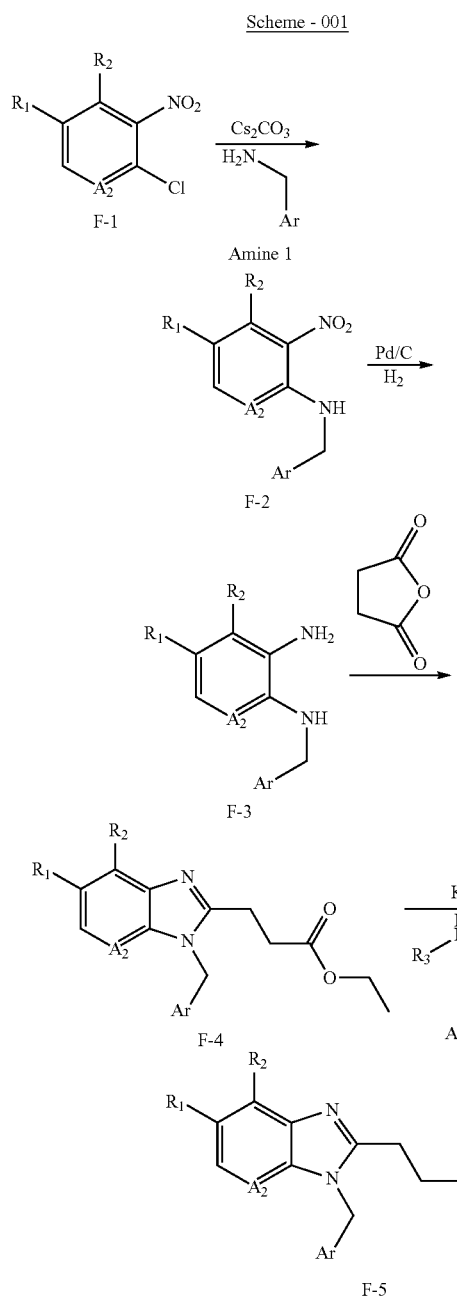

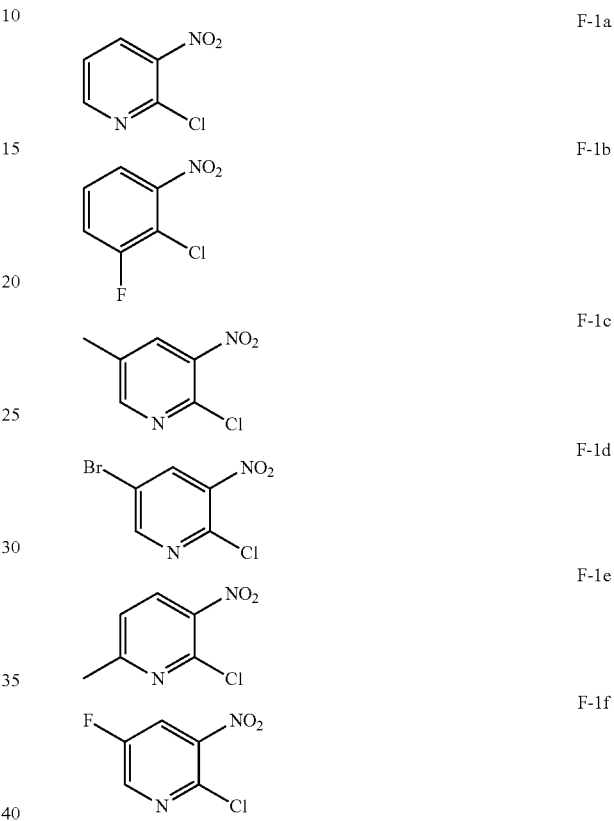

The above synthesis (Scheme 001) is illustrated by the preparation of 3-(3-benzyl-3H-imidazo[4,5-b]pyridin-2-yl)-N—((S)-1-phenyl-ethyl)-propionamide (Ex. 1) described below.

Synthesis of benzyl-(3-nitro-pyridin-2-yl)-amine

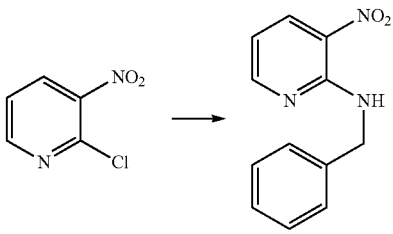 [SMILES: O=[N+]([O-])c1cccnc1Cl ; O=[N+]([O-])c1cccnc1NCc1ccccc1]

reduction with iron in HCl. Intermediate F-3 was reacted with succinic anhydride in dioxane at reflux, and then treated with $H_2SO_4$ and EtOH under reflux. The obtained ester, of general formula F-4, was treated with K$^t$OBu and the required Amine 2 in the MW at 150° C. to afford the final compounds of general formula F-5.

F-1 could be any of the following intermediates:

Commercially available 2-chloro-3-nitro-pyridine of general formula F-1 was reacted with $Cs_2CO_3$ and the required Amine 1 in methanol at reflux to yield the aralkyl-(3-nitro-pyridin-2-yl)-amine derivatives of general formula F-2, which was hydrogenated over Pd/C in EtOH to afford N'2'-aralkyl-pyridine-2,3-diamine of general formula F-3. This diamine could alternatively be obtained through a In a round bottom flask fitted with magnetic stirrer and reflux condenser, a solution of 2-chloro-3-nitropyridine (580 mg, 3.70 mmol) in dioxane (10 ml) was treated with $Cs_2CO_3$ (2.41 g, 7.40 mmol) and 4-fluorobenzylamine (850 µl, 7.40 mmol) and heated to 80° C. for 2 hours. The mixture was allowed to cool down to r.t., filtered and washed with EtOAc. The filtrate was purified by column chromatography with a gradient of EtOAc and cyclohexane, product eluted with 10% EtOAc. Product fractions were combined and evaporated to provide the title compound (913 mg, 100%).

LCMS Method: 3, RT: 4.45 min, MI: 248 [M+1]

$^1$H-NMR, Method 1: (CDCl$_3$) 8.50 (br 1H), 8.45 (dd 1H), 8.43 (s 1H), 7.37-7.32 (m 2H), 7.03 (tt 2H), 6.71-6.68 (m 1H), 4.83 (d 2H).

Synthesis of N'2'-benzyl-pyridine-2,3-diamine

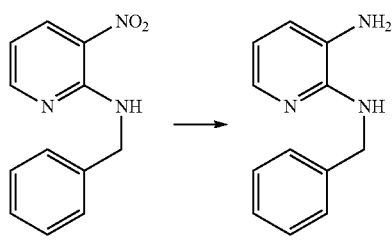 [SMILES: O=[N+]([O-])c1cccnc1NCc1ccccc1 ; Nc1cccnc1NCc1ccccc1]

To a round bottom flask fitted with magnetic stirrer and containing benzyl-(3-nitro-pyridin-2-yl)-amine (912 mg, 3.69 mmol) and 10% Pd/C (90 mg) was added MeOH (10 ml), whilst stirring under N$_2$. Mixture was purged with more N$_2$ and a double balloon filled with H$_2$ was fitted onto the flask. Suspension was allowed to stir at r.t. for 90 min under an atmosphere of H$_2$ and subsequently filtered through Celite®. The filtrate was evaporated under reduced pressure to provide the title compound (800 mg, 100%).

LCMS Method: 3, RT: 1.71 min, MI: 218 [M+1]

$^1$H-NMR, Method 1: (DMSO) 7.42-7.38 (m 2H), 7.31 (dd 1H), 7.15 (t 2H), 6.93 (br 1H), 6.83 (d 1H), 6.50 (dd 1H), 5.22 (br 2H), 4.59 (d 2H).

Synthesis of N'2'-(4-fluoro-benzyl)-pyridine-2,3-diamine (Example of alternative reduction method)

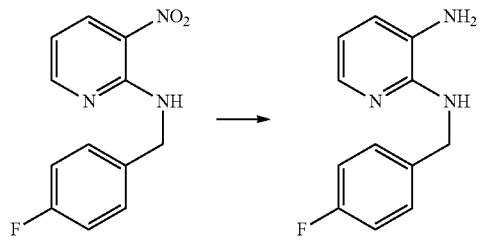 [SMILES: O=[N+]([O-])c1cccnc1NCc1ccc(F)cc1 ; Nc1cccnc1NCc1ccc(F)cc1]

In a round bottom flask fitted with magnetic stirrer and reflux condenser, HCl conc. (45 ml) was added to a stirred solution of (4-fluoro-benzyl)-(3-nitro-pyridin-2-yl)-amine (3.15 g, 12.73 mmol) and Fe powder (2.85 g, 50.95 mmol) in EtOH (135 ml). The reaction was stirred at 40° C. for 1 h, and then allowed to cool down overnight. Reaction crude was basified to pH 8 with NaHCO$_3$ aqueous solution and then extracted into DCM (2×450 ml). The organic phases were combined, filtered through a silicone treated filter paper and concentrated under reduced pressure to afford the title compound (2.67 g, 96%).

Synthesis of 3-(3-benzyl-3H-imidazo[4,5-b]pyridin-2-yl)-propionic acid ethyl ester

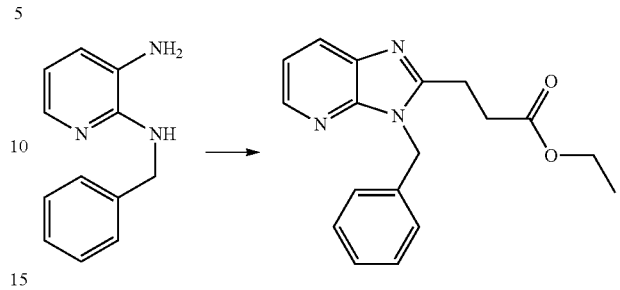

In a round bottom flask fitted with magnetic stirrer and reflux condenser, to a stirred solution of N'2'-benzyl-pyridine-2,3-diamine (9.7 g, 48.6 mmol) in dioxane was added succinic anhydride (5.84 g, 58.3 mmol) and the reaction mixture was heated to 80° C. for 16 hours with stirring under N$_2$. The dioxane was removed under reduced pressure and the resulting crude treated with EtOH (100 ml). To this mixture was added conc. H$_2$SO$_4$ (3 ml) cautiously with stirring. After addition, the mixture was heated at reflux under N$_2$ for 20 hours. The mixture was cooled to r.t. and poured into saturated NaHCO$_3$ aqueous solution and extracted (×3) with Et$_2$O. Organic phases were washed with brine and dried over anhydrous MgSO$_4$. The solvent was removed under reduced pressure and the crude material (16.35 g) was purified by column chromatography with a gradient of DCM and Et$_2$O to give the title compound (1.98 g, 13%).

LCMS Method: 4, RT: 1.09 min, MI: 310 [M+1]

$^1$H-NMR, Method 2: (DMSO) 8.30 (d 1H), 8.01 (d 1H), 7.36-7.18 (m 6H), 5.54 (s 2H), 4.03 (q 2H), 3.09 (t 2H), 2.87 (t 2H), 1.14 (t 3H)

Synthesis of 3-(3-benzyl-3H-imidazo[4,5-b]pyridin-2-yl)-N—((S)-1-phenyl-ethyl)-propionamide (Ex. 1)

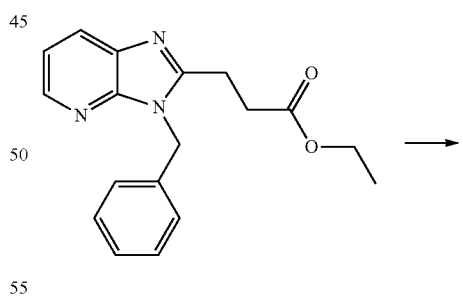

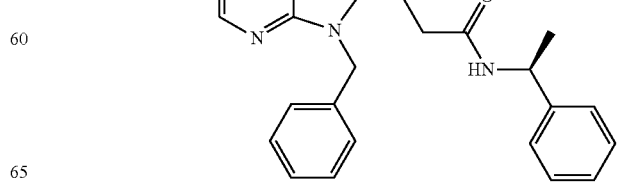

To a 10 ml MW vial fitted with a magnetic stirrer was added 3-(3-benzyl-3H-imidazo [4,5-b]pyridin-2-yl)-propionic acid ethyl ester (154 mg, 0.5 mmol), (S)-1-phenylethylamine (121 mg, 1 mmol) and K'OBu (56 mg, 0.5 mmol). The reaction mixture was heated at 150° C. for 45 min in the MW. Reaction crude was treated with HOAc (8 drops) and MeOH (1 ml) and purified by reverse phase mass-directed preparative HPLC using Method 8 to afford the title compound (3 mg, 2%).

The following compounds of general formula F-5 were prepared according to the general synthesis shown in Scheme 001:

| Example | SM | Amine 1 | Amine 2 | | Characterisation |
|---|---|---|---|---|---|
| 1 | F-1a | benzylamine | (S)-1-phenylethylamine | LCMS Method: 4, RT: 1.10 min, MI: 385 [M + 1] | $^1$H NMR, Method 2: (DMSO) 8.49-8.40 (m 1H), 8.32-8.29 (m 1H), 8.02-7.99 (m 1H), 7.34-7.15 (m 9H), 5.50 (s 2H), 4.91-4.86 (m 1H), 3.09-2.98 (m 2H), 2.79-2.67 (m 2H), 1.32 (d 3H) |
| 3 | F-1a | benzylamine | 2-thiophenemethylamine | LCMS Method: 4, RT: 1.04 min, MI: 377 [M + 1] | $^1$H-NMR, Method 2: (DMSO) 8.63-8.59 (m 1H), 8.32-8.29 (m 1H), 7.99 (d 1H), 7.43-7.17 (m 7H), 6.95-6.90 (m 2H), 5.54 (s 2H), 4.41 (d 2H), 3.07 (t 2H), 2.72 (t 2H) |
| 4 | F-1a | benzylamine | (R)-1-phenylethylamine | LCMS Method: 4, RT: 1.10 min, MI: 386 [M + 1] | $^1$H-NMR, Method 2: (DMSO) 8.49-8.40 (m 1H), 8.32-8.29 (m 1H), 8.02-7.99 (m 1H), 7.34-7.15 (m 9H), 5.50 (s 2H), 4.91-4.86 (m 1H), 3.09-2.98 (m 2H), 2.79-2.67 (m 2H), 1.32 (d 3H) |
| 5 | F-1a | benzylamine | 2-methylbenzylamine | LCMS Method: 4, RT: 1.10 min, MI: 386 [M + 1] | $^1$H-NMR, Method 2: (DMSO) 8.38-8.29 (m 2H), 8.02-7.98 (m 1H), 7.36-7.01 (m 10H), 5.53 (s 2H), 4.22 (d 2H), 3.09 (t 2H), 2.76 (t 2H), 2.21 (s 3H) |
| 6 | F-1a | 3-(trifluoromethoxy)benzylamine | 3-(trifluoromethoxy)benzylamine | LCMS Method: 4, RT: 1.26 min, MI: 540 [M + 1] | $^1$H-NMR, Method 2: (DMSO) 8.60 (t 1H), 8.31 (dd 1H), 8.00 (dd 1H), 7.33 (m 9H), 5.60 (s 2H), 4.32 (d 2H), 3.12 (t 2H), 2.80 (t 2H) |

General Synthesis of 3-(3-aralkyl-3H-imidazo[4,5-b]pyridin-2-yl)-propionamide of general formula F-5 (Scheme 002-A)

F-1 could be any of the following intermediates:

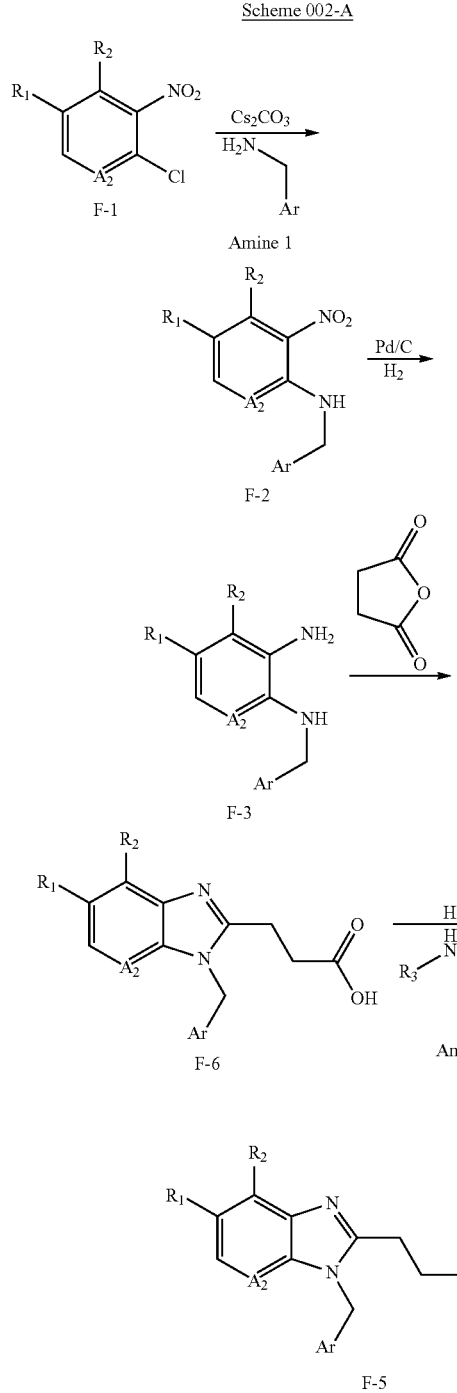

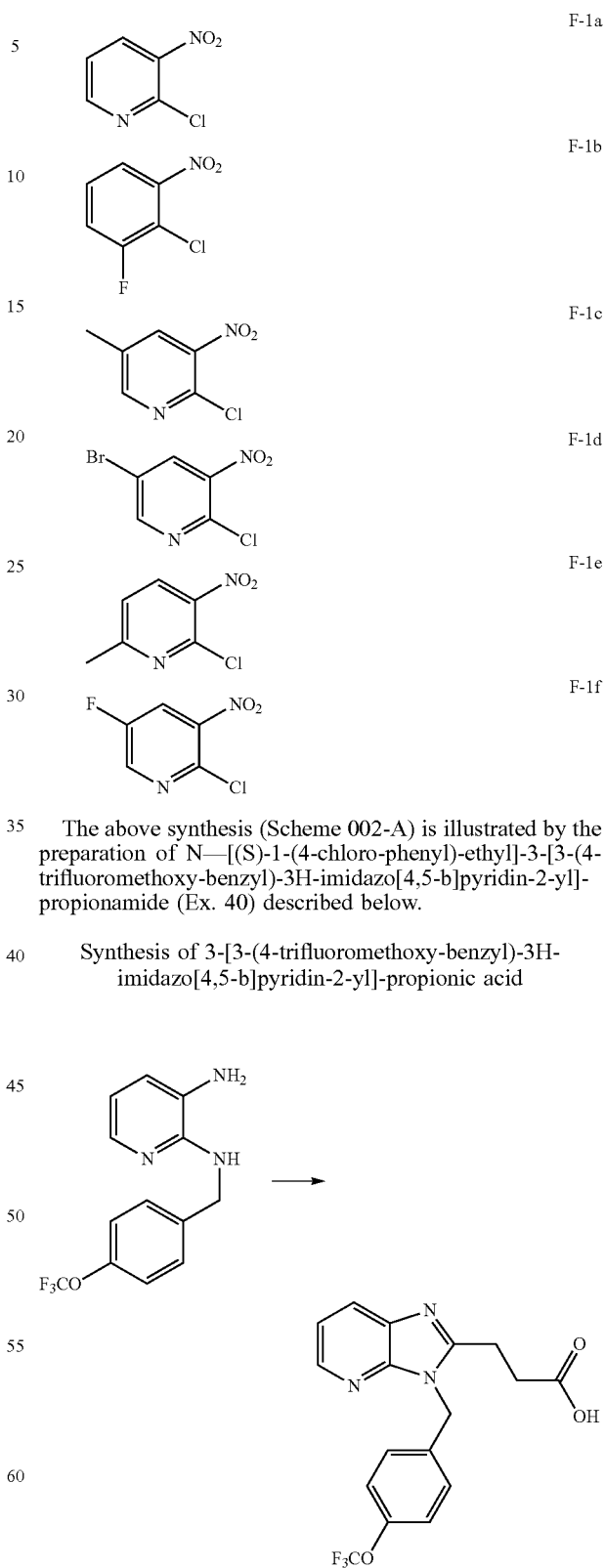

The above synthesis (Scheme 002-A) is illustrated by the preparation of N—[(S)-1-(4-chloro-phenyl)-ethyl]-3-[3-(4-trifluoromethoxy-benzyl)-3H-imidazo[4,5-b]pyridin-2-yl]-propionamide (Ex. 40) described below.

Synthesis of 3-[3-(4-trifluoromethoxy-benzyl)-3H-imidazo[4,5-b]pyridin-2-yl]-propionic acid Intermediates F-2 and F-3 were prepared as in Scheme 001. Intermediate F-3 was reacted with succinic anhydride in dioxane at reflux, and then treated with HOAc. The obtained carboxylic acid, of general formula F-6, was treated with HBTU, Et₃N and the required amine 2 at r.t. to afford the final compounds of general formula F-5.

In a round bottom flask fitted with a magnetic stirrer and reflux condenser, a solution of N'2'-(4-trifluoromethoxy-benzyl)-pyridine-2,3-diamine (2.5 g, 8.83 mmol) in dioxane (50 ml) was treated with succinic anhydride (880 mg, 8.83 mmol) and heated at 80° C. for 5 hours under $N_2$. The reaction mixture was then treated with HOAc (25 ml) and heated to reflux overnight. Reaction crude was allowed to cool down, then solvent was evaporated under reduced pressure and azeotroped from toluene and $CHCl_3$ to give a dark solid. This solid was stirred in $Et_2O$ (100 ml) for 2 hours and filtered. The solid was washed with $Et_2O$ (50 ml) and dried to afford the title compound (1.89 g, 59%).

LCMS Method: 1, RT: 3.79 min, MI: 366 [M+1]

Synthesis of N—[(S)-1-(4-chloro-phenyl)-ethyl]-3-[3-(4-trifluoromethoxy-benzyl)-3H-imidazo[4,5-b]pyridin-2-yl]-propionamide (Ex. 40)

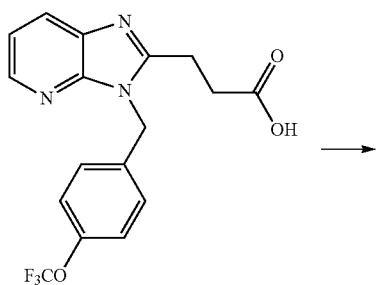

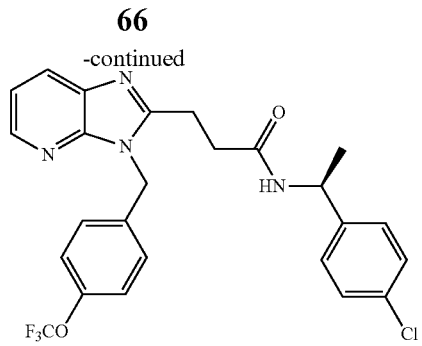

In a round bottom flask fitted with a magnetic stirrer, 3-[3-(4-trifluoromethoxy-benzyl)-3H-imidazo[4,5-b]pyridin-2-yl]-propionic acid (73 mg, 0.2 mmol), $Et_3N$ (70 µl, 0.5 mmol) and (S)-1-(4-chlorophenyl)ethylamine (31 mg, 0.20 mmol) were dissolved in DMF (2 ml). Finally, HBTU (83 mg, 0.22 mmol) was added in. Reaction mixture was allowed to stir at r.t. for 1 hour, then diluted with EtOAc, washed with water and brine, dried and evaporated under reduced pressure. The crude product was purified by reverse phase mass-directed preparative HPLC using either LCMS Method 5 or 6. Required product fractions were concentrated in the Genevac™ to afford the title compound (79 mg, 79%).

The following compounds of general formula F-5 were prepared according to the general synthesis shown in Scheme 002-A:

| Example | SM | Amine 1 | Amine 2 | Characterisation | |
|---|---|---|---|---|---|
| 7 | F-1a | 4-F3CO-benzyl-NH2 | HO-CH(Ph)-CH2-NH2 | LCMS Method: 1, RT: 4.02 min, MI: 485 [M + 1] | ¹H-NMR, Method 1: (DMSO) 8.38 (d 1H), 8.31 (dd 1H), 8.01 (dd 1H), 7.31-7.17 (m 10H), 5.54 (s 2H), 4.87-4.81 (m 2H), 3.59-3.50 (m 2H), 3.13-3.00 (m 2H), 2.86-2.73 (m 2H) |
| 8 | F-1a | 4-F3CO-benzyl-NH2 | (1S,2R)-1-amino-2-hydroxyindane | LCMS Method: 1, RT: 4.30 min, MI: 497 [M + 1] | ¹H-NMR, Method 1: (CDCl₃) 8.36 (dd 1H), 8.00 (dd 1H), 7.31-7.16 (m 9H), 6.47 (d 1H), 5.57 (d 1H), 5.44 (d 1H), 5.39-5.36 (m 1H), 4.73 (td 1H), 3.48-3.40 (m 1H), 3.15 (dd 1H), 3.05-2.97 (m 2H), 2.82-2.79 (m 2H) |
| 9 | F-1a | 4-F3CO-benzyl-NH2 | (1S,2S)-1-amino-2-hydroxyindane | LCMS Method: 1, RT: 4.17 min, MI: 497 [M + 1] | ¹H-NMR, Method 1: (DMSO) 8.34-8.31 (m 2H), 8.01 (dd 1H), 7.38-7.33 (m 4H), 7.30 (dd 1H), 7.18-7.15 (m 2H), 7.11-7.03 (m 2H), 5.61 (s 2H), 5.28 (d 1H), 5.02 (t 1H), 4.22-4.16 (m 1H), 3.22-3.06 (m 3H), 2.87-2.65 (m 3H) |
| 10 | F-1a | 4-F3CO-benzyl-NH2 | 4-(3-dimethylaminopropoxy)benzylamine | LCMS Method: 1, RT: 2.79 min, MI: 556 [M + 1] | ¹H-NMR, Method 1: (DMSO) 8.44 (t 1H), 8.31 (dd 1H), 8.02 (dd 1H), 7.33 (br 4H), 7.28 (dd 1H), 7.12 (dt 2H), 6.79 (dt 2H), 5.57 (s 2H), 4.20 (d 2H), 3.94 (t2 H), 3.10 (t 2H), 2.77 (t 2H), 2.44 (t 2H), 2.21 (s 6H), 1.88-1.82 (m 2H) |

-continued

| Example | SM | Amine 1 | Amine 2 | Characterisation | |
|---|---|---|---|---|---|
| 11 | F-1a | 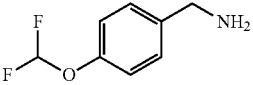 | 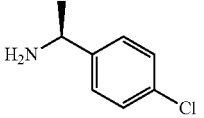 | LCMS Method: 1, RT: 4.50 min, MI: 418 [M + 1] | ¹H-NMR, Method 1: (DMSO) 8.46 (d 1H), 8.30 (dd 1H), 8.01 (dd 1H), 7.30-7.24 (m 7H), 7.18 (t 1H), 7.12-7.10 (m 2H), 5.49 (s 2H), 4.92-4.83 (m 1H), 3.12-2.98 (m 2H), 2.82-2.67 (m 2H), 1.31 (d 3H) |
| 12 | F-1a | 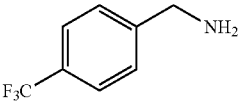 | 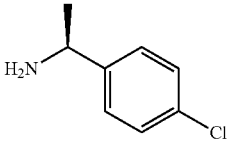 | LCMS Method: 1, RT: 4.81 min, MI: 487 [M + 1] | ¹H-NMR, Method 1: (DMSO) 8.46 (d 1H), 8.31 (dd 1H), 8.04 (dd 1H), 7.68 (d 2H), 7.36 (d 2H), 7.31-7.24 (m 5H), 5.61 (s 2H), 4.90-4.82 (m 1H), 3.11-2.97 (m 2H), 2.83-2.67 (m 2H), 1.31 (d 3H) |
| 13 | F-1a | 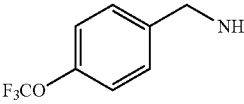 | 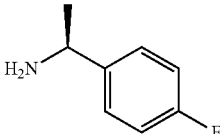 | LCMS Method: 1, RT: 4.64 min, MI: 487 [M + 1] | ¹H-NMR, Method 1: (DMSO) 8.44 (d 1H), 8.31 (dd 1H), 8.03 (dd 1H), 7.31 (br 4H), 7.31-7.27 (m 3H), 7.04 (tt 2H), 5.54 (s 2H), 4.89 (m 1H), 3.13-3.00 (m 2H), 2.82-2.68 (m 2H), 1.32 (d 3H) |
| 14 | F-1a | 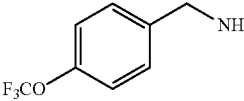 | 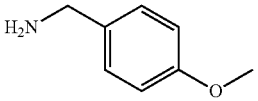 | LCMS Method: 1, RT: 4.42 min, MI: 485 [M + 1] | ¹H-NMR, Method 1: (CDCl₃) 8.38 (dd 1H), 7.93 (dd 1H), 7.25-7.23 (m 3H), 7.15-7.13 (m 2H), 7.06 (dt 2H), 6.73 (dt 2H), 6.46 (t 1H), 5.54 (s 2H), 4.31 (d 2H), 3.76 (s 3H), 3.15 (t 2H), 2.86 (t 2H) |
| 15 | F-1a | 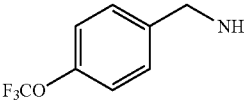 | 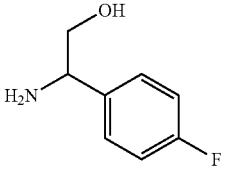 | LCMS Method: 1, RT: 4.10 min, MI: 503 [M + 1] | ¹H-NMR, Method 1: (DMSO) 8.38 (d 1H), 8.30 (dd 1H), 8.01 (dd 1H), 7.32-7.26 (m 7H), 7.05 (tt 2H), 5.53 (s 2H), 4.86 (t 1H), 4.82 (q 1H), 3.52 (t 2H), 3.12-2.99 (m 2H), 2.84-2.71 (m 2H) |
| 16 | F-1a | 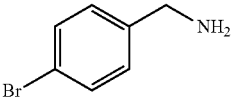 | 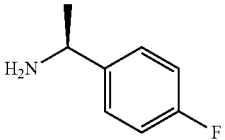 | LCMS Method: 1, RT: 4.51 min, MI: 481/483 [M + 1] | ¹H-NMR, Method 1: (DMSO) 8.43 (d 1H), 8.32 (dd 1H), 8.03 (dd 1H), 7.51 (dt 2H), 7.31-7.28 (m 3H), 7.14 (dt 2H), 7.04 (tt 2H), 5.49 (s 2H), 4.92-4.85 (m 1H), 3.11-2.98 (m 2H), 2.80-2.67 (m 2H), 1.32 (d 3H) |
| 17 | F-1a | 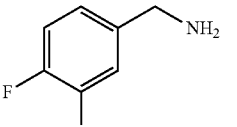 | 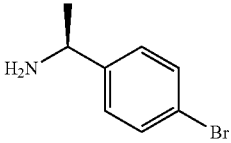 | LCMS Method: 1, RT: 4.58 min, MI: 499/501 [M + 1] | ¹H-NMR, Method 1: (DMSO) 8.45 (d 1H), 8.30 (dd 1H), 8.02 (dd 1H), 7.40-7.27 (m 5H), 7.24-7.20 (m 2H), 7.01-6.98 (m 1H), 5.48 (s 2H), 4.87-4.81 (m 1H), 3.12-2.98 (m 2H), 2.82-2.67 (m 2H), 1.30 (d 3H) |
| 18 | F-1a | 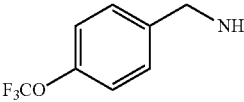 | 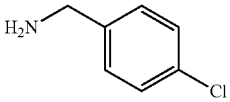 | LCMS Method: 1, RT: 4.77 min, MI: 489/491 [M + 1] | ¹H-NMR, Method 1: (CDCl₃) 8.40 (dd 1H), 7.91 (dd 1H), 7.28-7.23 (m 3H), 7.15-7.12 (m 4H), 7.06-7.04 (m 2H), 6.78 (t 1H), 5.53 (s 2H), 4.34 (d 2H), 3.15 (t 2H), 2.87 (t 2H) |

| Example | SM | Amine 1 | Amine 2 | | Characterisation |
|---|---|---|---|---|---|
| 19 | F-1a | 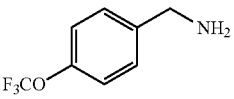 | 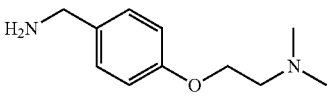 | LCMS Method: 1, RT: 2.71 min, MI: 542 [M + 1] | ¹H-NMR, Method 1: (DMSO) 8.43 (t 1H), 8.31 (dd 1H), 8.02 (dd 1H), 7.33 (br 4H), 7.28 (dd 1H), 7.12 (d 2H), 6.80 (d 2H), 5.57 (s 2H), 4.19 (d 2H), 4.00 (t 2H), 3.10 (t 2H), 2.76 (t 2H), 2.62 (t 2H), 2.22 (s 6H) |
| 20 | F-1a | 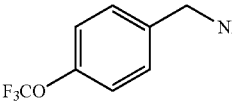 | 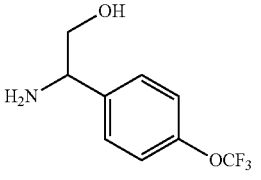 | LCMS Method: 1, RT: 4.56 min, MI: 569 [M + 1] | ¹H-NMR, Method 1: (DMSO) 8.47 (d 1H), 8.31 (dd 1H), 8.02 (dd 1H), 7.41 (d 2H), 7.30 (s 4H), 7.28 (dd 1H), 7.21 (d 2H), 5.54 (s 2H), 4.94 (br 1H), 4.87 (q 1H), 3.58 (d 2H), 3.15-3.01 (m 2H), 2.89-2.74 (m 2H) |
| 21 | F-1a | 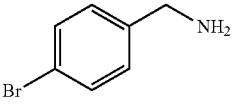 | 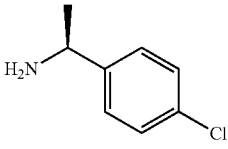 | LCMS Method: 1, RT: 4.76 min, MI: 497/499 [M + 1] | ¹H-NMR, Method 1: (DMSO) 8.47 (d 1H), 8.34 (dd 1H), 8.05 (dd 1H), 7.51 (dt 2H), 7.32 (dd 1H), 7.28 (s 4H), 7.15 (dt 2H), 5.50 (s 2H), 4.90-4.83 (m 1H), 3.13-3.00 (m 2H), 2.81-2.68 (m 2H), 1.31 (d 3H) |
| 22 | F-1a | 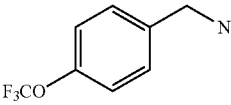 | 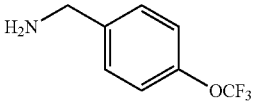 | LCMS Method: 1, RT: 4.95 min, MI: 539 [M + 1] | ¹H-NMR, Method 1: (DMSO) 8.56 (t 1H), 8.31 (dd 1H), 8.03 (dd 1H), 7.37-7.31 (m 6H), 7.29 (dd 1H), 7.23-7.21 (m 2H), 5.57 (s 2H), 4.29 (d 2H), 3.11 (t 2H), 2.78 (t 2H) |
| 23 | F-1a | 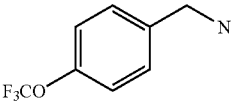 | 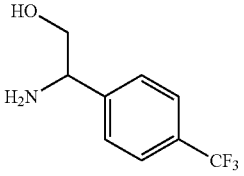 | LCMS Method: 1, RT: 4.49 min, MI: 553 [M + 1] | ¹H-NMR, Method 1: (CDCl₃) 8.37 (dd 1H), 7.62 (dd 1H), 7.40-7.30 (m 5H), 7.21-7.10 (m 5H), 5.49 (d 1H), 5.41 (d 1H), 5.12-5.07 (m 1H), 3.94 (ddd 2H), 3.14 (t 2H), 3.00-2.93 (m 1H), 2.84-2.77 (m 1 H) |
| 24 | F-1a | 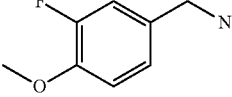 | 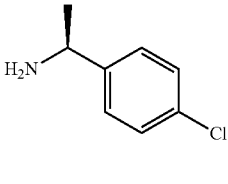 | LCMS Method: 1, RT: 4.34 min, MI: 467 [M + 1] | ¹H-NMR, Method 1: (DMSO) 8.46 (d 1H), 8.32 (dd 1H), 8.01 (dd 1H), 7.31-7.26 (m 5H), 7.13-7.07 (m 2H), 6.96 (d 1H), 5.42 (s 2H), 4.91-4.83 (m 1H), 3.78 (s 3H), 3.13-2.99 (m 2H), 2.82-2.67 (m 2H), 1.32 (d 3H) |
| 25 | F-1a | 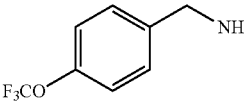 | 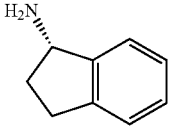 | LCMS Method: 1, RT: 4.76 min, MI: 481 [M + 1] | ¹H-NMR, Method 1: (DMSO) 8.35-8.31 (m 2H), 8.01 (dd 1H), 7.38-7.33 (m 4H), 7.29 (dd 1H), 7.24-7.16 (m 2H), 7.14-7.08 (m 2H), 5.61 (s 2H), 5.28 (q 1H), 3.21-3.07 (m 2H), 2.94-2.87 (m 1H), 2.83-2.68 (m 3H), 2.39-2.31 (m 1H), 1.81-1.72 (m 1H) |
| 26 | F-1c | 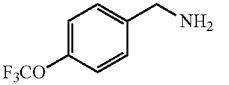 | 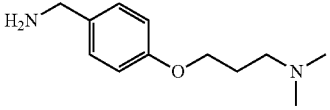 | LCMS Method: 1, RT: 2.83 min, MI: 570 [M + 1] | ¹H-NMR, Method 1: (DMSO) 8.42 (t 1H), 8.15 (d 1H), 7.81 (d 1H), 7.31 (s 4H), 7.12 (d 2H), 6.80 (d 2H), 5.53 (s 2H), 4.19 (d 2H), 3.97 (t 2H), 3.07 (t 2H), 2.87 (t 2H), 2.74 (t 2H), 2.55 (s 6H), 2.42 (s 3H), 2.01-1.94 (m 2H) |

-continued

| Example | SM | Amine 1 | Amine 2 | Characterisation | |
|---|---|---|---|---|---|
| 27 | F-1a | 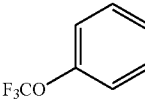 | 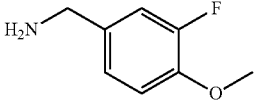 | LCMS Method: 1, RT: 4.46 min, MI: 503 [M + 1] | ¹H-NMR, Method 1: (DMSO) 8.47 (t 1H), 8.31 (dd 1H), 8.01 (dd 1H), 7.36 (s 4H), 7.28 (dd 1H), 7.10 (dd 1H), 7.03-6.96 (m 2H), 5.57 (s 2H), 4.21 (d 2H), 3.79 (s 3H), 3.11 (t 2H), 2.77 (t 2H) |
| 28 | F-1a | 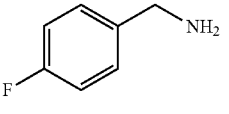 | 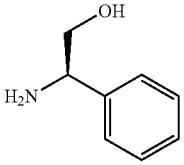 | LCMS Method: 1, RT: 3.44 min, MI: 419 [M + 1] | ¹H-NMR, Method 1: (MeOD) 8.36 (dd 1H), 8.03 (dd 1H), 7.34 (dd 1H), 7.24-7.18 (m 7H), 7.01 (tt 2H), 5.51 (s 2H), 4.96-4.92 (m 1H), 3.74-3.64 (m 2H), 3.17-3.13 (m 2H), 2.84 (t 2H) |
| 29 | F-1a | 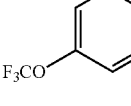 | 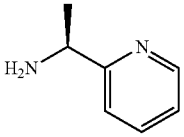 | LCMS Method: 1, RT: 3.13 min, MI: 470 [M + 1] | ¹H-NMR, Method 1: (DMSO) 8.49-8.46 (m 2H), 8.31 (dd 1H), 8.03 (dd 1H), 7.62 (td 1H), 7.34 (br 1H), 7.32 (s 4H), 7.29 (dd 1H), 7.20 (ddd 1H), 5.55 (s 2H), 4.96-4.88 (m 1H), 3.15-3.00 (m 2H), 2.87-2.72 (m 2H), 1.36 (d 3H) |
| 30 | F-1a | 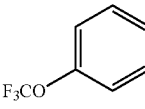 | 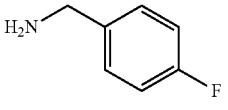 | LCMS Method: 1, RT: 4.53 min, MI: 473 [M + 1] | ¹H-NMR, Method 1: (CDCl₃) 8.40 (dd 1H), 7.93 (dd 1H), 7.28-7.23 (m 3H), 7.15-7.09 (m 4H), 6.87 (tt 2H), 6.66 (t 1H), 5.54 (s 2H), 4.35 (d 2H), 3.16 (t 2H), 2.88 (t 2H) |
| 31 | F-1a | 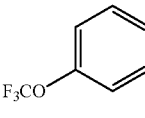 | 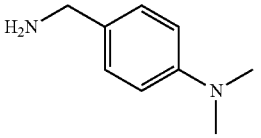 | LCMS Method: 1, RT: 3.17 min, MI: 498 [M + 1] | ¹H-NMR, Method 1: (DMSO) 8.33-8.29 (m 2H), 8.01 (dd 1H), 7.32 (s 4H), 7.27 (dd 1H), 7.00 (d 2H), 6.58 (d 2H), 5.57 (s 2H), 4.12 (d 2H), 3.08 (t 2H), 2.83 (s 6H), 2.73 (t 2H) |
| 32 | F-1a | 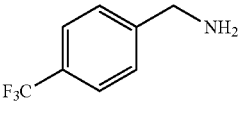 | 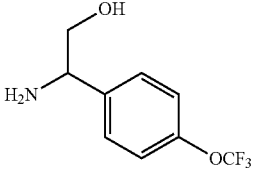 | LCMS Method: 1, RT: 4.52 min, MI: 553 [M + 1] | ¹H-NMR, Method 1: (CDCl₃) 8.37 (dd 1H), 7.68 (dd 1H), 7.53 (d 2H), 7.27-7.23 (m 5H), 7.21 (dd 1H), 6.99 (d 2H), 5.55 (d 1H), 5.48 (d 1H), 5.08-5.04 (m 1H), 3.93 (ddd 2H), 3.12 (t 2H), 2.98-2.76 (m 2H) |
| 33 | F-1a | 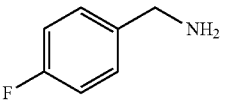 | 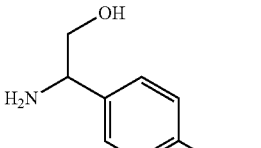 | LCMS Method: 1, RT: 4.10 min, MI: 503 [M + 1] | ¹H-NMR, Method 1: (1H 400 CDCl3) 8.38 (dd 1H), 7.83 (dd 1H), 7.29 (dt 2H), 7.23 (dd 1H), 7.18-7.14 (m 2H), 7.09-7.05 (m 3H), 6.97 (tt 2H), 5.45 (s 2H), 5.08-5.04 (m 1H), 3.90 (ddd 2H), 3.23-3.07 (m 2H), 2.92-2.76 (m 2H) |
| 34 | F-1a | 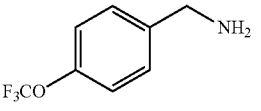 | 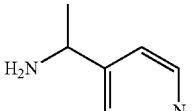 | LCMS Method: 1, RT: 2.70 min, MI: 470 [M + 1] | ¹H-NMR, Method 1: (DMSO) 8.55 (d 1H), 8.39 (dd 2H), 8.31 (dd 1H), 8.05 (dd 1H), 7.31 (s 4H), 7.30-7.26 (m 3H), 5.54 (s 2H), 4.89-4.82 (m 1H), 3.15-3.00 (m 2H), 2.89-2.70 (m 2H), 1.33 (d 3H) |

| Example | SM | Amine 1 | Amine 2 | Characterisation | |
|---|---|---|---|---|---|
| 35 | F-1a | 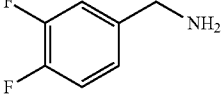 | 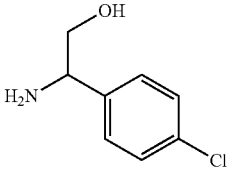 [SMILES: NC(CO)c1ccc(Cl)cc1] | LCMS Method: 1, RT: 3.96 min, MI: 471 [M + 1] | 1H-NMR, Method 1: (DMSO) 8.40 (d 1H), 8.30 (dd 1H), 8.01 (dd 1H), 7.39-7.26 (m 7H), 7.01-6.98 (m 1H), 5.48 (s 2H), 4.88 (t 1H), 4.80 (q 1H), 3.53 (t 2H), 3.12-2.99 (m 2H), 2.85-2.71 (m 2H) |
| 36 | F-1a | 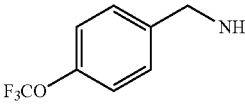 | 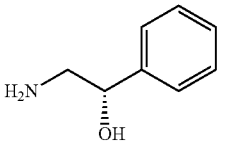 | LCMS Method: 1, RT: 4.10 min, MI: 485 [M + 1] | 1H-NMR, Method 1: (DMSO) 8.31 (dd 1H), 8.07 (t 1H), 8.01 (dd 1H), 7.36-7.19 (m 10H), 5.57 (s 2H), 5.45 (br 1H), 4.59 (t 1H), 3.29-3.23 (m 2H), 3.06-3.00 (m 2H), 2.71-2.68 (m 2H) |
| 37 | F-1a | 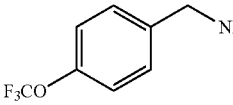 | 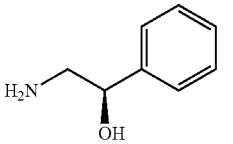 | LCMS Method: 1, RT: 4.10 min, MI: 485 [M + 1] | 1H-NMR, Method 1: (CDCl3) 8.37 (dd 1H), 7.97 (d 1H), 7.35-7.33 (m 2H), 7.31-7.28 (m 2H), 7.25-7.21 (m 4H), 7.17-7.15 (m 2H), 6.52 (br 1H), 5.55 (d 1H), 5.48 (d 1H), 4.87 (dd 1H), 3.77-3.71 (m 1H), 3.31-3.17 (m 2H), 3.12-3.05 (m 1H), 2.86-2.74 (m 2H) |
| 38 | F-1a | 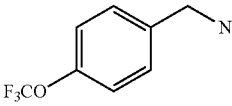 | 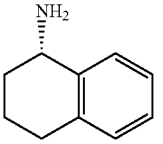 | LCMS Method: 1, RT: 4.93 min, MI: 495 [M + 1] | 1H-NMR, Method 1: (DMSO) 8.34 (d 1H), 8.32 (dd 1H), 8.00 (dd 1H), 7.37-7.32 (m 4H), 7.29 (dd 1H), 7.14-6.99 (m 4H), 5.60 (s 2H), 4.96 (m 1H), 3.21-3.05 (m 2H), 2.83-2.66 (m 4H), 1.86-1.84 (m 2H), 1.73-1.59 (m 2H) |
| 39 | F-1a | 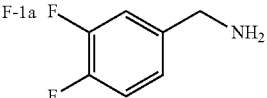 | 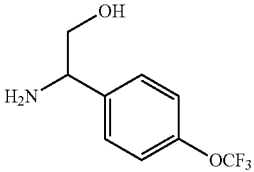 | LCMS Method: 1, RT: 4.25 min, MI: 521 [M + 1] | 1H-NMR, Method 1: (CDCl3) 8.38 (dd 1H), 7.82 (dd 1H), 7.28 (dt 2H), 7.24 (dd 1H), 7.11-6.98 (m 5H), 6.93-6.89 (m 1H), 5.44 (d 1H), 5.40 (d 1H), 5.08-5.04 (m 1H), 3.91 (ddd 2H), 3.22-3.07 (m 2H), 2.96-2.79 (m 2H) |
| 40 | F-1a | 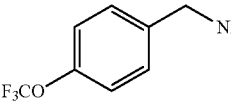 | 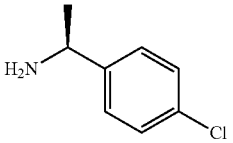 | LCMS Method: 2, RT: 7.8 min, MI: 503/505 [M + 1] | 1H-NMR, Method 1: (DMSO) 8.47 (d 1H), 8.31 (dd 1H), 8.03 (dd 1H), 7.31-7.25 (m 9H), 5.53 (s 2H), 4.90-4.83 (m 1H), 3.13-2.99 (m 2H), 2.83-2.69 (m 2H), 1.31 (d 3H) |
| 41 | F-1a | 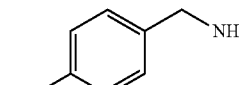 | 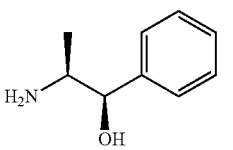 | LCMS Method: 1, RT: 4.27 min, MI: 498 [M + 1] | 1H-NMR, Method 1: (CDCl3) 8.35 (dd 1H), 7.91 (dd 1H), 7.34-7.32 (m 2H), 7.28-7.15 (m 8H), 6.34 (d 1H), 5.58 (d 1H), 5.45 (d 1H), 4.91 (d 1H), 4.34-4.26 (m 1H), 3.31-3.23 (m 1H), 3.07-3.00 (m 1H), 2.86-2.71 (m 2H), 0.96 (d 3H) |
| 42 | F-1a | 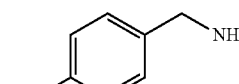 | 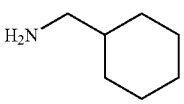 | LCMS Method: 1, RT: 4.86 min, MI: 461 [M + 1] | 1H-NMR, Method 1: (DMSO) 8.30 (dd 1H), 7.98 (dd 1H), 7.90 (t 1H), 7.33 (br 4H), 7.27 (dd 1H), 5.57 (s 2H), 3.05 (t 2H), 2.87 (t 2H), 2.68 (t 2H), 1.60-1.57 (m 5H), 1.35-1.26 (m 1H), 1.15-1.03 (m 3H), 0.82-0.73 (m 2H) |

| Example | SM | Amine 1 | Amine 2 | Characterisation | |
|---|---|---|---|---|---|
| 43 | F-1a | 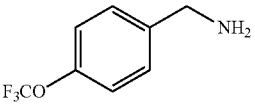 | 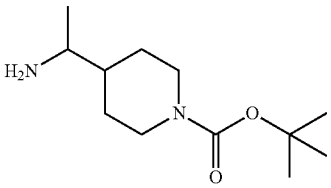 | LCMS Method: 1, RT: 4.83 min, MI: 576 [M + 1] | ¹H-NMR, Method 1: (CDCl₃) 8.37 (dd 1H), 7.95 (dd 1H), 7.25-7.23 (m 3H), 7.16-7.14 (m 2H), 6.04 (d 1H), 5.57 (d 1H), 5.50 (d 1H), 4.05 (br 2H), 3.87-3.78 (m 1H), 3.20-3.04 (m 2H), 2.83-2.79 (m 2H), 2.54-2.48 (m 2H), 1.53-1.50 (m 2H), 1.44 (s 9H), 1.43-1.33 (m 1H), 1.17-1.05 (m 2H), 1.02 (d 3H) |
| 44 | F-1a | 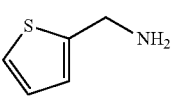 | 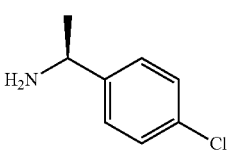 | LCMS Method: 1, RT: 4.24 min, MI: 425 [M + 1] | ¹H-NMR, Method 1: (DMSO) 8.48 (d 1H), 8.34 (dd 1H), 8.00 (dd 1H), 7.43 (dd 1H), 7.32-7.27 (m 5H), 7.11 (dd 1H), 6.97 (dd 1H), 5.66 (s 2H), 4.92-4.85 (m 1H), 3.22-3.08 (m 2H), 2.83-2.69 (m 2H), 1.32 (d 3H) |
| 45 | F-1a | 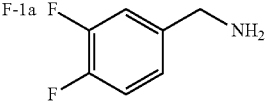 | 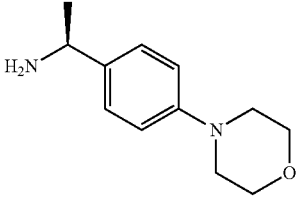 | LCMS Method: 1, RT: 3.80 min, MI: 506 [M + 1] | ¹H-NMR, Method 1: (DMSO) 8.31-8.29 (m 2H), 8.01 (dd 1H), 7.40-7.30 (m 2H), 7.28 (dd 1H), 7.10 (d 2H), 7.01-6.97 (m 1H), 6.79 (d 2H), 5.49 (s 2H), 4.85-4.78 (m 1H), 3.72 (t 4H), 3.08-3.01 (m 6H), 2.79-2.66 (m 2H), 1.29 (d 3H) |
| 46 | F-1a | 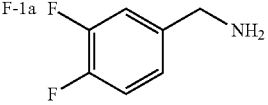 | 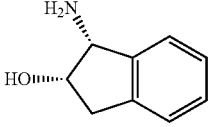 | LCMS Method: 1, RT: 3.88 min, MI: 449 [M + 1] | ¹H-NMR, Method 1: (CDCl₃) 8.35 (dd 1H), 8.01 (dd 1H), 7.31-7.20 (m 5H), 7.15-7.04 (m 2H), 6.97-6.94 (m 1H), 6.44 (d 1H), 5.52 (d 1H), 5.39 (d 1H), 5.39-5.36 (m 1H), 4.73 (dt 1H), 3.46-3.39 (m 1H), 3.18-3.13 (m 1H), 3.05-2.96 (m 2H), 2.87-2.76 (m 2H) |
| 47 | F-1a | 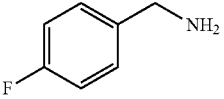 | 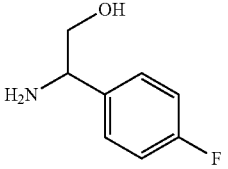 | LCMS Method: 1, RT: 3.57 min, MI: 437 [M + 1] | ¹H-NMR, Method 1: (DMSO) 8.38 (d 1H), 8.31 (dd 1H), 8.01 (dd 1H), 7.33-7.23 (m 5H), 7.14 (tt 2H), 7.06 (tt 2H), 5.49 (s 2H), 4.87 (t 1H), 4.82 (q 1H), 3.53 (t 2H), 3.12-2.99 (m 2H), 2.83-2.70 (m 2H) |
| 48 | F-1a | 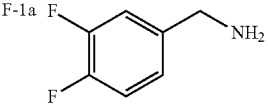 | 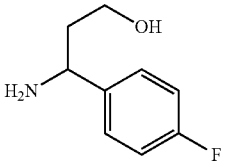 | LCMS Method: 1, RT: 3.77 min, MI: 469 [M + 1] | — |
| 49 | F-1a | 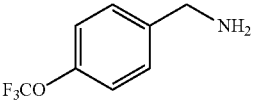 [SMILES: NCc1ccc(OC(F)(F)F)cc1] | 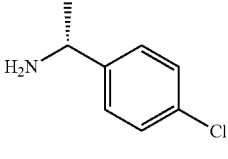 | LCMS Method: 1, RT: 4.93 min, MI: 503 [M + 1] | ¹H-NMR, Method 1: (DMSO) 8.48 (d 1H), 8.32 (dd 1H), 8.04 (dd 1H), 7.31-7.25 (m 9H), 5.54 (s 2H), 4.90-4.83 (m 1H), 3.12-3.02 (m 2H), 2.83-2.71 (m 2H), 1.31 (d 3H) |
| 50 | F-1a | 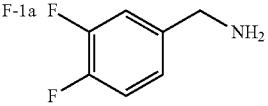 | 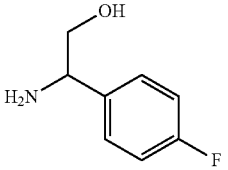 | LCMS Method: 1, RT: 3.74 min, MI: 455 [M + 1] | ¹H-NMR, Method 1: (DMSO) 8.38 (d 1H), 8.31 (dd 1H), 8.01 (dd 1H), 7.40-7.27 (m 5H), 7.05 (tt 2H), 7.02-6.98 (m 1H), 5.49 (s 2H), 4.86 (t 1H), 4.82 (q 1H), 3.53 (t 2H), 3.11-3.02 (m 2H), 2.85-2.72 (m 2H) |

| Example | SM | Amine 1 | Amine 2 | Characterisation | |
|---|---|---|---|---|---|
| 51 | F-1a | 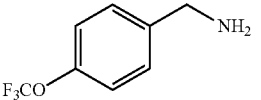 | 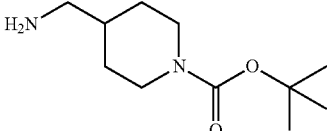 | LCMS Method: 1, RT: 4.72 min, MI: 562 [M + 1] | — |
| 52 | F-1c | 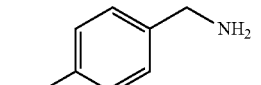 | 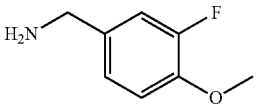 | LCMS Method: 1, RT: 4.53 min, MI: 517 [M + 1] | $^1$H-NMR, Method 1: (DMSO) 8.46 (t 1H), 8.15 (d 1H), 7.81 (d 1H), 7.32 (s 4H), 7.09 (dd 1H), 7.03-6.95 (m 2H), 5.53 (s 2H), 4.20 (d 2H), 3.80 (s 3H), 3.08 (t 2H), 2.75 (t 2H), 2.42 (s 3H) |
| 53 | F-1c | 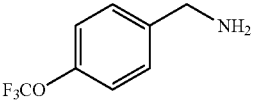 | 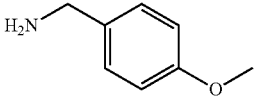 | LCMS Method: 1, RT: 4.45 min, MI: 499 [M + 1] | $^1$H-NMR, Method 1: (DMSO) 8.41 (t 1H), 8.15 (d 1H), 7.82 (d 1H), 7.31 (s 4H), 7.11 (d 2H), 6.79 (d 2H), 5.53 (s 2H), 4.18 (d 2H), 3.70 (s 3H), 3.06 (t 2H), 2.73 (t 2H), 2.42 (s 3H) |
| 54 | F-1a | 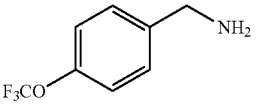 [SMILES: NCc1ccc(OC(F)(F)F)cc1] | 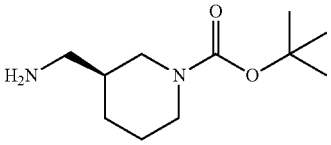 | LCMS Method: 1, RT: 4.80 min, MI: 562 [M + 1] | $^1$H-NMR, Method 1: (CDCl$_3$) 8.38 (dd 1H), 7.99 (d 1H), 7.26-7.23 (m 3H), 7.15-7.13 (m 2H), 6.57 (br 1H), 5.55 (s 2H), 3.70 (d 1H), 3.60 (br 1H), 3.20 (br 1H), 3.15 (t 2H), 2.99 (br 1H), 2.85 (t 2H), 2.72 (br 1H), 2.48 (br 2H), 1.69-1.53 (m 2H), 1.43 (s 9H), 1.38-1.27 (m 1H), 1.15 (br 1H) |
| 55 | F-1a | 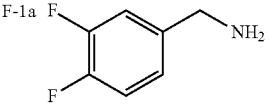 | 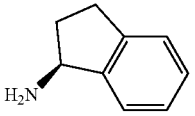 | LCMS Method: 1, RT: 4.35 min, MI: 433 [M + 1] | $^1$H-NMR, Method 1: (CDCl$_3$) 8.38 (dd 1H), 7.92 (dd 1H), 7.25 (dd 1H), 7.22-7.17 (m 2H), 7.14-7.03 (m 4H), 6.99-6.96 (m 1H), 6.34 (d 1H), 5.54 (d 1H), 5.49 (d 1H), 5.41 (q 1H), 3.23-3.09 (m 2H), 2.95-2.78 (m 4H), 2.55-2.48 (m 1H), 1.77-1.68 (m 1H) |
| 56 | F-1a | 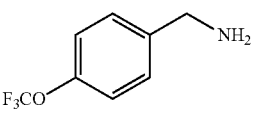 [SMILES: NCc1ccc(OC(F)(F)F)cc1] | 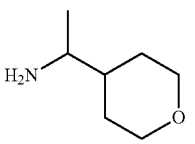 | LCMS Method: 1, RT: 3.97 min, MI: 477 [M + 1] | $^1$H-NMR, Method 1: (CDCl$_3$) 8.37 (dd 1H), 7.95 (dd 1H), 7.26-7.22 (m 3H), 7.16-7.14 (m 2H), 6.01 (d 1H), 5.57 (d 1H), 5.50 (d 1H), 3.90-3.79 (m 3H), 3.26-3.05 (m 4H), 2.87-2.75 (m 2H), 1.50-1.38 (m 3H), 1.33-1.16 (m 2H), 1.03 (d 3H) |
| 57 | F-1a | 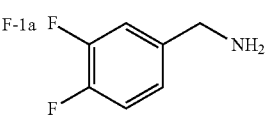 | 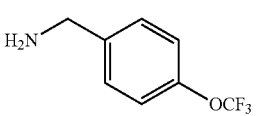 | LCMS Method: 1, RT: 4.65 min, MI: 491 [M + 1] | $^1$H-NMR, Method 1: (CDCl$_3$) 8.39 (dd 1H), 7.92 (dd 1H), 7.28-7.24 (m 1H), 7.17-7.01 (m 6H), 6.97-6.94 (m 1H), 6.60 (t 1H), 5.48 (s 2H), 4.40 (d 2H), 3.15 (t 2H), 2.89 (t 2H) |
| 58 | F-1a | 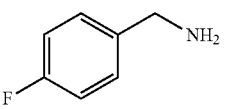 | 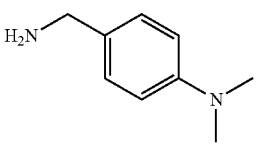 | LCMS Method: 1, RT: 2.67 min, MI: 432 [M + 1] | $^1$H-NMR, Method 1: (DMSO) 8.33-8.31 (m 2H), 8.00 (dd 1H), 7.29-7.25 (m 3H), 7.15 (tt 2H), 7.01 (d 2H), 6.60 (d 2H), 5.52 (s 2H), 4.13 (d 2H), 3.08 (t 2H), 2.84 (s 6H), 2.72 (t 2H) |

| Example | SM | Amine 1 | Amine 2 | Characterisation | |
|---|---|---|---|---|---|
| 59 | F-1a | 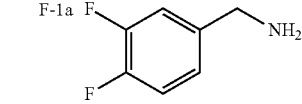 | 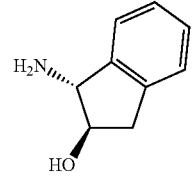 | LCMS Method: 1, RT: 3.76 min, MI: 449 [M + 1] | ¹H-NMR, Method 1: (CDCl₃) 8.39 (dd 1H), 7.95 (dd 1H), 7.34 (d 1H), 7.28-7.19 (m 3H), 7.15-7.03 (m 3H), 6.98-6.95 (m 1H), 5.49 (s 2H), 5.06 (t 1H), 4.36 (q 1H), 3.27 (dd 1H), 3.18 (t 2H), 3.05-2.88 (m 3H) |
| 60 | F-1a | 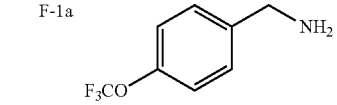 | 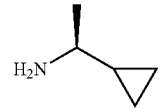 | LCMS Method: 1, RT: 4.35 min, MI: 433 [M + 1] | ¹H-NMR, Method 1: (CDCl₃) 8.37 (dd 1H), 7.98 (dd 1H), 7.25-7.22 (m 3H), 7.15-7.13 (m 2H), 5.98 (d 1H), 5.54 (s 2H), 3.39-3.29 (m 1H), 3.13 (td 2H), 2.86-2.74 (m 2H), 1.11 (d 3H), 0.77-0.68 (m 1H), 0.45-0.39 (m 1H), 0.33-0.26 (m 1H), 0.21-0.10 (m 2H) |
| 61 | F-1d | 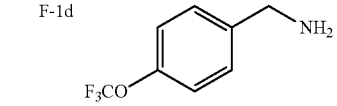 | 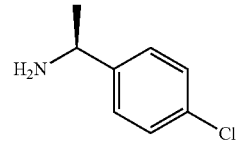 | LCMS Method: 1, RT: 5.64 min, MI: 580/582 [M + 1] | — |
| 62 | F-1a | 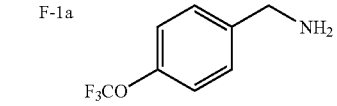 | 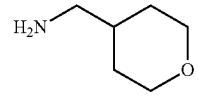 | LCMS Method: 1, RT: 3.81 min, MI: 463 [M + 1] | ¹H-NMR, Method 1: (CDCl₃) 8.40 (dd 1H), 7.97 (dd 1H), 7.28-7.25 (m 3H), 7.17-7.15 (m 2H), 6.30 (br 1H), 5.56 (s 2H), 3.87 (dd 2H), 3.25 (td 2H), 3.17-3.09 (m 4H), 2.85 (t 2H), 1.70-1.58 (m 1H), 1.49-1.45 (m 2H), 1.30-1.16 (m 2H) |
| 63 | F-1a | 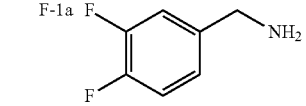 | 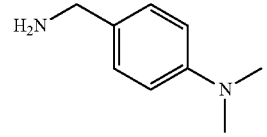 | LCMS Method: 1, RT: 2.76 min, MI: 450 [M + 1] | ¹H-NMR, Method 1: (DMSO) 8.33-8.29 (m 2H), 8.01 (dd 1H), 7.41-7.32 (m 2H), 7.28 (dd 1H), 7.03-6.99 (m 3H), 6.59 (d 2H), 5.52 (s 2H), 4.13 (d 2H), 3.08 (t 2H), 2.83 (s 6H), 2.73 (t 2H) |
| 64 | F-1a | 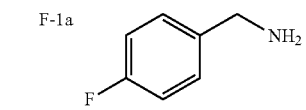 | 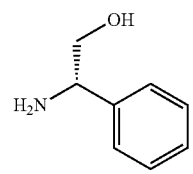 | LCMS Method: 1, RT: 3.44 min, MI: 419 [M + 1] | ¹H-NMR, Method 1: (MeOD) 8.36 (dd 1H), 8.03 (dd 1H), 7.34 (dd 1H), 7.22-7.18 (m 7H), 7.01 (tt 2H), 5.51 (s 2H), 4.96-4.93 (m 1H), 3.74-3.64 (m 2H), 3.17-3.13 (m 2H), 2.84 (t 2H) |
| 65 | F-1a | 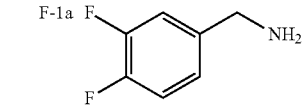 | 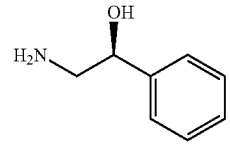 | LCMS Method: 1, RT: 3.72 min, MI: 437 [M + 1] | ¹H-NMR, Method 1: (CDCl₃) 8.36 (dd 1H), 7.93 (dd 1H), 7.35-7.33 (m 2H), 7.30-7.28 (m 2H), 7.25-7.19 (m 2H), 7.14-7.07 (m 1H), 7.06-7.01 (m 1H), 6.96-6.93 (m 1H), 6.56 (t 1H), 5.49 (d 1H), 5.42 (d 1H), 4.86 (dd 1H), 3.76-3.70 (m 1H), 3.30-3.14 (m 2H), 3.10-3.03 (m 1H), 2.86-2.74 (m 2H) |

| Example | SM | Amine 1 | Amine 2 | | Characterisation |
|---|---|---|---|---|---|
| 66 | F-1a | 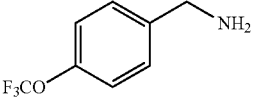 | 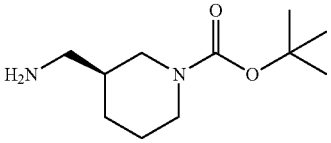 | LCMS Method: 1, RT: 4.81 min, MI: 562 [M + 1] | ¹H-NMR, Method 1: (CDCl₃) 8.36 (dd 1H), 7.98 (d 1H), 7.25-7.21 (m 3H), 7.15-7.13 (m 2H), 6.57 (br 1H), 5.54 (s 2H), 3.70 (dd 1H), 3.61 (br 1H), 3.22 (br 1H), 3.13 (t 2H), 2.96 (br 1H), 2.84 (t 2H), 2.71 (br 1H), 2.25 (br 1H), 1.68-1.53 (m 3H), 1.43 (s 9H), 1.38-1.27 (m 1H), 1.15 (br 1H) |
| 67 | F-1a | 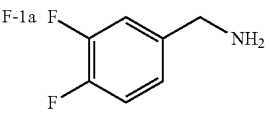 | 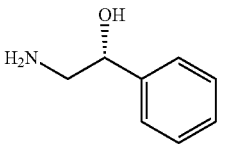 | LCMS Method: 1, RT: 3.70 min, MI: 437 [M + 1] | ¹H-NMR, Method 1: (CDCl₃) 8.37 (dd 1H), 7.97 (dd 1H), 7.35-7.27 (m 4H), 7.25-7.22 (m 2H), 7.14-7.02 (m 2H), 6.97-6.94 (m 1H), 6.49 (t 1H), 5.50 (d 1H), 5.43 (d 1H), 4.87 (dd 1H), 3.77-3.71 (m 1H), 3.31-3.16 (m 2H), 3.12-3.04 (m 1H), 2.87-2.75 (m 2H) |
| 68 | F-1a | 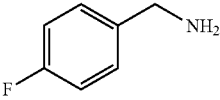 | 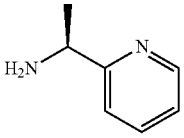 | LCMS Method: 1, RT: 2.57 min, MI: 404 [M + 1] | ¹H-NMR, Method 1: (DMSO) 8.49-8.47 (m 2H), 8.31 (dd 1H), 8.02 (dd 1H), 7.62 (td 1H), 7.33 (d 1H), 7.29-7.24 (m 3H), 7.21 (ddd 1H), 7.14 (tt 2H), 5.49 (s 2H), 4.95-4.88 (m 1H), 3.14-3.00 (m 2H), 2.85-2.71 (m 2H), 1.36 (d 3H) |
| 69 | F-1a | 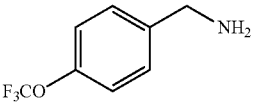 | 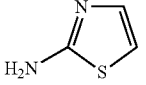 | LCMS Method: 1, RT: 4.31 min, MI: 448 [M + 1] | ¹H-NMR, Method 1: (DMSO) 12.24 (s 1H), 8.31 (dd 1H), 8.01 (dd 1H), 7.46 (d 1H), 7.38-7.33 (m 4H), 7.27 (dd 1H), 7.18 (d 1H), 5.60 (s 2H), 3.20 (t 2H), 3.08 (t 2H) |
| 70 | F-1d | 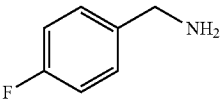 | 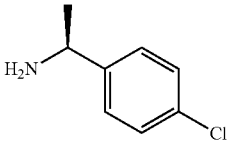 | LCMS Method: 1, RT: 5.23 min, MI: 515/517 [M + 1] | ¹H-NMR, Method 1: (DMSO) 8.45 (d 1H), 8.41 (d 1H), 8.29 (d 1H), 7.30-7.23 (m 6H), 7.14 (tt 2H), 5.47 (s 2H), 4.90-4.82 (m 1H), 3.12-2.99 (m 2H), 2.80-2.67 (m 2H), 1.31 (d 3H) |
| 71 | F-1a | 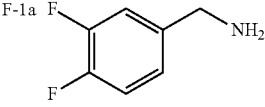 | 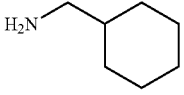 | LCMS Method: 1, RT: 4.46 min, MI: 413 [M + 1] | ¹H-NMR, Method 1: (CDCl₃) 8.40 (dd 1H), 7.99 (dd 1H), 7.28 (dd 1H), 7.14-7.03 (m 2H), 7.00-6.97 (m 1H), 6.13 (br 1H), 5.52 (s 2H), 3.16 (t 2H), 3.05 (t 2H), 2.85 (t 2H), 1.63-1.56 (m 5H), 1.40-1.31 (m 1H), 1.16-1.03 (m 3H), 0.86-0.77 (m 2H) |
| 72 | F-1a | 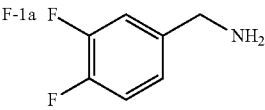 | 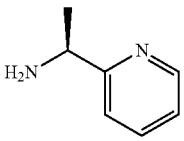 | LCMS Method: 1, RT: 2.80 min, MI: 422 [M + 1] | ¹H-NMR, Method 1: (CDCl₃) 8.45 (dd 1H), 8.35 (dd 1H), 7.98 (dd 1H), 7.59 (td 1H), 7.24 (dd 1H), 7.17-6.99 (m 5H), 6.95-6.92 (m 1H), 5.48 (s 2H), 5.11-5.04 (m 1H), 3.13 (t 2H), 2.91 (t 2H), 1.41 (d 3H) |
| 73 | F-1a | 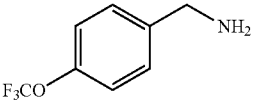 [SMILES: NCc1ccc(OC(F)(F)F)cc1] | 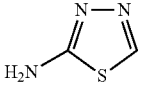 | LCMS Method: 1, RT: 3.98 min, MI: 449 [M + 1] | ¹H-NMR, Method 1: (DMSO) 12.71 (s 1H), 9.14 (s 1H), 8.31 (dd 1H), 8.01 (dd 1H), 7.38-7.33 (m 4H), 7.27 (dd 1H), 5.60 (s 2H), 3.22 (t 2H), 3.13 (t 2H) |

| Example | SM | Amine 1 | Amine 2 | Characterisation | |
|---|---|---|---|---|---|
| 74 | F-1a | 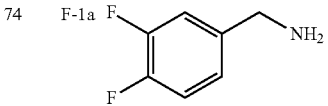 | 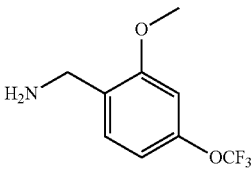 | LCMS Method: 1, RT: 4.74 min, MI: 521 [M + 1] | ¹H-NMR, Method 1: (DMSO) 8.41 (t 1H), 8.33 (dd 1H), 8.04 (dd 1H), 7.41-7.33 (m 2H), 7.31 (dd 1H), 7.20 (d 1H), 7.06-7.02 (m 1H), 6.94 (d 1H), 6.73 (dq 1H), 5.52 (s 2H), 4.19 (d 2H), 3.81 (s 3H), 3.12 (t 2H), 2.80 (t 2H) |
| 75 | F-1a | 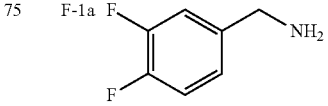 | 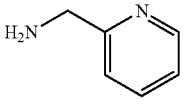 | LCMS Method: 1, RT: 2.61 min, MI: 408 [M + 1] | ¹H-NMR, Method 1: (DMSO) 8.61 (t 1H), 8.46 (dd 1H), 8.32 (dd 1H), 8.04 (dd 1H), 7.64 (td 1H), 7.42-7.33 (m 2H), 7.31-7.27 (m 2H), 7.24-7.21 (m 1H), 7.05-7.02 (m 1H), 5.52 (s 2H), 4.35 (d 2H), 3.12 (t 2H), 2.82 (t 2H) |
| 76 | F-1a | 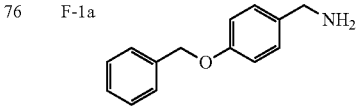 | 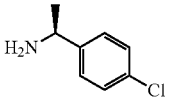 | LCMS Method: 1, RT: 5.02 min, MI: 525 [M + 1] | ¹H-NMR, Method 1: (DMSO) 8.47 (d 1H), 8.36 (dd 1H), 8.04 (dd 1H), 7.43-7.29 (m 10H), 7.17 (d 2H), 6.95 (d 2H), 5.45 (s 2H), 5.05 (s 2H), 4.91-4.83 (m 1H), 3.14-3.04 (m 2H), 2.81-2.68 (m 2H), 1.32 (d 3H) |
| 77 | F-1a | 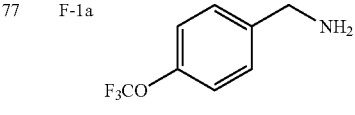 | 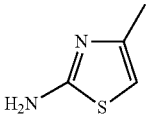 | LCMS Method: 1, RT: 4.49 min, MI: 462 [M + 1] | ¹H-NMR, Method 1: (DMSO) 12.15 (br 1H), 8.31 (d 1H), 8.01 (d 1H), 7.35 (br 4H), 7.28-7.24 (m 1H), 6.71 (s 1H), 5.59 (s 2H), 3.19 (t 2H), 3.05 (t 2H), 2.25 (s 3H) |
| 78 | F-1a | 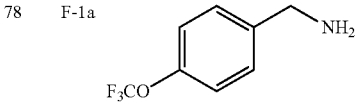 | 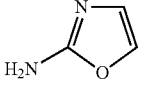 | LCMS Method: 1, RT: 3.81 min, MI: 432 [M + 1] | ¹H-NMR, Method 1: (DMSO) 11.31 (br 1H), 8.30 (dd 1H), 8.01 (dd 1H), 7.83 (d 1H), 7.34 (s 4H), 7.26 (dd 1H), 7.07 (d 1H), 5.59 (s 2H), 3.17-3.12 (m 2H), 3.06-2.97 (m 2H) |
| 79 | F-1e | 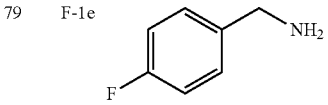 | 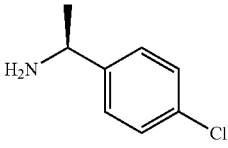 | LCMS Method: 1, RT: 4.34 min, MI: 451 [M + 1] | ¹H-NMR, Method 1: (DMSO) 8.44 (d 1H), 7.89 (d 1H), 7.31-7.19 (m 6H), 7.16-7.12 (m 3H), 5.44 (s 2H), 4.90-4.82 (m 1H), 3.05-2.92 (m 2H), 2.77-2.63 (m 2H), 2.57 (s 3H), 1.31 (d 3H) |
| 80 | F-1a | 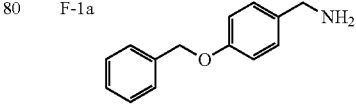 | 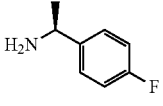 | LCMS Method: 1, RT: 4.77 min, MI: 509 [M + 1] | ¹H-NMR, Method 1: (DMSO) 8.44 (d 1H), 8.34 (dd 1H), 8.02 (dd 1H), 7.43-7.35 (m 4H), 7.33-7.27 (m 4H), 7.16 (dt 2H), 7.05 (tt 2H), 6.95 (dt 2H), 5.43 (s 2H), 5.05 (s 2H), 4.93-4.86 (m 1H), 3.14-3.00 (m 2H), 2.80-2.67 (m 2H), 1.32 (d 3H) |
| 81 | F-1a | 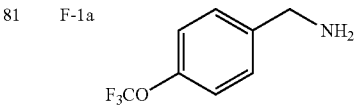 | 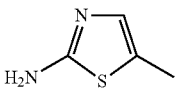 | LCMS Method: 1, RT: 4.50 min, MI: 462 [M + 1] | ¹H-NMR, Method 1: (DMSO) 12.04 (br 1H), 8.31 (d 1H), 8.01 (d 1H), 7.35 (br 4H), 7.27 (dd 1H), 7.11 (d 1H), 5.60 (s 2H), 3.19 (t 2H), 3.04 (t 2H), 2.31 (br 3H) |

| Example | SM | Amine 1 | Amine 2 | Characterisation | |
|---|---|---|---|---|---|
| 82 | F-1a | 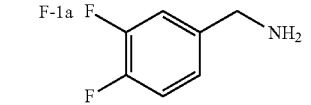 | 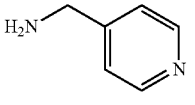 | LCMS Method: 1, RT: 2.58 min, MI: 408 [M + 1] | ¹H-NMR, Method 1: (DMSO) 8.61 (t 1H), 8.46 (dq 1H), 8.32 (dd 1H), 8.04 (dd 1H), 7.64 (td 1H), 7.42-7.33 (m 2H), 7.31-7.27 (m 2H), 7.24-7.21 (m 1H), 7.05-7.02 (m 1H), 5.52 (s 2H), 4.35 (d 2H), 3.12 (t 2H), 2.82 (t 2H) |

General Synthesis of 3-(3-aralkyl-3H-imidazo[4,5-b]pyridin-2-yl)-propionamide of general formula F-5 (Scheme 002-B)

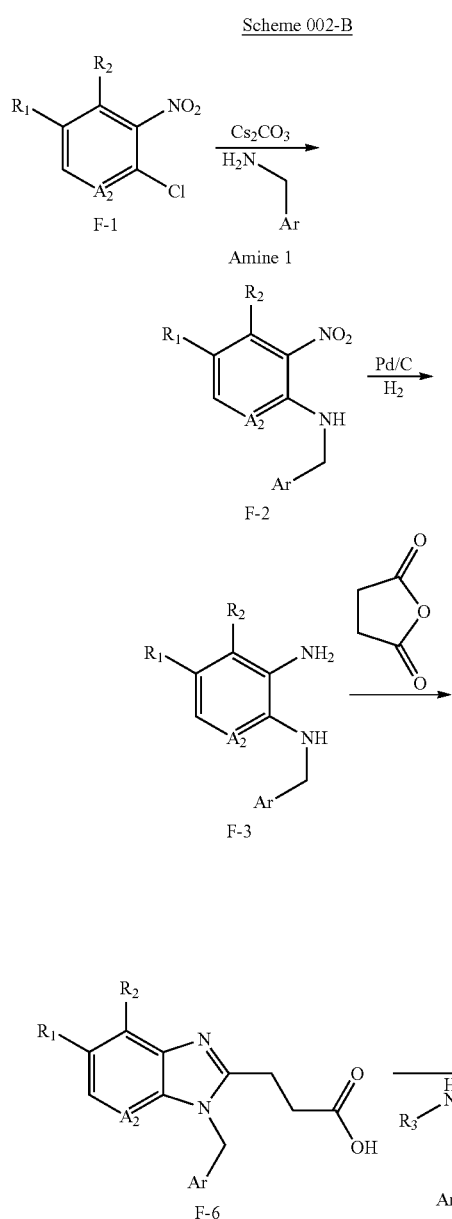

Intermediates F-2 and F-3 were prepared as in Scheme 001. Intermediate F-6 was prepared as in Scheme 002-A. Intermediate F-6, was treated with CDI and the required amine 2 in DMF at r.t. to afford the final compounds of general formula F-5.

F-1 could be any of the following intermediates:

The above synthesis (Scheme 002-A) is illustrated by the preparation of N—[(S)-1-(4-bromo-phenyl)-ethyl]-3-[3-(4-fluoro-benzyl)-3H-imidazo[4,5-b]pyridin-2-yl]-propionamide (Ex. 83) described below.

Synthesis of N—[(S)-1-(4-bromo-phenyl)-ethyl]-3-[3-(4-fluoro-benzyl)-3H-imidazo[4,5-b]pyridin-2-yl]-propionamide (Ex. 83)

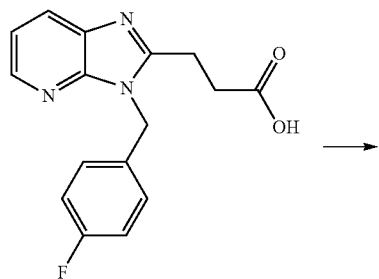

→

-continued

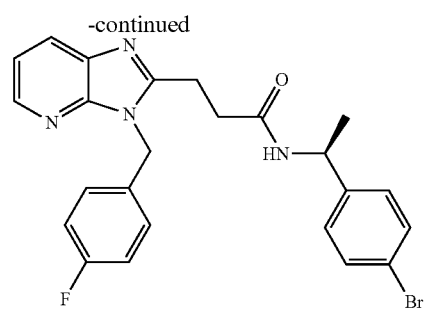

In a round bottom flask fitted with a magnetic stirrer, 3-[3-(4-fluoro-benzyl)-3H-imidazo[4,5-b]pyridin-2-yl]-propionic acid (500 mg, 1.67 mmol) and CDI (410 mg, 2.51 mmol) were dissolved in anhydrous DMF (7 ml) and stirred at r.t. for 30 min. (S)-(−)-1-(4-bromophenyl)ethylamine (670 mg, 3.34 mmol) was then added and the reaction stirred over the weekend at r.t. Reaction mixture was quenched with water (30 ml) and extracted with EtOAc (40 ml×2). Organic phases were combined, washed with brine (30 ml), dried and concentrated under reduced pressure to afford a brown oily crude material which was purified on silica gel by column chromatography with a gradient of MeOH and DCM, product eluted with 3% MeOH. Required product fractions were combined and concentrated under reduced pressure to afford the title compound (688 mg, 86%).

The following compounds of general formula F-5 were prepared according to the general synthesis shown in Scheme 002-B:

| Example | SM | Amine 1 | Amine 2 | Characterisation | |
|---|---|---|---|---|---|
| 83 | F-1a | 4-fluorobenzylamine | (S)-1-(4-bromophenyl)ethylamine | LCMS Method: 1, RT: 4.47 min, MI: 481/483 [M + 1] | $^1$H-NMR, Method 1: (DMSO) 8.45 (d 1H), 8.31 (dd 1H), 8.01 (dd 1H), 7.40 (dt 2H), 7.29-7.21 (m 5H), 7.13 (tt 2H), 5.48 (s 2H), 4.88-4.80 (m 1H), 3.11-2.97 (m 2H), 2.80-2.66 (m 2H), 1.30 (d 3H) |
| 84 | F-1a | 4-methoxybenzylamine | (S)-1-(4-chlorophenyl)ethylamine | LCMS Method: 1, RT: 4.19 min, MI: 449 [M + 1] | $^1$H-NMR, Method 1: (DMSO) 8.46 (d 1H), 8.32 (d 1H), 8.00 (d 1H), 7.31-7.26 (m 5H), 7.15 (d 2H), 6.86 (d 2H), 5.42 (s 2H), 4.91-4.84 (m 1H), 3.70 (s 3H), 3.11-2.98 (m 2H), 2.80-2.66 (m 2H), 1.32 (d 3H) |
| 85 | F-1a | 3,4-difluorobenzylamine | (S)-1-(4-methylphenyl)ethylamine | LCMS Method: 4, RT: 1.19 min, MI: 436 [M + 1] | $^1$H-NMR, Method 1: (DMSO) 8.29 (dd 1H), 7.99 (dd 1H), 7.38-7.26 (m 3H), 7.12 (d 2H), 7.04-6.97 (m 3H), 5.49 (s 2H), 4.89-4.80 (m 1H), 3.08-3.03 (m 2H), 2.76-2.70 (m 2H), 2.23 (s 3H), 1.28 (d 3H) |
| 86 | F-1a | 3,4-difluorobenzylamine | (S)-1-phenylethylamine | LCMS Method: 4, RT: 1.14 min, MI: 422 [M + 1] | $^1$H-NMR, Method 1: (DMSO) 8.44-8.39 (m 2H), 8.29 (dd 1H), 7.99 (dd 1H), 7.19-7.16 (m 8H), 7.02-6.98 (m 1H), 5.49 (s 2H), 4.93-4.84 (m 1H), 3.09-3.04 (m 2H), 2.78-2.72 (m 2H), 1.31 (d 3H) |

-continued

| Example | SM | Amine 1 | Amine 2 | Characterisation | |
|---|---|---|---|---|---|
| 87 | F-1a | 4-fluorobenzylamine | (S)-1-phenylethylamine | LCMS Method: 1, RT: 4.04 min, MI: 403 [M + 1] | $^1$H-NMR, Method 1: (MeOD) 8.41 (d 1 H), 8.30 (dd 1H), 8.00 (dd 1H), 7.30-7.21 (m 5H), 7.12 (tt 2H), 7.03 (tt 2H), 5.47 (s 2H), 4.90-4.83 (m 1H), 3.10-2.96 (m 2H), 2.78-2.64 (m 2H), 1.30 (d 3H) |
| 88 | F-1a | 4-fluorobenzylamine | (S)-1-(4-fluorophenyl)ethylamine | LCMS Method: 1, RT: 4.09 min, MI: 421 [M + 1] | $^1$H-NMR, Method 1: (DMSO) 8.42 (d 1H), 8.31 (dd 1H), 8.01 (dd 1H), 7.31-7.23 (m 5H), 7.13 (tt 2H), 7.04 (tt 2H), 5.48 (s 2H), 4.91-4.84 (m 1H), 3.11-2.98 (m 2H), 2.79-2.66 (m 2H), 1.31 (d 3H) |
| 89 | F-1a | 3,4-difluorobenzylamine | (S)-1-phenylpropylamine | LCMS Method: 4, RT: 1.20 min, MI: 436 [M + 1] | $^1$H-NMR, Method 1: (DMSO) 8.34 (br d 1H), 8.29 (dd 1H), 7.97 (dd 1H), 7.38-7.18 (m 8H), 7.02-6.99 (m 1H), 5.48 (s 2H), 4.70-4.62 (m 1H), 3.08-3.03 (m 2H), 2.78-2.73 (m 2H), 1.67-1.61 (m 2H), 0.78 (t 3H) |
| 90 | F-1a | 4-methoxybenzylamine | (S)-1-(4-methylphenyl)ethylamine | LCMS Method: 4, RT: 1.17 min, MI: 430 [M + 1] | $^1$H-NMR, Method 1: (DMSO) 8.37-8.30 (m 2H), 8.01-7.97 (m 1H), 7.29-7.24 (m 1H), 7.17-7.13 (m 4H), 7.06-7.02 (m 2H), 6.89-6.84 (m 2H), 5.42 (s 2H), 4.90-4.83 (m 1H), 3.70 (s 3H), 3.11-3.01 (m 2H), 2.78-2.66 (m 2H), 2.25 (s 3H), 1.30 (d 3H) |
| 91 | F-1b | 4-methoxybenzylamine | 4-methoxybenzylamine | LCMS Method: 4, RT: 1.11 min, MI: 449 [M + 1] | $^1$H-NMR, Method 1: (DMSO) 8.41 (t 1H), 7.41 (d 1H), 7.15 (m 5H), 6.88 (d 2H), 6.79 (d 2H), 4.20 (d 2H), 3.70 (s 3H), 3.32 (s 3H), 3.09 (t 2H), 2.74 (t 2H) |
| 92 | F-1a | 4-methoxybenzylamine | (S)-1-phenylethylamine | LCMS Method: 1, RT: 3.90 min, MI: 415 [M + 1] | $^1$H-NMR, Method 1: (MeOD) 8.36 (dd 1H), 8.01 (dd 1H), 7.34 (dd 1H), 7.20-7.16 (m 5H), 7.11 (dt 2H), 6.83 (dt 2H), 5.46 (s 2H), 4.94 (q 1H), 3.73 (s 3H), 3.19-3.05 (m 2H), 2.75 (t 2H), 1.39 (d 3H) |
| 93 | F-1a | 4-methoxybenzylamine | (S)-1-phenylpropylamine | LCMS Method: 4, RT: 1.16 min, MI: 430 [M + 1] | $^1$H-NMR, Method 1: (DMSO) 8.38-8.30 (m 2H), 8.00-7.95 (m 1H), 7.30-7.11 (m 8H), 6.89-6.83 (m 2H), 5.42 (s 2H), 4.72-4.63 (m 1H), 3.70 (s 3H), 3.04 (t 2H), 2.74 (t 2H), 1.70-1.59 (m 2H), 0.81 (t 3H) |
| 94 | F-1a | 4-fluorobenzylamine | 4-fluorobenzylamine | LCMS Method: 1, RT: 3.98 min, MI: 407 [M + 1] | $^1$H-NMR, Method 1: (MeOD) 8.36 (dd 1H), 8.00 (dd 1H), 7.34 (dd 1H), 7.26-7.22 (m 2H), 7.19-7.16 (m 2H), 7.03 (tt 2H), 6.91 (tt 2H), 5.56 (s 2H), 4.30 (br 2H), 3.16 (t 2H), 2.79 (t 2H) |

| Example | SM | Amine 1 | Amine 2 | | Characterisation |
|---|---|---|---|---|---|
| 95 | F-1a | 3,4-difluorobenzylamine | (S)-1-(4-fluorophenyl)ethylamine | LCMS Method: 4, RT: 1.14 min, MI: 440 [M + 1] | ¹H-NMR, Method 1: (DMSO) 8.42 (d 1H), 8.30 (d 1H), 8.00 (d 1H), 7.35-7.27 (m, rotameric forms 4H), 7.16-7.00 (m, rotameric forms 3H), 6.26 (d 1H), 5.49 (s 2H), 4.71-4.67 (m, rotameric forms 1H), 3.10-2.95 (m 2H), 2.78-2.70 (m 2H), 1.32-1.26 (m 3H) |
| 96 | F-1a | 4-methoxybenzylamine | (S)-1-(4-fluorophenyl)ethylamine | LCMS Method: 4, RT: 1.12 min, MI: 434 [M + 1] | ¹H-NMR, Method 1: (DMSO) 8.42 (br d 1H), 8.33-8.30 (m 1H), 8.02-7.98 (m 1H), 7.33-7.01 (m 7H), 6.89-6.84 (m 2H), 5.42 (s 2H), 4.92-4.85 (m 1H), 3.70 (s 3H), 3.12-3.00 (m 2H), 2.82-2.65 (m 2H), 1.31 (d 3H) |
| 97 | F-1a | 4-fluorobenzylamine | 4-methoxybenzylamine | LCMS Method: 4, RT: 1.06 min, MI: 420 [M + 1] | ¹H-NMR, Method 2: (DMSO) 8.38 (t 1H), 8.30 (dd 1H), 7.99 (dd 1H), 7.10 (m 7H), 6.78 (d 2H), 5.52 (s 2H), 4.18 (d 2H), 3.71 (s 3H), 3.07 (t 2H), 2.72 (t 2H) |
| 98 | F-1a | 3-(trifluoromethoxy)benzylamine | 4-methoxybenzylamine | LCMS Method: 4, RT: 1.17 min, MI: 484 [M + 1] | ¹H-NMR, Method 1: (DMSO) 8.38 (m 3H), 8.02 (d 1H), 7.32 (m 7H), 6.79 (m 2H), 5.60 (m 2H), 4.20 (m 2H), 3.71 (s 3H), 3.10 (m 2H), 2.75 (m 2H) |
| 99 | F-1a | 4-methoxybenzylamine | (S)-1-phenylbutylamine | LCMS Method: 4, RT: 1.23 min, MI: 444 [M + 1] | ¹H-NMR, Method 1: (DMSO) 8.38-8.30 (m 2H), 7.95-7.99 (m 1H), 7.30-7.11 (m 8H), 6.89-6.83 (m 2H), 5.42 (s 2H), 4.81-4.72 (m 1H), 3.70 (s 3H), 3.08-3.01 (m 2H), 2.79-2.67 (m 2H), 1.65-1.51 (m 2H), 1.34-1.10 (m 2H), 0.81 (t 3H) |
| 100 | F-1a | 3,4-difluorobenzylamine | 4-methoxybenzylamine | LCMS Method: 4, RT: 1.09 min, MI: 437 [M + 1] | ¹H-NMR, Method 2: (DMSO) 8.38 (t 1H), 8.30 (dd 1H), 7.99 (dd 1H), 7.26 (m 3H), 7.11 (d 2H), 7.01 (m 1H), 6.78 (d 2H), 5.52 (s 2H), 4.18 (d 2H), 3.71 (s 3H), 3.08 (t 2H), 2.73 (t 2H) |
| 101 | F-1f | 2-methoxybenzylamine | 4-methoxybenzylamine | LCMS Method: 4, RT: 1.15 min, MI: 449 [M + 1] | ¹H-NMR, Method 1: (DMSO) 8.40 (t 1H), 8.34 (t 1H), 7.95 (dd 1H), 7.17 (d 2H), 7.14 (d 2H), 6.87 (d 2H), 6.81 (d 2H), 5.44 (s 2H), 4.18 (d 2H), 3.71 (s 3H), 3.70 (s 3H), 3.09 (t 2H), 2.72 (t 2H) |
| 102 | F-1a | 4-methoxybenzylamine | N-methylbenzylamine | LCMS Method: 4, RT: 1.13 min, MI: 415 [M + 1] | ¹H-NMR, Method 2: (DMSO) 8.29 (m 1H), 7.97 (m 1H), 7.19 (m 6H), 6.86 (d 2H), 4.51 and 5.47 (2 × s, rotamers 2H), 3.70 (s 3H), 3.08 (m 2H), 2.95 (m 5H) |

| Example | SM | Amine 1 | Amine 2 | | Characterisation |
|---|---|---|---|---|---|
| 103 | F-1a | 4-methylbenzylamine | 4-methoxybenzylamine | | LCMS Method: 4, RT: 1.11 min, MI: 415 [M + 1] | ¹H-NMR, Method 2: (DMSO) 8.37 (t 1H), 8.30 (dd 1H), 7.98 (dd 1H), 7.25 (dd 2H), 7.07 (m 6H), 6.78 (d 2H), 5.48 (s 2H), 4.18 (d 2H), 3.71 (s 3H), 2.75 (t 2H), 2.70 (t 2H), 2.25 (s 3H) |
| 104 | F-1a | 4-methoxybenzylamine | (S)-N-methyl-1-phenylethylamine | | LCMS Method: 4, RT: 1.20 min, MI: 429 [M + 1] | ¹H-NMR, Method 2: (DMSO) 8.32-8.30 (m 1H), 8.01-7.96 (m 1H), 7.42-7.17 (m 8H), 6.88 (d 2H), 5.49 (s 2H), 5.28, 5.78 (q 1H), 3.70 (s 3H), 3.25-2.70 (m 4H), 2.68 (s 3H), 1.54 (3H d) |
| 105 | F-1a | 4-methoxybenzylamine | (1-methyl-1H-indol-5-yl)methanamine | | LCMS Method: 4, RT: 1.08 min, MI: 454 [M + 1] | — |
| 106 | F-1a | 4-methoxybenzylamine | 2-methylbenzylamine | | LCMS Method: 4, RT: 1.10 min, MI: 415 [M + 1] | ¹H-NMR, Method 2: (DMSO) 8.35 (t 1H), 8.30 (d 1H), 7.98 (d 1H), 7.25 (d 1H), 7.02 (m 6H), 6.86 (d 2H), 5.45 (s 2H), 4.22 (d 2H), 3.70 (s 3H), 3.07 (t 2H), 2.73 (t 2H), 2.21 (s 3H) |
| 107 | F-1a | 4-methoxybenzylamine | 3,4-difluorobenzylamine | | LCMS Method: 4, RT: 1.09 min, MI: 437 [M + 1] | ¹H-NMR, Method 2: (DMSO) 8.54 (t 1H), 8.31 (dd 1H), 7.97 (dd 1H), 7.10 (m 6H), 6.86 (d 2H), 5.45 (s 2H), 4.25 (d 2H), 3.70 (s 3H), 3.09 (t 2H), 2.74 (t 2H) |
| 108 | F-1a | 4-methoxybenzylamine | 4-methylphenethylamine | | LCMS Method: 4, RT: 1.15 min, MI: 430 [M + 1] | ¹H-NMR, Method 1: (DMSO) 8.33-8.30 (m 1H), 8.04-7.96 (m 2H), 7.28-7.23 (m 1H), 7.18-7.14 (m 2H), 7.07-7.01 (m 4H), 6.91-6.85 (m 2H), 5.45 (s 2H), 3.71 (s 3H), 3.33-3.18 (m 2H), 3.07-2.99 (m 2H), 2.74-2.60 (m 4H), 2.24 (s 3H) |
| 109 | F-1c | 4-fluorobenzylamine | 4-methoxybenzylamine | | LCMS Method: 1, RT: 3.89 min, MI: 433 [M + 1] | ¹H-NMR, Method 1: (DMSO) 8.40 (t 1H), 8.16 (d 1H), 7.81 (d 1H), 7.27-7.23 (m 2H), 7.17-7.11 (m 4H), 6.80 (dt 2H), 5.48 (s 2H), 4.19 (d 2H), 3.71 (s 3H), 3.06 (t 2H), 2.72 (t 2H), 2.42 (s 3H) |
| 110 | F-1a | 3-fluorobenzylamine | 4-methoxybenzylamine | | LCMS Method: 4, RT: 1.06 min, MI: 419 [M + 1] | ¹H-NMR, Method 2: (DMSO) 8.38 (t 1H), 8.30 (dd 1H), 8.00 (dd 1H), 7.33 (m 1H), 7.26 (dd 2H), 6.99 (m 5H), 6.78 (d 2H), 5.56 (s 2H), 4.18 (d 2H), 3.71 (s 3H), 3.07 (t 2H), 2.73 (t 2H) |
| 111 | F-1a | benzylamine | cyclohexylmethanamine | | LCMS Method: 1, RT: 4.18 min, MI: 377 [M + 1] | ¹H-NMR, Method 1: (DMSO) 8.30 (d 1H), 7.97 (d 1H), 7.89 (t 1H), 7.34-7.24 (m 4H), 7.20-7.18 (m 2H), 5.54 (s 2H), 3.04 (t 2H), 2.87 (t 2H), 2.66 (t 2H), 1.60-1.58 (m 5H), 1.36-1.26 (m 1H), 1.15-1.04 (m 3H), 0.82-0.74 (m 2H) |

| Example | SM | Amine 1 | Amine 2 | Characterisation | |
|---|---|---|---|---|---|
| 112 | F-1a |  | 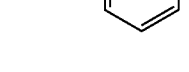 | LCMS Method: 4, RT: 1.09 min, MI: 415 [M + 1] | ¹H-NMR, Method 2: (DMSO) 1.31 (d 3H), 2.72 (m 2H), 3.03 (m 2H), 3.70 (s 3H), 4.84 (m 1H), 5.42 (s 2H), 6.85 (d 2H), 7.14 (m 8H), 7.98 (dd 1H), 8.30 (dd 1H), 8.38 (d 1H) |
| 113 | F-1a | 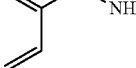 | 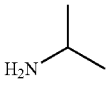 | LCMS Method: 4, RT: 0.98 min, MI: 353 [M + 1] | ¹H-NMR, Method 2: (DMSO) 8.29 (dd 1H), 7.96 (dd 1H), 7.78 (d 1H), 7.23 (dd 2H), 7.15 (d 2H), 6.87 (d 2H), 5.45 (s 2H), 3.76 (m 1H), 3.71 (s 3H), 3.01 (t 2H), 2.60 (t 2H), 1.01 (d 6H) |
| 114 | F-1a |  |  | LCMS Method: 4, RT: 1.07 min, MI: 419 [M + 1] | ¹H-NMR, Method 2: (DMSO) 8.50 (t 1H), 8.31 (dd 1H), 7.98 (dd 1H), 7.04 (m 7H), 6.86 (d 2H), 5.44 (s 2H), 4.29 (d 2H), 3.70 (s 3H), 3.07 (t 2H), 2.74 (t 2H) |
| 115 | F-1a | 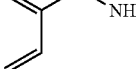 | 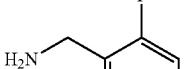 | LCMS Method: 4, RT: 1.11 min, MI: 415 [M + 1] | ¹H-NMR, Method 2: (DMSO) 8.45 (t 1H), 8.30 (dd 1H), 7.97 (m 1H), 7.24 (dd 1H), 7.00 (m 6H), 6.86 (d 2H), 5.45 (s 2H), 4.22 (d 2H), 3.70 (s 3H), 3.07 (t 2H), 2.73 (t 2H), 2.22 (s 3H) |
| 116 | F-1a |  | 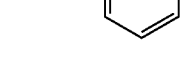 | LCMS Method: 4, RT: 1.08 min, MI: 446 [M + 1] | ¹H-NMR, Method 2: (DMSO) 8.30 (dd 1H), 7.96 (m 2H), 7.23 (dd 1H), 7.15 (d 2H), 7.07 (d 2H), 6.87 (d 2H), 6.78 (d 2H), 5.45 (s 2H), 3.71 (s 3H), 3.70 (s 3H), 3.18 (m 2H), 3.02 (t 2H), 2.59 (m 4H) |
| 117 | F-1a | 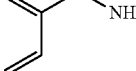 | 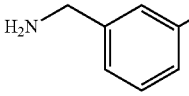 | LCMS Method: 4, RT: 1.07 min MI: 420 | ¹H-NMR, Method 2: (DMSO) 8.52 (t 1H), 8.31 (dd 1H), 7.97 (dd 1H), 7.24 (m 2H), 7.17 (d 2H), 6.99 (m 3H), 6.86 (d 2H), 5.45 (s 2H), 4.41 (d 2H), 3.70 (s 3H), 3.09 (t 2H), 2.75 (t 2H) |
| 118 | F-1a |  |  | LCMS Method: 4, RT: 1.13 min MI: 416 | ¹H-NMR, Method 2: (DMSO) 8.38 (t 1H), 8.30 (dd 1H), 7.99 (dd 1H), 7.25 (dd 2H), 6.94 (m 6H), 6.78 (d 2H), 5.49 (s 2H), 4.18 (d 2H), 3.71 (s 3H), 3.05 (t 2H), 2.71 (t 2H), 2.24 (s 3H) |
| 119 | F-1a | 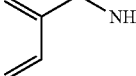 | 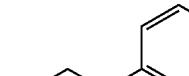 | LCMS Method: 4, RT: 1.17 min MI: 434 | ¹H-NMR, Method 2: (DMSO) 8.32-8.30 (m 1H), 8.03-8.00 (m 1H), 7.19-7.08 (m 7H), 6.89-6.86 (m 2H), 5.48, (s 2H), 4.60 and 4.48 (s 2H, rotamers), 3.70 (s 3H), 3.14-3.09 (m 2H), 2.94 (s 3H), 2.98-2.91 (m 2H) |
| 120 | F-1a |  |  | LCMS Method: 4, RT: 1.33 min MI: 539 | ¹H-NMR, Method 2: (DMSO) 8.53 (t 1H), 8.28 (dd 1H), 8.03 (dd 1H), 7.44 (d 2H), 7.30 (m 6H), 6.83 (d 2H), 5.59 (s 2H), 4.27 (d 2H), 3.03 (t 2H), 2.77 (t 2H) |

General Synthesis of 3-(3-aralkyl-3H-imidazo[4,5-b]pyridin-2-yl)-propionamide of general formula F-5 (Scheme 002-C)

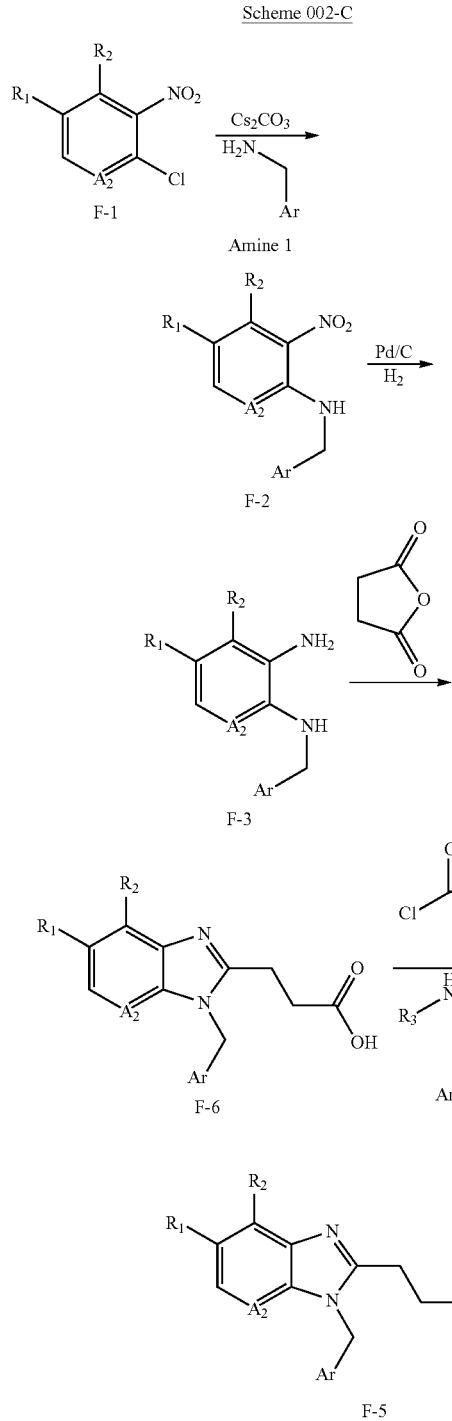

F-1 could be any of the following intermediates:

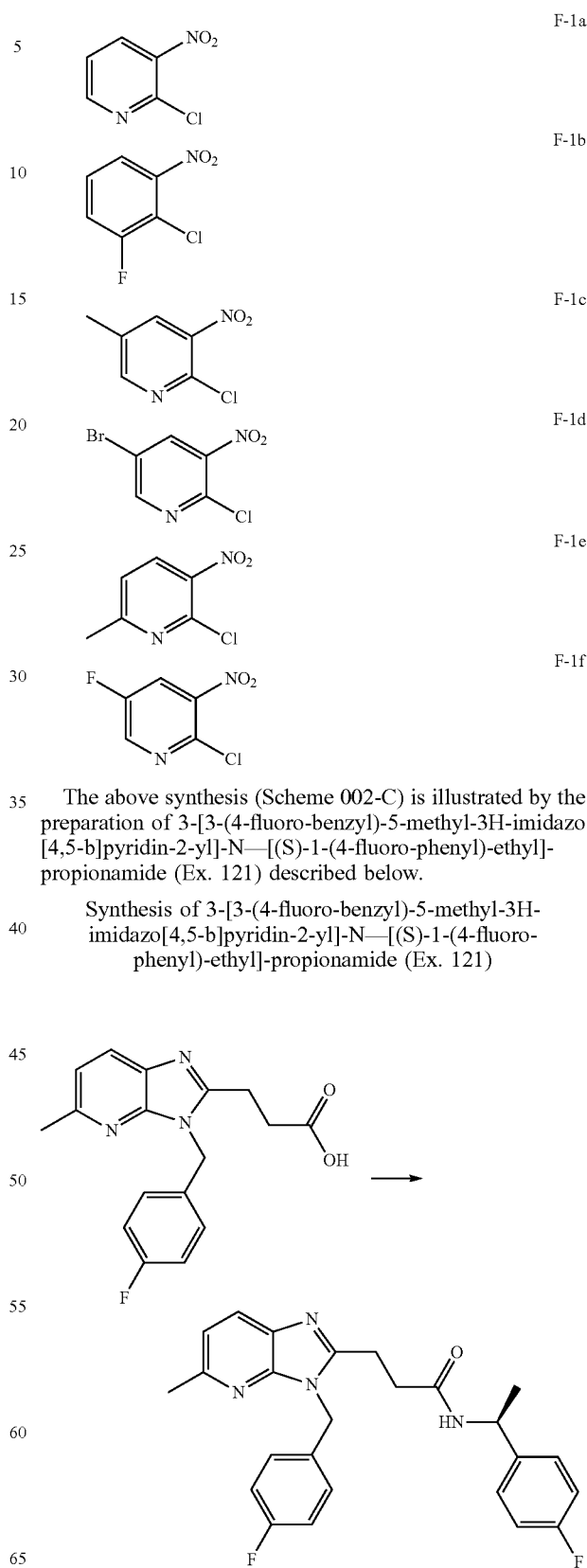

The above synthesis (Scheme 002-C) is illustrated by the preparation of 3-[3-(4-fluoro-benzyl)-5-methyl-3H-imidazo[4,5-b]pyridin-2-yl]-N—[(S)-1-(4-fluoro-phenyl)-ethyl]-propionamide (Ex. 121) described below.

Synthesis of 3-[3-(4-fluoro-benzyl)-5-methyl-3H-imidazo[4,5-b]pyridin-2-yl]-N—[(S)-1-(4-fluoro-phenyl)-ethyl]-propionamide (Ex. 121)

Intermediates F-2 and F-3 were prepared as in Scheme 001. Intermediate F-6 was prepared as in Scheme 002-A. Intermediate F-6, was treated with oxalyl chloride and the required Amine 2 in DCM at r.t. to afford the final compounds of general formula F-5.

In a round bottom flask fitted with magnetic stirrer, 3-[3-(4-fluoro-benzyl)-5-methyl-3H-imidazo[4,5-b]pyridin-2-yl]-propionic acid (360 mg, 1.150 mmol) were suspended in DCM (15 ml). This suspension was cooled in an ice bath and then treated with 2 drops of DMF followed by dropwise addition of oxalyl chloride (0.5 ml, 5.75 mmol). The resultant solution was warmed to r.t. whilst stirring for 1 hour. The solution was evaporated and azeotroped from DCM and the crude acid chloride was redissolved in DCM (5 ml). In a separate round bottom flask fitted with magnetic stirrer, a solution of (S)-1-(4-fluoro-phenyl)-ethylamine (310 μl, 2.30 mmol) in pyridine (4 ml) was treated with the aforementioned acid chloride solution and stirred at r.t. for 5 hours. Reaction mixture was diluted with DCM, washed with water and brine, dried and evaporated under reduced pressure. The crude product was dissolved in MeOH and half of the solution was purified by reverse phase mass-directed preparative HPLC using either LCMS method 5 or 6. Product fractions were combined and evaporated in the Genevac™ to afford the title compound (66 mg, 24%).

LCMS Method: 5 LCMS1, RT: 3.94 min, MI: 435 [M+1]

$^1$H NMR, Method 1: (DMSO) 8.43 (d 1H), 7.89 (d 1H), 7.31-7.28 (m 2H), 7.23-7.19 (m 2H), 7.17-7.12 (m 3H), 7.04 (tt 2H), 5.44 (s 2H), 4.91-4.84 (m 1H), 3.04-2.91 (m 2H), 2.77-2.63 (m 2H), 2.56 (s 3H), 1.31 (d 3H).

General Synthesis of 3-(3-aralkyl-3H-imidazo[4,5-c]pyridin-2-yl)-propionamide of general formula F-12 (Scheme 003)

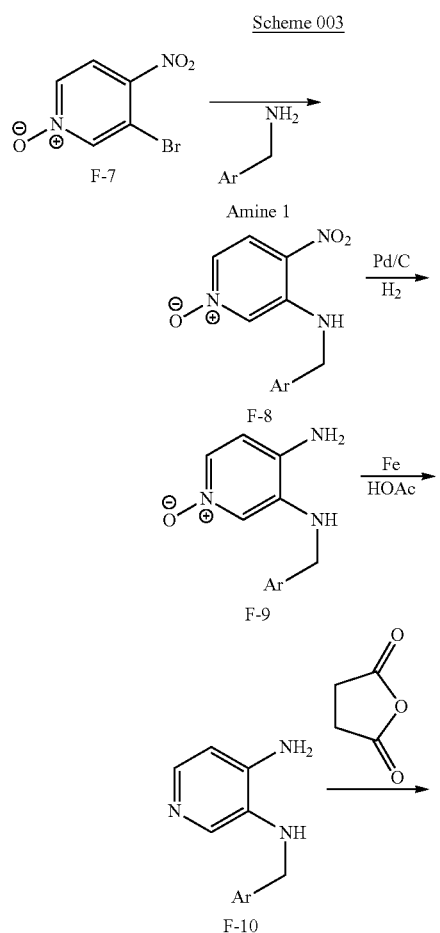

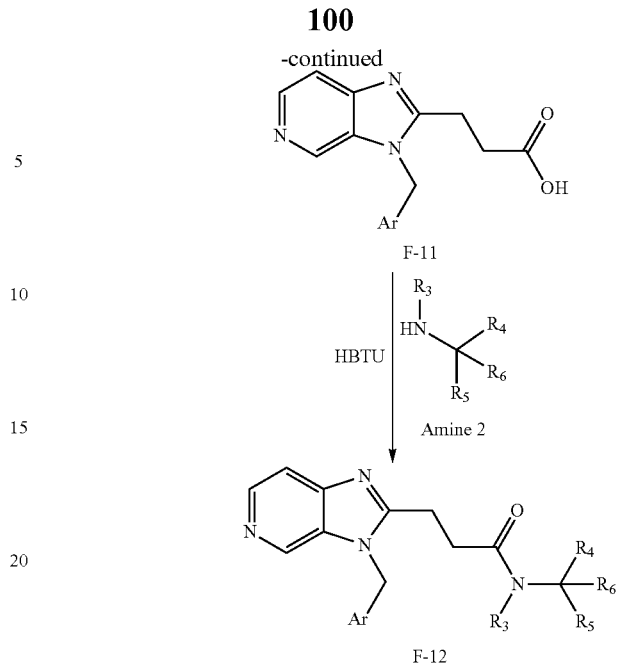

Commercially available 3-bromo-4-nitro-pyridine 1-oxide of formula F-7 was reacted with the required amine 1 in propanol at 90° C. to yield the aralkyl-(4-nitro-1-oxy-pyridin-3-yl)-amine derivative of general formula F-8, which was hydrogenated over Pd/C in EtOH to afford N'3'-aralkyl-1-oxy-pyridine-3,4-diamine of general formula F-9. This was treated with Fe powder in HOAc at reflux to yield N'3'-aralkyl-pyridine-3,4-diamine of general formula F-10. This intermediate was reacted with succinic anhydride in dioxane at reflux, and then treated with HOAc. The obtained carboxylic acid, of general formula F-11, was treated with HBTU and the required amine 2 in DCM to afford the final compounds of general formula F-12. The final compounds could alternatively have been obtained from treatment of the same carboxylic acid with CDI and the required Amine 2 as described in Scheme 002-B.

The above synthesis (Scheme 003) is illustrated by the preparation of N—[(S)-1-(4-chloro-phenyl)-ethyl]-3-[3-(4-trifluoromethoxy-benzyl)-3H-imidazo[4,5-c]pyridin-2-yl]-propionamide (Ex. 122) described below.

Synthesis of (4-nitro-1-oxy-pyridin-3-yl)-(4-trifluoromethoxy-benzyl)-amine

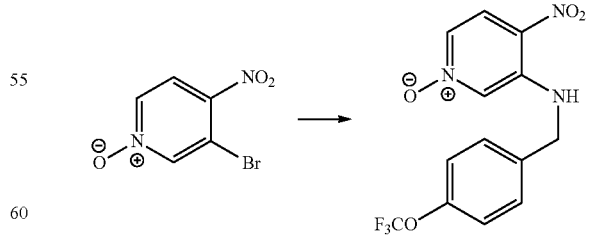

In a round bottom flask fitted with magnetic stirrer and reflux condenser, 3-bromo-4-nitro-pyridine 1-oxide (5.3 g, 24.25 mmol) and 4-(trifluoromethoxy)benzylamine (9.28 g, 48.55 mmol) were dissolved in propanol (50 ml) and heated to 90° C. for 5 hours. Reaction mixture was allowed to cool overnight whilst stirring, with a solid crashing out of the reaction crude. This solid was filtered off, washed with IPA (2×10 ml) and dried in vacuo to afford the title compound (4.64 g, 58%).

LCMS Method: 2, RT: 6.50 min, MI: 330 [M+1]

¹H NMR, Method 1: (DMSO) 8.82 (t 1H), 8.05 (d 1H), 7.94 (d 1H), 7.52 (d 2H), 7.49 (dd 1H), 7.36 (d 2H), 4.68 (d 2H).

Synthesis of 1-oxy-N'3'-(4-trifluoromethoxy-benzyl)-pyridine-3,4-diamine

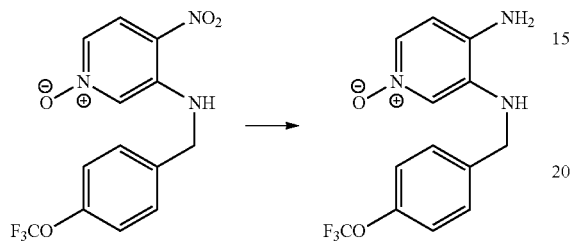

In a round bottom flask fitted with magnetic stirrer, (4-nitro-1-oxy-pyridin-3-yl)-(4-trifluoromethoxy-benzyl)-amine (3.36 g, 10.2 mmol) were added in and flask was purged with $N_2$. Pd/C (400 mg) was added and solids were suspended in MeOH (200 ml). Mixture was purged with more $N_2$ and a double balloon filled with $H_2$ was fitted onto the flask. Suspension was allowed to stir at r.t. overnight under an atmosphere of $H_2$ and subsequently filtered through Celite® to remove the catalyst. Filtrate was concentrated at reduced pressure to afford the title compound (3 g, 98%).

LCMS Method: 1, RT: 2.70 min, MI: 300 [M+1]

Synthesis of N'3'-(4-trifluoromethoxy-benzyl)-pyridine-3,4-diamine

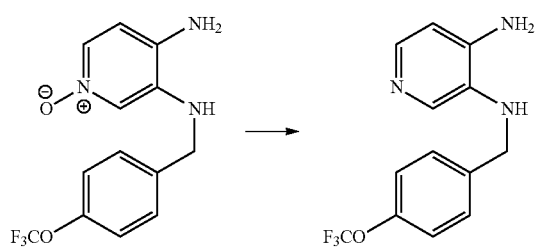

In a round bottom flask fitted with a magnetic stirrer and a reflux condenser, 1-oxy-N'3'-(4-trifluoromethoxy-benzyl)-pyridine-3,4-diamine (3.01 g, 10.05 mmol) and Fe powder (800 mg, 15 mmol) were dissolved in HOAc (40 ml) and heated at 90° C. overnight. Reaction crude was quenched with NaOH 2N aqueous solution until pH 7, and then extracted with EtOAc. Organic phases were combined, washed with 10% EDTA solution, filtered through a silicone treated filter paper and concentrated under reduced pressure. Crude material was purified by column chromatography with a gradient of cyclohexane and EtOAc, followed by a gradient of EtOAc and MeOH, product eluted with 20% MeOH in EtOAc. Product fractions were combined and concentrated under reduced pressure to afford the title compound (2.86 g, 100%).

LCMS Method: 1, RT: 2.51 min, MI: 284 [M+1]

Synthesis of 3-[3-(4-trifluoromethoxy-benzyl)-3H-imidazo[4,5-c]pyridin-2-yl]-propionic acid

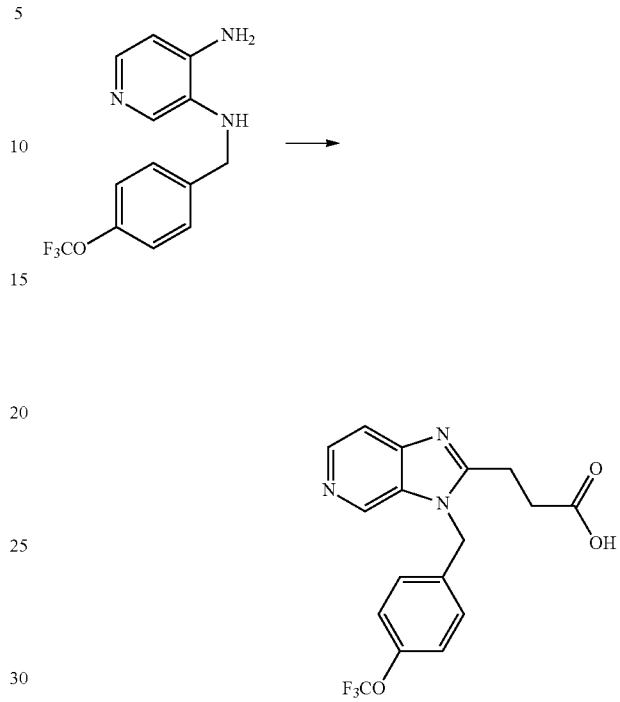

In a round bottom flask, fitted with a magnetic stirrer and reflux condenser, N'3'-(4-trifluoromethoxy-benzyl)-pyridine-3,4-diamine (2.86 g, 10.1 mmol) and succinic anhydride (1 g, 10.1 mmol) were dissolved in dioxane (70 ml) and HOAc (35 ml). This mixture was heated at 80° C. over the weekend. The reaction mixture was treated then with further HOAc (25 ml) and heated to reflux for a further 24 hours. Reaction crude was allowed to cool down and then concentrated under reduced pressure. Crude material was dissolved in MeOH (30 ml) and filtered through SCX (25 g) previously soaked in MeOH. Title compound was released off the SCX resin with ammonia in MeOH 0.4 M. Eluent was concentrated under reduced pressure and recrystallized in DCM to afford the title compound (1.16 g, 31%).

LCMS Method: 1, RT: 2.34 min, MI: 366 [M+1]

Synthesis of N—[(S)-1-(4-chloro-phenyl)-ethyl]-3-[3-(4-trifluoromethoxy-benzyl)-3H-imidazo[4,5-c]pyridin-2-yl]-propionamide (Ex. 122)

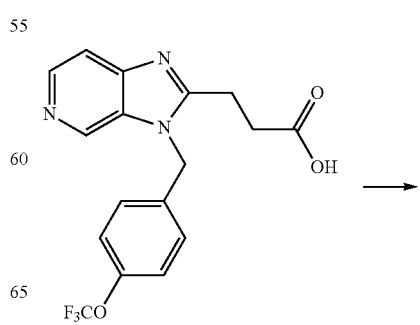

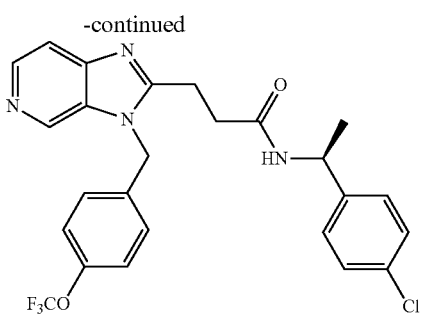

In a round bottom flask fitted with a magnetic stirrer, 3-[3-(4-trifluoromethoxy-benzyl)-3H-imidazo[4,5-c]pyridin-2-yl]-propionic acid (100 mg, 0.27 mmol), Hunig's base (100 μl, 0.54 mmol) and (S)-1-(4-chloro-phenyl)-ethylamine (50 μl, 0.324 mmol) were dissolved in DCM (20 ml). Mixture was cooled with an ice bath, and then HBTU (204 mg, 0.54 mmol) was added. Reaction mixture was allowed to stir at r.t. for 1 hour until complete conversion. Crude mixture was concentrated under reduced pressure and purified by column chromatography with a gradient of EtOAc and cyclohexane, required product eluted with neat EtOAc. Required product fractions were combined and concentrated under reduced pressure to afford a solid which was further purified by reverse phase mass-directed preparative HPLC, using either LCMS Method 5 or 6. Required fractions were concentrated in the Genevac™ to afford the title compound (28 mg, 30%).

The following compounds of general formula F-12 were prepared according to the general synthesis shown in Scheme 003:

| Example | SM | Amine 1 | Amine 2 | Characterisation | |
|---|---|---|---|---|---|
| 122 | F-7 | 4-F3CO-benzyl-NH2 | (S)-1-(4-Cl-phenyl)ethylamine | LCMS Method: 1, RT: 3.05 min, MI: 503/505 [M + 1] | $^1$H-NMR, Method 1: (CDCl$_3$) 8.63 (s 1H), 8.47 (d 1H), 7.61 (dd 1H), 7.16-7.06 (m 8H), 6.47 (d 1H), 5.41 (d 1H), 5.36 (d 1H), 5.00-4.93 (m 1H), 3.21-3.08 (m 2H), 2.95-2.83 (m 2H), 1.39 (d 3H) |
| 123 | F-7 | 4-F3CO-benzyl-NH2 | (S)-2-hydroxy-1-phenyl-ethylamine | LCMS Method: 1, RT: 2.61 min, MI: 485 [M + 1] | $^1$H-NMR, Method 1: (CDCl$_3$) 8.55 (d 1H), 8.34 (d 1H), 7.20-7.00 (10H), 5.34 (s 2H), 5.07-5.03 (m 1H), 3.98-3.87 (m 2H), 3.65 (br 2H), 3.25-3.03 (m 3H), 2.88-2.82 (m 1H) |
| 124 | F-7 | 4-F3CO-benzyl-NH2 | (S)-1-(4-F-phenyl)ethylamine | LCMS Method: 1, RT: 2.94 min, MI: 487 [M + 1] | $^1$H-NMR, Method 1: (CDCl$_3$) 8.63 (d 1H), 8.45 (d 1H), 7.60 (dd 1H), 7.16-7.07 (m 6H), 6.82 (tt 2H), 6.56 (d 1H), 5.42 (d 1H), 5.37 (d 1H), 5.02-4.95 (m 1H), 3.21-3.08 (m 2H), 2.94-2.83 (m 2H), 1.38 (d 3H) |
| 125 | F-7 | 4-F3CO-benzyl-NH2 | (S)-1-[4-(4-methylpiperazin-1-yl)phenyl]ethylamine | LCMS Method: 1, RT: 2.05 min, MI: 284 [M + 1] | $^1$H-NMR, Method 1: (CDCl$_3$) 8.62 (s 1H), 8.45 (d 1H), 7.63 (d 1H), 7.16-7.00 (m 6H), 6.67 (d 2H), 6.25 (d 1H), 5.43 (d 1H), 5.37 (d 1H), 4.98-4.91 (m 1H), 3.19-3.14 (m 6H), 2.93-2.81 (m 2H), 2.72 (t 4H), 2.43 (s 3H), 1.37 (d 3H) |
| 126 | F-7 | 4-F3CO-benzyl-NH2 | 2-hydroxy-1-(4-OCF3-phenyl)ethylamine | LCMS Method: 1, RT: 2.95 min, MI: 569 [M + 1] | $^1$H-NMR, Method 1: (CDCl$_3$) 8.60 (s 1H), 8.40 (d 1H), 7.39 (dd 1H), 7.26-7.21 (m 2H), 7.15-7.13 (m 2H), 7.07-7.05 (m 2H), 6.99-6.97 (m 2H), 5.37 (s 2H), 5.07-5.03 (m 1H), 3.91 (ddd 2H), 3.18 (t 2H), 3.03-2.96 (m 1H), 2.91-2.84 (m 1H) |
| 127 | F-7 | 4-F-benzyl-NH2 | 1-phenyl-propylamine | LCMS Method: 4, RT: 1.05 min, MI: 418 [M + 1] | $^1$H-NMR, Method 2: (DMSO) 8.86 (br s1 H), 8.45-8.34 (m 2H), 7.64-7.60 (m 1H), 7.34-7.16 (m 9H), 5.61 (s 2H), 4.77-4.68 (m 1H), 3.16 (t 2H), 2.85 (t 2H), 1.79-1.63 (m 2H), 0.86 (t 3H) |

-continued

| Example | SM | Amine 1 | Amine 2 | Characterisation | |
|---|---|---|---|---|---|
| 128 | F-7 | 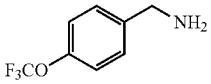 | 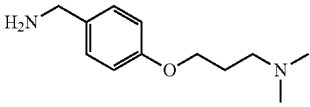 | LCMS Method: 1, RT: 2.06 min, MI: 278 [M + 1] | ¹H-NMR, Method 1: (DMSO) 8.82 (s 1H), 8.43 (t 1H), 8.32 (d 1H), 7.60 (d 1H), 7.36-7.31 (m 4H), 7.10 (dt 2H), 6.77 (dt 2H), 5.66 (s 2H), 4.19 (d 2H), 3.94 (t 2H), 3.14 (t 2H), 2.79 (t 2H), 2.40 (t 2H), 2.19 (s 6H), 1.87-1.80 (m 2H) |
| 129 | F-7 | 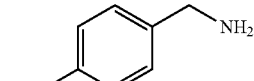 | 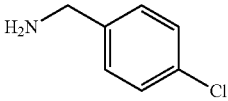 | LCMS Method: 1, RT: 2.96 min, MI: 489/491 [M + 1] | ¹H-NMR, Method 1: (CDCl₃) 8.64 (d 1H), 8.45 (d 1H), 7.58 (dd 1H), 7.20-7.04 (m 8H), 6.66 (t 1H), 5.44 (s 2H), 4.35 (d 2H), 3.17 (t 2H), 2.93 (t 2H) |
| 130 | F-7 | 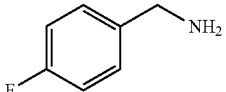 | 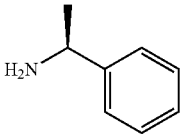 | LCMS Method: 4, RT: 0.99 min, MI: 404 [M + 1] | ¹H-NMR, Method 1: (DMSO) 8.81 (s 1H), 8.43 (br d 1H), 8.30 (d 1H), 7.60-7.57 (m 1H), 7.29-7.12 (m 9H), 5.56 (s 2H), 4.92-4.85 (m 1H), 3.15-3.07 (m 2H), 2.83-2.70 (m 2H), 1.33 (d 3H) |
| 131 | F-7 | 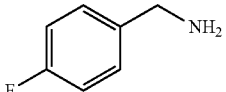 | 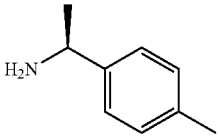 | LCMS Method: 4, RT: 1.07 min, MI: 418 [M + 1] | ¹H-NMR, Method 1: (DMSO) 8.81 (s 1H), 8.37 (br d 1H), 8.30 (d 1H), 7.59-7.56 (m 1H), 7.28-7.00 (m 8H), 5.56 (s 2H), 4.89-4.82 (m 1H), 3.14-3.07 (m 2H), 2.80-2.72 (m 2H), 2.24 (s 3H), 1.30 (d 3H) |
| 132 | F-7 | 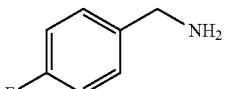 | 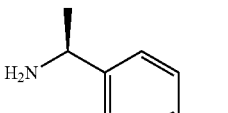 | LCMS Method: 4, RT: 1.03 min, MI: 422 [M + 1] | ¹H-NMR, Method 1: (DMSO) 8.81 (s 1H), 8.45 (br d 1H), 8.31 (d 1H), 7.60-7.56 (m 1H), 7.32-6.98 (m 8H), 5.56 (s 2H), 4.94-4.84 (m 1H), 3.20-3.02 (m 2H), 2.87-2.69 (m 2H), 1.32 (d 3H) |
| 133 | F-7 | 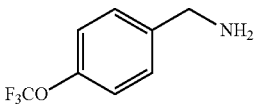 | 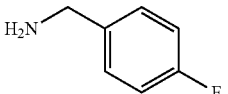 | LCMS Method: 1, RT: 2.85 min, MI: 473 [M + 1] | ¹H-NMR, Method 1: (CDCl₃) 8.63 (s 1H), 8.43 (d 1H), 7.57 (d 1H), 7.18-7.06 (m 6H), 6.84 (t 2H), 6.76 (br 1H), 5.45 (s 2H), 4.34 (d 2H), 3.16 (t 2H), 2.92 (t 2H) |
| 134 | F-7 | 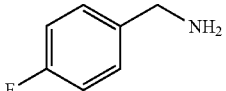 | 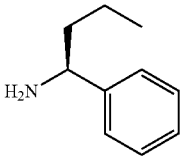 | LCMS Method: 4, RT: 1.03 min, MI: 422 [M + 1] | ¹H-NMR, Method 1: (DMSO) 8.81 (s 1H), 8.45 (br d 1H), 8.31 (d 1H), 7.60-7.56 (m 1H), 7.32-6.98 (m 8H), 5.56 (s 2H), 4.94-4.84 (m 1H), 3.20-3.02 (m 2H), 2.87-2.69 (m 2H), 1.32 (d 3H) |
| 135 | F-7 | 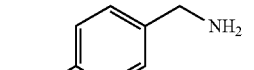 | 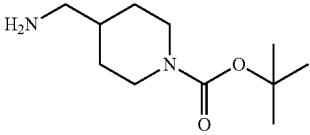 | LCMS Method: 1, RT: 3.00 min, MI: 562 [M + 1] | ¹H-NMR, Method 1: (CDCl₃) 8.67 (s 1H), 8.45 (d 1H), 7.60 (dd 1H), 7.20-7.13 (m 4H), 6.20 (t 1H), 5.48 (s 2H), 4.02 (br 2H), 3.17 (t 2H), 3.11 (br 2H), 2.89 (t 2H), 2.57 (t 2H), 2.39 (br 1H), 1.55 (br 2H), 1.44 (s 9H), 1.09-1.01 (m 2H) |
| 136 | F-7 | 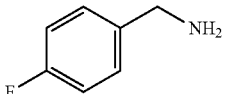 | 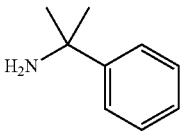 | LCMS Method: 1, RT: 1.04 min, MI: 418 [M + 1] | ¹H-NMR, Method 1: (DMSO) 8.82 (s 1H), 8.34-8.30 (m 1H), 8.20 (br s 1H), 7.64-7.61 (m 1H), 7.26-7.04 (m 9H), 5.54 (s 2H), 3.06 (br t 2H), 2.80 (br t 2H), 1.51 (s 6H) |

General Synthesis of 3-(1-aralkyl-1H-pyrrolo[2,3-b]pyridin-2-yl)-propionamide of general formula F-17
(Scheme 004)

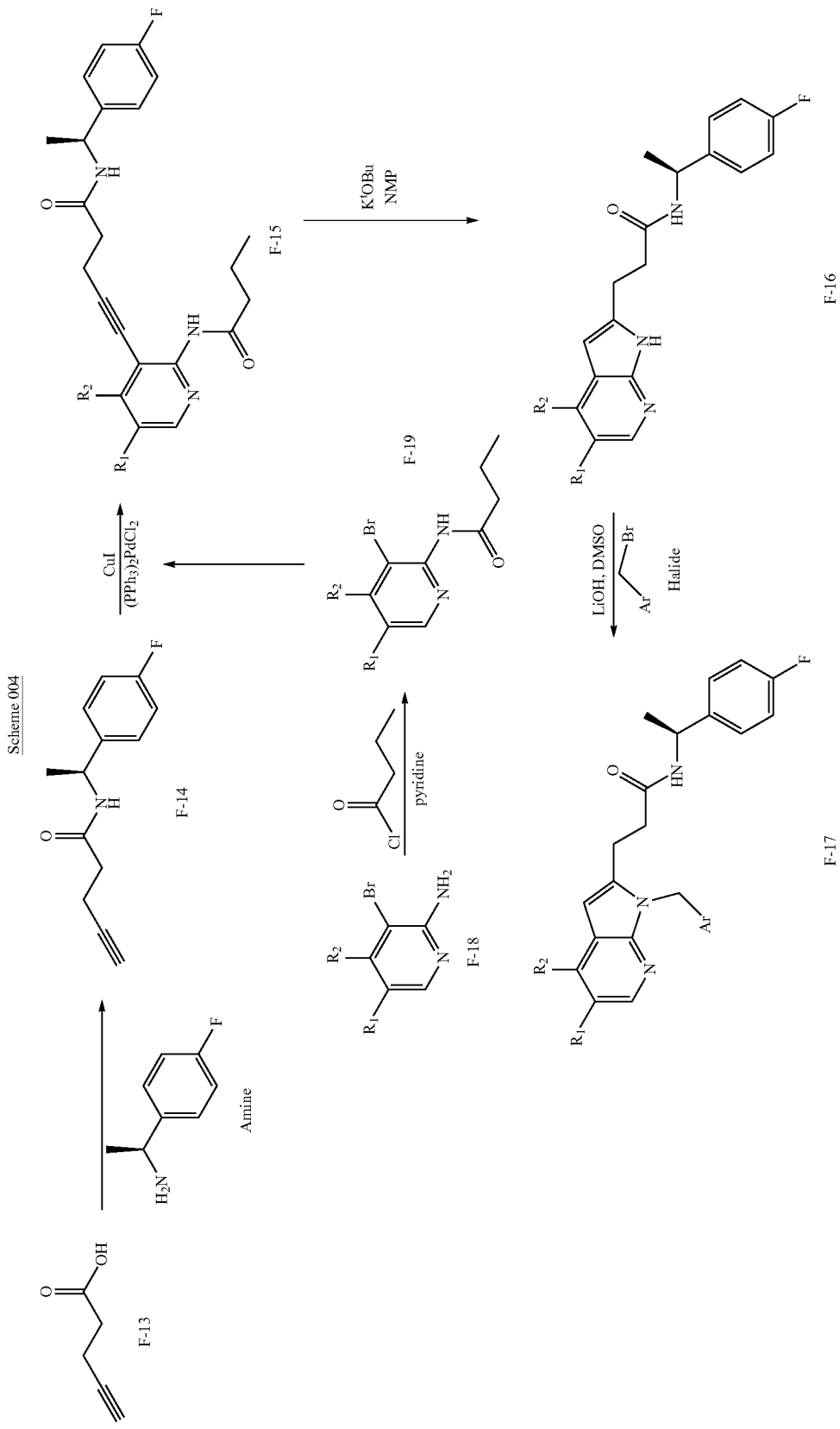

Commercially available 4-pentynoic acid of formula F-13 was reacted with the required amine and HBTU in DMF at r.t. to afford the pent-4-ynoic acid [(S)-1-(4-fluoro-phenyl)-ethyl]-amide of formula F-14. This intermediate was submitted to a Sonogashira coupling with N-(3-bromo-pyridin-2-yl)-butyramide of general formula F-19 to yield the 5-(2-butyrylamino-pyridin-3-yl)-pent-4-ynoic acid [(S)-1-(4-fluoro-phenyl)-ethyl]-amide of general formula F-15. This was treated with KtOBu in NMP at 50° C. to yield the N—[(S)-1-(4-fluoro-phenyl)-ethyl]-3-(1H-pyrrolo[2,3-b]pyridin-2-yl)-propionamide of general formula F-16 which was subsequently reacted with the required halide and LiOH in DMSO to afford the final compounds of general formula F-17.

F-18 could be any of the following intermediates:

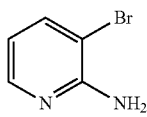
F-18a

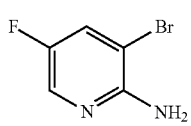
F-18b

The above synthesis (Scheme 004) is illustrated by the preparation of N—[(S)-1-(4-fluoro-phenyl)-ethyl]-3-[1-(4-trifluoromethoxy-benzyl)-1H-pyrrolo[2,3-b]pyridin-2-yl]-propionamide (Ex. 137) described below.

Synthesis of N-(3-bromo-pyridin-2-yl)-butyramide

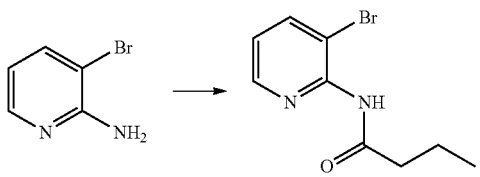

In a round bottom flask fitted with magnetic stirrer, 2-amino-3-bromopyridine (5.72 g, 33.09 mmol) was dissolved in pyridine (30 ml). This solution was cooled with an ice bath and butyryl chloride (3.5 ml, 33.5 mmol) was added dropwise. Reaction mixture was allowed to stir at 10° C. for 2 hours and then at r.t. overnight. Reaction crude was diluted with EtOAc and washed (×3) with water. Organic phase was, filtered through a silicone treated filter paper and concentrated under reduced pressure. The crude product was purified by column chromatography with a gradient of MeOH and DCM, required product eluted with 3% of MeOH. Product fractions were combined and concentrated under reduced pressure to afford the title compound (5.72 g, 71%) as an oil which crystallized upon standing.

LCMS Method: 1, RT: 2.84 min, MI: 243 [M+1]

$^1$H NMR, Method 1: (CDCl$_3$) 8.36 (dd 1H), 7.86 (dd 2H), 6.95 (dd 1H), 2.64 (t 2H), 1.82-1.72 (m 2H), 1.02 (t 3H).

Synthesis of pent-4-ynoic acid [(S)-1-(4-fluoro-phenyl)-ethyl]-amide

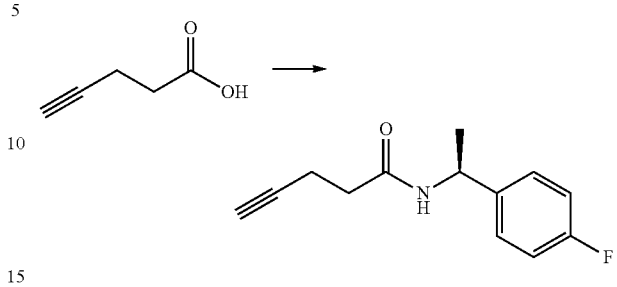

In a round bottom flask fitted with magnetic stirrer, 4-pentynoic acid (1.5 g, 15.3 mmol) and (S)-1-(4-fluoro-phenyl)-ethylamine (1.8 ml, 16.83 mmol) were dissolved in DCM (50 ml) and then treated with Hunig's base (5.4 ml, 30.6 mmol) and HBTU (11.6 g, 30.6 mmol). This mixture was allowed to stir overnight at r.t. Reaction crude was concentrated under reduced pressure and purified by column chromatography with a gradient of EtOAc and cyclohexane, required product eluted with 40% EtOAc. Required product fractions were combined and concentrated under reduced pressure to afford the title compound (3.21 g, 96%).

LCMS Method: 1, RT: 3.78 min, MI: 220 [M+1]

Synthesis of 5-(2-butyrylamino-pyridin-3-yl)-pent-4-ynoic acid [(S)-1-(4-fluoro-phenyl)-ethyl]-amide

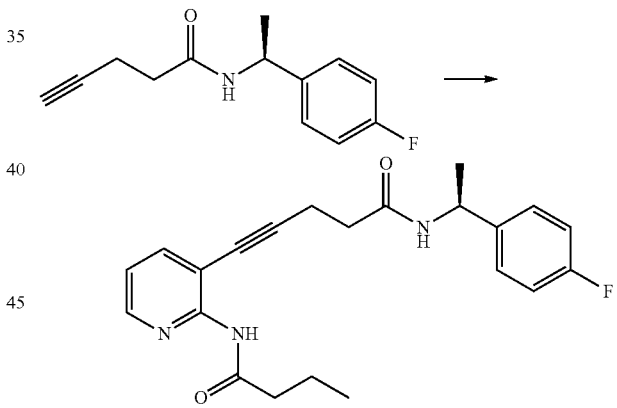

In a round bottom flask fitted with magnetic stirrer, pent-4-ynoic acid [(S)-1-(4-fluoro-phenyl)-ethyl]-amide (2.65 g, 12.1 mmol), N-(3-bromo-pyridin-2-yl)-butyramide (2.67 g, 11 mmol), Pd(PPh$_3$)$_2$Cl$_2$ (231 mg, 0.33 mmol), CuI (100 mg, 0.55 mmol) and TBAI (4 g, 11 mmol) were dissolved in anhydrous DMF (25 ml) and treated with Et$_3$N (4.6 ml, 33 mmol). This mixture was allowed to stir under N$_2$ at r.t. for 4 days. Reaction crude was quenched with water and extracted with EtOAc. Organic phases were combined, filtered through a silicone treated filter paper and concentrated under reduced pressure. Crude material was purified by column chromatography with a gradient of EtOAc and cyclohexane, required product eluted with 75% EtOAc. Required product fractions were combined and concentrated under reduced pressure to afford the title compound (2.8 g, 67%)

LCMS Method: 1, RT: 3.45 min, MI: 382 [M+1]

¹H NMR, Method 1: (CDCl₃) 8.31 (dd 1H), 7.74 (dd 1H), 7.21-7.15 (m 3H), 6.92 (tt 2H), 6.35 (s 1H), 5.92 (d 1H), 3.59 (t 2H), 3.37 (td 2H), 2.60 (t 2H), 1.87-1.78 (m 2H), 1.57-1.54 (m 1H), 1.43 (d 3H), 1.07 (t 3H).

Synthesis of N—[(S)-1-(4-fluoro-phenyl)-ethyl]-3-(1H-pyrrolo[2,3-b]pyridin-2-yl)-propionamide

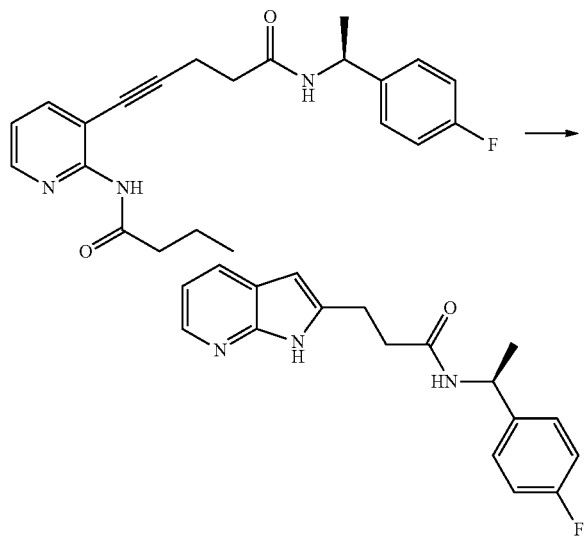

In a round bottom flask fitted with magnetic stirrer and reflux condenser, 5-(2-butyrylamino-pyridin-3-yl)-pent-4-ynoic acid [(S)-1-(4-fluoro-phenyl)-ethyl]-amide (2.82 g, 7.4 mmol) and KtOBu (913 mg, 8.14 mmol) were dissolved in NMP (25 ml). Mixture was heated at 50° C. for 24 hours. Reaction crude was quenched with water and extracted with EtOAc. Organic phases were combined, filtered through a silicone treated filter paper and concentrated under reduced pressure. Residue obtained was purified by column chromatography with a gradient of EtOAc and cyclohexane, required product eluted with neat EtOAc. Required fractions were combined and concentrated under reduced pressure to afford the title compound (2.3 g, 100%)

LCMS Method: 1, RT: 2.68 min, MI: 312 [M+1]

Synthesis of N—[(S)-1-(4-fluoro-phenyl)-ethyl]-3-[1-(4-trifluoromethoxy-benzyl)-1H-pyrrolo[2,3-b]pyridin-2-yl]-propionamide (Ex. 137)

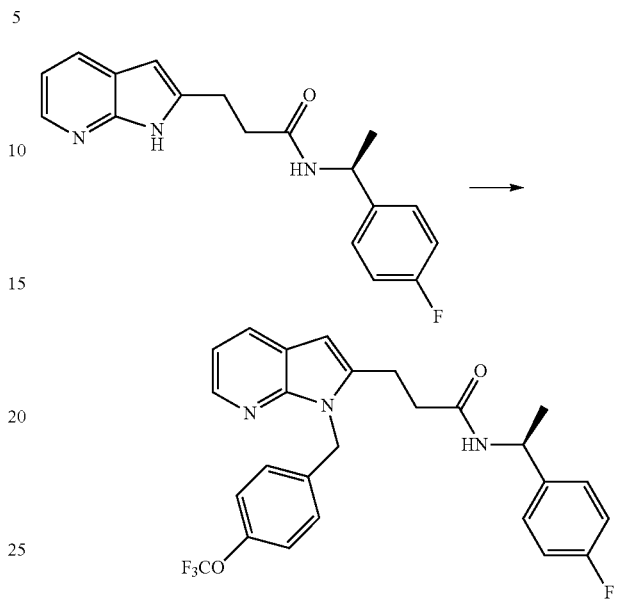

In a round bottom flask fitted with magnetic stirrer, N—[(S)-1-(4-fluoro-phenyl)-ethyl]-3-(1H-pyrrolo[2,3-b]pyridin-2-yl)-propionamide (500 mg, 1.60 mmol), 4-(trifluoromethoxy)benzyl bromide (490 mg, 1.92 mmol) and LiOH×H₂O (90 mg, 2.15 mmol) were dissolved in DMSO (8 ml). This mixture was allowed to stir at r.t. for 3 hours. Reaction crude was quenched with water and extracted with EtOAc. Organic phases were combined, filtered through a silicone treated filter paper and concentrated under reduced pressure. Residue obtained was purified by column chromatography with a gradient of EtOAc and cyclohexane, required product eluted with neat EtOAc. Product fractions were combined and concentrated under reduced pressure to afford a solid which was further purified by reverse phase mass-directed preparative HPLC, using either LCMS Method 5 or 6. Required fractions were concentrated in the Genevac™ to afford the title compound (208 mg, 27%)

The following compounds of general formula F-17 were prepared according to the general synthesis shown in Scheme 004:

| Example | SM | Halide | Amine | Characterisation | |
|---|---|---|---|---|---|
| 137 | F-18a | 4-(trifluoromethoxy)benzyl bromide | (S)-1-(4-fluorophenyl)ethylamine | LCMS Method: 1, RT: 5.26 min, MI: 486 [M + 1] | ¹H-NMR, Method 1: (CDCl₃) 8.28 (dd 1H), 7.83 (dd 1H), 7.15-7.02 (m 7H), 6.92 (tt 2H), 6.22 (s 1H), 5.58-5.47 (m 3H), 5.09-5.02 (m 1H), 3.03-2.99 (m 2H), 2.55-2.39 (m 2H), 1.40 (d 3H) |
| 138 | F-18a | 4-chlorobenzyl chloride | (S)-1-(4-fluorophenyl)ethylamine | LCMS Method: 1, RT: 5.06 min, MI: 436 [M + 1] | ¹H-NMR, Method 1: (DMSO) 8.41 (d 1H), 8.18 (dd 1H), 7.89 (dd 1H), 7.35-7.31 (m 2H), 7.30-7.25 (m 2H), 7.10-7.02 (m 5H), 6.28 (s 1H), 5.50 (s 2H), 4.94-4.87 (m 1H), 2.89 (t 2H), 2.55 (t 2H), 1.32 (d 3H) |

| Example | SM | Halide | Amine | Characterisation | |
|---|---|---|---|---|---|
| 139 | F-18b | F₃CO—C₆H₄—CH₂Br | H₂N—CH(CH₃)—C₆H₄—F | LCMS Method: 1, RT: 5.48 min, MI: 504 [M + 1] | ¹H-NMR, Method 1: (DMSO) 8.42 (d 1H), 8.16 (dd 1H), 7.82 (dd 1H), 7.29-7.26 (m 4H), 7.13 (dt 2H), 7.07 (tt 2H), 6.30 (s 1H), 5.53 (s 2H), 4.94-4.87 (m 1H), 2.91 (t 2H), 2.56 (t 2H), 1.32 (d 3H) |
| 140 | F-18a | F—C₆H₄—CH₂Br | H₂N—CH(CH₃)—C₆H₄—F | LCMS Method: 1, RT: 4.81 min, MI: 420 [M + 1] | ¹H-NMR, Method 1: (CDCl₃) 8.28 (dd 1H), 7.82 (dd 1H), 7.16-7.11 (m 2H), 7.08 (dd 1H), 7.03-6.99 (m 2H), 6.95-6.87 (m 4H), 6.21 (s 1H), 5.50 (q 3H), 5.09-5.02 (m 1H), 3.03-2.99 (m 2H), 2.51-2.37 (m 2H), 1.40 (d 3H) |
| 141 | F-18b | Cl—C₆H₄—CH₂Cl | H₂N—CH(CH₃)—C₆H₄—F | LCMS Method: 1, RT: 5.35 min, MI: 454 [M + 1] | ¹H-NMR, Method 1: (DMSO) 8.41 (d 1H), 8.17 (dd 1H), 7.82 (dd 1H), 7.34 (dt 2H), 7.29-7.26 (m 2H), 7.10-7.02 (m 4H), 6.29 (s 1H), 5.49 (s 2H), 4.94-4.87 (m 1H), 2.89 (t 2H), 2.54 (t 2H), 1.32 (d 3H) |

General Synthesis of 2-(3-aralkyl-3H-imidazo[4,5-b]pyridin-2-ylsulfanyl)-acetamide of general formula F-23, 2-(3-aralkyl-3H-imidazo[4,5-b]pyridine-2-sulfinyl)-acetamide of general formula F-24 2-(3-aralkyl-3H-imidazo[4,5-b]pyridine-2-sulfonyl)-acetamide of general formula F-25 (Scheme 005)

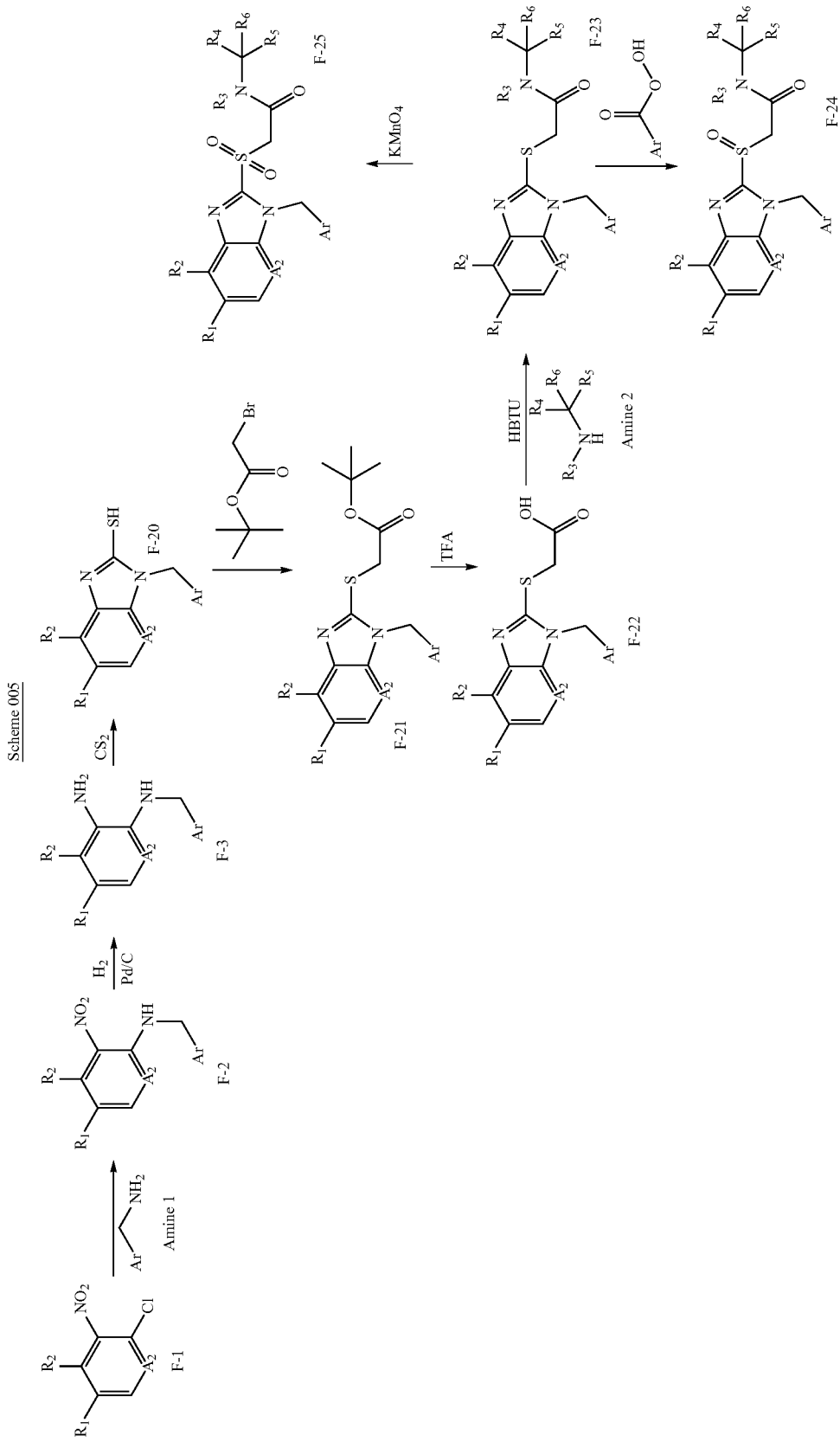

Intermediates F-2 and F-3 were prepared as in Scheme 001. Intermediate F-3 was treated with CS₂ to give the thiol intermediates of general formula F-20. Treatment of this intermediate with tert-butyl bromoacetate and K₂CO₃ afforded the ester of general formula F-21, which was hydrolyzed with TFA to the corresponding carboxylic acid of general formula F-22. The obtained acid was treated with HBTU and the required Amine 2 at r.t. to afford the final compounds of general formula F-23. Treatment of the final compound of general formula F-23 with a peroxide afforded the final compounds of general formula F-24. Treatment of the final compound of general formula F-23 with KMnO₄ afforded the final compounds of general formula F-25.

F-1 was the following intermediate:

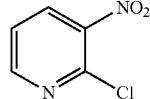

F-1a

The above synthesis (Scheme 005) is illustrated by the preparation of Examples 145, 148, 149 and 150 described below.

Synthesis of 3-(4-trifluoromethoxy-benzyl)-3H-imidazo[4,5-b]pyridine-2-thiol

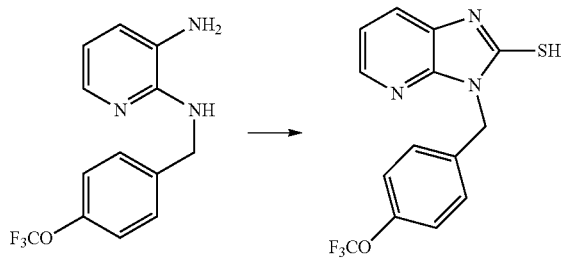 [SMILES: Nc1cccnc1NCc1ccc(OC(F)(F)F)cc1 ; FC(F)(F)Oc1ccc(Cn2c(S)nc3cccnc32)cc1]

In a round bottom flask fitted with magnetic stirrer and reflux condenser, N'2'-(4-trifluoromethoxy-benzyl)-pyridine-2,3-diamine (200 mg, 0.92 mmol) was dissolved in EtOH and CS₂ (160 µl, 2.76 mmol) was added in. The reaction mixture was heated to reflux overnight. Reaction mixture was allowed to cool down to r.t. and after a few hours a solid precipitated out of solution. This solid was filtered to afford the title compound (150 mg, 63%).

LCMS Method: 1, RT: 4.06 min, MI: 260 [M+1]

¹H NMR, Method 1: (DMSO) 13.13 (bs 1H), 8.20 (dd 1H), 7.58 (dd 1H), 7.48-7.44 (m 2H), 7.23 (dd 1H), 7.15 (tt 2H), 5.45 (s 2H).

Synthesis of [3-(4-trifluoromethoxy-benzyl)-3H-imidazo[4,5-b]pyridin-2-ylsulfanyl]-acetic acid tert-butyl ester

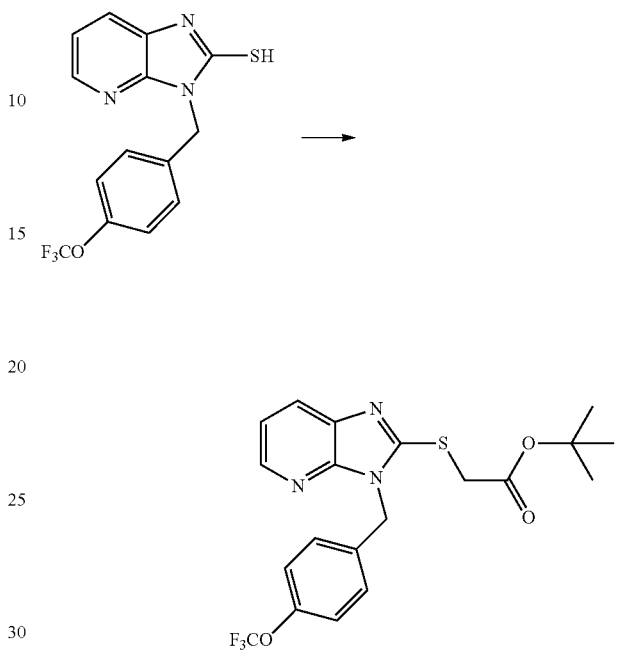

In a round bottom flask fitted with magnetic stirrer and reflux condenser, 3-(4-trifluoromethoxy-benzyl)-3H-imidazo[4,5-b]pyridine-2-thiol (150 mg, 0.58 mmol), tert-butyl bromoacetate (85 µl, 0.58 mmol) and K₂CO₃ (120 mg, 0.87 mmol) were dissolved in acetone (4 ml) and refluxed for 5 hours. Reaction crude was allowed to cool down overnight. Solvent was evaporated under reduced pressure, crude material taken up in water and extracted with EtOAc. Organic phases were combined and washed with diluted NaOH aqueous solution. Organic phases were dried and concentrated under reduced pressure to afford the title compound (210 mg, 100%).

LCMS Method: 1, RT: 5.25 min, MI: 374 [M+1]

¹H NMR, Method 1: (CDCl₃) 8.29 (dd 1H), 7.88 (dd 1H), 7.37-7.34 (m 2H), 7.18 (dd 1H), 6.99 (tt 2H), 5.40 (s 2H), 4.13 (s 2H), 1.45 (s 9H).

Synthesis of [3-(4-trifluoromethoxy-benzyl)-3H-imidazo[4,5-b]pyridin-2-ylsulfanyl]-acetic acid

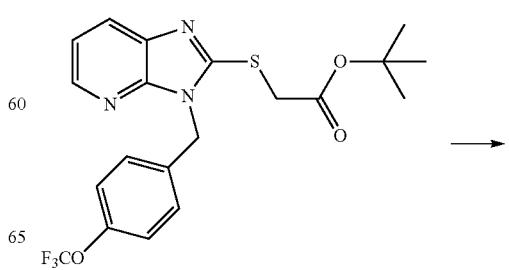

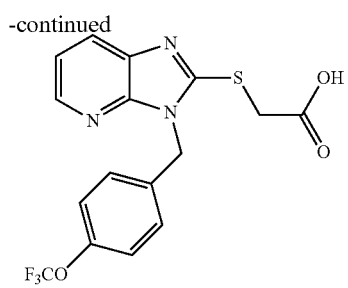

In a round bottom flask fitted with a magnetic stirrer, [3-(4-trifluoromethoxy-benzyl)-3H-imidazo[4,5-b]pyridin-2-ylsulfanyl]acetic acid tert-butyl ester (216 mg, 0.58 mmol) was dissolved in DCM (4 ml) and TFA (2 ml) was added in. Reaction mixture was stirred at r.t. overnight. The solvent had evaporated off overnight so DCM (3 ml) was added. This solution was then poured onto Et$_2$O (10 ml). The solution was concentrated under reduced pressure to afford the title compound (200 mg, 111%). The title compound was found to contain additional impurities but was used in subsequent reactions without further purification.

LCMS Method: 1, RT: 4.01 min, MI: 318 [M+1]

$^1$H NMR, Method 1: (DMSO) 8.28 (dd 1H), 7.97 (dd 1H), 7.37-7.34 (m 2H), 7.27 (dd 1H), 7.18 (tt 2H), 5.41 (s 2H), 4.22 (s 2H).

Synthesis of N—[(S)-1-(4-fluoro-phenyl)-ethyl]-2-[3-(4-trifluoromethoxy-benzyl)-3H-imidazo[4,5-b]pyridin-2-ylsulfanyl]-acetamide (Ex. 145)

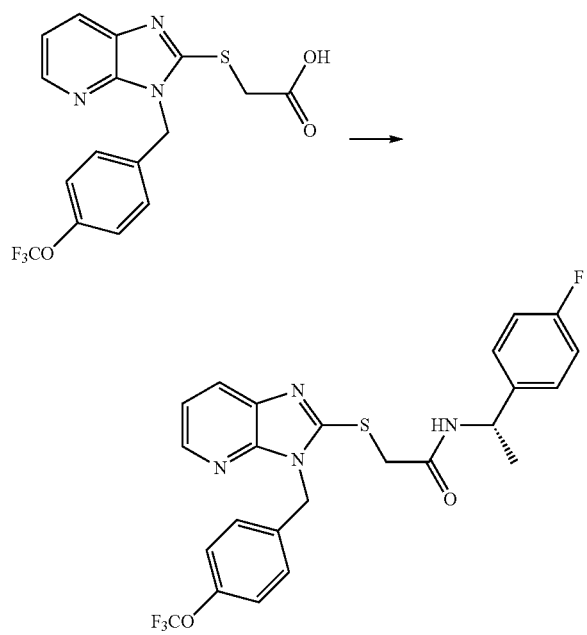

In a round bottom flask fitted with magnetic stirrer, [3-(4-trifluoromethoxy-benzyl)-3H-imidazo[4,5-b]pyridin-2-ylsulfanyl]-acetic acid (60 mg, 0.189 mmol) and (S)-1-(4-fluorophenyl)ethylamine (26 μl, 0.19 mmol) were dissolved in anhydrous DMF (3 ml) and then treated with HBTU (79 mg, 0.21 mmol) and Et$_3$N (80 μl, 0.57 mmol). This mixture was stirred at r.t. for 18 h. Reaction crude was diluted with EtOAc (15 ml) and washed with water (15 ml) and brine (10 ml). The organic phase was dried and concentrated under reduced pressure to give 146 mg of an orange oil, which was purified by reverse phase mass-directed preparative HPLC, using either LCMS Method 5 or 6. Required product fractions were concentrated in the Genevac™ to afford the title compound (15 mg, 19%).

Synthesis of N—[(S)-1-(4-fluoro-phenyl)-ethyl]-2-[3-(4-trifluoromethoxy-benzyl)-3H-imidazo[4,5-b]pyridine-2-sulfinyl]-acetamide (Ex. 148 and 149)

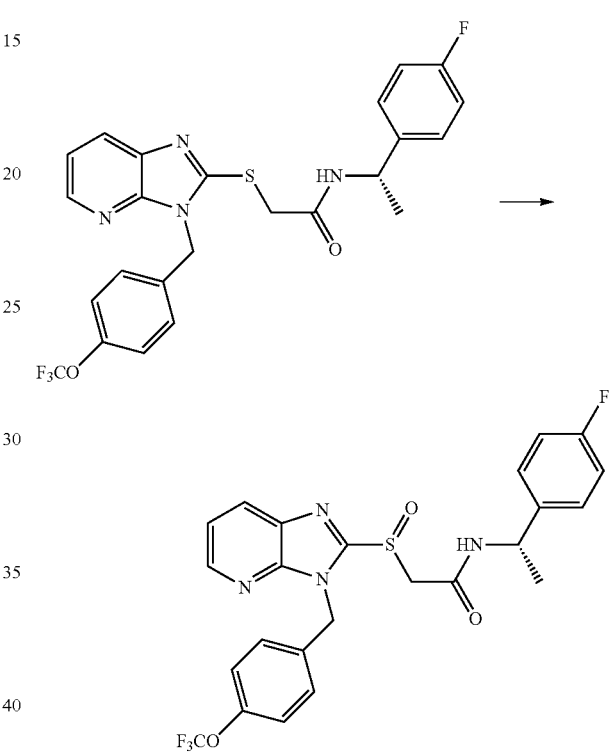

In a round bottom flask fitted with magnetic stirrer, N—[(S)-1-(4-fluoro-phenyl)-ethyl]-2-[3-(4-trifluoromethoxy-benzyl)-3H-imidazo[4,5-b]pyridin-2-ylsulfanyl]-acetamide (230 mg, 0.46 mmol) was dissolved in anhydrous DCM (100 ml). This solution was cooled to 0° C. and flushed with N$_2$. A solution of 3-chloroperoxybenzoic acid, 77% in DCM (8 ml) was added dropwise at 0° C. and under N$_2$. This mixture was stirred at r.t. for 6 hours. Solvent was evaporated under reduced pressure and residue extracted with brine (50 ml) and EtOAc (50 ml). Organic phases were dried and concentrated under reduced pressure to afford 242 mg of a crude material which was purified by reverse phase mass-directed preparative HPLC, using either LCMS Method 5 or 6. Required product fractions were concentrated in the Genevac™ to afford the title compound as two separate diastereoisomers of which the stereochemistry at the sulfoxide was unknown. For diastereoisomer A (r.t. 4.73 min), 32 mg were afforded (14% yield). For diastereoisomer B (r.t. 4.83 min), 10.5 mg were afforded (5% yield).

LCMS Method (diastereoisomer A): 1, RT: 4.73 min, MI: 521 [M+1]

LCMS Method (diastereoisomer B): 1, RT: 4.83 min, MI: 521 [M+1]

123

Synthesis of N—[(S)-1-(4-fluoro-phenyl)-ethyl]-2-[3-(4-trifluoromethoxy-benzyl)-3H-imidazo[4,5-b]pyridine-2-sulfonyl]-acetamide (Ex. 150)

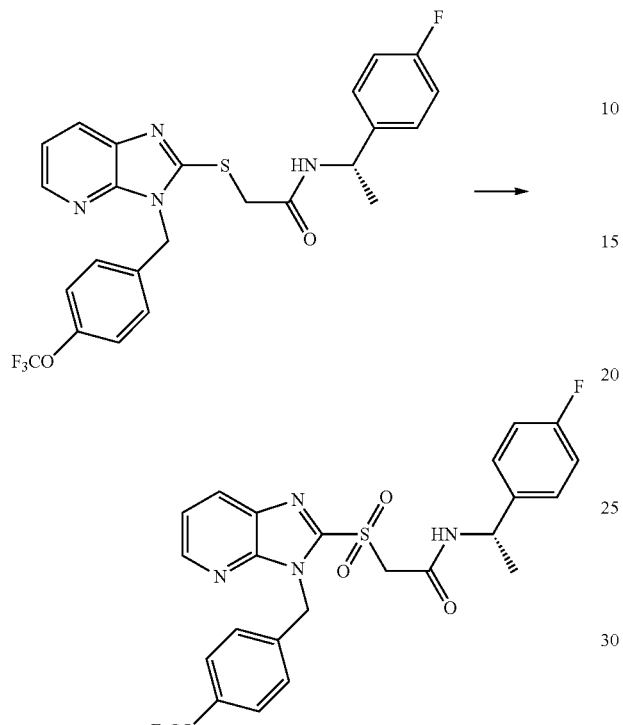

In a round bottom flask fitted with magnetic stirrer, N—[(S)-1-(4-fluoro-phenyl)-ethyl]-2-[3-(4-trifluoromethoxy-benzyl)-3H-imidazo[4,5-b]pyridin-2-ylsulfanyl]-acetamide (132 mg, 0.26 mmol) was dissolved in acetic acid (10 ml) and KMnO$_4$ 0.1 M aqueous solution (3.54 ml, 0.35 mmol) was added dropwise over 15 min and then stirred for 2.5 hours at r.t. Sodium sulfite was added to decolourise. The reaction mixture was then concentrated under reduced pressure. The solid was dissolved in DCM and the insoluble material filtered off. The filtrate was concentrated under reduced pressure and purified by reverse phase mass-directed preparative HPLC, using either LCMS Method 5 or 6. Required product fractions were concentrated in the Genevac™ to afford the title compound (31 mg, 22%).

Amine 2 used in the HBTU coupling step for the synthesis of Ex. 147 was made according to the following synthetic scheme:

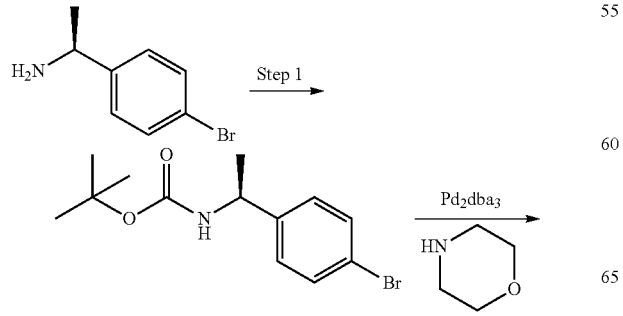

124

-continued

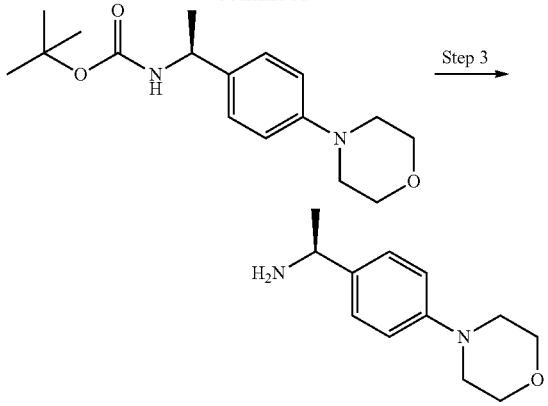

Step 1: Synthesis of [(S)-1-(4-bromo-phenyl)-ethyl]carbamic acid tert-butyl ester

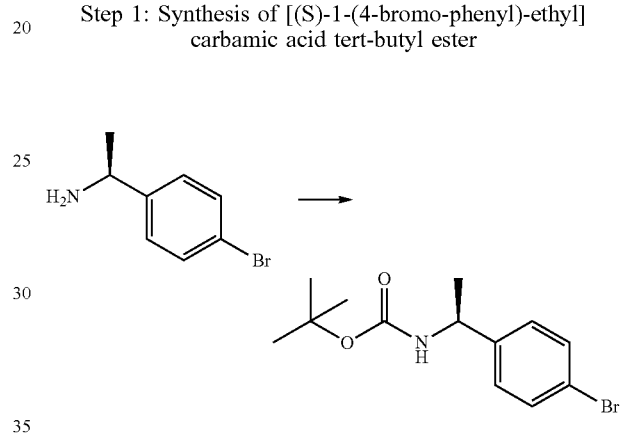

In a round bottom flask fitted with magnetic stirrer, a solution of (S)-1-(4-bromo-phenyl)-ethylamine (600 mg, 3 mmol) in DCM (15 ml) was cooled in an ice bath and treated with NEt$_3$ (460 µl, 3.3 mmol) and di-tert-butyldicarbonate (680 mg, 3.15 mmol). The reaction mixture was warmed to r.t. and stirred for 2 hours. Reaction crude was diluted with DCM and washed with ice-cold 1M HCl aqueous solution, saturated NaHCO$_3$ aqueous solution and brine, dried and evaporated in vacuo to afford the title compound (923 mg, 100%).

LCMS Method: 1, RT: 5.21 min, MI: 244/246 [M+1]

Step 2: Synthesis of [(S)-1-(4-morpholin-4-yl-phenyl)-ethyl]carbamic acid tert-butyl ester

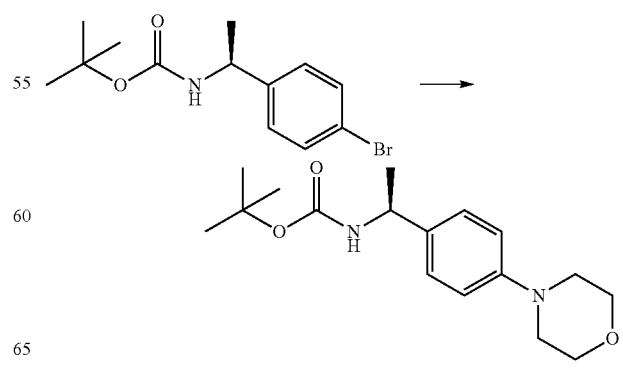

In a MW vial fitted with magnetic stirrer, a mixture of [(S)-1-(4-bromo-phenyl)-ethyl]-carbamic acid tert-butyl ester (900 mg, 3 mmol), morpholine (800 µl, 9.2 mmol), Pd$_2$dba$_3$ (35 mg, 0.06 mmol), X-Phos (86 mg, 0.18 mmol) and Na$^t$OBu (433 mg, 4.5 mmol) in dioxane (12 ml) was heated to 90° C. in the MW for 2 hours. Reaction crude was diluted with EtOAc, washed with water and brine, dried and concentrated under reduced pressure. The crude product was purified by column chromatography with a gradient of EtOAc and cyclohexane, product eluted with 30% EtOAc. Product fractions were combined and concentrated under reduced pressure to afford the title compound (730 mg, 79%).

LCMS Method: 1, RT: 4.27 min, MI: 307 [M+1]

Step 3: Synthesis of (S)-1-(4-morpholin-4-yl-phenyl)-ethylamine

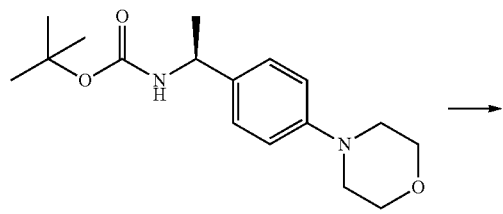

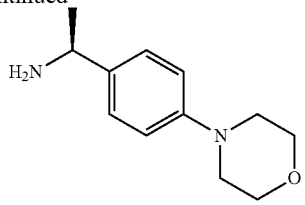

In a round bottom flask fitted with magnetic stirrer, acetyl chloride (1.5 ml, 21.1 mmol) was added to MeOH (10 ml), whilst stirring in an ice bath. The resultant 2M HCl solution was added to a flask containing [(S)-1-(4-morpholin-4-yl-phenyl)-ethyl]-carbamic acid tert-butyl ester and the mixture was stirred for 2 hours at r.t. Reaction crude was concentrated under reduced pressure and the resultant solid triturated in Et$_2$O. The suspension was filtered and the solid product dried to afford the title compound (550 mg, 83%).

LCMS Method: 1, RT: 1.65 min, MI: 207 [M+1]

$^1$H NMR, Method 1: (CD$_3$OD) 7.77-7.73 (m 2H), 7.69-7.66 (m 2H), 4.56 (q 1H), 4.10 (t 4H), 3.65 (t 4H), 1.65 (d 3H).

The following compounds were prepared according to the general synthesis shown in Scheme 005:

| Example | General formula | Amine 1 | Amine 2 | Characterisation | |
|---|---|---|---|---|---|
| 142 | F-23 | (4-trifluoromethoxy-benzyl)amine | (S)-2-amino-2-phenyl-ethanol | LCMS Method: 1, RT: 4.55 min, MI: 503 [M + 1] | $^1$H-NMR, Method 1: (DMSO) 8.75 (d 1H), 8.27 (d 1H), 7.96 (d 1H), 7.40-7.19 (m 10H), 5.45 (s 2H), 4.90 (t 1H), 4.83 (q 1H), 4.26 (d 1H), 4.20 (d 1H), 3.61-3.51 (m 2H) |
| 143 | F-23 | (4-fluoro-benzyl)amine | (S)-2-amino-2-phenyl-ethanol | LCMS Method: 1, RT: 4.04 min, MI: 437 [M + 1] | $^1$H-NMR, Method 1: (CDCl$_3$) 8.74 (d 1H), 8.34 (dd 1H), 7.80 (dd 1H), 7.36-7.32 (m 2H), 7.24-7.18 (m 6H), 6.99 (tt 2H), 5.41 (d 1H), 5.36 (d 1H), 5.07-5.03 (m 1H), 3.98 (d 1H), 3.88 (d 1H), 3.87-3.79 (m 2H), 2.83 (br 1H) |
| 144 | F-23 | (4-trifluoromethoxy-benzyl)amine | (S)-1-(4-chloro-phenyl)-ethylamine | LCMS Method: 1, RT: 5.50 min, MI: 521 [M + 1] | $^1$H-NMR, Method 1: (CDCl$_3$) 8.44 (d 1H), 8.37 (dd 1H), 7.81 (dd 1H), 7.39 (dt 2H), 7.27 (dd 1H), 7.17-7.08 (m 6H), 5.43 (d 1H), 5.44 (d 1H), 5.00-4.93 (m 1H), 3.95 (d 1H), 3.88 (d 1H), 1.38 (d 3H) |
| 145 | F-23 | (4-trifluoromethoxy-benzyl)amine | (S)-1-(4-fluoro-phenyl)-ethylamine | LCMS Method: 1, RT: 5.26 min, MI: 505 [M + 1] | $^1$H-NMR, Method 1: (CDCl$_3$) 8.42 (d 1H), 8.35 (dd 1H), 7.79 (dd 1H), 7.38 (dt 2H), 7.25 (dd 1H), 7.16-7.10 (m 4H), 6.84 (tt 2H), 5.39 (s 2H), 5.01-4.94 (m 1H), 3.93 (d 1H), 3.86 (d 1H), 1.38 (d 3H) |
| 146 | F-23 | (4-fluoro-benzyl)amine | (S)-1-(4-fluoro-phenyl)-ethylamine | LCMS Method: 1, RT: 4.79 min, MI: 439 [M + 1] | $^1$H-NMR, Method 1: (CDCl$_3$) 8.45 (d 1H), 8.35 (dd 1H), 7.79 (dd 1H), 7.36-7.32 (m 2H), 7.24 (dd 1H), 7.13-7.08 (m 2H), 6.99 (tt 2H), 6.83 (tt 2H), 5.37 (s 2H), 5.01-4.93 (m 1H), 3.92 (d 1H), 3.85 (d 1H), 1.38 (d 3H) |

-continued

| Example | General formula | Amine 1 | Amine 2 | Characterisation | |
|---|---|---|---|---|---|
| 147 | F-23 | 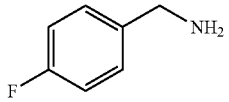 | 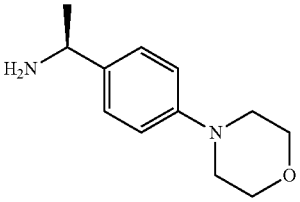 | LCMS Method: 1, RT: 4.38 min, MI: 506 [M + 1] | ¹H-NMR, Method 1: (CDCl₃) 8.33 (dd 1H), 8.28 (d 1H), 7.79 (dd 1H), 7.34-7.31 (m 2H), 7.22 (dd 1H), 7.04 (d 2H), 6.99 (tt 2H), 6.68 (d 2H), 5.36 (s 2H), 4.98-4.91 (m 1H), 3.95 (d 1H), 3.85 (d 1H), 3.84 (t 4H), 3.06 (t 4H), 1.36 (d 3H) |
| 148 | F-24 | 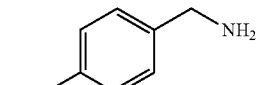 | 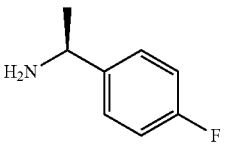 | LCMS Method: 1, RT: 4.83 min, MI: 521 [M + 1] | ¹H-NMR, Method 1: (CDCl₃) 8.58 (dd 1H), 8.10 (dd 1H), 7.50 (dt 2H), 7.39 (dd 1H), 7.22-7.15 (m 4H), 7.00-6.94 (m 3H), 5.87 (d 1H), 5.79 (d 1H), 5.04-4.97 (m 1H), 4.30 (d 1H), 4.17 (d 1H), 1.30 (d 3H) |
| 149 | F-24 | 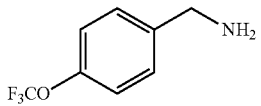 | 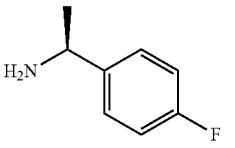 | LCMS Method: 1, RT: 4.73 min, MI: 521 [M + 1] | — |
| 150 | F-25 | 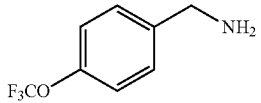 | 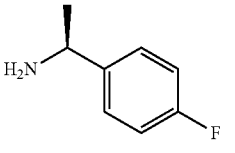 | LCMS Method: 1, RT: 5.15 min, MI: 537 [M + 1] | ¹H NMR, Method 1: (CDCl₃) 8.65 (dd 1H), 8.06 (dd 1H), 7.56 (dt 2H), 7.43 (dd 1H), 7.16-7.12 (m 4H), 6.86 (tt 2H), 5.83 (s 2H), 5.05-4.98 (m 1H), 4.48 (d 1H), 4.44 (d 1H), 1.43 (d 3H) |

General Synthesis of 2-(3-aralkyl-3H-imidazo[4,5-b]pyridin-2-yloxy)-acetamide of general formula F-30 (Scheme 006-A)

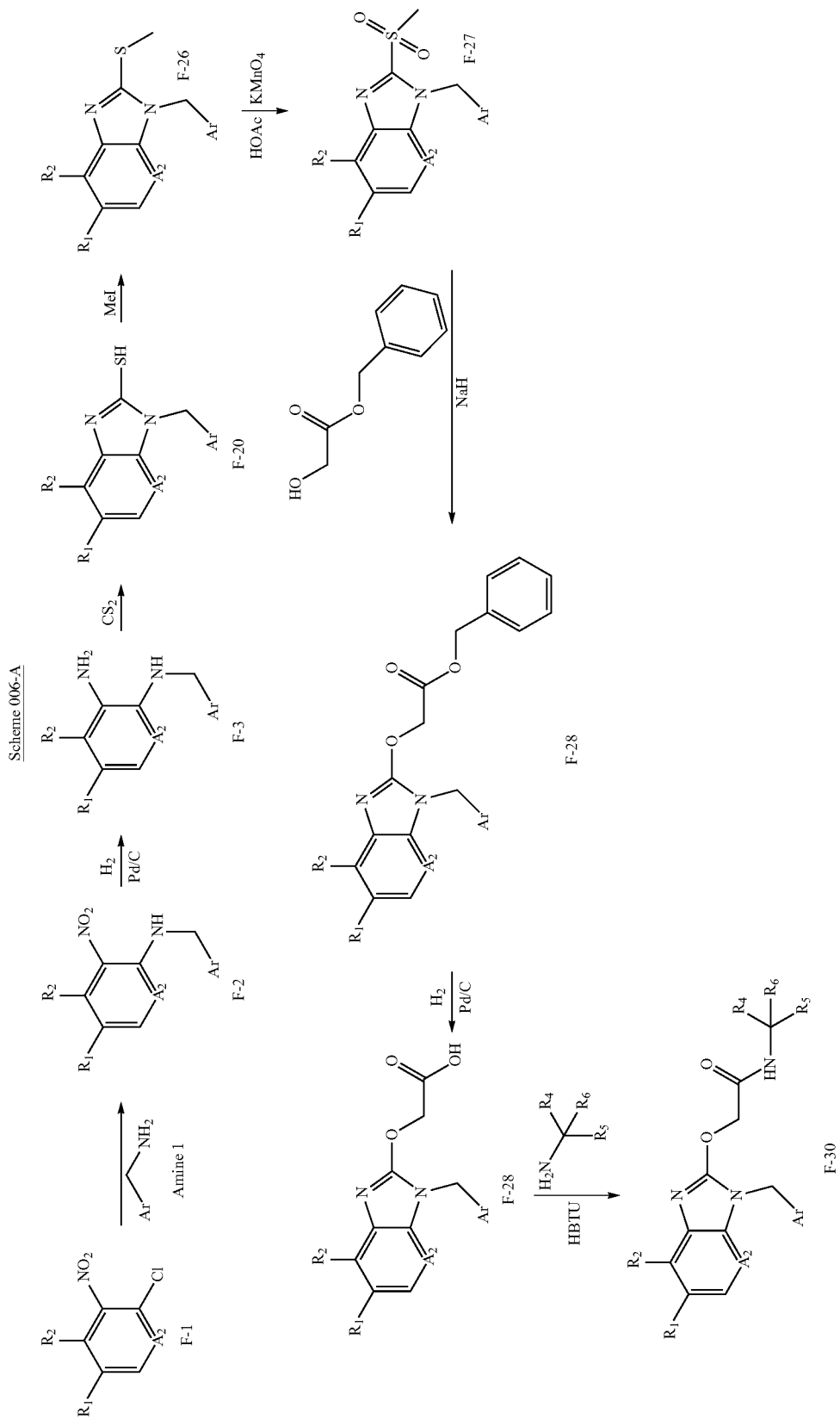

Intermediates F-2 and F-3 were prepared as in Scheme 001. Intermediate F-20 was prepared as in Scheme 005. Intermediate F-20 was treated with MeI to afford the methylated analogue of general formula F-26. Oxidation with KMnO₄ of the methylated analogue yielded the sulfone of general formula F-27. Reaction of this intermediate with hydroxy-acetic acid benzyl ester and NaH afforded the ester of general formula F-28. Hydrogenation of this ester afforded the carboxylic acid of general formula F-29. The obtained acid was treated with HBTU and the required amine 2 at r.t. to afford the final compounds of general formula F-30.

F-1 was specifically the following intermediate:

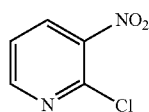

F-1a

The above synthesis (Scheme 006-A) is illustrated by the preparation of N—[(S)-1-(4-chloro-phenyl)-ethyl]-2-[3-(4-trifluoromethoxy-benzyl)-3H-imidazo[4,5-b]pyridin-2-yloxy]-acetamide (Ex. 152) described below.

Synthesis of 2-methylsulfanyl-3-(4-trifluoromethoxy-benzyl)-3H-imidazo[4,5-b]pyridine

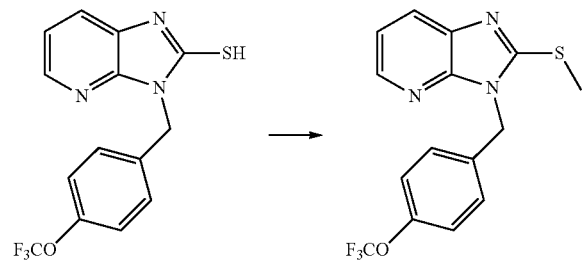 [SMILES: FC(F)(F)Oc1ccc(Cn2c(S)nc3cccnc32)cc1 ; CSc1nc2cccnc2n1Cc1ccc(OC(F)(F)F)cc1]

In a round bottom flask fitted with magnetic stirrer, 3-(4-trifluoromethoxy-benzyl)-3H-imidazo[4,5-b]pyridine-2-thiol (680 mg, 2.09 mmol) were dissolved in acetone (30 ml). This solution was cooled down to 0° C. with an ice bath and then K₂CO₃ (144 mg, 1.05 mmol) and MeI (65 μl, 1.05 mmol) were added in. Ice bath was removed and reaction mixture was allowed to stir at r.t. for 1.5 hours. After that time, K₂CO₃ (144 mg, 1.05 mmol) and MeI (65 μl, 1.05 mmol) were added in again and mixture was allowed to stir overnight at r.t. Reaction mixture was concentrated under reduced pressure and then dissolved in EtOAc (150 ml) and washed with water (100 ml) and brine (100 ml). Organic phase was dried and concentrated under reduced pressure to give 600 mg of crude material. This material was purified by column chromatography with a gradient of EtOAc and cyclohexane, required product eluted with 45% EtOAc. Required product fractions were combined and concentrated under reduced pressure to afford the title compound (603 mg, 85%).

LCMS Method: 1, RT: 4.89 min, MI: 340 [M+1]

¹H NMR, Method 1: (CDCl₃) 8.28 (dd 1H), 7.93 (dd 1H), 7.38 (d 2H), 7.20 (dd 1H), 7.15 (d 2H), 5.40 (s 2H), 2.79 (s 3H).

Synthesis of 2-methanesulfonyl-3-(4-trifluoromethoxy-benzyl)-3H-imidazo[4,5-b]pyridine

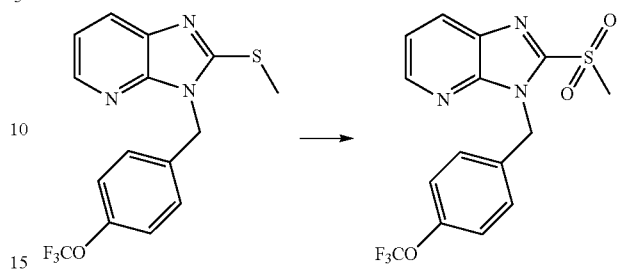

In a round bottom flask fitted with magnetic stirrer, 2-methylsulfanyl-3-(4-trifluoromethoxy-benzyl)-3H-imidazo[4,5-b]pyridine (571 mg, 1.68 mmol) was dissolved in HOAc (50 ml) and KMnO₄ 0.1 M aqueous solution (24 ml, 2.39 mmol) was added dropwise at r.t. over 15 min and then stirred for 3 hours at r.t. Sodium sulphite was added to decolourise. Reaction crude was diluted with water (250 ml), adjusted to pH 8 with Na₂CO₃ (extra 50 ml of water added to ensure solution remained homogeneous) and extracted with DCM (4×150 ml). Organic phases were combined and washed with brine (150 ml), dried and concentrated under reduced pressure. Crude material was purified by column chromatography with a gradient of EtOAc and cyclohexane, product eluted with 40% EtOAc. Required product fractions were combined and concentrated under reduced pressure to afford the title compound (220 mg, 35%).

LCMS Method: 1, RT: 4.78 min, MI: 372 [M+1]

¹H NMR, Method 1: (DMSO) 8.64 (dd 1H), 8.39 (dd 1H), 7.55 (dd 1H), 7.42 (d 2H), 7.34 (d 2H), 5.87 (s 2H), 3.62 (s 3H).

Synthesis of [3-(4-trifluoromethoxy-benzyl)-3H-imidazo[4,5-b]pyridin-2-yloxy]-acetic acid benzyl ester

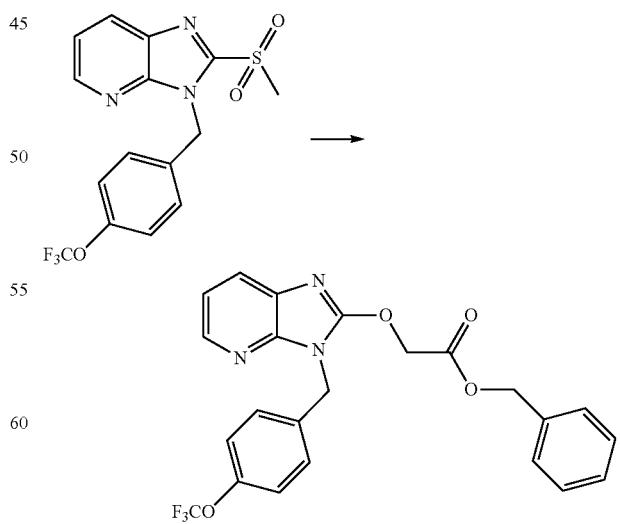

A previously dried round bottom flask fitted with a magnetic stirrer was charged with NaH (19 mg, 0.81 mmol)

and then benzyl glycolate (230 µl, 1.62 mmol) in anhydrous THF (3 ml) were added in dropwise. Immediately after the addition was complete, a solution of 2-methanesulfonyl-3-(4-trifluoromethoxy-benzyl)-3H-imidazo[4,5-b]pyridine (90 mg, 0.24 mmol) in anhydrous THF (3 ml) was added. Reaction was left stirring under $N_2$ at r.t. over the weekend. The reaction was quenched with water and a white solid crashed out of solution. This solid was filtered off and dried to afford the title compound (76 mg, 69%).

LCMS Method: 1, RT: 5.51 min, MI: 458 [M+1]

$^1$H NMR, Method 1: (DMSO) 8.17 (dd 1H), 7.84 (dd 1H), 7.43 (d 2H), 7.40-7.36 (m 1H), 7.32 (s 4H), 7.27 (d 2H), 7.22 (dd 1H), 5.34 (s 2H), 5.29 (s 2H), 5.22 (s 2H).

Synthesis of [3-(4-trifluoromethoxy-benzyl)-3H-imidazo[4,5-b]pyridin-2-yloxy]-acetic acid

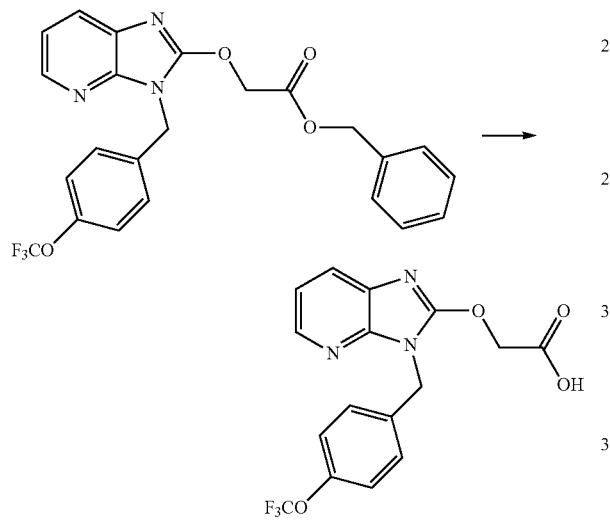

To a round bottom flask fitted with magnetic stirrer and containing [3-(4-trifluoromethoxy-benzyl)-3H-imidazo[4,5-b]pyridin-2-yloxy]-acetic acid benzyl ester (64 mg, 0.14 mmol) and 10% Pd/C (7 mg) was added EtOAc (5 ml), whilst stirring under $N_2$. Mixture was purged with more $N_2$ and a double balloon filled with $H_2$ was fitted onto the flask. Suspension was allowed to stir at r.t. for 2 hours under an atmosphere of $H_2$ and subsequently filtered through Celite® with EtOAc. Filtrate was evaporated under reduced pressure to afford the title compound (50 mg, 100%).

$^1$H NMR, Method 1: (CDCl$_3$) 8.22 (dd 1H), 7.80 (dd 1H), 7.44 (d 2H), 7.17-7.13 (m 3H), 5.34 (s 2H), 5.15 (s 2H).

Synthesis of N—[(S)-1-(4-chloro-phenyl)-ethyl]-2-[3-(4-trifluoromethoxy-benzyl)-3H-imidazo[4,5-b]pyridin-2-yloxy]-acetamide (Ex. 152)

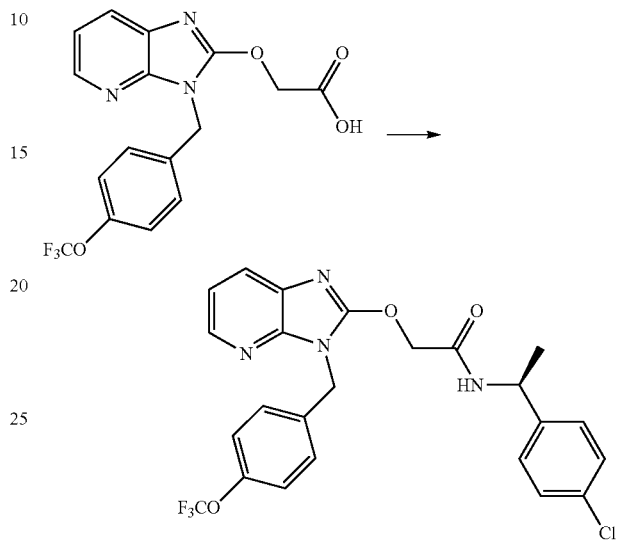

In a round bottom flask fitted with a magnetic stirrer, [3-(4-trifluoromethoxy-benzyl)-3H-imidazo[4,5-b]pyridin-2-yloxy]-acetic acid (24 mg, 0.07 mmol), Et$_3$N (30 µl, 0.2 mmol) and (S)-1-(4-chloro-phenyl)-ethylamine (10 µl, 0.07 mmol) were dissolved in anhydrous DMF (2 ml). Mixture was cooled with an ice bath, and then HBTU (27 mg, 0.07 mmol) was added. This mixture was allowed to stir at r.t. overnight. Reaction mixture was diluted with EtOAc (15 ml) and washed with water (15 ml) and brine (10 ml). Organic phase was dried and concentrated under reduced pressure to give a crude material which was purified by reverse phase mass-directed preparative HPLC, using either LCMS Method 5 or 6. Required product fractions were concentrated in the Genevac™ to afford the title compound (10 mg, 33%).

The following compounds of general formula F-30 were prepared according to the general synthesis shown in Scheme 006-A:

| Example | Amine 1 | Amine 2 | Characterisation | |
|---|---|---|---|---|
| 151 | ![structure] 4-F$_3$CO-benzyl-NH$_2$ | ![structure] H$_2$N-CH(Ph)-CH$_2$OH | LCMS Method: 1, RT: 4.40 min, MI: 487 [M + 1] | $^1$H-NMR, Method 1: (DMSO) 8.58 (d 1H), 8.14 (dd 1H), 7.80 (dd 1H), 7.49 (dt 2H), 7.35-7.28 (m 6H), 7.23 (dt 1H), 7.19 (dd 1H), 5.34 (s 2H), 5.11 (d 1H), 5.07 (d 1H), 4.96-4.87 (m 2H), 4.04 (m 2H), 3.65-3.55 (m 2H) |
| 152 | ![structure] 4-F$_3$CO-benzyl-NH$_2$ | ![structure] (S)-H$_2$N-CH(CH$_3$)-(4-Cl-Ph) | LCMS Method: 1, RT: 5.27 min, MI: 505 [M + 1] | $^1$H-NMR, Method 1: (CDCl$_3$) 8.26 (dd 1H), 7.80 (dd 1H), 7.31 (d 2H), 7.25-7.18 (m 3H), 7.12-7.09 (m 4H), 6.21 (d 1H), 5.33 (s 2H), 5.14-5.06 (m 1H), 5.03 (d 2H), 1.36 (d 3H) |

| Example | Amine 1 | Amine 2 | | Characterisation |
|---|---|---|---|---|
| 153 | 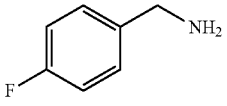 | 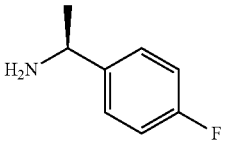 | LCMS Method: 1, RT: 4.57 min, MI: 423 [M + 1] | ¹H-NMR, Method 1: (CDCl$_3$) 8.26 (dd 1H), 7.80 (dd 1H), 7.26-7.18 (m 3H), 7.14-7.10 (m 2H), 6.97-6.89 (m 4H), 6.10 (d 1H), 5.30 (s 2H), 5.16-5.08 (m 1H), 5.03 (d 2H), 1.36 (d 3H) |
The aforementioned compounds in Scheme 006-A could have alternatively been obtained through the following synthetic route (Scheme 006-B):
Scheme 006-B
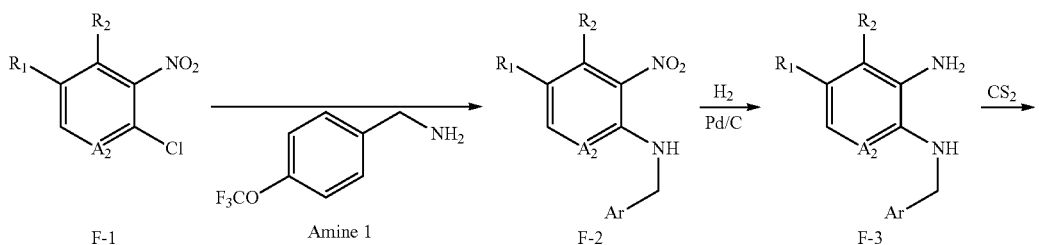
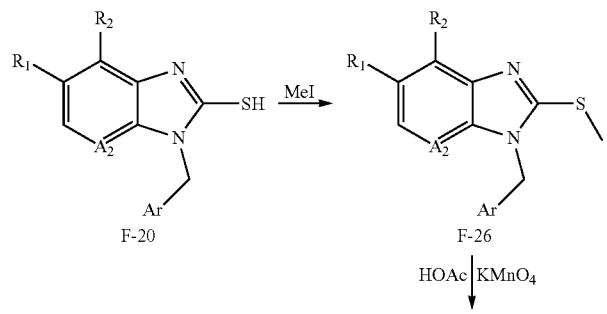
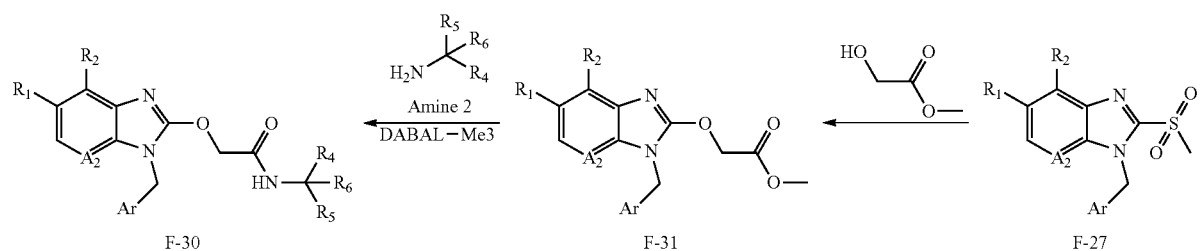

Intermediates F-2 and F-3 were prepared as in Scheme 001. Intermediate F-20 was prepared as in Scheme 005. Intermediate F-26 and F-27 were prepared as in scheme 006-A. Intermediate F-31 was prepared following the same procedure as for intermediate F-28 in scheme 006-A, using hydroxy-acetic acid methyl ester as the ester. Intermediate F-31 was treated with DABAL-Me₃ and the required amine 2 at reflux to afford the final compounds of general formula F-30.

F-1 was the following intermediate:

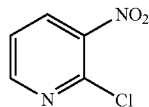

F-1a

The above synthesis (Scheme 006-B) is illustrated by the preparation of 2-[3-(4-fluoro-benzyl)-3H-imidazo[4,5-b]pyridin-2-yloxy]-N—[(S)-1-(4-fluoro-phenyl)-ethyl]-acetamide (Ex. 153) described below.

Synthesis of 2-[3-(4-fluoro-benzyl)-3H-imidazo[4,5-b]pyridin-2-yloxy]-N—[(S)-1-(4-fluoro-phenyl)-ethyl]-acetamide (Ex. 153)

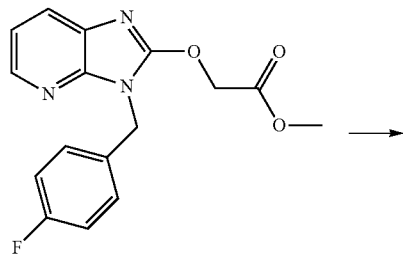

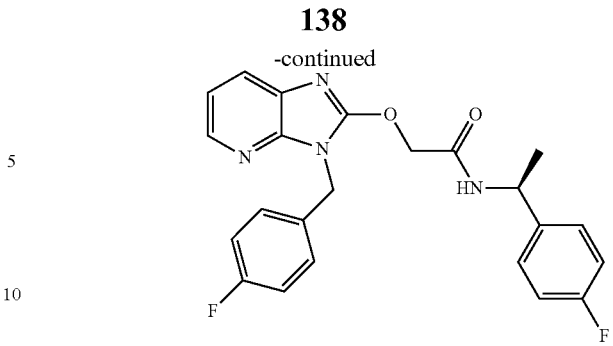

-continued

In a round bottom flask fitted with magnetic stirrer and reflux condenser, to a stirred suspension of DABAL-Me₃ (26 mg, 0.1 mmol) in anhydrous THF (1 ml) under an atmosphere of N₂, (S)-1-(4-fluoro-phenyl)-ethylamine (13 μl, 0.1 mmol) was added in. The solution was stirred and warmed to 40° C. for 1 hour. A solution of [3-(4-fluoro-benzyl)-3H-imidazo[4,5-b]pyridin-2-yloxy]-acetic acid methyl ester (22 mg, 0.07 mmol) in anhydrous THF (0.75 ml) was added and mixture was refluxed overnight. The reaction was cooled to r.t. and cautiously quenched with 2M HCl aqueous solution (1.5 ml) and stirred at r.t. for 30 minutes. The solution was transferred to a larger flask and the water evaporated. Crude material was purified by column chromatography. Required product fractions were combined and concentrated under reduced pressure to afford the title compound (1 mg, 3%).

The aforementioned compounds in Scheme 006-A could have alternatively been obtained through the following synthetic route (Scheme 006-C):

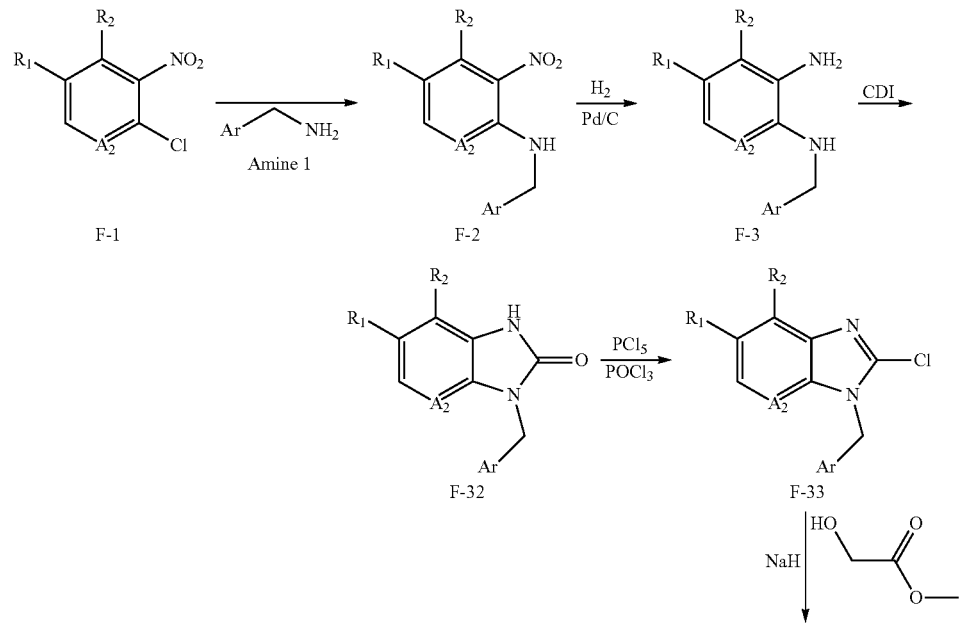

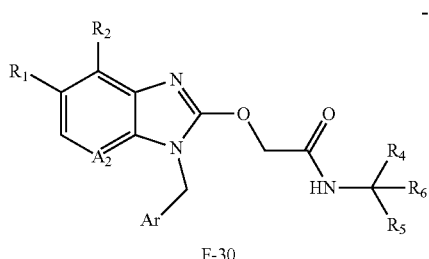 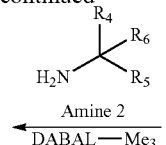 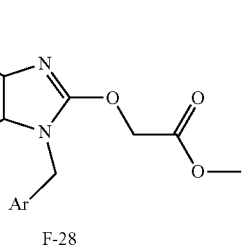

F-30        F-28

Intermediates F-2 and F-3 were prepared as in Scheme 001. Intermediate F-3 was treated with CDI to give the oxo intermediates of general formula F-32. This intermediate was treated with $POCl_3$ and $PCl_5$ to afford the chlorinated analogues of general formula F-33. Reaction of this intermediate with hydroxy-acetic acid methyl ester and NaH afforded the ester of general formula F-28. Final compounds of general formula F-30 were prepared from intermediate F-28 as in Scheme 006-B.

F-1 was the following intermediate:

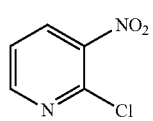

F-1a

The above synthesis (Scheme 006-C) is illustrated by the preparation of [3-(4-fluoro-benzyl)-3H-imidazo[4,5-b]pyridin-2-yloxy]-acetic acid methyl ester described below.

Synthesis of 3-(4-fluoro-benzyl)-1,3-dihydro-imidazo[4,5-b]pyridin-2-one

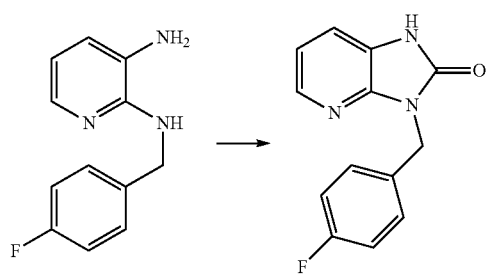 [SMILES: Nc1cccnc1NCc1ccc(F)cc1 ; O=c1[nH]c2cccnc2n1Cc1ccc(F)cc1]

In a round bottom flask fitted with magnetic stirrer, N'2'-(4-fluoro-benzyl)-pyridine-2,3-diamine (600 mg, 2.76 mmol) and CDI (896 mg, 5.52 mmol) were dissolved in anhydrous THF (70 ml). This mixture was allowed to stir at r.t. for 24 hours. Reaction crude was concentrated under reduced pressure and the residue diluted in EtOAc (50 ml), and then washed with water (50 ml) and brine (50 ml). Organic phase was filtered through a silicone treated filter paper and concentrated under reduced pressure to give 800 mg of crude product. This was purified by column chromatography with a gradient of EtOAc and cyclohexane, product eluted with 30 to 70% EtOAc. Required product fractions were concentrated under reduced pressure to afford the title compound (458 mg, 68%).

LCMS Method: 1, RT: 3.48 min, MI: 244 [M+1]

$^1$H-NMR, Method 1: ($CDCl_3$) 9.91 (br 1H), 8.08 (dd 1H), 7.50-7.47 (m 2H), 7.31 (dd 1H), 7.02-6.97 (m 3H), 5.15 (s 2H).

Synthesis of 2-chloro-3-(4-fluoro-benzyl)-3H-imidazo[4,5-b]pyridine

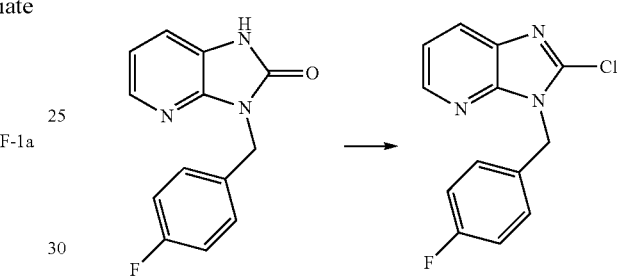

In a round bottom flask fitted with magnetic stirrer and reflux condenser, 3-(4-fluoro-benzyl)-1,3-dihydro-imidazo[4,5-b]pyridin-2-one (458 mg, 1.88 mmol) was dissolved in $POCl_3$ (6 ml) and heated to reflux at 110° C. $PCl_5$ (392 mg, 1.88 mmol) was added to the refluxing suspension and mixture was refluxed for 20 hours. Reaction crude was cooled down to r.t. and quenched by gradually adding the crude solution to a stirring flask of water. It was then basified with 6M NaOH aqueous solution. This was extracted with EtOAc (250 ml), organic phases were filtered through a silicone treated filter paper and concentrated under reduced pressure to give 400 mg of crude product. This material was purified by column chromatography with a gradient of EtOAc and cyclohexane, product eluted with 20% EtOAc. Required product fractions were combined and concentrated under reduced pressure to afford the title compound (184 mg, 38%).

LCMS Method: 4LCMS1, RT: 4.37 min, MI: 262 [M+1]
$^1$H-NMR, Method 1: ($CDCl_3$) 8.41 (dd 1H), 7.98 (dd 1H), 7.38-7.35 (m 2H), 7.28 (dd 1H), 7.00 (tt 2H), 5.48 (s 2H).

Synthesis of [3-(4-fluoro-benzyl)-3H-imidazo[4,5-b]pyridin-2-yloxy]-acetic acid methyl ester

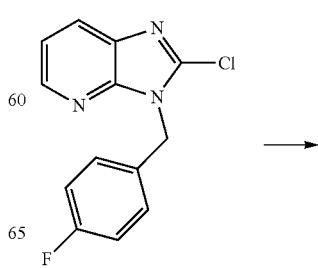

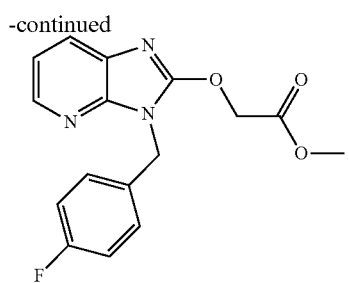

In a round bottom flask, fitted with magnetic stirrer and reflux condenser, methyl glycolate (90 μl, 1 mmol) was dissolved in DMF (4 ml) and allowed to stir at r.t. under $N_2$. NaH 60% in oil (50 mg, 1.25 mmol) was then added and the mixture was stirred at 40° C. for 1 h under $N_2$. 2-Chloro-3-(4-fluoro-benzyl)-3H-imidazo[4,5-b]pyridine (131 mg, 0.5 mmol) was added and mixture stirred at 80° C. overnight. Reaction crude was concentrated under reduced pressure and then partitioned between water and DCM. Organic phases were filtered through a silicone treated filter paper and concentrated under reduced pressure. Crude material was purified by column chromatography with a gradient of EtOAc and cyclohexane, product eluted with 70% EtOAc. Required product fractions were combined and concentrated under reduced pressure to afford the title compound (42 mg, 26%).

LCMS Method: 1, RT: 4.19 min, MI: 316 [M+1]
$^1$H-NMR, Method 1: (CDCl$_3$) 8.20 (dd 1H), 7.74 (dd 1H), 7.44-7.40 (m 2H), 7.12 (dd 1H), 6.98 (tt 2H), 5.30 (s 2H), 5.12 (s 2H), 3.79 (s 3H).

General Synthesis of 2-(3-aralkyl-3H-imidazo[4,5-b]pyridin-2-ylsulfanyl)-propionamide of general formula F-35 (Scheme 007)

Scheme 007

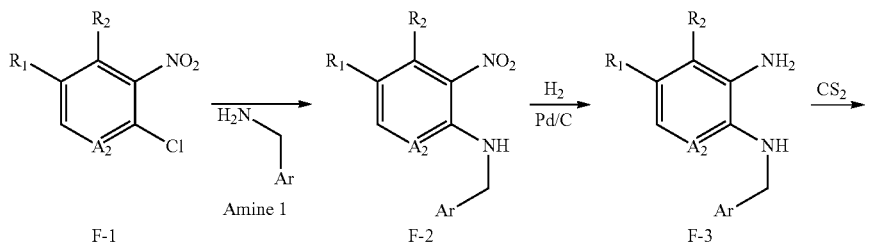

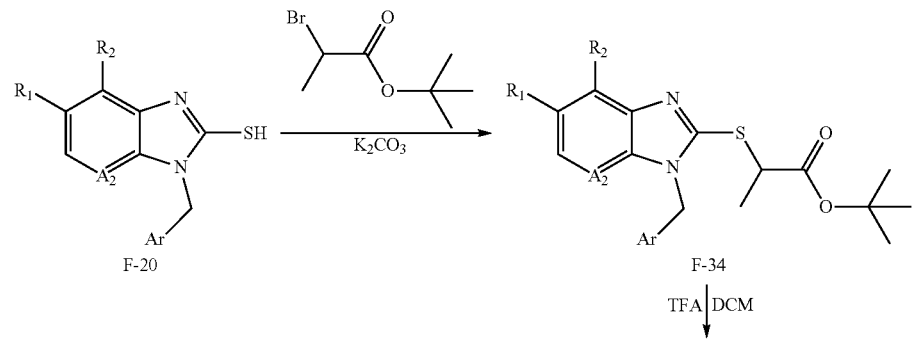

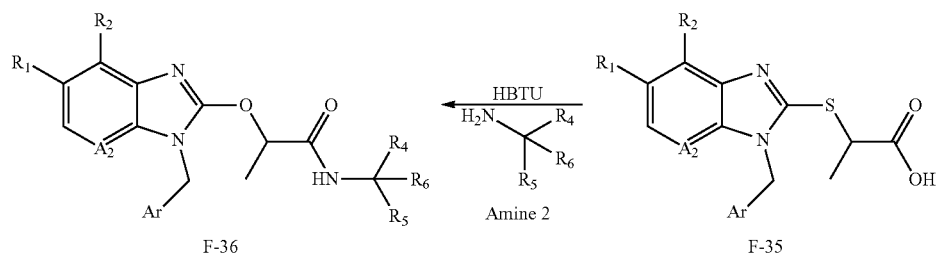

Intermediates F-2 and F-3 were prepared as in Scheme 001. Intermediate F-20 was prepared as in Scheme 005. Treatment of intermediate F-20 with tert-butyl 2-bromopropionate afforded the ester of general formula F-34. Hydrolysis of this ester with TFA yielded the carboxylic acid of general formula F-35. Reaction of this acid with the required amine 2 and HBTU afforded the final compounds of general formula F-36.

F-1 was the following intermediate:

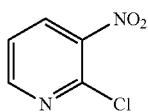

F-1a

The above synthesis (Scheme 007) is illustrated by the preparation of N—((R)-2-hydroxy-1-phenyl-ethyl)-2-[3-(4-trifluoromethoxy-benzyl)-3H-imidazo[4,5-b]pyridin-2-yl-sulfanyl]-propionamide (Ex. 154) described below.

Synthesis of 2-[3-(4-trifluoromethoxy-benzyl)-3H-imidazo[4,5-b]pyridin-2-ylsulfanyl]-propionic acid tert-butyl ester

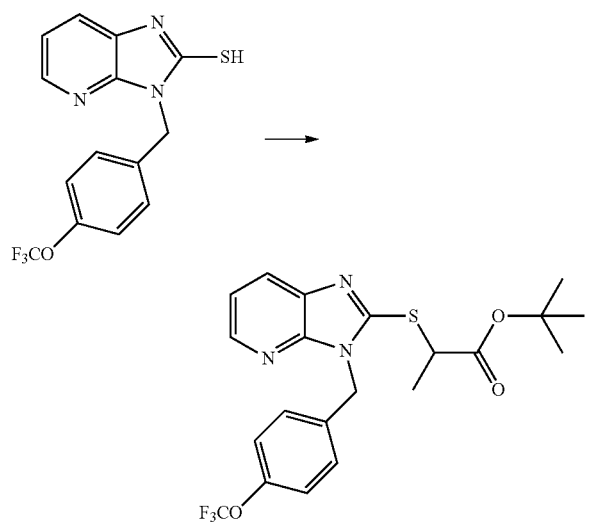

In a round bottom flask fitted with magnetic stirrer and reflux condenser, 3-(4-trifluoromethoxy-benzyl)-3H-imidazo[4,5-b]pyridine-2-thiol (150 mg, 0.46 mmol) and tort-butyl 2-bromopropionate (77 μl, 0.46 mmol) were refluxed for 2 h in acetone (5 ml) in the presence of $K_2CO_3$ (96 mg, 0.69 mmol). Heat was switched off and reaction mixture left stirring overnight. Solvent was concentrated under reduced pressure and residue taken up in water (20 ml) and extracted with EtOAc (20 ml). The organic layer was washed with 2M NaOH aqueous solution (20 ml) and subsequently dried and evaporated under reduced pressure to afford 224 mg of crude product. This was purified by column chromatography with a gradient of EtOAc and cyclohexane, product eluted with 30% EtOAc. Product fractions were concentrated under reduced pressure to afford the title compound (192 mg, 91%).

LCMS Method: 1, RT: 6.00 min, MI: 454 [M+1]

$^1$H-NMR, Method 1: (CDCl$_3$) 8.30 (dd 1H), 7.90 (dd 1H), 7.39 (dt 2H), 7.20 (dd 1H), 7.15 (d 2H), 5.46 (d 1H), 5.39 (d 1H), 4.70 (q 1H), 1.67 (d 3H), 1.41 (s 9H).

Synthesis of 2-[3-(4-trifluoromethoxy-benzyl)-3H-imidazo[4,5-b]pyridin-2-ylsulfanyl]-propionic acid

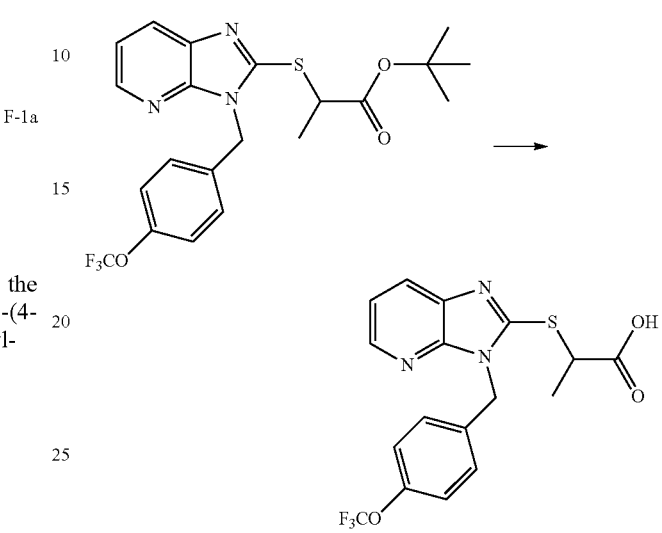

In a round bottom flask fitted with magnetic stirrer, 2-[3-(4-trifluoromethoxy-benzyl)-3H-imidazo[4,5-b]pyridin-2-ylsulfanyl]-propionic acid tert-butyl ester (97 mg, 0.21 mmol) was dissolved in DCM (2 ml) and TFA (1 ml) was added in. Mixture was stirred at r.t. overnight. The reaction mixture was concentrated under reduced pressure to afford the title compound (80 mg, 100%).

LCMS Method: 1, RT: 4.93 min, MI: 398 [M+1]

$^1$H-NMR, Method 1: (CDCl$_3$) 8.50 (dd 1H), 8.07 (dd 1H), 7.42 (dd 1H), 7.39 (dt 2H), 7.20 (d 2H), 5.58 (d 1H), 5.45 (d 1H), 4.47 (q 1H), 1.70 (d 3H).

Synthesis of N—((R)-2-hydroxy-1-phenyl-ethyl)-2-[3-(4-trifluoromethoxy-benzyl)-3H-imidazo[4,5-b]pyridin-2-ylsulfanyl]-propionamide (Ex. 154)

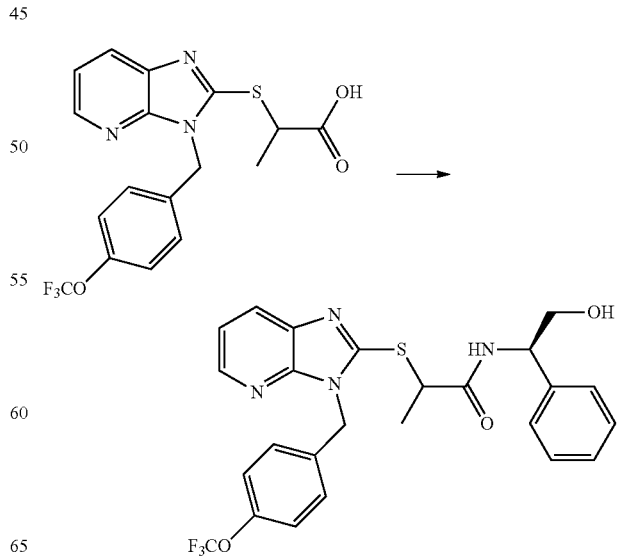

In a round bottom flask fitted with magnetic stirrer, a solution of 2-[3-(4-trifluoromethoxy-benzyl)-3H-imidazo[4,5-b]pyridin-2-ylsulfanyl]-propionic acid (97 mg, 0.24 mmol) and (R)-2-amino-2-phenyl-ethanol (37 µl, 0.27 mmol) in anhydrous DMF (3 ml) were treated with HBTU (102 mg, 0.27 mmol) and NEt$_3$ (34 µl, 0.47 mmol) and stirred at r.t. overnight. The reaction mixture was diluted with EtOAc (15 ml) and washed with NaHCO$_3$ aqueous solution (15 ml) and brine (10 ml). The organic layer was then filtered through a silicone treated filter paper and concentrated under reduced pressure. Crude material was purified by reverse phase mass-directed preparative HPLC, using LCMS Method 5 or 6. Product fractions were concentrated in the Genevac™ to afford the title compound (58 mg, 45%).

LCMS Method: 1, RT: 4.74 and 4.87 min, MI: 517 [M+1], 2 diastereoisomers.

General Synthesis of 3-[3-(4-hydroxy-benzyl)-3H-imidazo[4,5-b]pyridin-2-yl]-propionamide of general formula F-41 and 3-[3-(4-alkoxy-benzyl)-3H-imidazo[4,5-b]pyridin-2-yl]-propionamide of general formula F-42 (Scheme 008)

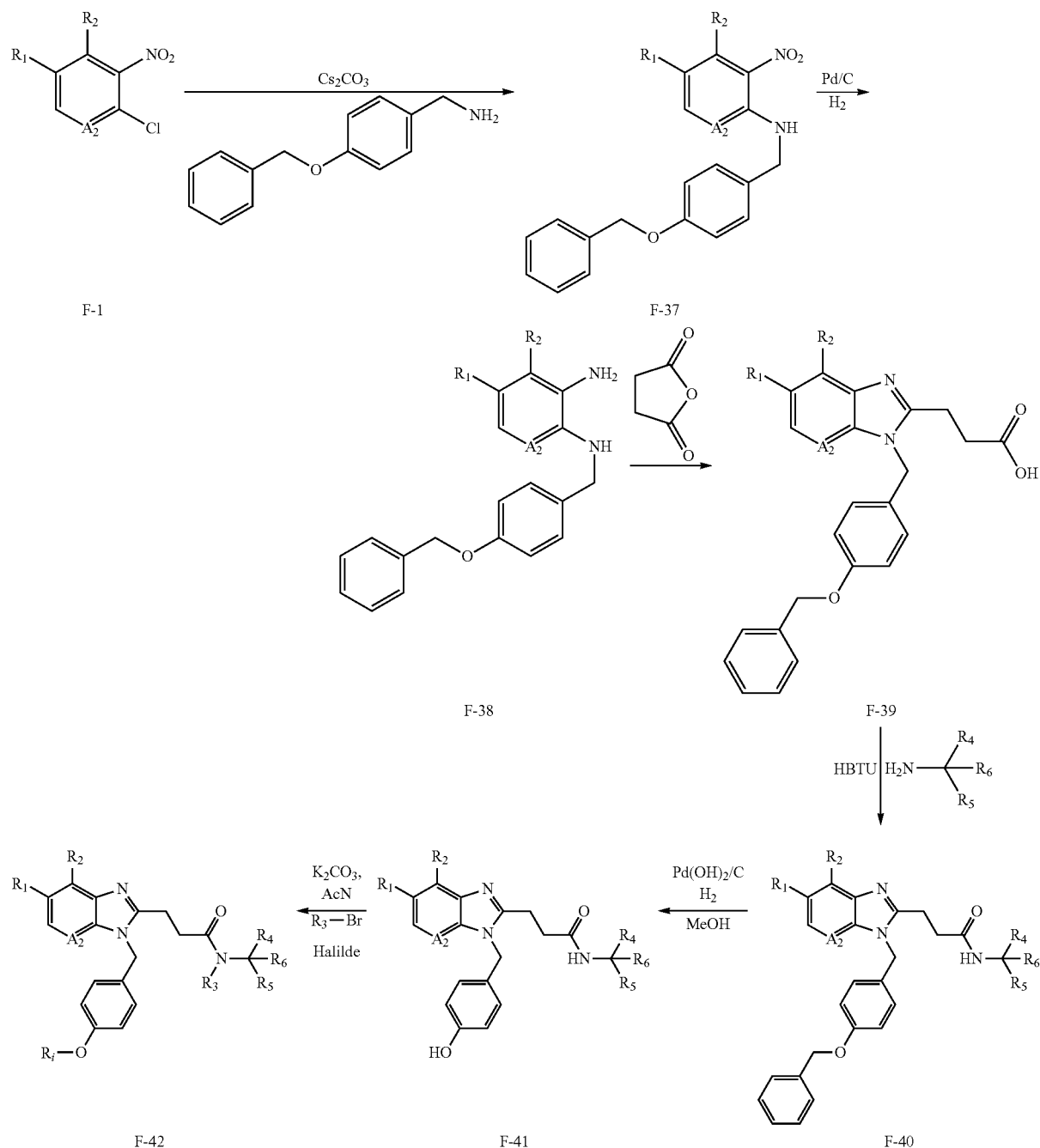

Intermediate F-37 was prepared following the same procedure as for intermediate F-2 in Scheme 001, using 4-benzyloxy-benzylamine as the amine. Intermediate F-38 was prepared following the same procedure as for intermediate F-3 in Scheme 001. Intermediates F-39 and F-40 were prepared following the same procedure as for intermediates F-6 and F-5 in Scheme 002-A. Hydrogenation of intermediate F-40 over Pd(OH)₂/C afforded the 3-[3-(4-hydroxy-benzyl)-3H-imidazo[4,5-b]pyridin-2-yl]-propionamide of general formula F-41. Treatment of this intermediate with K₂CO₃ and the required halide afforded the final compounds of general formula F-42.

F-1 was the following intermediate:

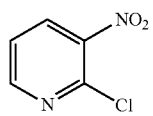

F-1a

The above synthesis (Scheme 008) is illustrated by the preparation of N—[(S)-1-(4-fluoro-phenyl)-ethyl]-3-[3-(4-isobutoxy-benzyl)-3H-imidazo[4,5-b]pyridin-2-yl]-propionamide (Ex. 156) described below.

Synthesis of N—[(S)-1-(4-fluoro-phenyl)-ethyl]-3-[3-(4-hydroxy-benzyl)-3H-imidazo[4,5-b]pyridin-2-yl]-propionamide (Ex. 155)

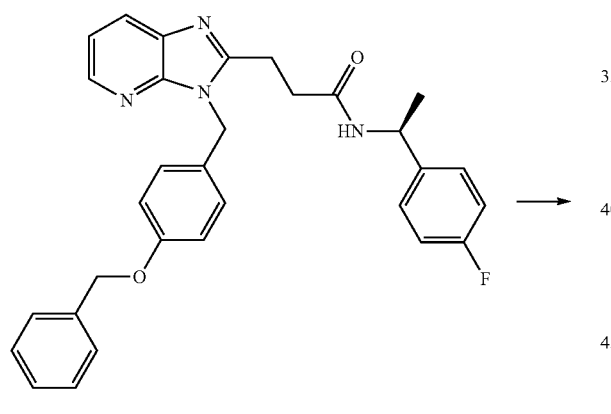

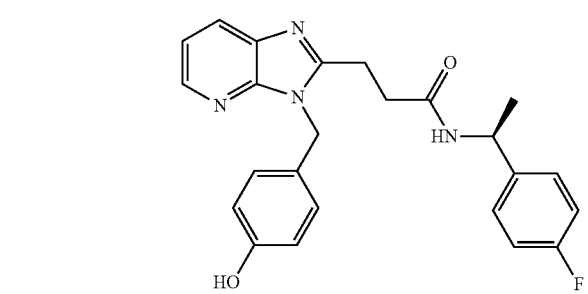

In a round bottom flask fitted with magnetic stirrer, 3-[3-(4-benzyloxy-benzyl)-3H-imidazo[4,5-b]pyridin-2-yl]-N—[(S)-1-(4-fluoro-phenyl)-ethyl]-propionamide (410 mg, 0.81 mmol) and 20% Pd(OH)₂/C (50 mg) were purged with N₂ and then treated with MeOH (20 ml). The suspension was stirred under a H₂ atmosphere for 24 hours at r.t. Suspension was filtered through Celite® with MeOH. The filtrate was concentrated under reduced pressure to afford the title compound (340 mg, 100% yield). From this material, 90 mg were further purified by reverse phase mass-directed preparative HPLC, using LCMS Method 5 or 6. Product fractions were concentrated in the Genevac™ to the title compound (38 mg).

Synthesis of N—[(S)-1-(4-fluoro-phenyl)-ethyl]-3-[3-(4-isobutoxy-benzyl)-3H-imidazo[4,5-b]pyridin-2-yl]-propionamide (Ex. 156)

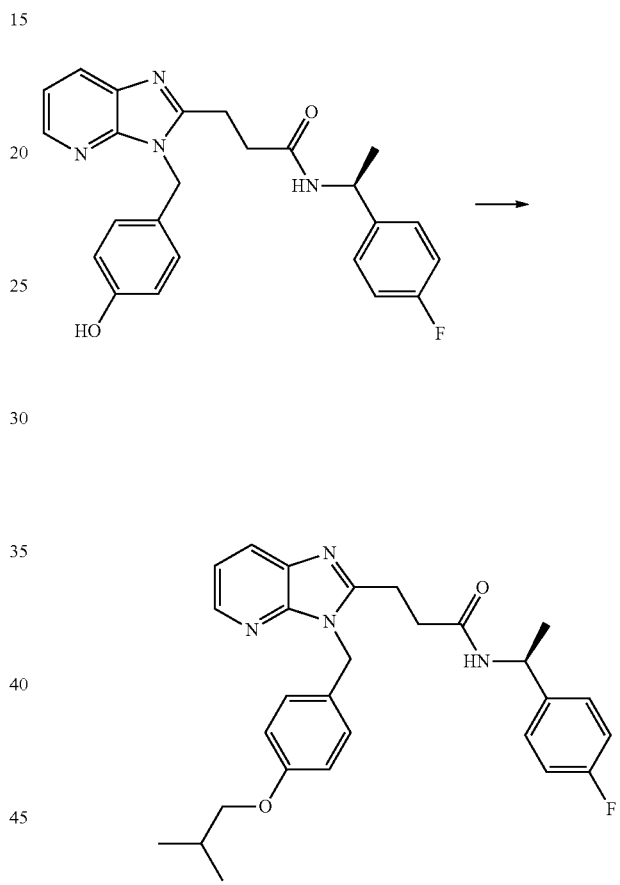

In a round bottom flask fitted with magnetic stirrer and reflux condenser, a mixture of N—[(S)-1-(4-fluoro-phenyl)-ethyl]-3-[3-(4-hydroxy-benzyl)-3H-imidazo[4,5-b]pyridin-2-yl]-propionamide (65 mg, 0.15 mmol) and K₂CO₃ (26 mg, 0.19 mmol) in acetonitrile (1.5 ml) was treated with isobutyl bromide (18 μl, 0.17 mmol) and heated to 90° C. in a sealed tube overnight. The reaction mixture was treated with additional isobutyl bromide and K₂CO₃ and heated for a further 24 hours. The reaction mixture was diluted with EtOAc, washed with saturated NH₄Cl aqueous solution and brine, dried and concentrated under reduced pressure. Crude product was purified by reverse phase mass-directed preparative HPLC, using either LCMS Method 5 or 6. Product fractions were concentrated in the Genevac™ to afford the title compound (16 mg, 23%).

The following compounds were prepared according to the general synthesis shown in Scheme 008:

| Example | General formula | Halide | Amine | Characterisation | |
|---|---|---|---|---|---|
| 155 | F-41 | None | 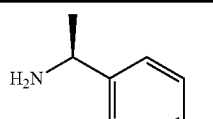 | LCMS Method: 1, RT: 3.40 min, MI: 419 [M + 1] | $^1$H-NMR, Method 1: (DMSO) 9.43 (bs 1H), 8.43 (d 1H), 8.35 (dd 1H), 8.02 (dd 1H), 7.32-7.28 (m 3H), 7.08-7.03 (m 4H), 6.68 (dt 2H), 5.38 (s 2H), 4.92-4.85 (m 1H), 3.14-3.01 (m 2H), 2.79-2.66 (m 2H), 1.31 (d 3H) |
| 156 | F-42 |  | 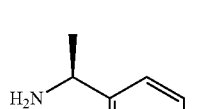 | LCMS Method: 1, RT: 4.89 min, MI: 475 [M + 1] | $^1$H-NMR, Method 1: (DMSO) 8.43 (d 1H), 8.32 (dd 1H), 8.00 (dd 1H), 7.32-7.25 (m 3H), 7.14 (d 2H), 7.05 (tt 2H), 6.86 (dt 2H), 5.41 (s 2H), 4.93-4.86 (m 1H), 3.68 (d 2H), 3.11-2.98 (m 2H), 2.79-2.66 (m 2H), 2.01-1.91 (m 1H), 1.32 (d 3H), 0.94 (d 6H) |

General Synthesis of (3-aralkyl-3H-imidazo[4,5-b]pyridin-2-ylmethyl)-urea of general formula F-46 and (3-aralkyl-3H-imidazo[4,5-b]pyridin-2-ylmethyl)-carbamate of general formula F-47 (Scheme 009)

Scheme 009

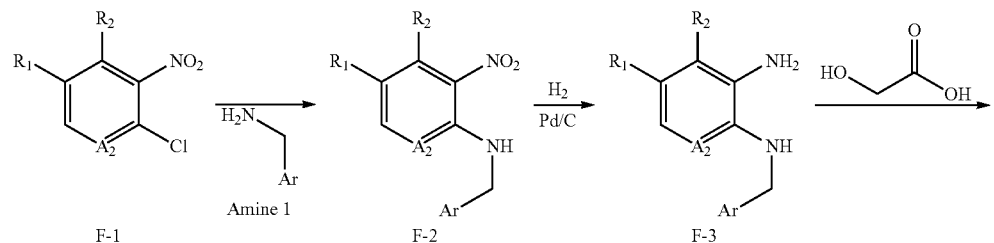

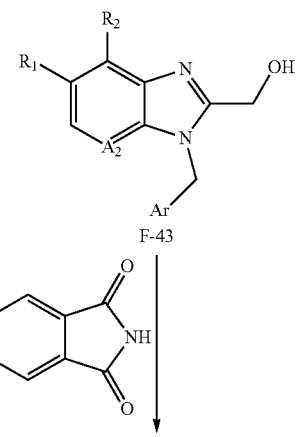

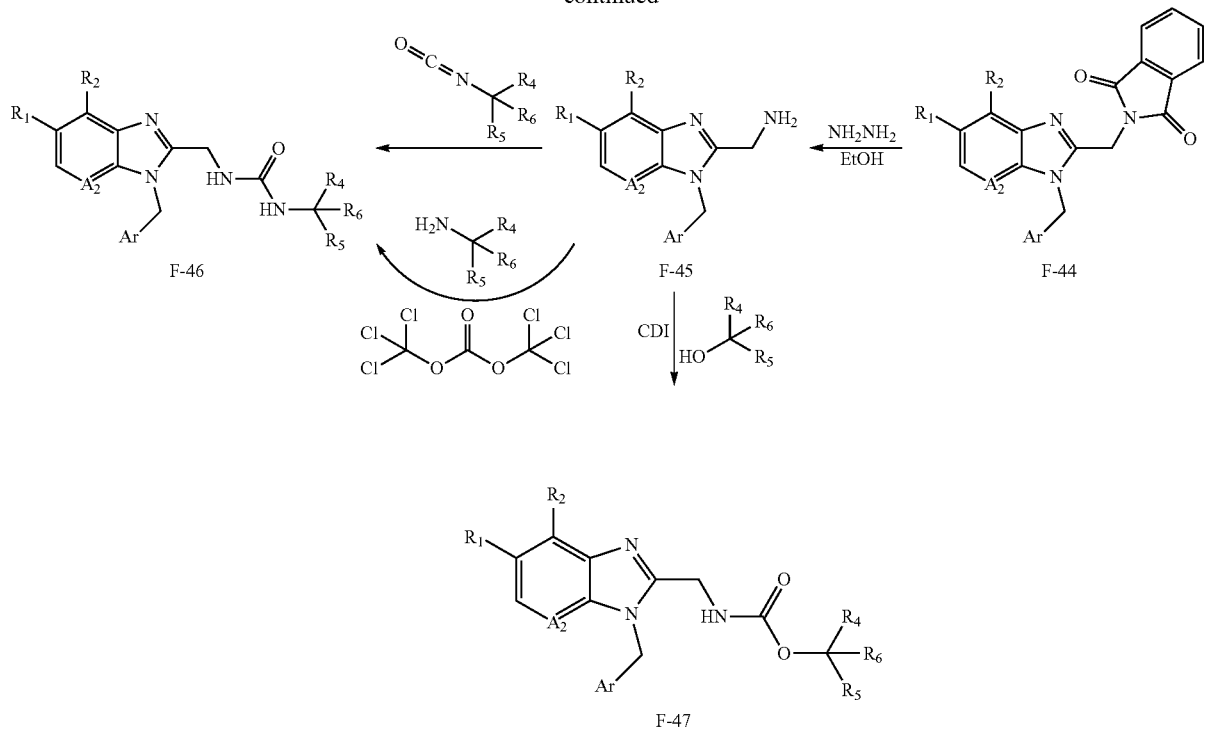

Intermediates F-2 and F-3 were prepared as in Scheme 001. Intermediate F-3 was reacted with glycolic acid to give the alcohol of general formula F-43, which was submitted to a Mitsunobu reaction with phthalimide to yield the imide of general formula F-44. Cleavage of the imide with hydrazine hydrate in ethanol afforded the primary amine of general formula F-45. Reaction of this intermediate with either the required isocyanate or with a mixture of triphosgene and the required amine afforded the ureas of general formula F-46. Finally, reaction of the same amine (F-45) with the required alcohol and CDI afforded the carbamates of general formula F-47.

F-1 was the following intermediate:

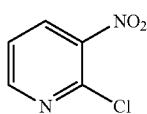

F-1a

The above synthesis (Scheme 009) is illustrated by the preparation of Example 161 and Example 162 described below.

Synthesis of [3-(4-fluoro-benzyl)-3H-imidazo[4,5-b]pyridin-2-yl]-methanol

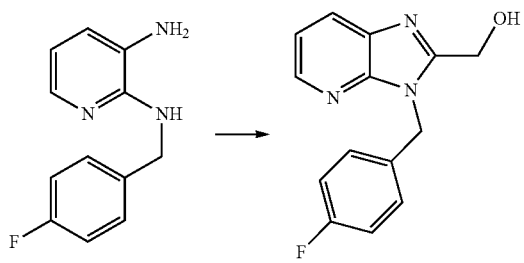 [SMILES: Nc1cccnc1NCc1ccc(F)cc1 ; OCc1nc2cccnc2n1Cc1ccc(F)cc1]

In a round bottom flask fitted with magnetic stirrer and reflux condenser, a mixture of N'2'-(4-fluoro-benzyl)-pyridine-2,3-diamine (2.56 g, 11.82 mmol) and glycolic acid (2.25 g, 29.55 mmol) was heated at 150° C. for 24 hours. Reaction crude was cooled and then treated with 2M HCl aqueous solution (20 ml). This mixture was sonicated to break up the thick oil and then stirred for a further 3 h. Aqueous ammonia (15 ml) was added followed by MeOH to give a black solution which was concentrated under reduced pressure. The crude product was purified by column chromatography with a gradient of MeOH and DCM, product eluted with 1 to 4% MeOH. Product fractions were combined and concentrated under reduced pressure to provide the title compound (2.38 g, 78%).

LCMS Method: 1, RT: 2.90 min, MI: 258 [M+1]

$^1$H-NMR, Method 1: (DMSO) 8.35 (dd 1H), 8.06 (dd 1H), 7.36-7.32 (m 2H), 7.29 (dd 1H), 7.14 (tt 2H), 5.80 (t 1H), 5.57 (s 2H), 4.72 (d 2H).

Synthesis of 2-[3-(4-fluoro-benzyl)-3H-imidazo[4,5-b]pyridin-2-ylmethyl]-isoindole-1,3-dione

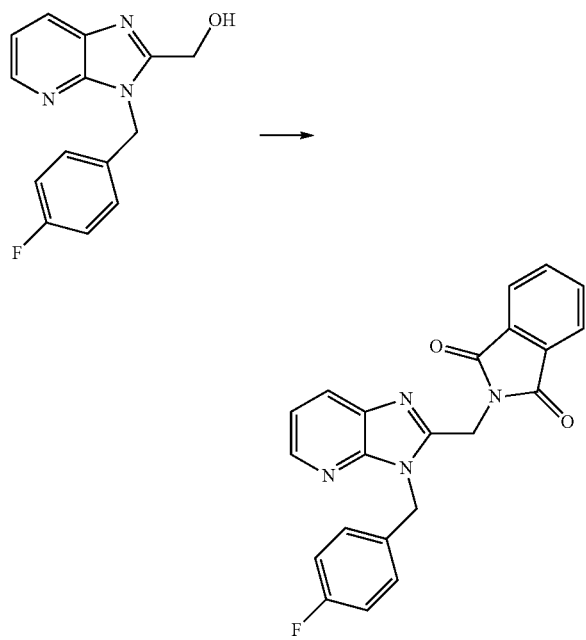

In a round bottom flask fitted with magnetic stirrer, [3-(4-fluoro-benzyl)-3H-imidazo[4,5-b]pyridin-2-yl]-methanol (2.38 g, 9.25 mmol), phthalimide (1.76 g, 12 mmol) and PPh$_3$ (3.2 g, 12.2 mmol) were dissolved in THF (100 ml) and the mixture was cooled to 0° C. with stirring under N$_2$. DIAD (2.4 ml, 12.2 mmol) was added dropwise and the reaction mixture was slowly allowed to reach r.t. and then stirred overnight. The suspension was filtered and the white solid obtained washed with Et$_2$O. The filtrate was evaporated, re-dissolved in EtOAc and washed with water and brine. The organic extract was dried and concentrated under reduced pressure and the crude product purified by column chromatography with a gradient of EtOAc and cyclohexane, product eluted with 30 to 100% EtOAc. Product fractions were combined and evaporated under reduced pressure to afford the title compound (2.15 g, 60%).

LCMS Method: 1, RT: 4.22 min, MI: 231 [M+1]

Synthesis of [3-(4-fluoro-benzyl)-3H-imidazo[4,5-b]pyridin-2-yl]-methylamine

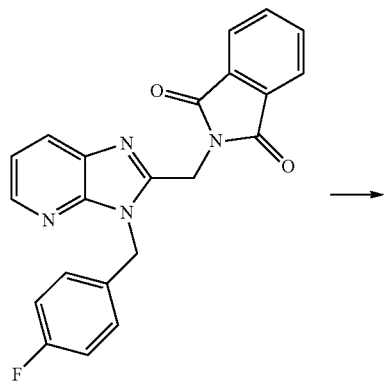

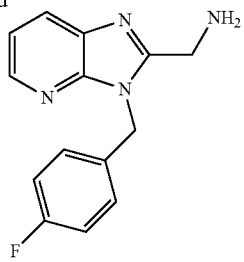

In a round bottom flask fitted with magnetic stirrer and reflux condenser, 2-[3-(4-fluoro-benzyl)-3H-imidazo[4,5-b]pyridin-2-ylmethyl]isoindole-1,3-dione (2.15 g, 5.56 mmol) in EtOH (80 ml) was treated with hydrazine hydrate (1.35 ml, 27.8 mmol) and heated to reflux overnight. The thick suspension was cooled in an ice bath and filtered. The obtained white solid was washed with cold EtOH. The filtrate was concentrated under reduced pressure and purified by column chromatography with a gradient of MeOH and DCM, product eluted with 5-10% MeOH. Product fractions were combined and concentrated under reduced pressure to afford the title compound (1.37 g, 97%).

LCMS Method: 1, RT: 2.05 min, MI: 257 [M+1]
$^1$H-NMR, Method 1: (DMSO) 8.32 (dd 1H), 8.03 (dd 1H), 7.32-7.26 (m 3H), 7.15 (tt 2H), 5.56 (s 2H), 3.94 (s 2H).

Synthesis of 1-[3-(4-fluoro-benzyl)-3H-imidazo[4,5-b]pyridin-2-ylmethyl]-3-((S)-1-phenyl-ethyl)-urea (Ex. 161)

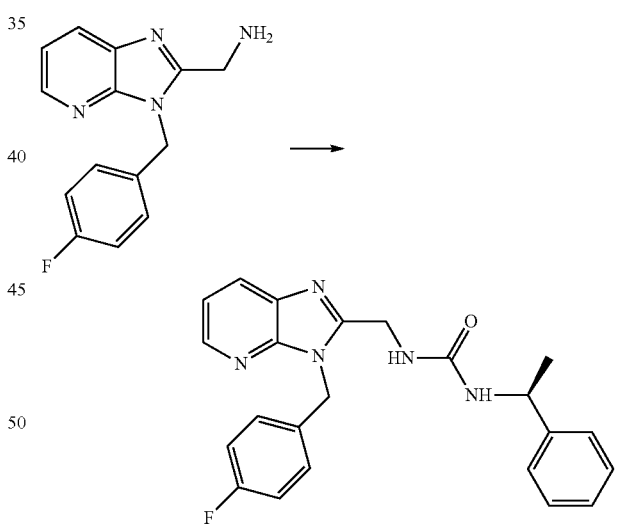

In a round bottom flask fitted with magnetic stirrer, a solution of [3-(4-fluoro-benzyl)-3H-imidazo[4,5-b]pyridin-2-yl]-methylamine (50 mg, 0.19 mmol) in DCM (4 ml) was treated with NEt$_3$ (200 µl, 1.47 mmol) and ((S)-1-isocyanato-ethyl)-benzene (31 µl, 0.22 mmol) and mixture was stirred at r.t. overnight. Reaction mixture was diluted with DCM, washed with brine, dried and concentrated under reduced pressure. The crude product was purified by reverse phase mass-directed preparative HPLC, using LCMS Method 5 or 6. Product fractions were combined and concentrated in the Genevac™ to afford the title compound (55 mg, 69%).

Synthesis of 1-[3-(3,4-difluoro-benzyl)-3H-imidazo[4,5-b]pyridin-2-ylmethyl]-3-((R)-2-hydroxy-1-phenyl-ethyl)-urea (Ex. 162)

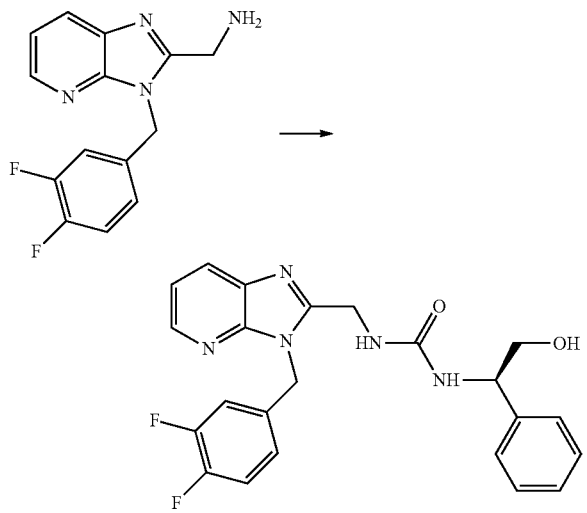

In a round bottom flask fitted with magnetic stirrer, to a solution of triphosgene (56 mg, 0.189 mmol) in dry DCM (1 ml) at 0° C. was added [3-(3,4-difluoro-benzyl)-3H-imidazo[4,5-b]pyridin-2-yl]-methylamine (140 mg, 0.51 mmol) in dry DCM (1 ml) dropwise (gave a bright pink solution). NEt$_3$ (141 µl, 1.02 mmol) in DCM (1 ml) was added immediately (reaction mixture turned yellow) and the resulting solution was stirred at 0° C. for 30 min. (R)-2-amino-2-phenyl-ethanol (105 mg, 0.77 mmol) was added and the reaction mixture stirred overnight. Reaction crude was concentrated under reduced pressure and triturated in EtOAc (15 ml). A white precipitate was filtered off and the filtrate concentrated under reduced pressure. Filtrate was purified by reverse phase mass-directed preparative HPLC, using LCMS Method 5 or 6. Product fractions were concentrated in the Genevac™ to give the title compound (10 mg, 5%).

The following compounds were prepared according to the general synthesis shown in Scheme 009:

| Example | General formula | Amine 1 | Amine 2 | Characterisation | |
|---|---|---|---|---|---|
| 157 | F-46 | 4-fluoro-benzylamine | (R)-1-(4-chlorophenyl)ethylamine | LCMS Method: 1, RT: 4.26 min, MI: 438 [M + 1] | $^1$H-NMR, Method 1: (DMSO) 8.34 (dd 1H), 8.05 (dd 1H), 7.37-7.33 (m 2H), 7.31-7.25 (m 5H), 7.12 (tt 2H), 6.73 (d 1H), 6.51 (t 1H), 5.50 (s 2H), 4.75-4.68 (m 1H), 4.53-4.42 (m 2H), 1.29 (d 3H) |
| 158 | F-46 | 3,4-difluoro-benzylamine | (R)-1-(4-bromophenyl)ethylamine | LCMS Method: 1, RT: 4.47 min, MI: 500 [M + 1] | $^1$H-NMR, Method 1: (DMSO) 8.34 (dd 1H), 8.06 (dd 1H), 7.48 (dt 2H), 7.39-7.28 (m 3H), 7.23 (dt 2H), 7.04-7.01 (m 1H), 6.71 (d 1H), 6.52 (t 1H), 5.50 (s 2H), 4.72-4.65 (m 1H), 4.56-4.44 (m 2H), 1.28 (d 3H) |
| 159 | F-46 | 4-fluoro-benzylamine | (R)-1-(4-methoxyphenyl)ethylamine | LCMS Method: 1, RT: 3.86 min, MI: 434 [M + 1] | $^1$H-NMR, Method 1: (DMSO) 8.34 (dd 1H), 8.05 (dd 1H), 7.31-7.26 (m 3H), 7.20 (dt 2H), 7.13 (tt 2H), 6.86 (dt 2H), 6.59 (d 1H), 6.48 (t 1H), 5.51 (s 2H), 4.72-4.65 (m 1H), 4.54-4.44 (m 2H), 3.72 (s 3H), 1.28 (d 3H) |
| 160 | F-46 | 4-fluoro-benzylamine | (R)-1-(4-fluorophenyl)ethylamine | LCMS Method: 1, RT: 3.99 min, MI: 422 [M + 1] | $^1$H-NMR, Method 1: (DMSO) 8.34 (dd 1H), 8.05 (dd 1H), 7.33-7.26 (m 5H), 7.15-7.10 (m 4H), 6.69 (d 1H), 6.50 (t 1H), 5.51 (s 2H), 4.77-4.70 (m 1H), 4.54-4.43 (m 2H), 1.30 (d 3H) |

-continued

| Example | General formula | Amine 1 | Amine 2 | Characterisation | |
|---|---|---|---|---|---|
| 161 | F-46 | 4-fluorobenzylamine | (S)-1-phenylethylamine | LCMS Method: 1, RT: 3.90 min, MI: 404 [M + 1] | $^1$H-NMR, Method 1: (DMSO) 8.34 (dd 1H), 8.05 (dd 1H), 7.32-7.26 (m 7H), 7.23-7.19 (m 1H), 7.13 (tt 2H), 6.68 (d 1H), 6.51 (t 1H), 5.51 (s 2H), 4.77-4.70 (m 1H), 4.55-4.44 (m 2H), 1.31 (d 3H) |
| 162 | F-46 | 3,4-difluorobenzylamine | (S)-2-amino-2-phenylethanol | LCMS Method: 1, RT: 3.50 min, MI: 437 [M + 1] | $^1$H-NMR, Method 1: (DMSO) 8.33 (dd 1H), 8.05 (dd 1H), 7.37-7.19 (m 8H), 7.05-7.02 (m 1H), 6.76-6.71 (m 2H), 5.51 (s 2H), 4.87 (t 1H), 4.69-4.64 (m 1H), 4.56-4.46 (m 2H), 3.58-3.49 (m 2H) |
| 163 | F-46 | 3,4-difluorobenzylamine | (S)-1-(4-morpholinophenyl)ethylamine | LCMS Method: 1, RT: 3.63 min, MI: 506 [M + 1] | $^1$H-NMR, Method 1: (DMSO) 8.33 (dd 1H), 8.05 (dd 1H), 7.38-7.28 (m 3H), 7.13 (d 2H), 7.04-7.01 (m 1H), 6.87 (d 2H), 6.52 (d 1H), 6.47 (t 1H), 5.51 (s 2H), 4.68-4.61 (m 1H), 4.56-4.45 (m 2H), 3.73 (t 4H), 3.05 (t 4H), 1.26 (d 3H) |
| 164 | F-47 | 4-fluorobenzylamine | (S)-2-amino-1-(4-fluorophenyl)ethanol | LCMS Method: 1, RT: 4.35 min, MI: 423 [M + 1] | $^1$H-NMR, Method 1: (DMSO) 8.35 (dd 1H), 8.06 (dd 1H), 7.92 (t 1H), 7.41-7.37 (m 2H), 7.31 (dd 1H), 7.27-7.11 (m 6H), 5.66 (q 1H), 5.51 (s 2H), 4.54-4.43 (m 2H), 1.42 (d 3H) |
| 165 | F-46 | 4-fluorobenzylamine | (S)-1-(3-methoxyphenyl)ethylamine | LCMS Method: 1, RT: 3.91 min, MI: 434 [M + 1] | $^1$H-NMR, Method 1: (DMSO) 8.34 (dd 1H), 8.04 (dd 1H), 7.31-7.26 (m 3H), 7.22 (t 1H), 7.13 (tt 2H), 6.86-6.85 (m 2H), 6.79-6.76 (m 1H), 6.68 (d 1H), 6.50 (t 1H), 5.51 (s 2H), 4.74-4.67 (m 1H), 4.54-4.44 (m 2H), 3.73 (s 3H), 1.29 (d 3H) |

General Synthesis of alkyl-carbamic acid 3-aralkyl-3H-imidazo[4,5-b]pyridin-2-ylmethyl ester of general formula F-48 (Scheme 010)

Scheme 010

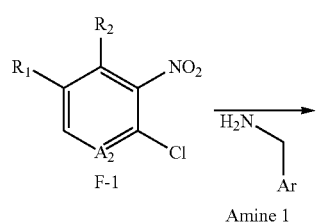

Amine 1

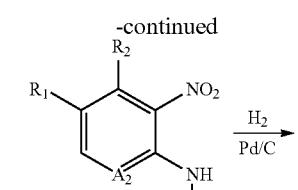

F-2

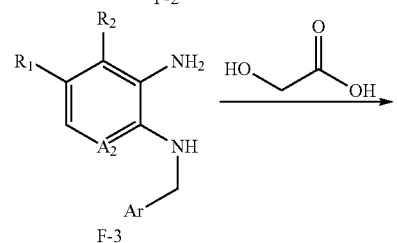

F-3

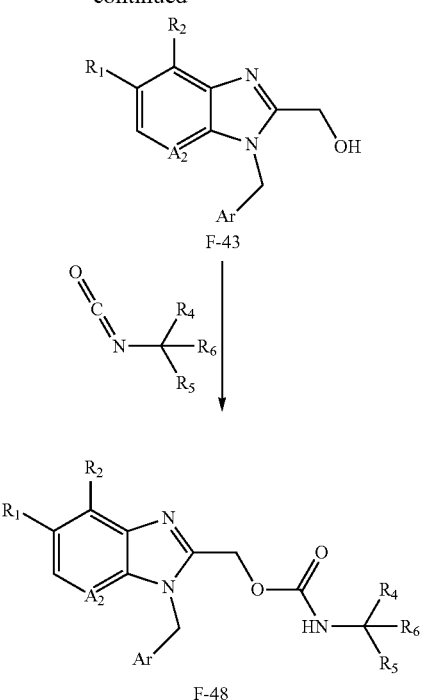

F-43

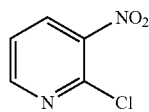

F-48

Intermediates F-2 and F-3 were prepared as in Scheme 001. Intermediate F-43 was prepared as in Scheme 009. Alcohol of general formula F-43 was reacted with the required isocyanate to afford the final compounds of general formula F-48.

F-1 was the following intermediate:

F-1a

The above synthesis (Scheme 010) is illustrated by the preparation of [(S)-1-(4-fluoro-phenyl)-ethyl]-carbamic acid 3-(4-fluoro-benzyl)-3H-imidazo[4,5-b]pyridin-2-ylmethyl ester (Ex. 166) described below.

Synthesis of [(S)-1-(4-fluoro-phenyl)-ethyl]carbamic acid 3-(4-fluoro-benzyl)-3H-imidazo[4,5-b]pyridin-2-ylmethyl ester (Ex. 166)

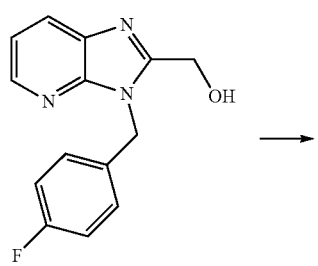

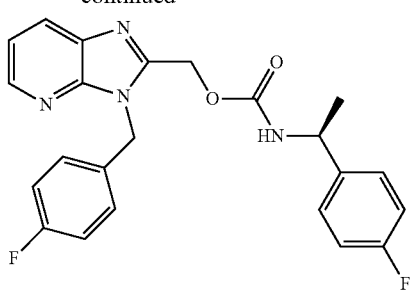

In a round bottom flask fitted with magnetic stirrer and reflux condenser, 1-fluoro-4-((S)-1-isocyanato-ethyl)-benzene (225 mg, 1.36 mmol) was added to a solution of [3-(4-fluoro-benzyl)-3H-imidazo[4,5-b]pyridin-2-yl]-methanol (70 mg, 0.27 mmol) in THF (1 ml) with ice-cooling. After 1.5 hours of stirring at 0° C., the ice-bath was removed and reaction crude heated to 40° C. overnight. Reaction crude was diluted with EtOAc (15 ml), washed with water (10 ml), filtered through a silicone treated filter paper and concentrated under reduced pressure to yield 174 mg of crude product. This material was purified by reverse phase mass-directed preparative HPLC using either LCMS Method 5 or 6 and concentrated in the Genevac™ to afford the title compound (4 mg, 4%).

LCMS Method: 1, RT: 4.55 min, MI: 423 [M+1]

$^{1}$H-NMR, Method 1: (CDCl$_3$) 8.44 (dd 1H), 8.08 (dd 1H), 7.29 (dd 1H), 7.24-7.21 (m 2H), 7.17-7.11 (m 2H), 7.03-6.92 (m 4H), 5.54 (s 2H), 5.32 (d 1H), 5.22 (d 1H), 4.91 (bs 1H), 4.80-4.73 (m 1H), 1.43 (d 3H).

General Synthesis of N-(4-amino-benzyl)-3-(3-aralkyl-3H-imidazo[4,5-b]pyridin-2-yl)-propionamide F-50 (Scheme 011)

Scheme 011

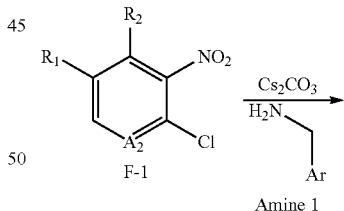

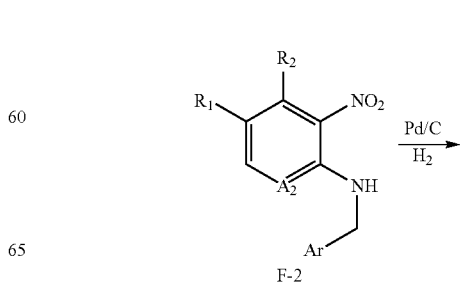

F-2

F-1 could be any of the following intermediates:

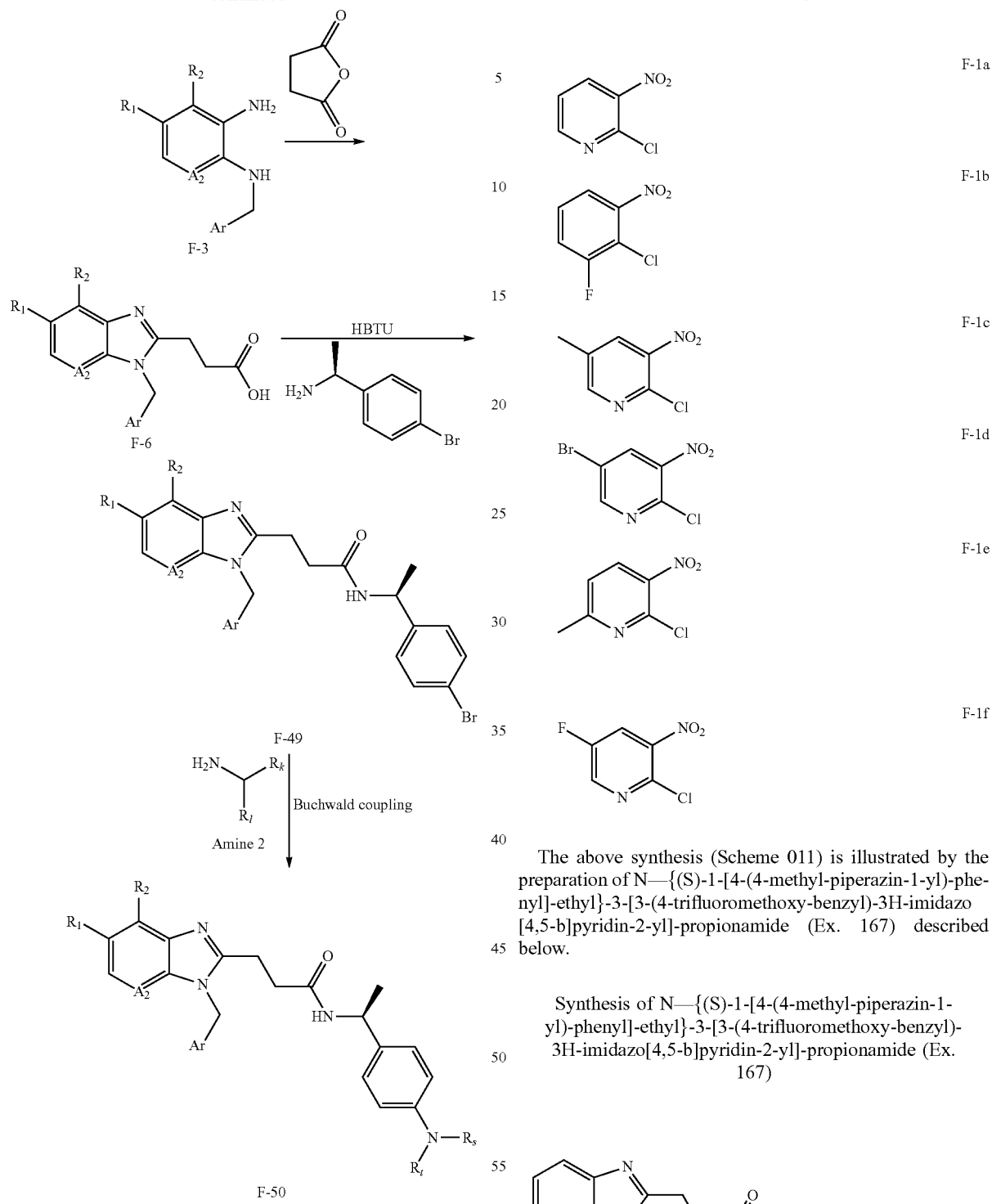

The above synthesis (Scheme 011) is illustrated by the preparation of N—{(S)-1-[4-(4-methyl-piperazin-1-yl)-phenyl]-ethyl}-3-[3-(4-trifluoromethoxy-benzyl)-3H-imidazo[4,5-b]pyridin-2-yl]-propionamide (Ex. 167) described below.

Synthesis of N—{(S)-1-[4-(4-methyl-piperazin-1-yl)-phenyl]-ethyl}-3-[3-(4-trifluoromethoxy-benzyl)-3H-imidazo[4,5-b]pyridin-2-yl]-propionamide (Ex. 167)

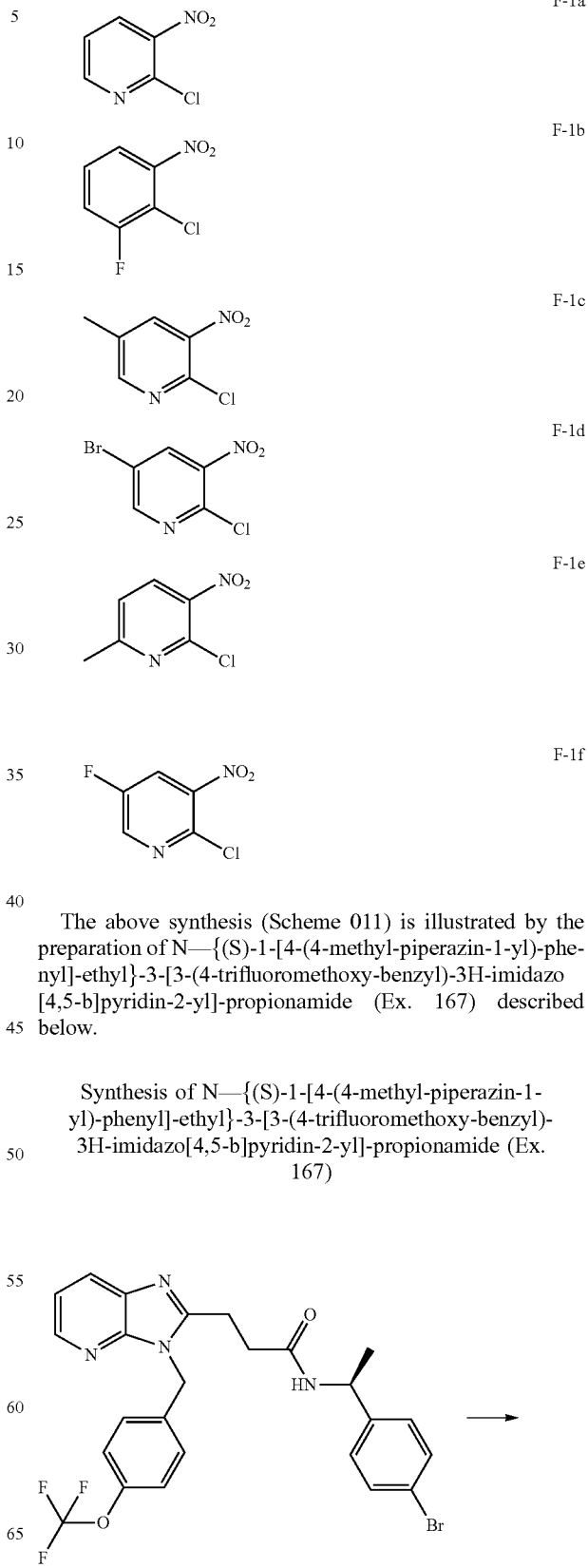

Intermediates F-2 and F-3 were prepared as in Scheme 001. Intermediate F-6 was prepared as in Scheme 002-A. Intermediate F-49 was prepared following the same procedure as for intermediate F-5 in Scheme 002-A, using (S)-1-(4-bromo-phenyl)-ethylamine as the required amine. Compounds of general formula F-49 were submitted to a Buchwald coupling with the required amine 2 to afford the final compounds of general formula F-50.

-continued

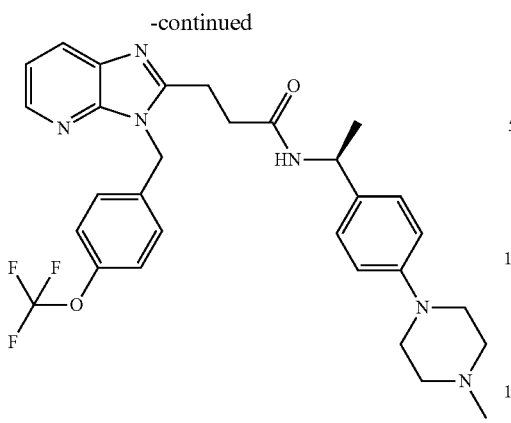

In a MW vial, N—[(S)-1-(4-bromo-phenyl)-ethyl]-3-[3-(4-trifluoromethoxy-benzyl)-3H-imidazo[4,5-b]pyridin-2-yl]-propionamide (218 mg, 0.39 mmol), 1-methylpiperazine (0.16 mL, 1.593 mmol), Pd$_2$(dba)$_3$ (20 mg, 0.02 mmol), X-Phos (19 mg, 0.04 mmol) and Na$^t$OBu (61 mg, 0.64 mmol) were dissolved in 4 mL of dioxane and heated in the MW to 140° C. for 1 hour. Solvent was concentrated under reduced pressure and the crude product was purified by reverse phase mass-directed preparative HPLC using either LCMS Method 5 or 6. Required product fractions were concentrated in the Genevac™ and material obtained was passed through an SCX cartridge. Required product was eluted with ammonia in MeOH solution. Eluent was concentrated under reduced pressure to afford the title compound (74 mg, 32%).

The following compounds of general formula F-50 were prepared according to the general synthesis shown in Scheme 011:

| Example | SM | Amine 1 | Amine 2 | Characterisation | |
|---|---|---|---|---|---|
| 167 | F-1a | 4-(trifluoromethoxy)benzylamine | 1-methylpiperazine | LCMS Method: 1, RT: 2.69 min, MI: 567 [M + 1] | $^1$H-NMR, Method 1: (DMSO) 8.31-8.28 (m 2H), 8.01 (dd 1H), 7.30 (s 4H), 7.27 (dd 1H), 7.08 (d 2H), 6.77 (d 2H), 5.53 (s 2H), 4.84-4.77 (m 1H), 3.11-2.98 (m 6H), 2.79-2.66 (m 2H), 2.45 (t 4H), 2.22 (s 3H), 1.28 (d 3H) |
| 168 | F-1a | 4-(trifluoromethoxy)benzylamine | (S)-3-(dimethylamino)pyrrolidine | LCMS Method: 1, RT: 2.78 min, MI: 581 [M + 1] | $^1$H-NMR, Method 1: (DMSO) 8.30 (dd 1H), 8.25 (d 1H), 8.02 (dd 1H), 7.30 (s 4H), 7.28 (dd 1H), 7.03 (d 2H), 6.37 (d 2H), 5.54 (s 2H), 4.82-4.75 (m, 1H), 3.28 (td 2H), 3.20-3.14 (m 1H), 3.05 (td 2H), 2.98 (t 1H), 2.83-2.76 (m 1H), 2.76-2.65 (m 2H), 2.22(s 6H), 2.18-2.10 (m 1H), 1.83-1.74 (m 1H), 1.27 (d 3H) |
| 169 | F-1a | 4-(trifluoromethoxy)benzylamine | (R)-3-(dimethylamino)pyrrolidine | LCMS Method: 1, RT: 2.78 min, MI: 581 [M + 1] | $^1$H-NMR, Method 1: (DMSO) 8.30 (dd 1H), 8.25 (d 1H), 8.02 (dd 1H), 7.30 (bs 4H), 7.28 (dd 1H), 7.03 (d 2H), 6.37 (d 2H), 5.54 (s 2H), 4.82-4.75 (m 1H), 3.36 (td 1H), 3.28 (td 1H), 3.20-3.13 (m 1H), 3.05 (td 2H), 2.97 (t 1H), 2.82-2.75 (m 1H), 2.75-2.66 (m 2H), 2.21 (s 6H), 2.17-2.10 (m 1H), 1.83-1.73 (m 1H), 1.28 (d 3H) |
| 170 | F-1a | 4-(trifluoromethoxy)benzylamine | homopiperazine | LCMS Method: 1, RT: 2.77 min, MI: 567 [M + 1] | $^1$H-NMR, Method 1: (DMSO) 8.30 (dd 1H), 8.24 (d 1H), 8.01 (dd 1H), 7.31 (s 4H), 7.28 (dd 1H), 7.00 (d 2H), 6.52 (d 2H), 5.54 (s 2H), 4.78 (m 1H), 3.47 (t 2H), 3.41 (t 2H), 3.08-3.03 (m 2H), 2.82 (t 2H), 2.77-2.66 (m 2H), 2.60 (t 2H), 1.75 (q 2H), 1.28 (d 3H) |
| 171 | F-1a | 4-(trifluoromethoxy)benzylamine | (2S,6S)-2,6-dimethylpiperazine | LCMS Method: 1, RT: 2.78 min, MI: 581 [M + 1] | $^1$H-NMR, Method 1: (DMSO) 8.31-8.29 (m 2H), 8.02 (dd 1H), 7.30 (s 4H), 7.28 (dd 1H), 7.05 (d 2H), 6.74 (d 2H), 5.54 (s 2H), 4.80 (m 1H), 3.43 (d 2H), 3.07-3.03 (m 2H), 2.87-2.78 (m 2H), 2.77-2.65 (m 2H), 2.06 (td 2H), 1.28 (d 3H), 1.02 (d 6H) |

| Example | SM | Amine 1 | Amine 2 | Characterisation | |
|---|---|---|---|---|---|
| 172 | F-1a | 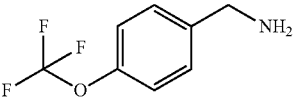 | 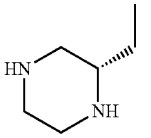 | LCMS Method: 1, RT: 2.79 min, MI: 581 [M + 1] | $^1$H-NMR, Method 1: (DMSO) 8.31-8.29 (m 2H), 8.02 (dd 1H), 7.30 (s 4H), 7.28 (dd 1H), 7.07(d 2H), 6.76 (d 2H), 5.54 (s 2H), 4.80 (m 1H), 3.43 (t 2H), 3.05 (td 2H), 2.97 (dt 1H), 2.79-2.66 (m 4H), 2.59-2.54 (m 1H), 2.53-2.46 (m 1H), 2.16 (t 1H), 1.41-1.33 (m 2H), 1.28 (d 3H), 0.93 (t 3H) |
| 173 | F-1a | 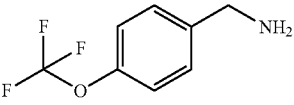 [SMILES: NCc1ccc(OC(F)(F)F)cc1] | 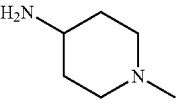 | LCMS Method: 1, RT: 2.66 min, MI: 581 [M + 1] | $^1$H-NMR, Method 1: (DMSO) 8.31 (dd 1H), 8.21 (d 1H), 8.01 (dd 1H), 7.31 (s 4H), 7.27 (dd 1H), 6.95 (d 2H), 6.44 (d 2H), 5.54 (s 2H), 5.27 (bs 1H), 4.78-4.75 (m 1H), 3.14-3.09 (m 1H), 3.05 (td 2H), 2.77-2.64 (m 4H), 2.20 (s 3H), 2.05 (t 2H), 1.86-1.83 (m 2H), 1.41-1.30 (m 2H), 1.26 (d 3H) |
| 174 | F-1a | 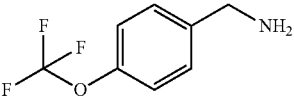 [SMILES: NCc1ccc(OC(F)(F)F)cc1] | 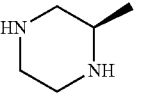 | LCMS Method: 1, RT: 2.71 min, MI: 567 [M + 1] | $^1$H-NMR, Method 1: (DMSO) 8.31-8.29 (m 2H), 8.01 (dd 1H), 7.30 (s 4H), 7.28 (dd 1H), 7.09 (d 2H), 6.76 (d 2H), 5.53 (s 2H), 4.83-4.77 (m 1H), 4.19 (bs 1H), 3.79 (d 1H), 3.49 (d 1H), 3.39 (d 1H), 3.12 (td 1H), 3.04 (td 2H), 2.79-2.67 (m 4H), 2.52 (td 1H), 1.28(d 3H), 1.18 (d 3H) |
| 175 | F-1a | 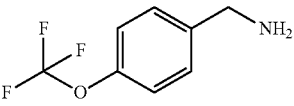 [SMILES: NCc1ccc(OC(F)(F)F)cc1] | 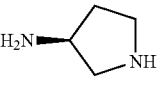 | LCMS Method: 1, RT: 2.70 min, MI: 553 [M + 1] | $^1$H-NMR, Method 1: (DMSO) 8.31 (dd 1H), 8.23 (d 1H), 8.01 (dd 1H), 7.32 (s 4H), 7.28 (dd 1H), 6.98 (d 2H), 6.45 (d 2H), 5.60 (t 1H), 5.55 (s 2H), 4.81-4.74 (m 1H), 4.49 (bs 1H), 3.86-3.30 (m 2H), 3.12-2.99 (m 3H), 2.93-2.61 (m 4H), 2.06-1.91 (m 1H), 1.54 (bs 1H), 1.27(d 3H) |
| 176 | F-1a | 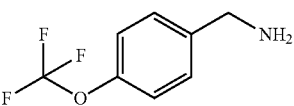 [SMILES: NCc1ccc(OC(F)(F)F)cc1] | 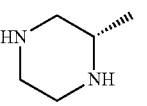 | LCMS Method: 1, RT: 2.70 min, MI: 567 [M + 1] | $^1$H-NMR, Method 1: (DMSO) 8.32-8.29 (m 2H), 8.02 (dd 1H), 7.30 (s 4H), 7.28 (dd 1H), 7.07 (d 2H), 6.76 (d 2H), 5.54 (s 2H), 4.84-4.77 (m 1H), 3.53 (bs 2H), 3.43 (d 2H), 3.05 (td 2H), 2.97 (dt 1H), 2.82-2.66 (m 4H), 2.16 (t 1H), 1.27 (d 3H), 1.03 (d 3H) |
| 177 | F-1a | 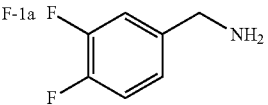 | 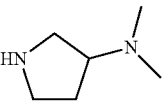 | LCMS Method: 1, RT: 2.53 min, MI: 533 [M + 1] | $^1$H-NMR, Method 1: (DMSO) 8.30 (dd 1H), 8.24 (d 1H), 8.01 (dd 1H), 7.40-7.30 (m 2H), 7.28 (dd 1H), 7.03 (d 2H), 7.00-6.97 (m 1H), 6.38 (d 2H), 5.49 (s 2H), 4.82-4.75 (m 1H), 3.39-3.33 (m 1H), 3.32-3.26 (m 1H), 3.21-3.13 (m 1H), 3.05 (td 2H), 2.99 (td 1H), 2.87-2.79 (m 1H), 2.77-2.65 (m 2H), 2.24 (s 6H), 2.18-2.11 (m 1H), 1.85-1.75 (m 1H), 1.28 (d 3H) |

| Example | SM | Amine 1 | Amine 2 | | Characterisation |
|---|---|---|---|---|---|
| 178 | F-1a | 4-F-C6H4-CH2-NH2 | azepane (HN-7-ring) | LCMS Method: 1, RT: 4.45 min, MI: 500 [M + 1] | ¹H-NMR, Method 1: (DMSO) 8.31 (dd 1H), 8.23 (d 1H), 8.00 (dd 1H), 7.28-7.23 (m 3H), 7.14 (tt 2H), 7.00 (d 2H), 6.50 (d 2H), 5.49 (s 2H), 4.82-4.75 (m 1H), 3.39 (t 4H), 3.11-2.98 (m 2H), 2.77-2.63 (m 2H), 1.69 (bs 4H), 1.43 (t 4H), 1.28 (d 3H) |
| 179 | F-1a | 3,4-di-F-C6H3-CH2-NH2 | 3-(trifluoromethyl)piperazine | LCMS Method: 1, RT: 3.12 min, MI: 573 [M + 1] | ¹H-NMR, Method 1: (DMSO) 8.33-8.29 (m 2H), 8.02 (dd 1H), 7.39-7.29 (m 2H), 7.27 (dd 1H), 7.09 (d 2H), 7.00-6.97 (m 1H), 6.79 (d 2H), 5.48 (s 2H), 4.85-4.78 (m 1H), 3.53-3.45 (m 2H), 3.40-3.37 (m 1H), 3.10-2.98 (m 3H), 2.82-2.58 (m 5H), 1.29 (d 3H) |
| 180 | F-1a | 4-F-C6H4-CH2-NH2 | pyrrolidine | LCMS Method: 1, RT: 4.04 min, MI: 472 [M + 1] | ¹H-NMR, Method 1: (DMSO) 8.31 (dd 1H), 8.23 (d 1H), 8.00 (dd 1H), 7.28-7.22 (m 3H), 7.13 (tt 2H), 7.03 (d 2H), 6.38 (d 2H), 5.49 (s 2H), 4.82-4.75 (m 1H), 3.16-3.14 (m 4H), 3.03 (td 2H), 2.71-2.67 (m 2H), 1.94-1.91 (m 4H), 1.27 (d 3H) |
| 181 | F-1a | 4-F-C6H4-CH2-NH2 | piperidin-4-yl-methanol | LCMS Method: 1, RT: 2.35 min, MI: 516 [M + 1] | — |
| 182 | F-1a | 3,4-di-F-C6H3-CH2-NH2 | 4-methylpiperazine | LCMS Method: 1, RT: 2.41 min, MI: 519 [M + 1] | ¹H-NMR, Method 1: (DMSO) 8.31-8.28 (m 2H), 8.01 (dd 1H), 7.40-7.30 (m 2H), 7.28 (dd 1H), 7.08 (d 2H), 7.01-6.98 (m 1H), 6.78 (d 2H), 5.49 (s 2H), 4.84-4.77 (m 1H), 3.09-3.00 (m 6H), 2.78-2.66 (m 2H), 2.45 (t 4H), 2.23 (s 3H), 1.28 (d 3H) |
| 183 | F-1a | 3,4-di-F-C6H3-CH2-NH2 | pyrrolidine | LCMS Method: 1, RT: 4.35 min, MI: 490 [M + 1] | ¹H-NMR, Method 1: (DMSO) 8.31 (dd 1H), 8.23 (d 1H), 8.01 (dd 1H), 7.40-7.30 (m 2H), 7.28 (dd 1H), 7.03 (d 2H), 7.00-6.98 (m 1H), 6.38 (d 2H), 5.50 (s 2H), 4.83-4.75 (m 1H), 3.16 (t 4H), 3.05 (td 2H), 2.76-2.66 (m 2H), 1.95-1.92 (m 4H), 1.28 (d 3H) |
| 184 | F-1a | 3,4-di-F-C6H3-CH2-NH2 | (3S)-3-methylpiperazine | LCMS Method: 1, RT: 2.47 min, MI: 519 [M + 1] | ¹H-NMR, Method 1: (DMSO) 8.31-8.29 (m 2H), 8.01 (dd 1H), 7.39-7.30 (m 2H), 7.28 (dd 1H), 7.07 (d 2H), 7.00-6.97 (m 1H), 6.75 (d 2H), 5.49 (s 2H), 4.84-4.77 (m 1H), 3.44-3.39 (m 2H), 3.08-3.03 (m 2H), 2.96 (dt 1H), 2.81-2.66 (m 4H), 2.49 (td 2H), 2.13 (t 1H), 1.28 (d 3H), 1.03 (d 3H) |
| 185 | F-1a | 4-F-C6H4-CH2-NH2 | morpholine | LCMS Method: 1, RT: 3.60 min, MI: 488 [M + 1] | ¹H-NMR, Method 1: (DMSO) 8.32-8.29 (m 2H), 8.01 (dd 1H), 7.29-7.23 (m 3H), 7.16-7.10 (m 4H), 6.80 (dt 2H), 5.49 (s 2H), 4.86-4.79 (m 1H), 3.73 (t 4H), 3.11-3.00 (m 6H), 2.77-2.65 (m 2H), 1.29 (d 3H) |

| Example | SM | Amine 1 | Amine 2 | | Characterisation |
|---|---|---|---|---|---|
| 186 | F-1a | 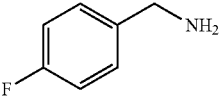 |  | LCMS Method: 1, RT: 2.64 min, MI: 486 [M + 1] | ¹H-NMR, Method 1: (DMSO) 8.32-8.27 (m 2H), 8.01 (dd 1H), 7.29-7.23 (m 3H), 7.14 (tt 2H), 7.07 (dt 2H), 6.77 (dt 2H), 5.49 (s 2H), 4.85-4.77 (m 1H), 3.06-3.02 (m 6H), 2.77-2.65 (m 2H), 1.62-1.57 (m 4H), 1.53-1.49 (m 2H), 1.29 (d 3H) |
| 187 | F-1a | 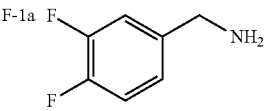 |  | LCMS Method: 1, RT: 2.69 min, MI: 504 [M + 1] | ¹H-NMR, Method 1: (DMSO) 8.30-8.26 (m 2H), 8.01 (dd 1H), 7.39-7.30 (m 2H), 7.28 (dd 1H), 7.06 (d 2H), 7.00-6.97 (m 1H), 6.76 (d 2H), 5.48 (s 2H), 4.83-4.76 (m 1H), 3.07-3.03 (m 6H), 2.78-2.65 (m 2H), 1.62-1.56 (m 4H), 1.53-1.48 (m 2H), 1.28 (d 3H) |
| 188 | F-1a | 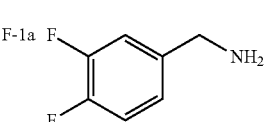 | 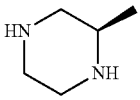 | LCMS Method: 1, RT: 2.47 min, MI: 519 [M + 1] | ¹H-NMR, Method 1: (DMSO) 8.31-8.29 (m 2H), 8.01 (dd 1H), 7.39-7.30 (m 2H), 7.28 (dd 1H), 7.07 (d 2H), 7.01-6.97 (m 1H), 6.76 (d 2H), 5.49 (s 2H), 4.84-4.77 (m 1H), 3.44-3.42 (m 4H), 3.06 (td 2H), 2.97 (d 1H), 2.83-2.66 (m 4H), 2.16 (t 1H), 1.28 (d 3H), 1.04 (d 3H) |
| 189 | F-1c | 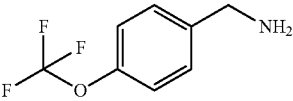 [SMILES: NCc1ccc(OC(F)(F)F)cc1] | 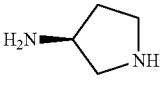 | LCMS Method: 1, RT: 2.77 min, MI: 567 [M + 1] | ¹H-NMR, Method 1: (DMSO) 8.24 (d 1H), 8.15 (d 1H), 7.81 (d 1H), 7.32-7.27 (m 4H), 6.97 (d 2H), 6.44 (d 2H), 5.60 (t 1H), 5.51 (s 2H), 4.80-4.73 (m 1H), 3.75 (bs 1H), 3.57-3.25 (m 1H), 3.07-2.97 (m 3H), 2.92-2.86 (m 1H), 2.81-2.75 (m 1H), 2.71 (q 2H), 2.61 (dd 1H), 2.41 (s 3H), 2.00-1.91 (m 1H), 1.56-1.47 (m 1H), 1.27 (d 3H) |
| 190 | F-1a | 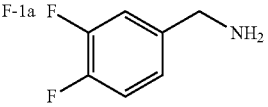 | 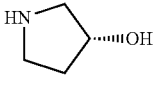 | LCMS Method: 1, RT: 3.60 min, MI: 506 [M + 1] | ¹H-NMR, Method 1: (DMSO) 8.30 (dd 1H), 8.23 (d 1H), 8.00 (dd 1H), 7.40-7.30 (m 2H), 7.28 (dd 1H), 7.02 (d 2H), 7.00-6.97 (m 1H), 6.35 (d 2H), 5.49 (s 2H), 4.91 (bs 1H), 4.82-4.75 (m 1H), 4.37 (bs 1H), 3.36-3.24 (m 2H), 3.19 (td 1H), 3.07-2.98 (m 3H), 2.76-2.64 (m 2H), 2.06-1.97 (m 1H), 1.89-1.82 (m 1H), 1.27 (d 3H) |
| 191 | F-1c | 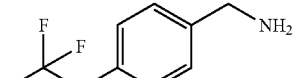 | 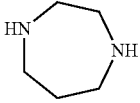 | LCMS Method: 1, RT: 2.81 min, MI: 581 [M + 1] | ¹H-NMR, Method 1: (DMSO) 8.27 (d 1H), 8.15 (d 1H), 7.83 (d 1H), 7.29 (s 4H), 7.00 (d 2H), 6.50 (d 2H), 5.51 (s 2H), 4.83-4.75 (m 1H), 3.47 (t 2H), 3.41-3.38 (m 3H), 3.09-2.97 (m 2H), 2.81 (t 2H), 2.78-2.64 (m 2H), 2.58 (t 2H), 2.41 (s 3H), 1.77-1.71 (m 2H), 1.28 (d 3H) |
| 192 | F-1c | 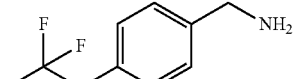 | 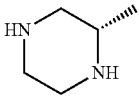 | LCMS Method: 1, RT: 2.80 min, MI: 581 [M + 1] | ¹H-NMR, Method 1: (DMSO) 8.31 (d 1H), 8.15 (d 1H), 7.83 (d 1H), 7.31-7.26 (m 4H), 7.06 (d 2H), 6.73 (d 2H), 5.50 (s 2H), 4.84-4.77 (m 1H), 3.41 (d 2H), 3.09-2.92 (m 3H), 2.79-2.64 (m 4H), 2.45 (td 1H), 2.42 (s 3H), 2.11 (t 1H), 1.28 (d 3H), 1.02 (d 3H) |

| Example | SM | Amine 1 | Amine 2 | Characterisation | |
|---|---|---|---|---|---|
| 193 | F-1a | 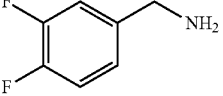 | 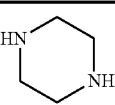 | LCMS Method: 1, RT: 2.43 min, MI: 505 [M + 1] | ¹H-NMR, Method 1: (DMSO) 8.30-8.28 (m 2H), 8.00 (dd 1H), 7.39-7.29 (m 2H), 7.27 (dd 1H), 7.08 (d 2H), 7.00-6.97 (m 1H), 6.77 (d 2H), 5.48 (s 2H), 4.84-4.76 (m 1H), 3.07-3.00 (m 6H), 2.87 (t 4H), 2.78-2.65 (m 2H), 1.28 (d 3H) |

General Synthesis of (3-(3-aralkyl-3H-imidazo[4,5-b]pyridin-2-yl-propionylamino)-acetic acid of general formula F-52 (Scheme 012)

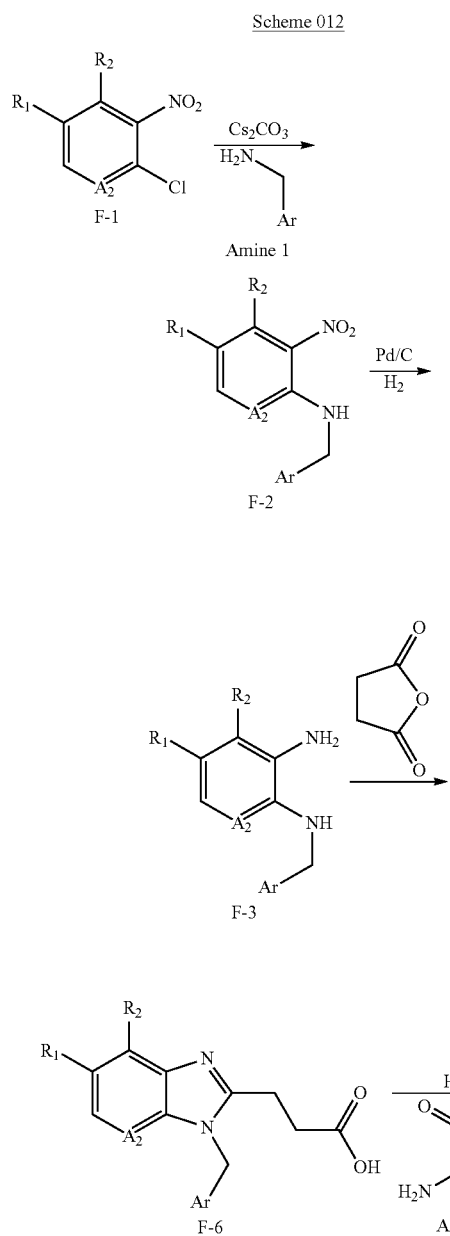

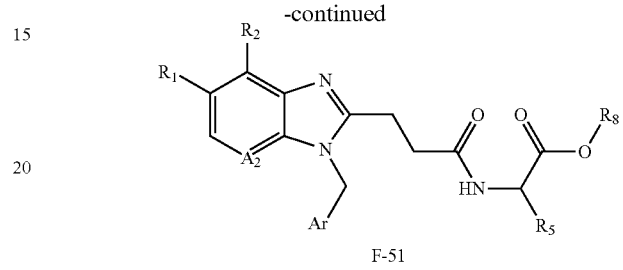

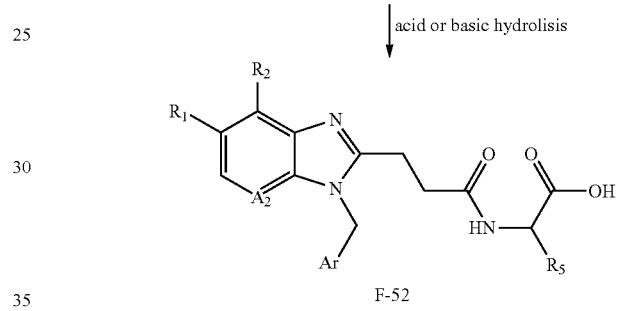

$R_8$ is (1-6C)alkyl.

Intermediates F-2 and F-3 were prepared as in Scheme 001. Intermediate F-6 was prepared as in Scheme 002-A. Intermediate F-51 was prepared following the same procedure as for intermediate F-5 in Scheme 002-A, using an α-amino acid as the required amine 2. Intermediate of general formula F-51 was hydrolysed in basic conditions (LiOH or NaOH in THF/water) or acid conditions (TFA in DCM) to afford the final compounds of general formula F-52.

F-1 could be any of the following intermediates:

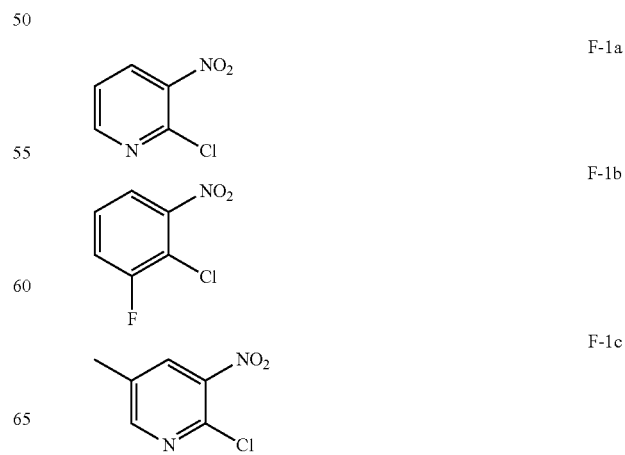

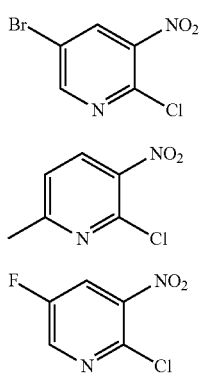

F-1d

F-1e

F-1f

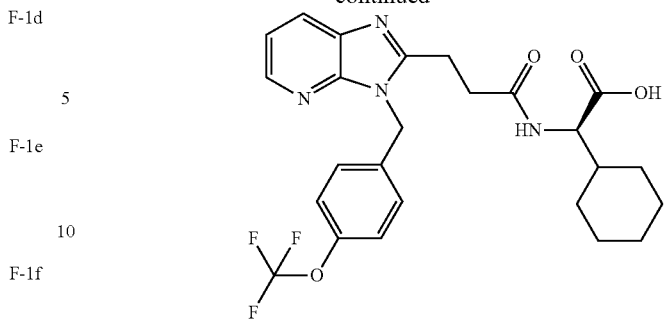

The above synthesis (Scheme 012) is illustrated by the preparation of (R)-cyclohexyl-{3-[3-(4-trifluoromethoxy-benzyl)-3H-imidazo[4,5-b]pyridin-2-yl]-propionylamino}-acetic acid (Ex. 194) described below.

Synthesis of (R)-cyclohexyl-{3-[3-(4-trifluoromethoxy-benzyl)-3H-imidazo[4,5-b]pyridin-2-yl]-propionylamino}-acetic acid (Ex. 194)

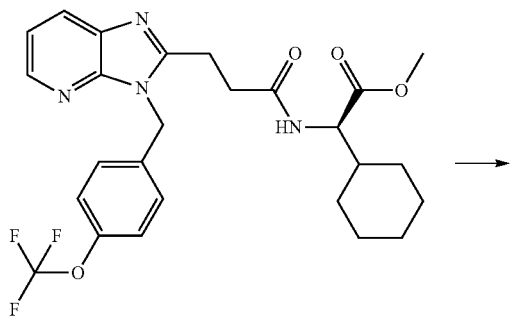

→

In a round bottom flask fitted with magnetic stirrer, (R)-cyclohexyl-{3-[3-(4-trifluoromethoxy-benzyl)-3H-imidazo[4,5-b]pyridin-2-yl]-propionylamino}-acetic acid methyl ester (130 mg, 0.25 mmol) was dissolved in THF (5 mL) and water (2.5 mL) and then treated with LiOH monohydrate (31 mg, 0.75 mmol). This mixture was allowed to stir at r.t. for 2 hours. Reaction crude was neutralized to pH 7 with HCl 2 N aqueous solution and concentrated under reduced pressure. Crude product was purified by column chromatography with a gradient of EtOAc/MeOH, required product eluted with 15% MeOH. Product fractions were combined and concentrated under reduced pressure, then further purified by reverse phase mass-directed preparative HPLC using LCMS Method 5. Product fractions were combined and concentrated in the Genevac™ to afford the title compound (31.5 mg, 23%).

The following compounds of general formula F-52 were prepared according to the general synthesis shown in Scheme 012:

| Example | SM | Amine 1 | Amine 2 | | Characterisation |
|---|---|---|---|---|---|
| 194 | F-1a | (4-trifluoromethoxybenzyl)amine | cyclohexylglycine methyl ester | LCMS Method: 1, RT: 4.42 min, MI: 505 [M + 1] | ¹H-NMR, Method 1: (DMSO) 12.53 (bs 1H), 8.30 (dd 1H), 8.13 (d 1H), 7.98 (dd 1H), 7.32 (s 4H), 7.27 (dd 1H), 5.57 (s 2H), 4.14 (dd 1H), 3.11-2.98 (m 2H), 2.87-2.80 (m 1H), 2.76-2.67 (m 1H), 1.68-1.49 (m 6H), 1.17-0.92 (m 5H) |
| 195 | F-1a | (4-trifluoromethoxybenzyl)amine | phenylalanine methyl ester | LCMS Method: 1, RT: 4.27 min, MI: 513 [M + 1] | ¹H-NMR, Method 1: (DMSO) 12.71 (bs 1H), 8.37-8.35 (m 2H), 8.05 (d 1H), 7.35-7.30 (m 5H), 7.19 (bs 2H), 7.18 (bs 2H), 7.17-7.11 (m 1H), 5.57 (s 2H), 4.44-4.39 (m 1H), 3.05-3.01 (m 3H), 2.84 (dd 1H), 2.73-2.69 (m 2H) |
| 196 | F-1a | (4-trifluoromethylbenzyl)amine | phenylalanine methyl ester | LCMS Method: 1, RT: 4.25 min, MI: 497 [M + 1] | ¹H-NMR, Method 1: (DMSO) 12.69 (bs 1H), 8.33 (d 1H), 8.29 (dd 1H), 8.00 (dd 1H), 7.69 (d 2H), 7.35 (d 2H), 7.28 (dd 1H), 7.18-7.11 (m 5H), 5.61 (s 2H), 4.44-4.38 (m 1H), 3.03 (dd 1H), 2.95 (t 2H), 2.83 (dd 1H), 2.69 (t 2H) |

| Example | SM | Amine 1 | Amine 2 | Characterisation | |
|---|---|---|---|---|---|
| 197 | F-1a | 4-(difluoromethoxy)benzylamine | methyl phenylalaninate | LCMS Method: 1, RT: 3.89 min, MI: 495 [M + 1] | ¹H-NMR, Method 1: (DMSO) 12.71 (bs 1H), 8.34 (d 1H), 8.31 (dd 1H), 7.99 (dd 1H), 7.20 (t 1H), 7.29-7.12 (m 10H), 5.49 (s 2H), 4.45-4.40 (m 1H), 3.04 (dd 1H), 2.98 (t 2H), 2.85 (dd 1H), 2.69 (t 2H) |
| 198 | F-1a | 3,4-difluorobenzylamine | methyl phenylalaninate | LCMS Method: 1, RT: 3.88 min, MI: 465 [M + 1] | ¹H-NMR, Method 1: (DMSO) 12.70 (bs 1H), 8.33 (d 1H), 8.31 (dd 1H), 7.99 (dd 1H), 7.41-7.28 (m 2H), 7.27 (dd 1H), 7.20-7.12 (m 5H), 6.99-6.96 (m 1H), 5.48 (s 2H), 4.44-4.39 (m 1H), 3.06-2.96 (m 3H), 2.84 (dd 1H), 2.69 (t 2H) |
| 199 | F-1a | 4-(trifluoromethoxy)benzylamine | methyl phenylalaninate | LCMS Method: 1, RT: 4.28 min, MI: 513 [M + 1] | ¹H-NMR, Method 1: (DMSO) 12.71 (bs 1H), 8.33 (d 1H), 8.30 (dd 1H), 7.99 (dd 1H), 7.34-7.26 (m 5H), 7.19-7.12 (m 5H), 5.54 (s 2H), 4.45-4.39 (m 1H), 3.04 (dd 1H), 2.97 (t 2H), 2.85 (dd 1H), 2.70 (t 2H) |
| 200 | F-1a | 4-(trifluoromethoxy)benzylamine | methyl tyrosinate | LCMS Method: 1, RT: 3.74 min, MI: 529 [M + 1] | ¹H-NMR, Method 1: (DMSO) 12.61 (bs 1H), 9.20 (bs 1H), 8.30 (dd 1H), 8.26 (d 1H), 8.00 (dd 1H), 7.34-7.30 (m 4H), 7.27 (dd 1H), 6.99 (d 2H), 6.62 (d 2H), 5.54 (s 2H), 4.36-4.30 (m 1H), 2.99 (t 2H), 2.91 (dd 1H), 2.73 (dd 1H), 2.70 (t 2H) |
| 201 | F-1a | (S)-1-(4-fluorophenyl)ethylamine | methyl phenylalaninate | LCMS Method: 1, RT: 3.87 min, MI: 461 [M + 1] | ¹H-NMR, Method 1: (DMSO) 12.70 (s 1H), 8.32 (d 1H), 8.25 (dd 1H), 7.94 (dd 1H), 7.38-7.35 (m 2H), 7.23-7.12 (m 8H), 5.99 (q 1H), 4.46 (m 1H), 3.04 (dd 1H), 2.98 (t 2H), 2.85 (dd 1H), 2.73-2.64 (m 2H), 2.03 (d 3H) |
| 202 | F-1a | thiophen-2-ylmethylamine | methyl phenylalaninate | LCMS Method: 1, RT: 3.55 min, MI: 435 [M + 1] | ¹H-NMR, Method 1: (DMSO) 12.70 (bs 1H), 8.35-8.32 (m 2H), 7.97 (dd 1H), 7.43 (dd 1H), 7.27 (dd 1H), 7.22-7.14 (m 5H), 7.09 (dd 1H), 6.97 (dd 1H), 5.66 (s 2H), 4.46-4.40 (m 1H) 3.08-3.02 (m 3H), 2.85 (dd 1H), 2.69 (t 2H) |

General Synthesis of 3-(3-aralkyl-3H-imidazo[4,5-b]pyridin-2-yl)-N-(2-hydroxy-ethyl)-propionamide of general formula F-53 (Scheme 013)

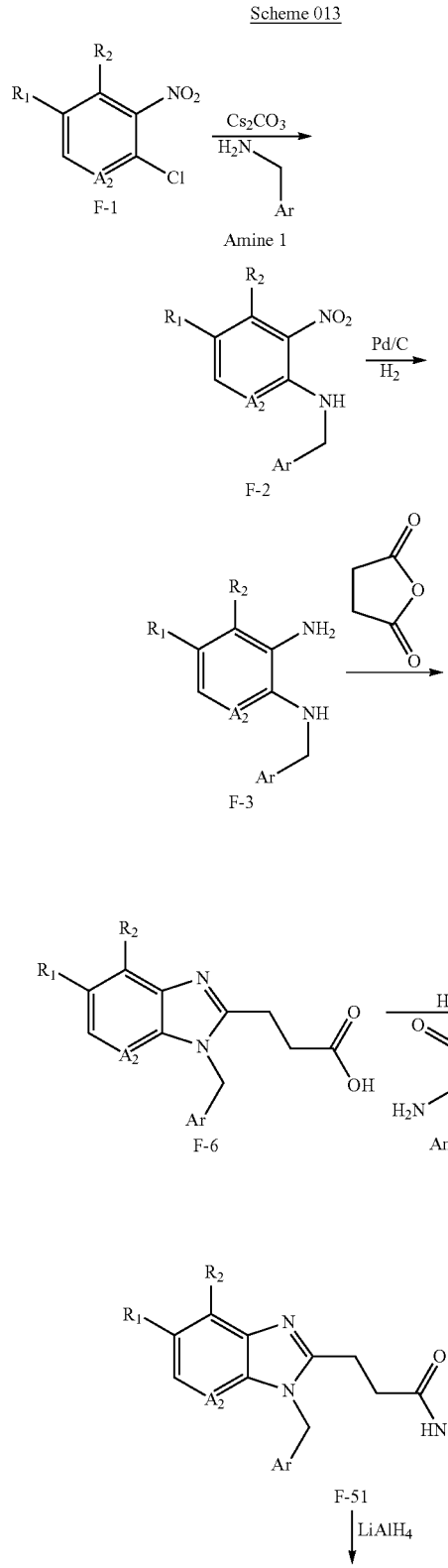

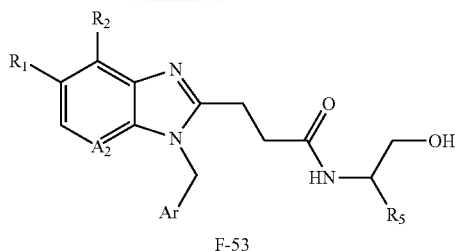

Intermediates F-2 and F-3 were prepared as in Scheme 001. Intermediate F-6 was prepared as in Scheme 002-A. Intermediate F-51 was prepared following the same procedure as for intermediate F-5 in Scheme 002-A, using an α-amino acid as the required amine 2. Compounds of general formula F-51 were reduced with LiAlH₄ to afford the final compounds of general formula F-53.

F-1 could be any of the following intermediates:

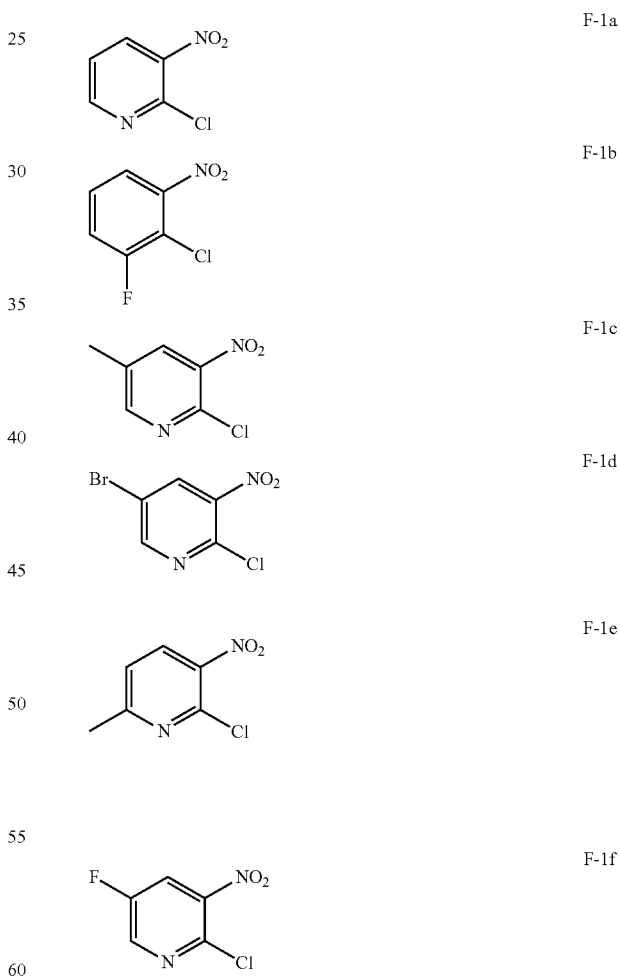

$R_8$ could be either methyl or tert-butyl.

The above synthesis (Scheme 013) is illustrated by the preparation of N—((R)-1-Hydroxymethyl-2-phenyl-ethyl)-3-[3-(4-trifluoromethoxy-benzyl)-3H-imidazo[4,5-b]pyridin-2-yl]-propionamide (Ex. 203) described below.

Synthesis of N—((R)-1-Hydroxymethyl-2-phenyl-ethyl)-3-[3-(4-trifluoromethoxy-benzyl)-3H-imidazo[4,5-b]pyridin-2-yl]-propionamide (Ex. 203)

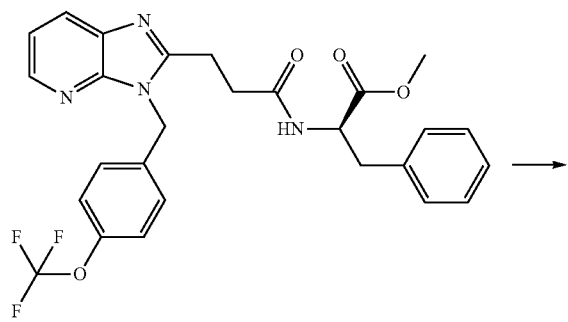

In a round bottom flask fitted with a magnetic stirrer and N$_2$ connection, LiAlH$_4$ (39 mg, 1.2 mmol) was dissolved in anhydrous THF (5 ml) under N$_2$ and cooled to 0° C. with an ice bath. Then, (R)-3-phenyl-2-{3-[3-(4-trifluoromethoxy-benzyl)-3H-imidazo[4,5-b]pyridin-2-yl]-propionylamino}-propionic acid methyl ester (180 mg, 0.34 mmol) dissolved in anhydrous THF (5 ml) was added in. Reaction mixture was allowed to stir whilst warming to r.t. overnight. Reaction crude was extracted with EtOAc and water, organic phase washed with brine, dried over MgSO$_4$ and filtered. Filtrate was concentrated under reduced pressure and purified by reverse phase mass-directed preparative HPLC using either LCMS Method 5 or 6. Required product fractions were concentrated in the Genevac™ to afford the title compound (20 mg, 12%).

The following compounds of general formula F-53 were prepared according to the general synthesis shown in Scheme 013:

| Example | SM | Amine 1 | Amine 2 | Characterisation | |
|---|---|---|---|---|---|
| 203 | F-1a | 4-OCF$_3$-benzyl-NH$_2$ | phenylalanine methyl ester | LCMS Method: 1, RT: 4.10 min, MI: 499 [M + 1] | — |
| 204 | F-1a | 4-OCF$_3$-benzyl-NH$_2$ | phenylalanine methyl ester | LCMS Method: 1, RT: 4.12 min, MI: 499 [M + 1] | — |
| 205 | F-1a | 4-OCF$_3$-benzyl-NH$_2$ | tyrosine tert-butyl ester | LCMS Method: 1, RT: 3.60 min, MI: 514 [M + 1] | $^1$H-NMR, Method 1: (DMSO) 9.13 (bs 1H), 8.30 (dd 1H), 7.99 (dd 1H), 7.79 (d 1H), 7.32 (s 4H), 7.27 (dd 1H), 6.96 (d 2H), 6.61 (d 2H), 5.55 (s 2H), 4.71 (bs 1H), 3.84-3.77 (m 1H), 3.31-3.24 (m 2H), 3.00 (t 2H), 2.71-2.62 (m 3H), 2.54-2.46 (m 1H) |

-continued

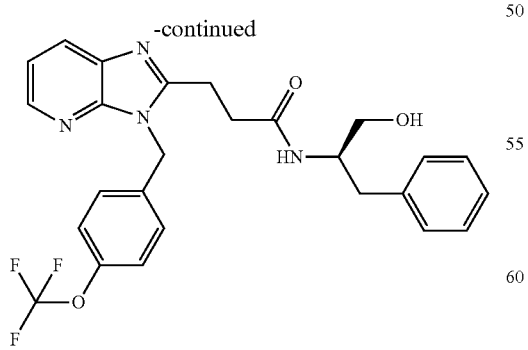

General Synthesis of N-(4-Aminomethyl-benzyl)-3-(3-aralkyl-3H-imidazo[4,5-b]pyridin-2-yl)-propionamide of general formula F-54 (Scheme 014)

Scheme 014

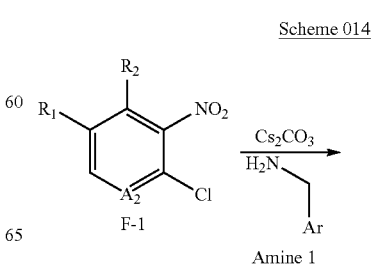

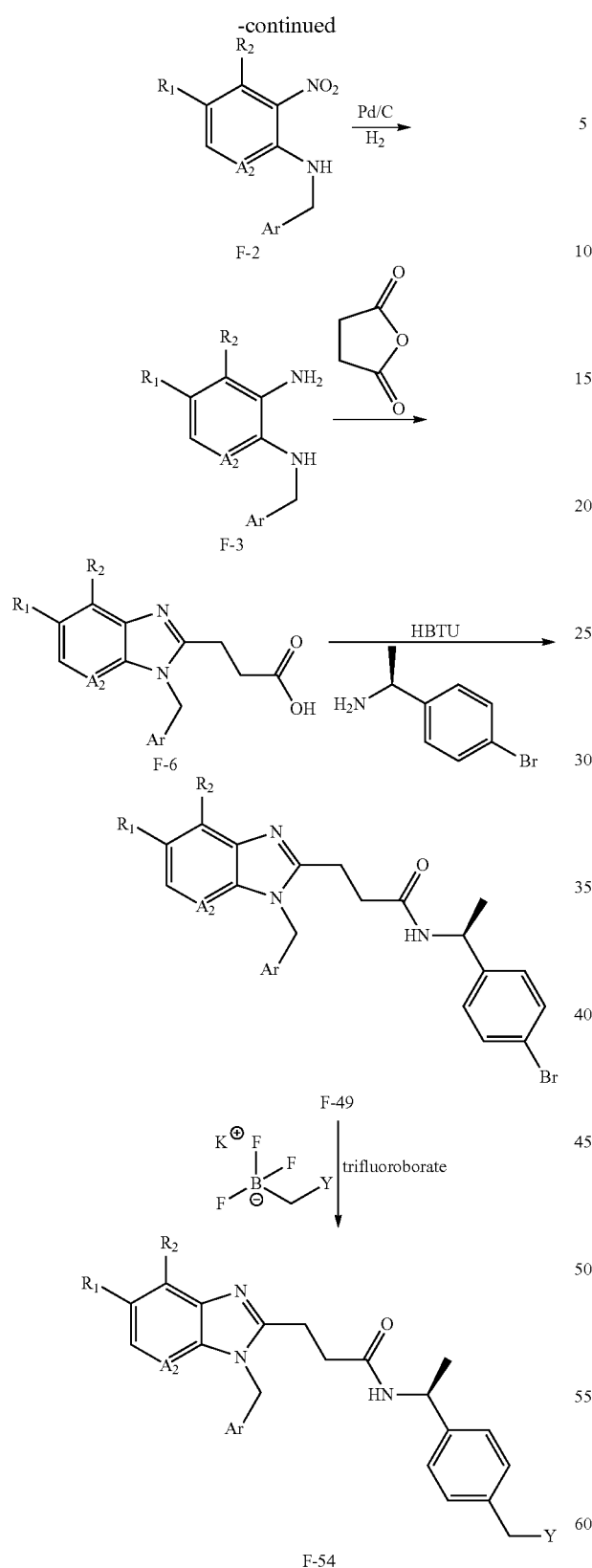

1-(4-bromo-phenyl)-ethylamine as the required amine. Compounds of general formula F-49 were submitted to a Molander coupling to afford the final compounds of general formula F-54.

F-1 could be any of the following intermediates:

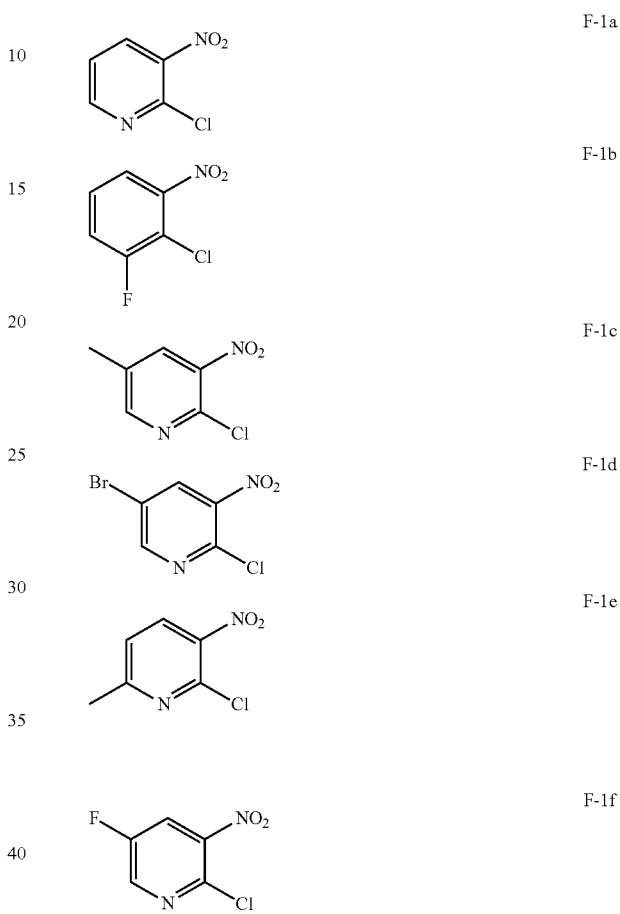

The above synthesis (Scheme 014) is illustrated by the preparation of 3-[3-(3,4-difluoro-benzyl)-3H-imidazo[4,5-b]pyridin-2-yl]-N—[(S)-1-(4-morpholin-4-ylmethyl-phenyl)-ethyl]-propionamide (Ex. 206) described below.

Synthesis of 3-[3-(3,4-difluoro-benzyl)-3H-imidazo[4,5-b]pyridin-2-yl]-N—[(S)-1-(4-morpholin-4-ylmethyl-phenyl)-ethyl]-propionamide (Ex. 206)

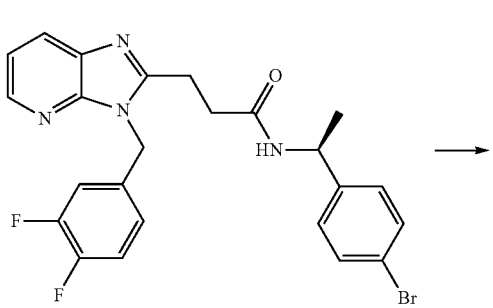

Intermediates F-2 and F-3 were prepared as in Scheme 001. Intermediate F-6 was prepared as in Scheme 002-A. Intermediate F-49 was prepared following the same procedure as for intermediate F-5 in Scheme 002-A, using (S)-

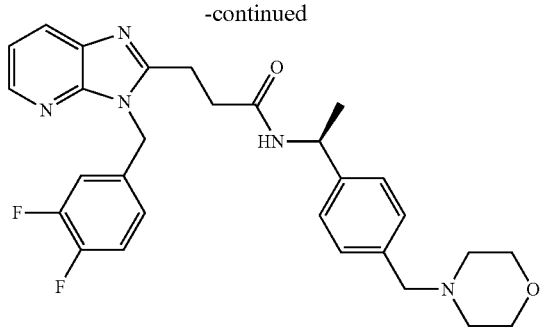

-continued

In a round bottom flask fitted with a magnetic stirrer and reflux condenser, N—[(S)-1-(4-bromomethyl-phenyl)-ethyl]-3-[3-(3,4-difluoro-benzyl)-3H-imidazo[4,5-b]pyridin-2-yl]-propionamide (100 mg, 0.20 mmol), potassium (morpholin-4-yl)methyltrifluoroborate (50 mg, 0.24 mmol) and $K_3PO_4$ (300 mg, 1.4 mmol) were dissolved in a 1:1 mixture of tert-BuOH and water (2 ml). Then, Pd(OAc)2 (1 mg, 0.002 mmol) and X-Phos (2 mg, 0.004 mmol) were added in. This mixture was heated to 110° C. for 20 hours. Reaction mixture was filtered through Celite® and the solvent concentrated under reduced pressure. Crude material was purified by reverse phase mass-directed preparative HPLC using LCMS Method 5 or 6. Required product fractions were concentrated in the Genevac™ to afford the title compound (21 mg, 21%).

The following compounds of general formula F-54 were prepared according to the general synthesis shown in Scheme 014:

| Example | SM | Amine | Trifluoroborate | | Characterisation |
|---|---|---|---|---|---|
| 206 | F-1a | 3,4-difluorobenzylamine | morpholinylmethyl-KF$_3$B | LCMS Method: 1, RT: 2.36 min, MI: 520 [M + 1] | $^1$H-NMR, Method 1: (DMSO) 8.40 (d 1H), 8.31 (dd 1H), 8.01 (dd 1H), 7.39-7.27 (m 3H), 7.20 (d 2H), 7.15 (d 2H), 7.01-6.98 (m 1H), 5.48 (s 2H), 4.92-4.84 (m 1H), 3.55 (t 4H), 3.39 (s 2H), 3.11-3.01 (m 2H), 2.81-2.69 (m 2H), 2.30 (bs 4H), 1.31 (d 3H) |
| 207 | F-1a | 3,4-difluorobenzylamine | diethylaminomethyl-KF$_3$B | LCMS Method: 1, RT: 2.50 min, MI: 506 [M + 1] | $^1$H-NMR, Method 1: (DMSO) 8.39 (d 1H), 8.30 (dd 1H), 8.01 (dd 1H), 7.39-7.25 (m 3H), 7.20-7.14 (m 4H), 7.01-6.98 (m 1H), 5.49 (s 2H), 4.92-4.84 (m 1H), 3.45 (s 2H), 3.12-3.02 (m 2H), 2.82-2.68 (m 2H), 2.42 (q 4H), 1.32 (d 3H), 0.95 (t 6H) |
| 208 | F-1a | 3,4-difluorobenzylamine | dimethylaminomethyl-KF$_3$B | LCMS Method: 1, RT: 2.40 min, MI: 478 [M + 1] | $^1$H-NMR, Method 1: (DMSO) 8.40 (d 1H), 8.30 (dd 1H), 8.01 (dd 1H), 7.39-7.30 (m 2H), 7.28 (dd 1H), 7.21 (d 2H), 7.14 (d 2H), 7.01 (m 1H), 5.49 (s 2H), 4.93-4.85 (m 1H), 3.32 (s 2H), 3.11-3.02 (m 2H), 2.82-2.69 (m 2H), 2.11 (s 6H), 1.32 (d 3H) |

General Synthesis of 3-(3-aralkyl-3H-imidazo[4,5-b]pyridin-2-yl)-N-(2-mercapto-ethyl)-propionamide of general formula F-56 (Scheme 015)

Scheme 015

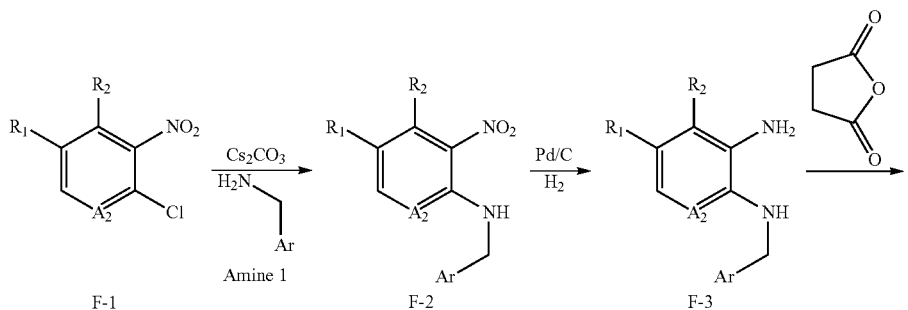

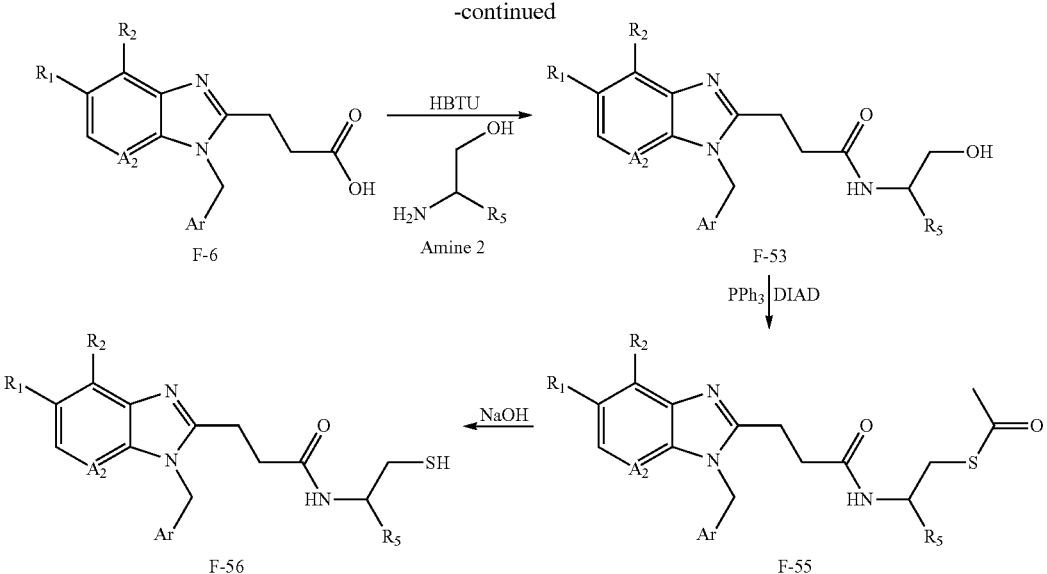

Intermediates F-2 and F-3 were prepared as in Scheme 001. Intermediate F-6 was prepared as in Scheme 002-A. Intermediate F-53 was prepared following the same procedure as for intermediate F-5 in Scheme 002-A, using an α-aminoalcohol as the required amine 2. Compounds of general formula F-53 were submitted to a Mitsunobu reaction with thioacetic acid. The obtained thioester, of general formula F-55, was hydrolyzed in basic media to afford the final compounds of general formula F-56.

F-1 was the following intermediate:

F-1a

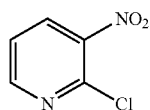

The above synthesis (Scheme 015) is illustrated by the preparation of N—((R)-2-mercapto-1-phenyl-ethyl)-3-[3-(4-trifluoromethoxy-benzyl)-3H-imidazo[4,5-b]pyridin-2-yl]-propionamide (Ex. 209) described below.

Synthesis of thioacetic acid S—((R)-2-phenyl-2-{3-[3-(4-trifluoromethoxy-benzyl)-3H-imidazo[4,5-b]pyridin-2-yl]-propionylamino}-ethyl) ester

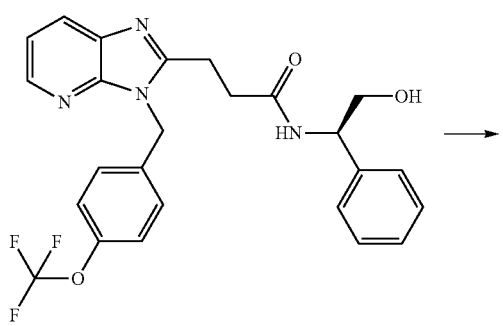

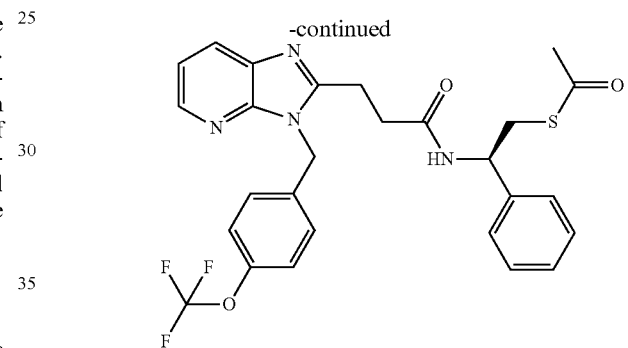

In a round bottom flask fitted with magnetic stirrer, PPh₃ (484 mg, 1.85 mmol) was dissolved in THF (7 ml) and solution cooled to 0° C. with an ice bath. Once cooled, DIAD (362 mg, 1.85 mmol) was added in and the mixture was stirred for 30 min. A solution of N—((R)-2-hydroxy-1-phenyl-ethyl)-3-[3-(4-trifluoromethoxy-benzyl)-3H-imidazo[4,5-b]pyridin-2-yl]-propionamide (416 mg, 0.86 mmol) in THF (14 ml) was added in dropwise. Then, thioacetic acid (0.13 ml, 1.85 mmol) was added in. Reaction mixture was stirred at r.t. for 3 hours and then solvent was concentrated under reduced pressure. Crude material was dissolved in EtOAc and washed with water and brine. Organic phase was dried and concentrated under reduced pressure. Residue was purified by column chromatography with a gradient of 50-80% EtOAc/cyclohexane. Product fractions were concentrated under reduced pressure to afford the title compound (138 mg, 30%).

LCMS Method: 1, RT: 4.82 min, MI: 543 [M+1]

187

Synthesis of N—((R)-2-mercapto-1-phenyl-ethyl)-3-[3-(4-trifluoromethoxy-benzyl)-3H-imidazo[4,5-b]pyridin-2-yl]-propionamide (Ex. 209)

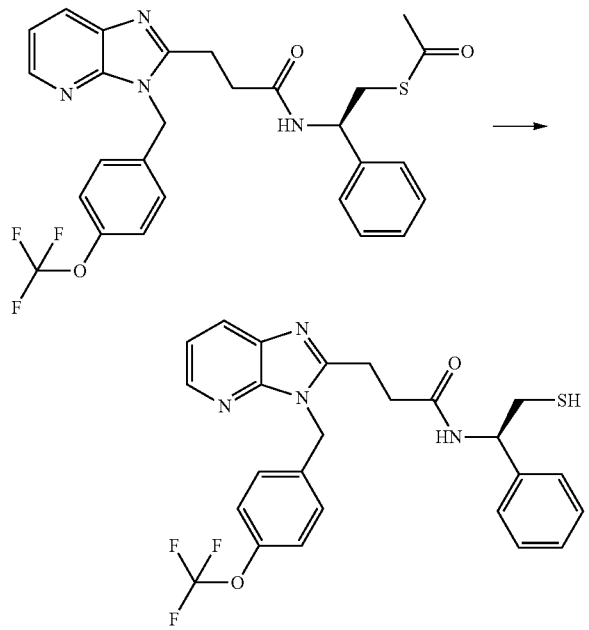

188

In a round bottom flask fitted with magnetic stirrer, thioacetic acid S—((R)-2-phenyl-2-{3-[3-(4-trifluoromethoxy-benzyl)-3H-imidazo[4,5-b]pyridin-2-yl]-propionylamino}-ethyl)ester was dissolved in MeOH and the solution was degassed with $N_2$ for 1 hour. Solution was cooled to 0° C. with an ice bath and 1M NaOH aqueous solution was then added at 0° C. under $N_2$. The reaction mixture was stirred for 2 h at 0° C. Reaction mixture was poured into 1M HCl aqueous solution (3 ml) and brine (10 ml). Aqueous phase was extracted with EtOAc and organic phase filtered through a silicone treated filter paper and concentrated under reduced pressure. Crude material was purified by reverse phase mass-directed preparative HPLC using LCMS Method 5 or 6. Product fractions were concentrated in the Genevac™ to afford the title compound (26 mg, 22%).

LCMS Method: 1, RT: 4.73 min, MI: 501 [M+1]

$^1$H-NMR, Method 1: (CDCl$_3$) 8.38 (dd 1H), 7.99 (dd 1H), 7.27 (dd 1H), 7.23-7.11 (m 10H), 5.49 (s 2H), 5.17 (dt 1H), 3.16-3.12 (m 2H), 2.97-2.90 (m 3H), 2.88-2.81 (m 1H), 1.18 (dd 1H).

General Synthesis of N-(2-amino-ethyl)-3-(3-aralkyl-3H-imidazo[4,5-b]pyridin-2-yl)-propionamide of general formula F-58 (Scheme 016)

Scheme 016

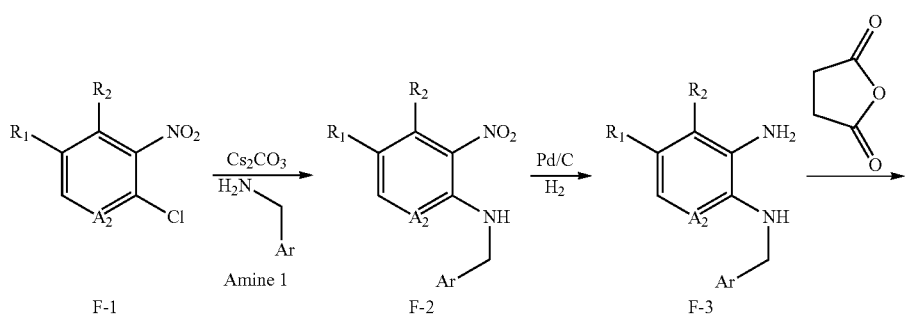

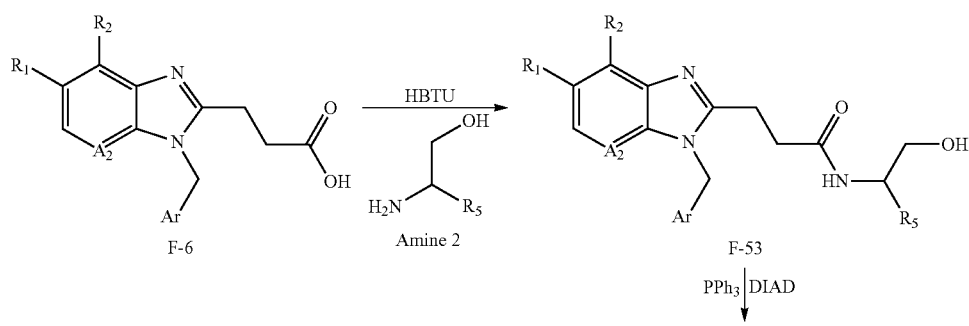

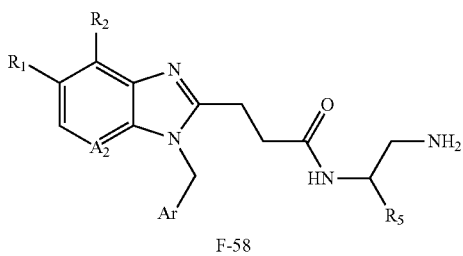

F-58

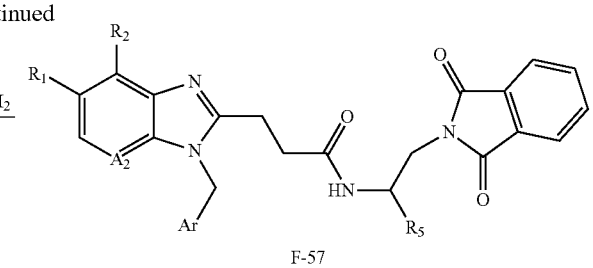

F-57

Intermediates F-2 and F-3 were prepared as in Scheme 001. Intermediate F-6 was prepared as in Scheme 002-A. Intermediate F-53 was prepared following the same procedure as for intermediate F-5 in Scheme 002-A, using an α-aminoalcohol as the required amine 2. Compounds of general formula F-53 were submitted to a Mitsunobu with phthalimide. The obtained intermediate, of general formula F-57, was treated with hydrazine in ethanol to afford the final compounds of general formula F-58.

F-1 was the following intermediate:

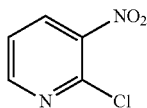

F-1a

The above synthesis (Scheme 016) is illustrated by the preparation of N—((R)-2-amino-1-phenyl-ethyl)-3-[3-(4-trifluoromethoxy-benzyl)-3H-imidazo[4,5-b]pyridin-2-yl]-propionamide (Ex. 210) described below.

Synthesis of N—[(R)-2-(1,3-dioxo-1,3-dihydro-isoindol-2-yl)-1-phenyl-ethyl]-3-[3-(4-trifluoromethoxy-benzyl)-3H-imidazo[4,5-b]pyridin-2-yl]-propionamide

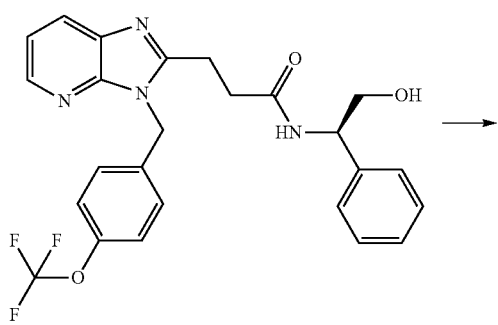

-continued

In a round bottom flask fitted with magnetic stirrer, PPh$_3$ (343 mg, 1.31 mmol), phthalimide (192 mg, 1.31 mmol) and N—((R)-2-hydroxy-1-phenyl-ethyl)-3-[3-(4-trifluoromethoxy-benzyl)-3H-imidazo[4,5-b]pyridin-2-yl]-propionamide (300 mg, 0.62 mmol) were dissolved in anhydrous THF and the reaction mixture cooled to 0° C., whilst stirring under N$_2$. DIAD (257 μl, 1.31 mmol) was then added dropwise and the reaction mixture allowed to stir over the weekend. Reaction crude was concentrated under reduced pressure, dissolved in EtOAc (40 ml) and washed with water (35 ml) and brine (35 ml). Organic phase was dried and concentrated under reduced pressure. Crude material was purified by column chromatography with a gradient of 0 to 50% EtOAc/cyclohexane and subsequently with a gradient of 0 to 5% MeOH/DCM when required product eluted. Product fractions were combined and concentrated under reduced pressure to afford the title compound (129 mg, 34%)

LCMS Method: 1, RT: 4.89 min, MI: 613 [M+1]

Synthesis of N—((R)-2-amino-1-phenyl-ethyl)-3-[3-(4-trifluoromethoxy-benzyl)-3H-imidazo[4,5-b]pyridin-2-yl]-propionamide (Ex. 210)

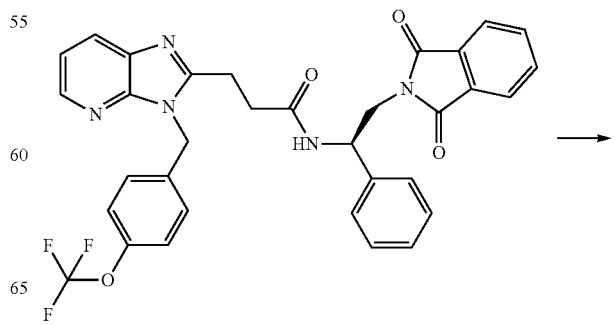

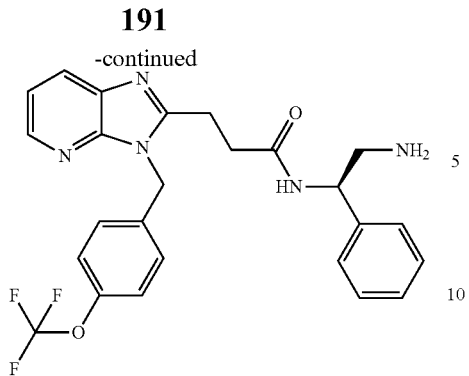

In a round bottom flask fitted with magnetic stirrer and reflux condenser, to a solution of N—[(R)-2-(1,3-dioxo-1,3-dihydro-isoindol-2-yl)-1-phenyl-ethyl]-3-[3-(4-trifluoromethoxy-benzyl)-3H-imidazo[4,5-b]pyridin-2-yl]-propionamide (129 mg, 0.21 mmol) in EtOH (6 ml) was added hydrazine monohydrate (51 μl, 1.05 mmol) and the solution was heated at reflux for 5 hours. Reaction crude was allowed to cool down to r.t. As the reaction mixture cooled, some 2,3-dihydro-phthalazine-1,4-dione precipitated out. The reaction mixture was then filtered and the filtrate was passed through a 5 g SCX cartridge. The SCX cartridge was flushed with MeOH and the product eluted using 2 M ammonia in MeOH solution. Eluent was concentrated under reduced pressure to give 72 mg of an oily solid. This solid was further purified by reverse phase mass-directed preparative HPLC using LCMS Method 7. Product fractions were concentrated in the Genevac™ to afford the title compound (4 mg, 4%).

LCMS Method: 1, RT: 2.74 min, MI: 484 [M+1]

General Synthesis of 3-(3-aralkyl-6-methyl-3H-imidazo[4,5-b]pyridin-2-yl)-propionamide of general formula F-63 (Scheme 017)

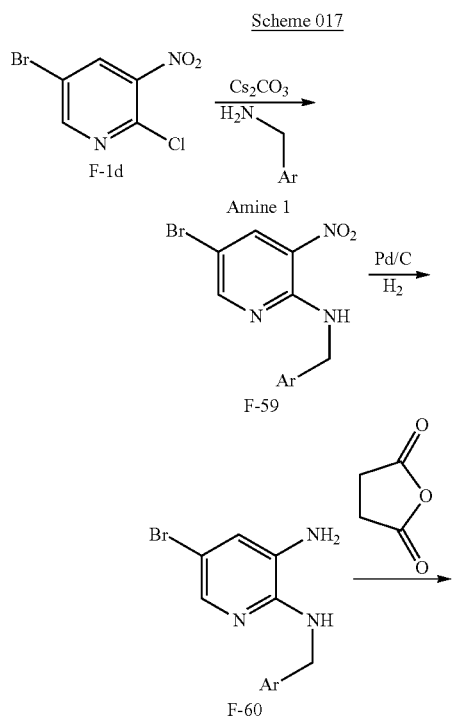

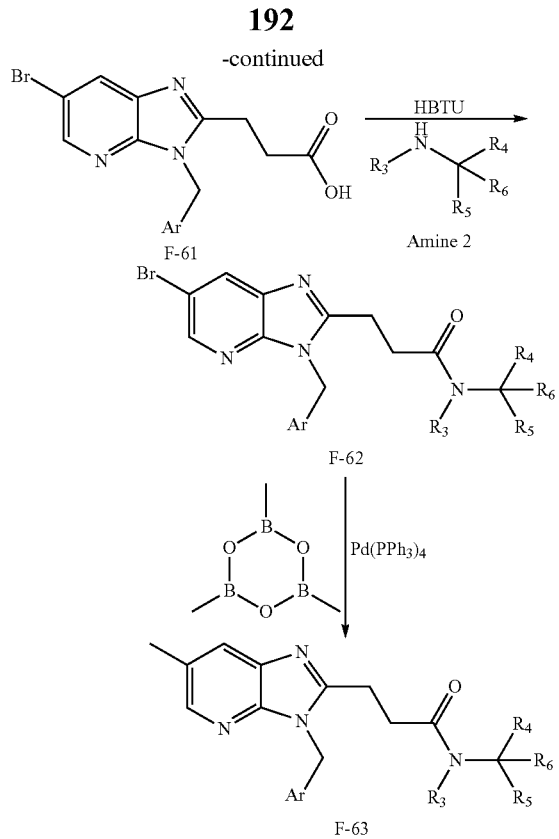

Commercially available 5-bromo-2-chloro-3-nitro-pyridine of formula F-1d was reacted with $Cs_2CO_3$ and the required amine 1 in methanol at reflux to yield the aralkyl-(5-bromo-3-nitro-pyridin-2-yl)-amine derivatives of general formula F-59. Intermediate F-60 was prepared following the same procedure as for intermediate F-3 in Scheme 001. Intermediates F-61 and F-62 were prepared following the same procedure as for intermediates F-6 and F-5, respectively, in Scheme 002-A. Compounds of general formula F-62 were treated with trimethylboroxine and $Pd(PPh_3)_4$ to afford the final compounds of general formula F-63.

The above synthesis (Scheme 017) is illustrated by the preparation of N—[(S)-1-(4-chloro-phenyl)-ethyl]-3-[6-methyl-3-(4-trifluoromethoxy-benzyl)-3H-imidazo[4,5-b]pyridin-2-yl]-propionamide (Ex. 211) described below.

Synthesis of N—[(S)-1-(4-chloro-phenyl)-ethyl]-3-[6-methyl-3-(4-trifluoromethoxy-benzyl)-3H-imidazo[4,5-b]pyridin-2-yl]-propionamide (Ex. 211)

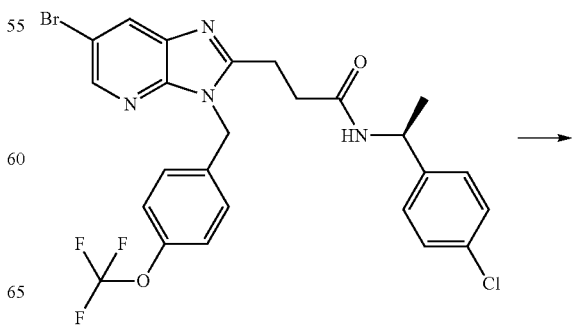

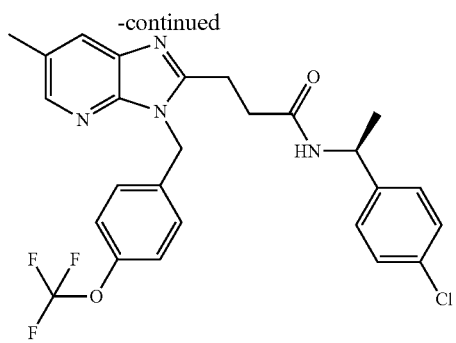

In a round bottom flask fitted with magnetic stirrer and reflux condenser, 3-[6-bromo-3-(4-trifluoromethoxy-benzyl)-3H-imidazo[4,5-b]pyridin-2-yl]-N—[(S)-1-(4-chlorophenyl)-ethyl]-propionamide (150 mg, 0.26 mmol) was dissolved in $K_3PO_4$ aqueous solution (0.5 ml) and dioxane (3 ml). Mixture was degassed with $N_2$ for 30 min, then $Pd(PPh_3)_4$ (15 mg, 0.01 mmol) and trimethylboroxine (36 mg, 0.28 mmol) were added in. This mixture was heated at 80° C. under $N_2$ overnight. Further 0.28 mmol of trimethylboroxine and an additional 0.01 mmol of $Pd(PPh_3)_4$ were added in and stirring was continued for 3 hours at 90° C. Reaction was allowed to cool down to r.t. Reaction mixture was filtered through Celite® and eluted with EtOAc. Filtrate was washed with water and brine, filtered through a silicone treated filter paper and concentrated under reduced pressure. Crude material was purified by reverse phase mass-directed preparative HPLC using LCMS Method 6. Required product fractions were concentrated in the Genevac™ to afford the title compound (27 mg, 21%).

The following compounds of general formula F-63 were prepared according to the general synthesis shown in Scheme 017:

| Example | Amine 1 | Amine 2 | Characterisation | |
|---|---|---|---|---|
| 211 | ![F-F-F-O-C6H4-CH2-NH2] | ![H2N-CH(CH3)-C6H4-Cl] | LCMS Method: 1, RT: 4.97 min, MI: 517 [M + 1] | $^1$H-NMR, Method 1: (CDCl$_3$) 8.21 (d 1H), 7.72 (d 1H), 7.19-7.06 (m 8H), 6.61 (d 1H), 5.58 (d 1H), 5.41 (d 1H), 5.01-4.94 (m 1H), 3.15-3.01 (m 2H), 2.88-2.76 (m 2H), 2.50 (s 3H), 1.38 (d 3H) |
| 212 | ![F-F-F-O-C6H4-CH2-NH2] | ![H2N-CH(CH3)-C6H4-OMe] | LCMS Method: 1, RT: 4.59 min, MI: 513 [M + 1] | $^1$H-NMR, Method 1: (DMSO) 8.34 (d 1H), 8.14 (d 1H), 7.82 (d 1H), 7.31-7.26 (m 4H), 7.16 (d 2H), 6.77 (d 2H), 5.50 (s 2H), 4.87-4.79 (m 1H), 3.69 (s 3H), 3.06-2.97 (m 2H), 2.77-2.64 (m 2H), 2.42 (s 3H), 1.29 (d 3H) |
| 213 | ![F-C6H4-CH2-NH2] | ![H2N-CH(CH3)-C6H4-Cl] | LCMS Method: 1, RT: 4.45 min, MI: 451 [M + 1] | $^1$H-NMR, Method 1: (DMSO) 8.44 (d 1H), 8.16 (d 1H), 7.81 (m 1H), 7.31-7.21 (m 6H), 7.13 (tt 2H), 5.45 (s 2H), 4.90-4.83 (m 1H), 3.08-2.95 (m 2H), 2.78-2.65 (m 2H), 2.43 (s 3H), 1.31 (d 3H) |

General Synthesis of N-(1-acyl-piperidin-4-ylm-ethyl)-3-(3-aralkyl-3H-imidazo[4,5-b]pyridin-2-yl)-propionamide of general formula F-66 and F66a (Scheme 018)

Scheme 018

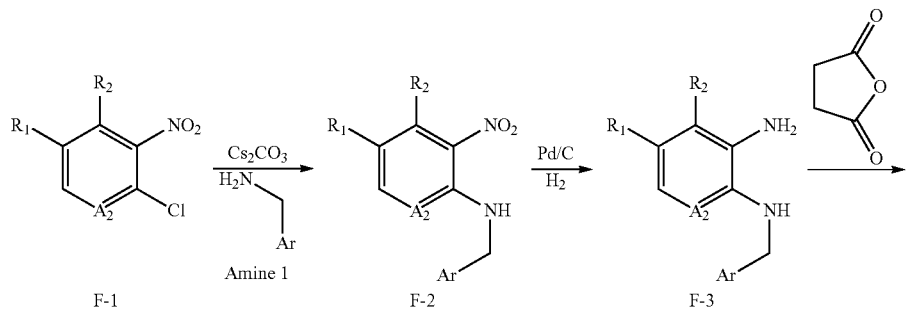

195
-continued
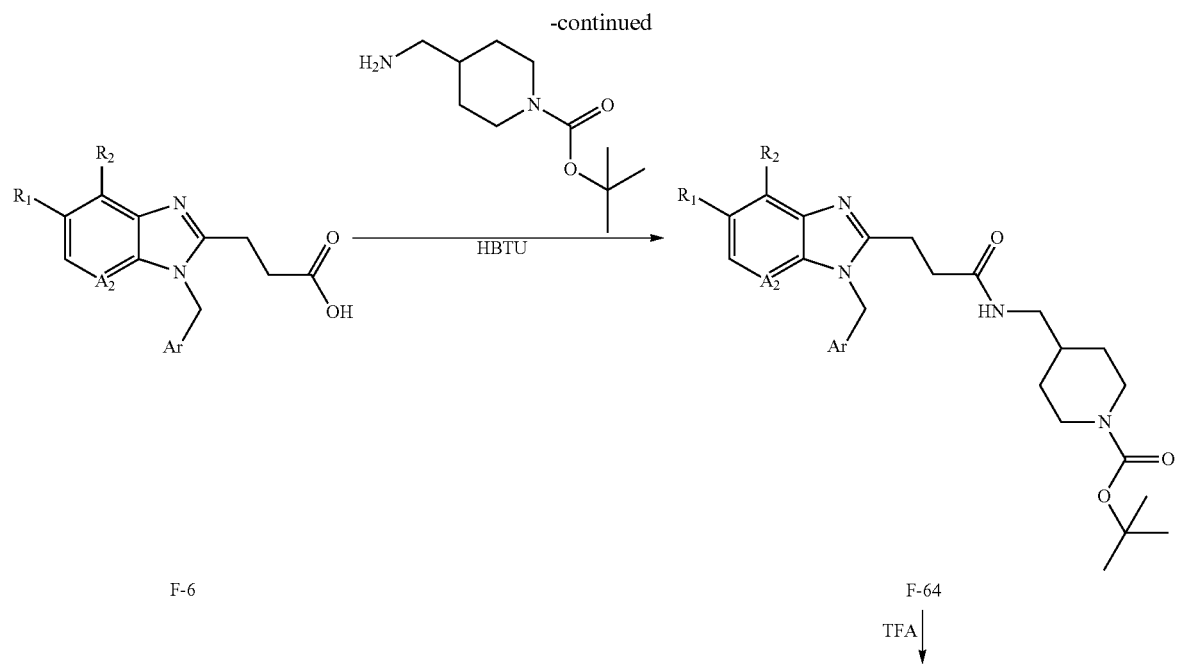
F-6
F-64
TFA
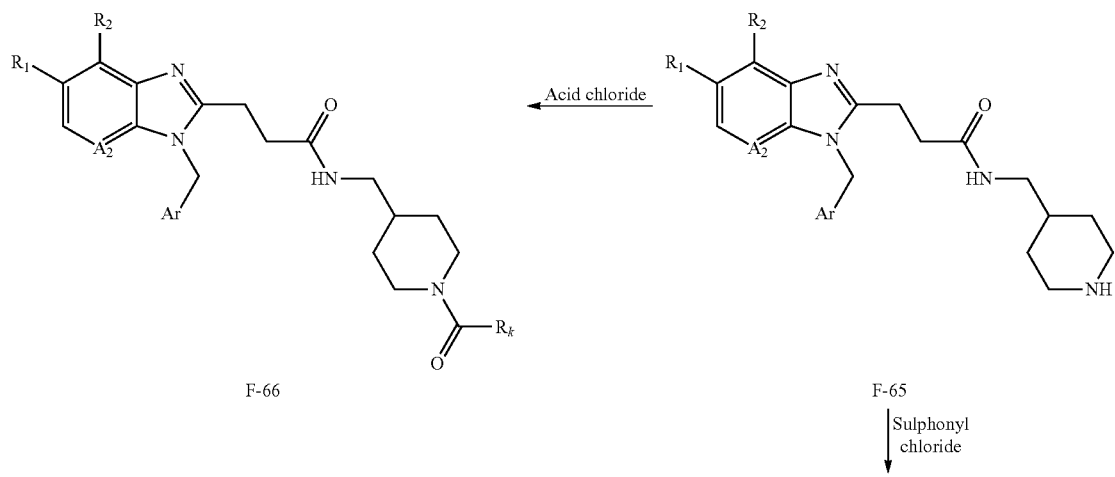
F-66
Acid chloride
F-65
Sulphonyl chloride
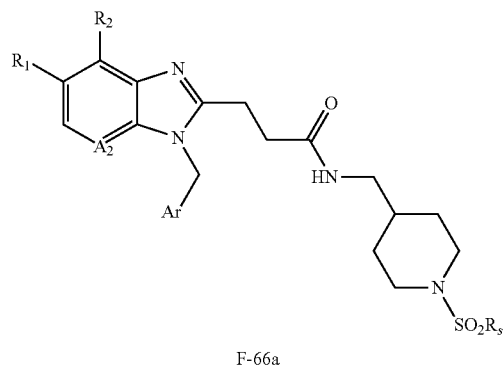
F-66a Intermediates F-2 and F-3 were prepared as in Scheme 001. Intermediate F-6 was prepared as in Scheme 002-A. Intermediate F-64 was prepared following the same procedure as for intermediate F-5 in scheme 002-A, using 4-aminomethyl-piperidine-1-carboxylic acid tert-butyl ester as the required amine. Compounds of general formula F-64 were treated with TFA to afford the deprotected analogues of general formula F-65. This was reacted with the required acid chloride or sulphonyl chloride to afford the final compounds of general formula F-66 and F-66a.

F-1 could be any of the following intermediates:

F-1a
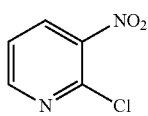

F-1b
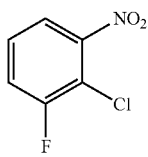

F-1c
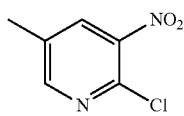

F-1d
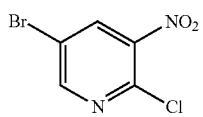

F-1e
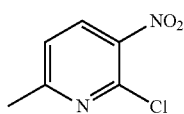

F-1f
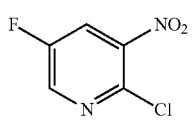

The above synthesis (Scheme 018) is illustrated by the preparation of N-(1-methanesulfonyl-piperidin-4-ylmethyl)-3-[3-(4-trifluoromethoxy-benzyl)-3H-imidazo[4,5-b]pyridin-2-yl]-propionamide (Ex. 214) described below.

Synthesis of N-piperidin-4-ylmethyl-3-[3-(4-trifluoromethoxy-benzyl)-3H-imidazo[4,5-b]pyridin-2-yl]-propionamide

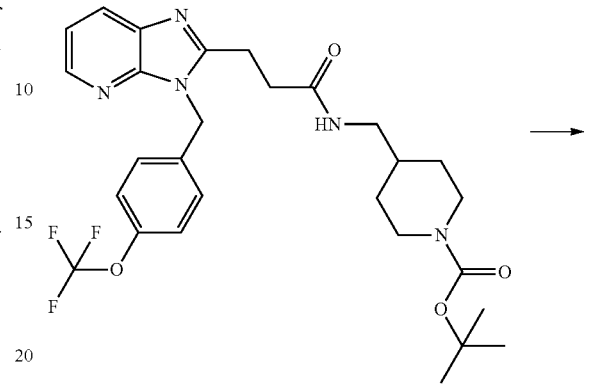

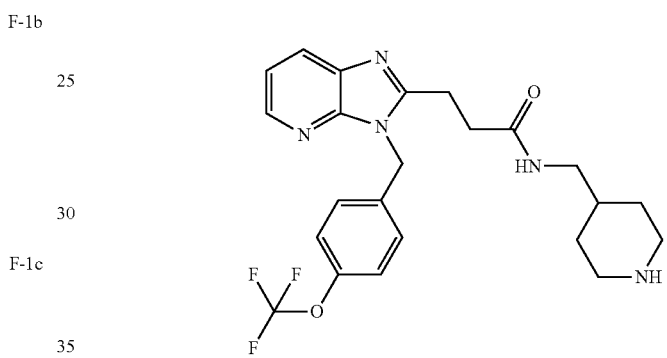

In a round bottom flask fitted with magnetic stirrer, 4-{3-[3-(4-trifluoromethoxy-benzyl)-3H-imidazo[4,5-b]pyridin-2-yl]-propionylamino}-methyl)-piperidine-1-carboxylic acid tert-butyl ester (461 mg, 0.82 mmol) was dissolved in DCM (4 ml) and TFA (2 ml) was added in. This mixture was allowed to stir at r.t. overnight. Solvent was concentrated under reduced pressure to afford the title compound (380 mg, 100%).

LCMS Method: 1, RT: 2.51 min, MI: 462 [M+1]

Synthesis of N-(1-methanesulfonyl-piperidin-4-ylmethyl)-3-[3-(4-trifluoromethoxy-benzyl)-3H-imidazo[4,5-b]pyridin-2-yl]-propionamide (Ex. 214)

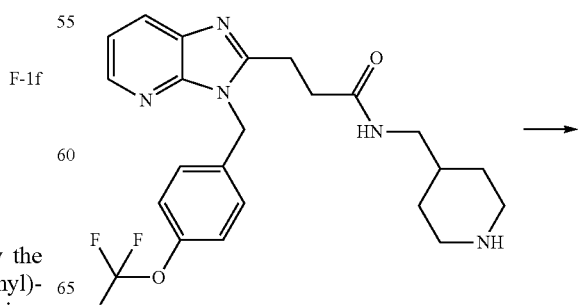

-continued

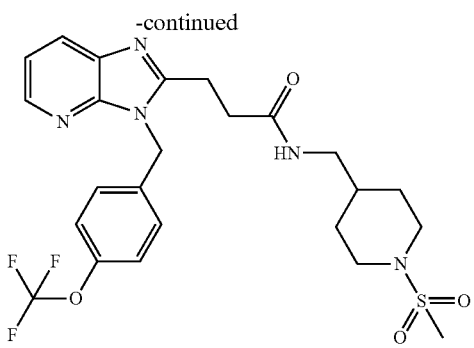

In a round bottom flask fitted with magnetic stirrer, N-piperidin-4-ylmethyl-3-[3-(4-trifluoromethoxy-benzyl)-3H-imidazo[4,5-b]pyridin-2-yl]-propionamide (126 mg, 0.27 mmol) was dissolved in DCM (3 ml) under $N_2$. To this solution was added $NEt_3$ (49 μl, 0.35 mmol) and methanesulphonyl chloride (23 μl, 0.30 mmol). This mixture was stirred overnight at r.t. Reaction crude was extracted with brine and organic phase was filtered through a silicone treated filter paper and concentrated under reduced pressure to give the crude product. This was purified by reverse phase mass-directed preparative HPLC using LCMS Method 5 or 6. Product fractions were concentrated in the Genevac™ to afford the title compound (25 mg, 17%).

The following compounds of general formula F-66 and F66a were prepared according to the general synthesis shown in Scheme 018:

Autotaxin (ATX) Activity
Quanta Red Assay

Measuring ATX activity using an enzyme coupled Quanta Red assay (Thermo Scientific—Pierce Protein Research Products, Product #15159) was determined as follows. 8 μL human recombinant ATX (final concentration 0.8 μg/mL) in 1× Assay buffer containing 50 mM Tris-HCl (pH 8.0), 5 mM $CaCl_2$ was added to an opaque black flat-bottom 384-well plate (Corning, #3575) containing 2 μL test compound in 40% DMSO (4% final DMSO concentration). 10 μL of Quanta Red, Horseradish peroxidase (HRP), Choline Oxidase (CO), Rac-1-Palmitoyl-glycero-3-phosphocholine solution (final concentration 1:250 for Quanta Red, 0.5 units/ml HRP, 0.5 units/ml CO, 15 μM Rac-1-Palmitoyl-glycero-3-phosphocholine) in 1× assay buffer (as described previously) was added to each well to start the reaction and the plate was incubated at room temperature for 2 hours. The reaction was stopped after 2 hours with a 20 μL addition of Quanta Red Stop solution (1:20 dilution in distilled water). The above-described mixture with DMSO alone was used as a positive control whereas that with DMSO alone without ATX was taken as a negative control.

For each test compound, ten concentrations were measured covering a range of 6.1 nM to 120 μM to determine $IC_{50}$ values. The top concentration was decreased to 1.2 μM when a test compound's $IC_{50}$ value was evaluated in low nanomolar range. Fluorescence was determined in a BMG Labtech Pherastar plus plate reader (λ emission=540 nm, λ excitation=590 nm). Data were analysed using Excel fit software. $IC_{50}$ values were determined in duplicate.

| Example | SM | Amine | Chloride | Characterisation | |
|---|---|---|---|---|---|
| 214 | F-1a | 4-(trifluoromethoxy)benzylamine | methanesulfonyl chloride | LCMS Method: 1, RT: 3.89 min, MI: 540 [M + 1] | ¹H-NMR, Method 1: (CDCl3) 8.38 (dd 1H), 7.96 (dd 1H), 7.28-7.24 (m 3H), 7.17-7.15 (m 2H), 6.43 (t 1H), 5.53 (s 2H), 3.71 (d 2H), 3.15-3.11 (m 4H), 2.84 (t 2H), 2.73 (s 3H), 2.50 (td 2H), 1.70-1.66 (m 2H), 1.57-1.50 (m 1H), 1.31-1.20 (m 2H) |
| 215 | F-1a | 4-(trifluoromethoxy)benzylamine | cyclopropanecarbonyl chloride | LCMS Method: 1, RT: 3.87 min, MI: 530 [M + 1] | ¹H-NMR, Method 1: (CDCl3) 8.36 (dd 1H), 7.94 (dd 1H), 7.25-7.22 (m 3H), 7.15-7.13 (m 2H), 6.48 (t 1H), 5.53 (s 2H), 4.50 (d 1H), 4.10 (d 1H), 3.21-2.90 (m 5H), 2.82 (t 2H), 2.43 (t 1H), 2.06 (bs 2H), 1.70-1.58 (m 2H), 1.13-0.99 (m 2H), 0.92 (bs 2H), 0.71 (dd 2H) |
| 216 | F-1a | 4-(trifluoromethoxy)benzylamine | acetyl chloride | LCMS Method: 1, RT: 3.57 min, MI: 504 [M + 1] | ¹H-NMR, Method 1: (CDCl3) 8.37 (dd 1H), 7.94 (dd 1H), 7.26-7.23 (m 3H), 7.15-7.13 (m 2H), 6.48 (t 1H), 5.53 (s 2H), 4.52 (dt 1H), 3.67 (dt 1H), 3.21-3.10 (m 3H), 3.05-2.98 (m 1H), 2.91-2.81 (m 3H), 2.39 (td 1H), 2.02 (s 3H), 1.66-1.58 (m 3H), 1.08-0.97 (m 2H) |

TABLE 1

ATX activity (Quanta Red assay)

| Example | Activity | Structure | Name |
|---|---|---|---|
| 1 | 68 nM | 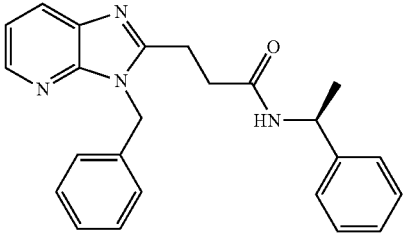 [SMILES: C[C@H](NC(=O)CCc1nc2cccnc2n1Cc1ccccc1)c1ccccc1] | 3-(3-Benzyl-3H-imidazo[4,5-b]pyridin-2-yl)-N-((S)-1-phenyl-ethyl)-propionamide |
| 3 | 855 nM | 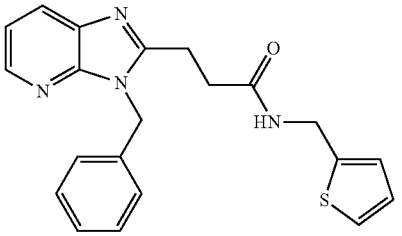 [SMILES: O=C(CCc1nc2cccnc2n1Cc1ccccc1)NCc1cccs1] | 3-(3-Benzyl-3H-imidazo[4,5-b]pyridin-2-yl)-N-thiophen-2-ylmethyl-propionamide |
| 4 | 2631 nM | 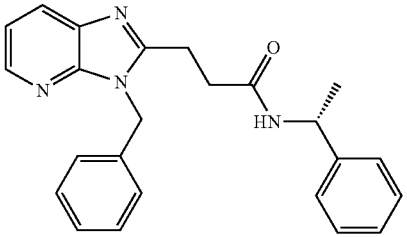 [SMILES: C[C@@H](NC(=O)CCc1nc2cccnc2n1Cc1ccccc1)c1ccccc1] | 3-(3-Benzyl-3H-imidazo[4,5-b]pyridin-2-yl)-N-((R)-1-phenyl-ethyl)-propionamide |
| 5 | 854 nM | 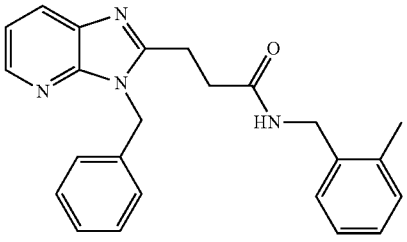 [SMILES: Cc1ccccc1CNC(=O)CCc1nc2cccnc2n1Cc1ccccc1] | 3-(3-Benzyl-3H-imidazo[4,5-b]pyridin-2-yl)-N-(2-methyl-benzyl)-propionamide |
| 6 | 476 nM | 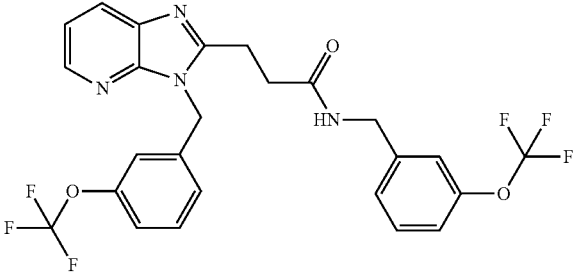 [SMILES: O=C(CCc1nc2cccnc2n1Cc1cccc(OC(F)(F)F)c1)NCc1cccc(OC(F)(F)F)c1] | N-(3-Trifluoromethoxy-benzyl)-3-[3-(3-trifluoromethoxy-benzyl)-3H-imidazo[4,5-b]pyridin-2-yl]-propionamide |

TABLE 1-continued

ATX activity (Quanta Red assay)

| Example | Activity | Structure | Name |
|---|---|---|---|
| 7 | 1 nM | 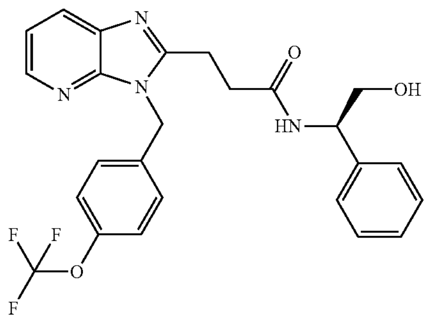 [SMILES: O=C(CCc1nc2cccnc2n1Cc1ccc(OC(F)(F)F)cc1)N[C@@H](CO)c1ccccc1] | N-((R)-2-Hydroxy-1-phenyl-ethyl)-3-[3-(4-trifluoromethoxy-benzyl)-3H-imidazo[4,5-b]pyridin-2-yl]-propionamide |
| 8 | 1 nM | 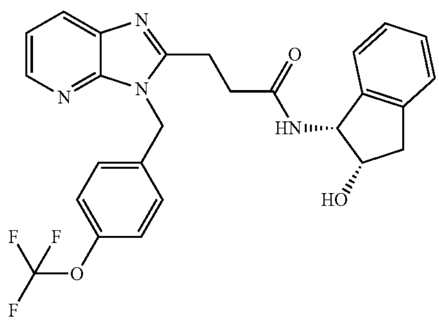 [SMILES: O=C(CCc1nc2cccnc2n1Cc1ccc(OC(F)(F)F)cc1)N[C@@H]1c2ccccc2C[C@@H]1O] | N-((1R,2S)-2-Hydroxy-indan-1-yl)-3-[3-(4-trifluoromethoxy-benzyl)-3H-imidazo[4,5-b]pyridin-2-yl]-propionamide |
| 9 | 1 nM | 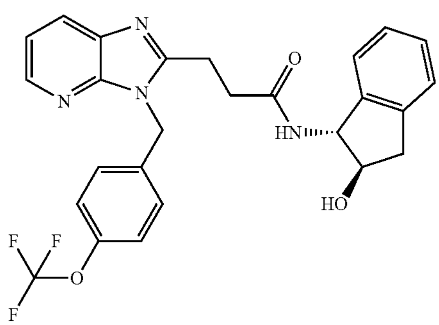 [SMILES: O=C(CCc1nc2cccnc2n1Cc1ccc(OC(F)(F)F)cc1)N[C@@H]1c2ccccc2C[C@H]1O] | N-((1R,2R)-2-Hydroxy-indan-1-yl)-3-[3-(4-trifluoromethoxy-benzyl)-3H-imidazo[4,5-b]pyridin-2-yl]-propionamide |
| 10 | 2 nM | 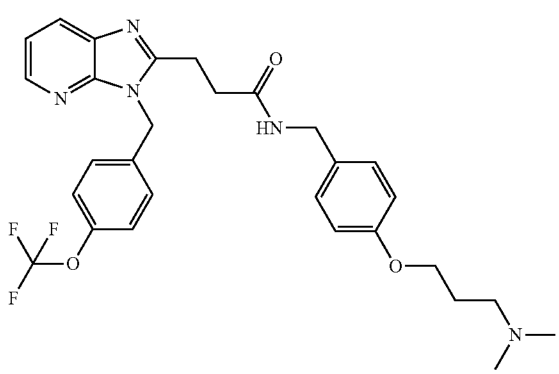 [SMILES: CN(C)CCCOc1ccc(CNC(=O)CCc2nc3cccnc3n2Cc2ccc(OC(F)(F)F)cc2)cc1] | N-[4-(3-Dimethylamino-propoxy)-benzyl]-3-[3-(4-trifluoromethoxy-benzyl)-3H-imidazo[4,5-b]pyridin-2-yl]-propionamide |

TABLE 1-continued

ATX activity (Quanta Red assay)

| Example | Activity | Structure | Name |
|---|---|---|---|
| 11 | 2 nM | 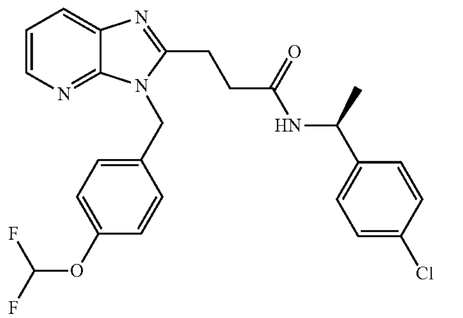 [SMILES: C[C@H](NC(=O)CCc1nc2cccnc2n1Cc1ccc(OC(F)F)cc1)c1ccc(Cl)cc1] | N-[(S)-1-(4-Chloro-phenyl)-ethyl]-3-[3-(4-difluoromethoxy-benzyl)-3H-imidazo[4,5-b]pyridin-2-yl]-propionamide |
| 12 | 2 nM | 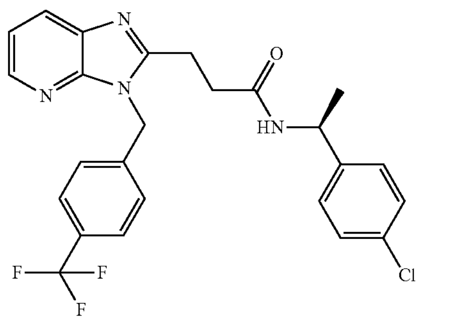 [SMILES: C[C@H](NC(=O)CCc1nc2cccnc2n1Cc1ccc(C(F)(F)F)cc1)c1ccc(Cl)cc1] | N-[(S)-1-(4-Chloro-phenyl)-ethyl]-3-[3-(4-trifluoromethyl-benzyl)-3H-imidazo[4,5-b]pyridin-2-yl]-propionamide |
| 13 | 2 nM | 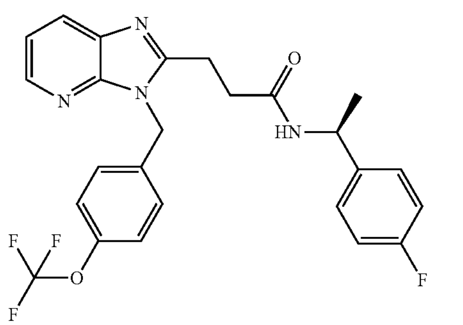 [SMILES: C[C@H](NC(=O)CCc1nc2cccnc2n1Cc1ccc(OC(F)(F)F)cc1)c1ccc(F)cc1] | N-[(S)-1-(4-Fluoro-phenyl)-ethyl]-3-[3-(4-trifluoromethoxy-benzyl)-3H-imidazo[4,5-b]pyridin-2-yl]-propionamide |
| 14 | 2 nM | 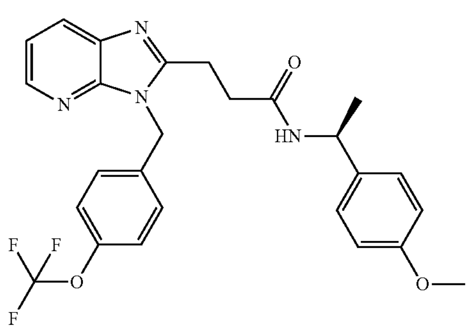 [SMILES: COc1ccc([C@H](C)NC(=O)CCc2nc3cccnc3n2Cc2ccc(OC(F)(F)F)cc2)cc1] | N-(4-Methoxy-benzyl)-3-[3-(4-trifluoromethoxy-benzyl)-3H-imidazo[4,5-b]pyridin-2-yl]-propionamide |

TABLE 1-continued

ATX activity (Quanta Red assay)

| Example | Activity | Structure | Name |
|---|---|---|---|
| 15 | 2 nM | 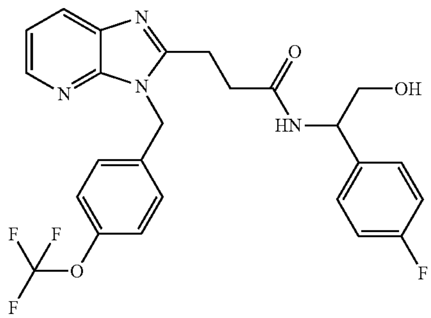 [SMILES: O=C(CCc1nc2cccnc2n1Cc1ccc(OC(F)(F)F)cc1)NC(CO)c1ccc(F)cc1] | N-[1-(4-Fluoro-phenyl)-2-hydroxy-ethyl]-3-[3-(4-trifluoromethoxy-benzyl)-3H-imidazo[4,5-b]pyridin-2-yl]-propionamide |
| 16 | 3 nM | 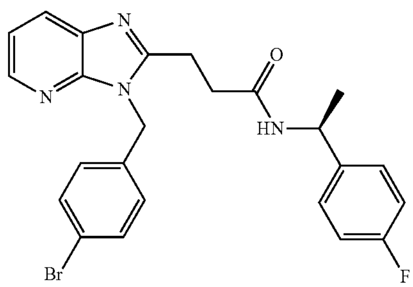 [SMILES: C[C@H](NC(=O)CCc1nc2cccnc2n1Cc1ccc(Br)cc1)c1ccc(F)cc1] | 3-[3-(4-Bromo-benzyl)-3H-imidazo[4,5-b]pyridin-2-yl]-N-[(S)-1-(4-fluoro-phenyl)-ethyl]-propionamide |
| 17 | 3 nM | 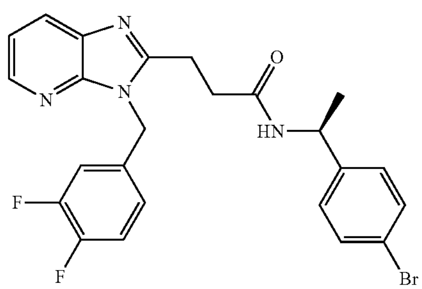 [SMILES: C[C@H](NC(=O)CCc1nc2cccnc2n1Cc1ccc(F)c(F)c1)c1ccc(Br)cc1] | N-[(S)-1-(4-Bromo-phenyl)-ethyl]-3-[3-(3,4-difluoro-benzyl)-3H-imidazo[4,5-b]pyridin-2-yl]-propionamide |
| 18 | 3 nM | 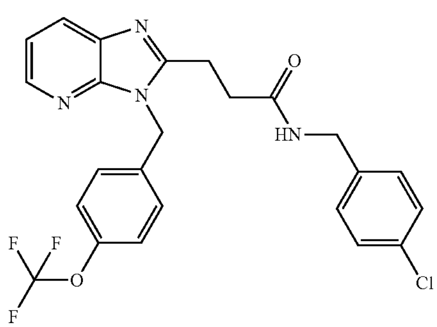 [SMILES: O=C(CCc1nc2cccnc2n1Cc1ccc(OC(F)(F)F)cc1)NCc1ccc(Cl)cc1] | N-(4-Chloro-benzyl)-3-[3-(4-trifluoromethoxy-benzyl)-3H-imidazo[4,5-b]pyridin-2-yl]-propionamide |

TABLE 1-continued

ATX activity (Quanta Red assay)

| Example | Activity | Structure | Name |
|---|---|---|---|
| 19 | 4 nM | 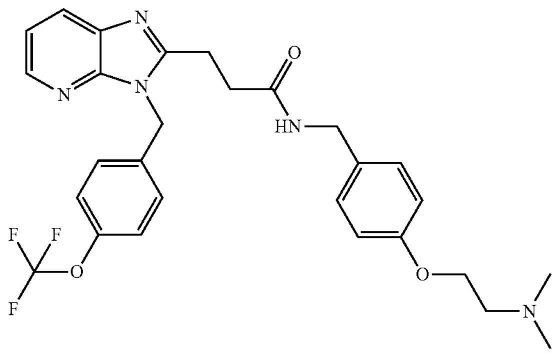 [SMILES: CN(C)CCOc1ccc(CNC(=O)CCc2nc3cccnc3n2Cc2ccc(OC(F)(F)F)cc2)cc1] | N-[4-(2-Dimethylamino-ethoxy)-benzyl]-3-[3-(4-trifluoromethoxy-benzyl)-3H-imidazo[4,5-b]pyridin-2-yl]-propionamide |
| 20 | 3 nM | 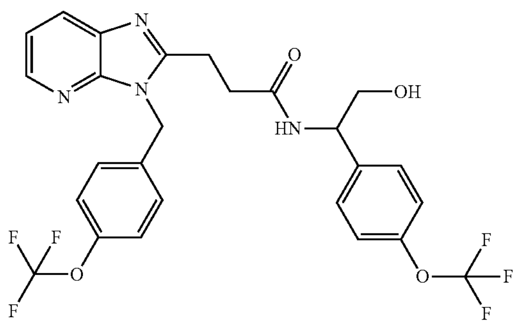 [SMILES: O=C(CCc1nc2cccnc2n1Cc1ccc(OC(F)(F)F)cc1)NC(CO)c1ccc(OC(F)(F)F)cc1] | N-[2-Hydroxy-1-(4-trifluoromethoxy-phenyl)-ethyl]-3-[3-(4-trifluoromethoxy-benzyl)-3H-imidazo[4,5-b]pyridin-2-yl]-propionamide |
| 21 | 5 nM | 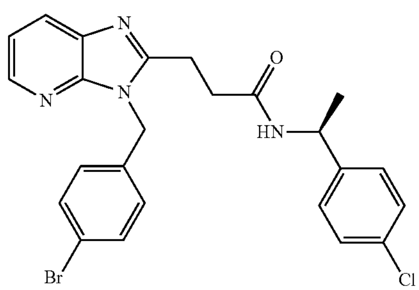 [SMILES: C[C@H](NC(=O)CCc1nc2cccnc2n1Cc1ccc(Br)cc1)c1ccc(Cl)cc1] | 3-[3-(4-Bromo-benzyl)-3H-imidazo[4,5-b]pyridin-2-yl]-N-[(S)-1-(4-chloro-phenyl)-ethyl]-propionamide |
| 22 | 4 nM | 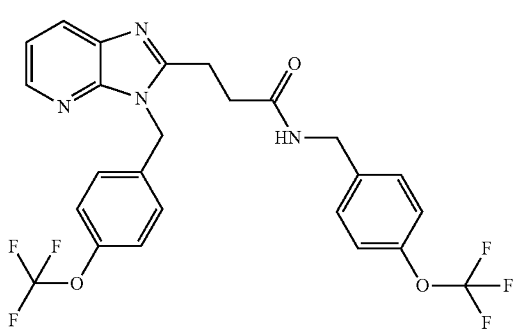 [SMILES: O=C(CCc1nc2cccnc2n1Cc1ccc(OC(F)(F)F)cc1)NCc1ccc(OC(F)(F)F)cc1] | N-(4-Trifluoromethoxy-benzyl)-3-[3-(4-trifluoromethoxy-benzyl)-3H-imidazo[4,5-b]pyridin-2-yl]-propionamide |

TABLE 1-continued

ATX activity (Quanta Red assay)

| Example | Activity | Structure | Name |
|---|---|---|---|
| 23 | 4 nM | 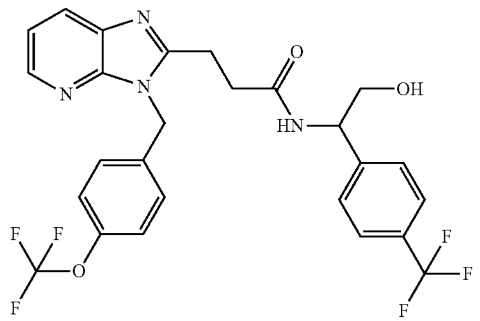 [SMILES: O=C(CCc1nc2cccnc2n1Cc1ccc(OC(F)(F)F)cc1)NC(CO)c1ccc(C(F)(F)F)cc1] | N-[2-Hydroxy-1-(4-trifluoromethyl-phenyl)-ethyl]-3-[3-(4-trifluoromethoxy-benzyl)-3H-imidazo[4,5-b]pyridin-2-yl]-propionamide |
| 24 | 4 nM | 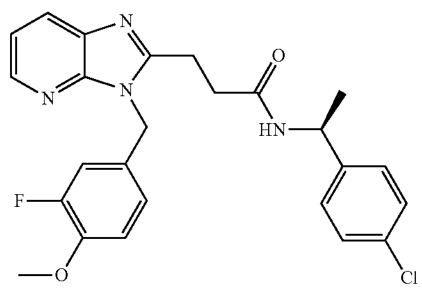 [SMILES: COc1ccc(Cn2c(CCC(=O)N[C@@H](C)c3ccc(Cl)cc3)nc3cccnc32)cc1F] | N-[(S)-1-(4-Chloro-phenyl)-ethyl]-3-[3-(3-fluoro-4-methoxy-benzyl)-3H-imidazo[4,5-b]pyridin-2-yl]-propionamide |
| 25 | 4 nM | 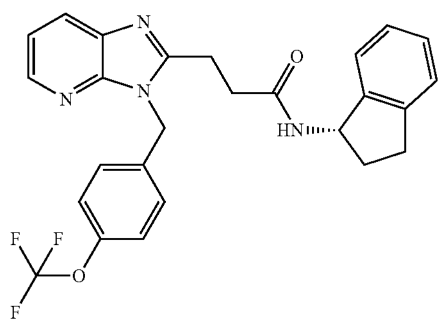 [SMILES: O=C(CCc1nc2cccnc2n1Cc1ccc(OC(F)(F)F)cc1)N[C@H]1CCc2ccccc21] | N-(S)-Indan-1-yl-3-[3-(4-trifluoromethoxy-benzyl)-3H-imidazo[4,5-b]pyridin-2-yl]-propionamide |
| 26 | 4 nM | 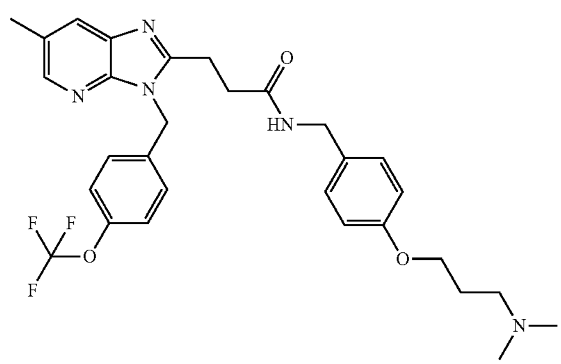 | N-[4-(3-Dimethylamino-propoxy)-benzyl]-3-[6-methyl-3-(4-trifluoromethoxy-benzyl)-3H-imidazo[4,5-b]pyridin-2-yl]-propionamide |

TABLE 1-continued

ATX activity (Quanta Red assay)

| Example | Activity | Structure | Name |
|---|---|---|---|
| 27 | 4 nM | 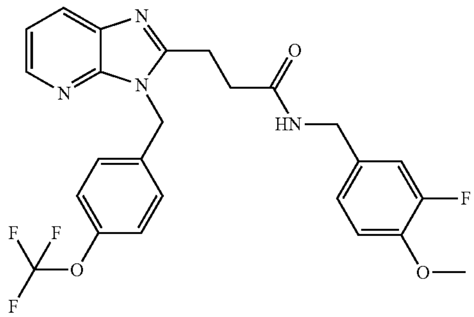 [SMILES: COc1ccc(CNC(=O)CCc2nc3cccnc3n2Cc2ccc(OC(F)(F)F)cc2)cc1F] | N-(3-Fluoro-4-methoxy-benzyl)-3-[3-(4-trifluoromethoxy-benzyl)-3H-imidazo[4,5-b]pyridin-2-yl]-propionamide |
| 28 | 5 nM | 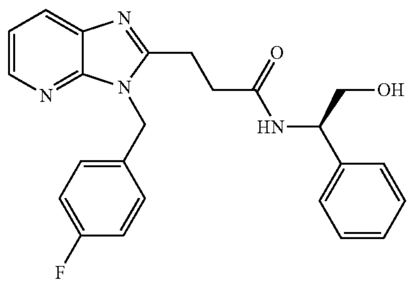 [SMILES: O=C(CCc1nc2cccnc2n1Cc1ccc(F)cc1)N[C@@H](CO)c1ccccc1] | 3-[3-(4-Fluoro-benzyl)-3H-imidazo[4,5-b]pyridin-2-yl]-N-((R)-2-hydroxy-1-phenyl-ethyl)-propionamide |
| 29 | 5 nM | 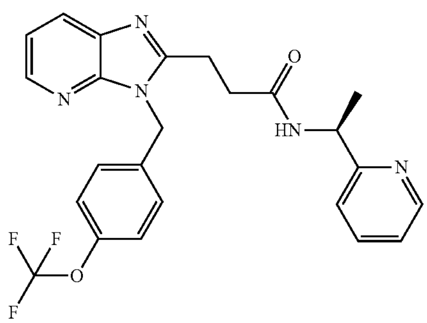 [SMILES: C[C@H](NC(=O)CCc1nc2cccnc2n1Cc1ccc(OC(F)(F)F)cc1)c1ccccn1] | N-((S)-1-Pyridin-2-yl-ethyl)-3-[3-(4-trifluoromethoxy-benzyl)-3H-imidazo[4,5-b]pyridin-2-yl]-propionamide |
| 30 | 5 nM | 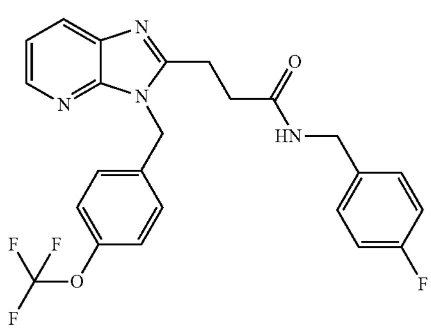 [SMILES: O=C(CCc1nc2cccnc2n1Cc1ccc(OC(F)(F)F)cc1)NCc1ccc(F)cc1] | N-(4-Fluoro-benzyl)-3-[3-(4-trifluoromethoxy-benzyl)-3H-imidazo[4,5-b]pyridin-2-yl]-propionamide |

TABLE 1-continued

ATX activity (Quanta Red assay)

| Example | Activity | Structure | Name |
|---|---|---|---|
| 31 | 6 nM | 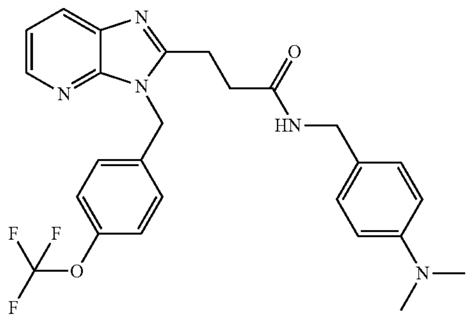 [SMILES: CN(C)c1ccc(CNC(=O)CCc2nc3cccnc3n2Cc2ccc(OC(F)(F)F)cc2)cc1] | N-(4-Dimethylamino-benzyl)-3-[3-(4-trifluoromethoxy-benzyl)-3H-imidazo[4,5-b]pyridin-2-yl]-propionamide |
| 32 | 6 nM | 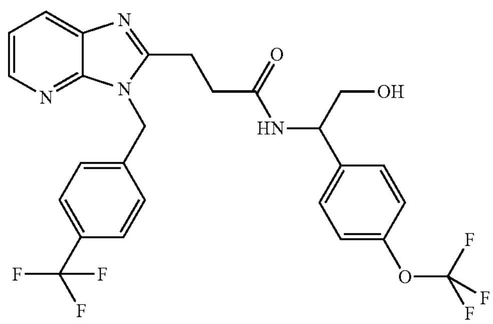 [SMILES: O=C(CCc1nc2cccnc2n1Cc1ccc(C(F)(F)F)cc1)NC(CO)c1ccc(OC(F)(F)F)cc1] | N-[2-Hydroxy-1-(4-trifluoromethoxy-phenyl)-ethyl]-3-[3-(4-trifluoromethyl-benzyl)-3H-imidazo[4,5-b]pyridin-2-yl]-propionamide |
| 33 | 6 nM | 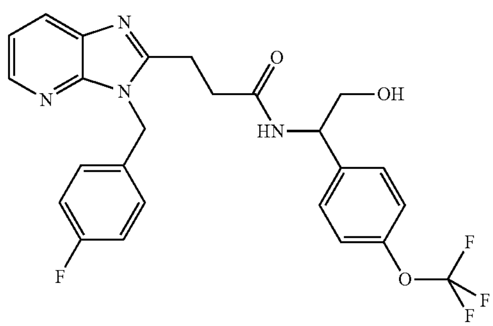 [SMILES: O=C(CCc1nc2cccnc2n1Cc1ccc(F)cc1)NC(CO)c1ccc(OC(F)(F)F)cc1] | 3-[3-(4-Fluoro-benzyl)-3H-imidazo[4,5-b]pyridin-2-yl]-N-[2-hydroxy-1-(4-trifluoromethoxy-phenyl)-ethyl]-propionamide |
| 34 | 6 nM | 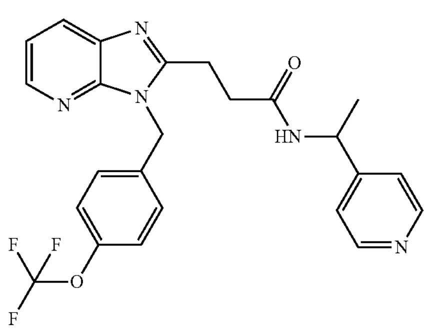 [SMILES: CC(NC(=O)CCc1nc2cccnc2n1Cc1ccc(OC(F)(F)F)cc1)c1ccncc1] | N-(1-Pyridin-4-yl-ethyl)-3-[3-(4-trifluoromethoxy-benzyl)-3H-imidazo[4,5-b]pyridin-2-yl]-propionamide |

TABLE 1-continued

ATX activity (Quanta Red assay)

| Example | Activity | Structure | Name |
|---|---|---|---|
| 35 | 7 nM | 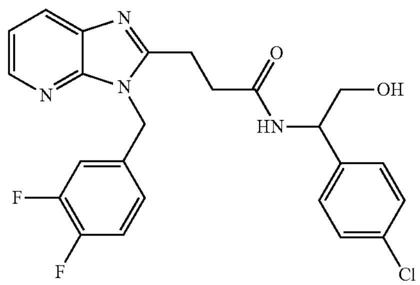 [SMILES: O=C(CCc1nc2cccnc2n1Cc1ccc(F)c(F)c1)NC(CO)c1ccc(Cl)cc1] | N-[1-(4-Chloro-phenyl)-2-hydroxy-ethyl]-3-[3-(3,4-difluoro-benzyl)-3H-imidazo[4,5-b]pyridin-2-yl]-propionamide |
| 36 | 7 nM | 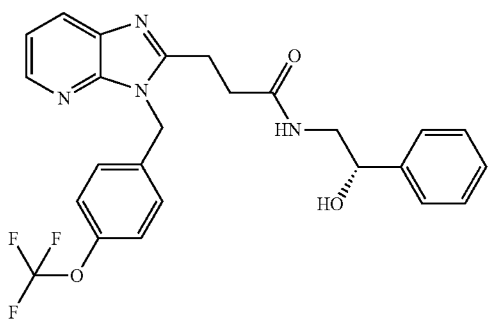 [SMILES: O=C(CCc1nc2cccnc2n1Cc1ccc(OC(F)(F)F)cc1)NC[C@@H](O)c1ccccc1] | N-((S)-2-Hydroxy-2-phenyl-ethyl)-3-[3-(4-trifluoromethoxy-benzyl)-3H-imidazo[4,5-b]pyridin-2-yl]-propionamide |
| 37 | 7 nM | 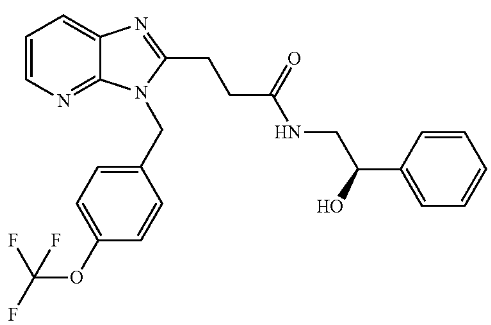 [SMILES: O=C(CCc1nc2cccnc2n1Cc1ccc(OC(F)(F)F)cc1)NC[C@H](O)c1ccccc1] | N-((R)-2-Hydroxy-2-phenyl-ethyl)-3-[3-(4-trifluoromethoxy-benzyl)-3H-imidazo[4,5-b]pyridin-2-yl]-propionamide |
| 38 | 9 nM | 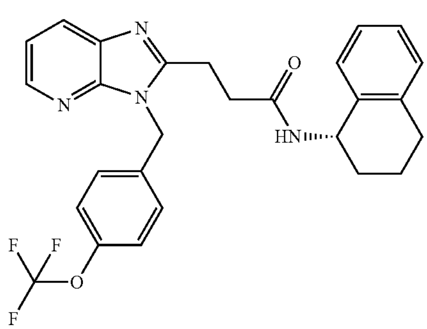 [SMILES: O=C(CCc1nc2cccnc2n1Cc1ccc(OC(F)(F)F)cc1)N[C@H]1CCCc2ccccc21] | N-(S)-1,2,3,4-Tetrahydro-naphthalen-1-yl-3-[3-(4-trifluoromethoxy-benzyl)-3H-imidazo[4,5-b]pyridin-2-yl]-propionamide |

TABLE 1-continued

ATX activity (Quanta Red assay)

| Example | Activity | Structure | Name |
|---|---|---|---|
| 39 | 7 nM | 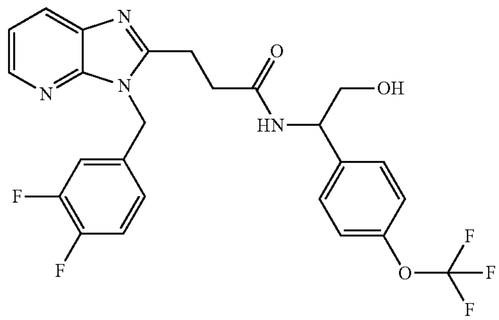 [SMILES: O=C(CCc1nc2cccnc2n1Cc1ccc(F)c(F)c1)NC(CO)c1ccc(OC(F)(F)F)cc1] | 3-[3-(3,4-Difluoro-benzyl)-3H-imidazo[4,5-b]pyridin-2-yl]-N-[2-hydroxy-1-(4-trifluoromethoxy-phenyl)-ethyl]-propionamide |
| 40 | 1 nM | 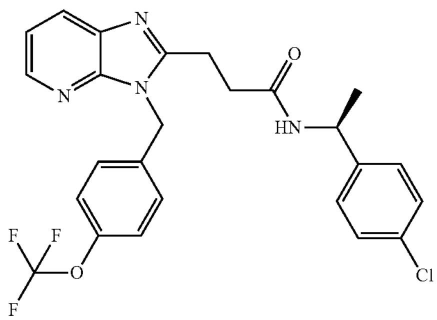 [SMILES: C[C@H](NC(=O)CCc1nc2cccnc2n1Cc1ccc(OC(F)(F)F)cc1)c1ccc(Cl)cc1] | N-[(S)-1-(4-Chloro-phenyl)-ethyl]-3-[3-(4-trifluoromethoxy-benzyl)-3H-imidazo[4,5-b]pyridin-2-yl]-propionamide |
| 41 | 10 nM | 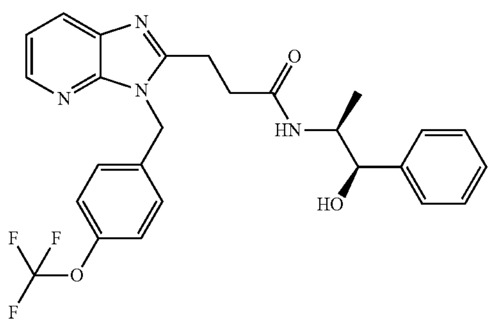 [SMILES: C[C@H](NC(=O)CCc1nc2cccnc2n1Cc1ccc(OC(F)(F)F)cc1)[C@H](O)c1ccccc1] | N-((1S,2R)-2-Hydroxy-1-methyl-2-phenyl-ethyl)-3-[3-(4-trifluoromethoxy-benzyl)-3H-imidazo[4,5-b]pyridin-2-yl]-propionamide |
| 42 | 11 nM | 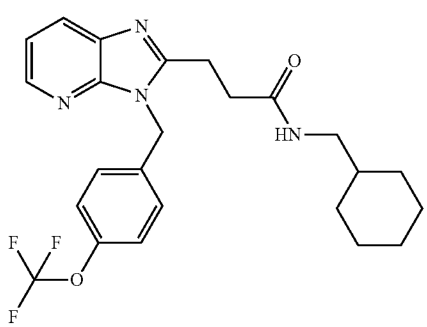 [SMILES: O=C(CCc1nc2cccnc2n1Cc1ccc(OC(F)(F)F)cc1)NCC1CCCCC1] | N-Cyclohexylmethyl-3-[3-(4-trifluoromethoxy-benzyl)-3H-imidazo[4,5-b]pyridin-2-yl]-propionamide |

TABLE 1-continued

ATX activity (Quanta Red assay)

| Example | Activity | Structure | Name |
|---|---|---|---|
| 43 | 11 nM | 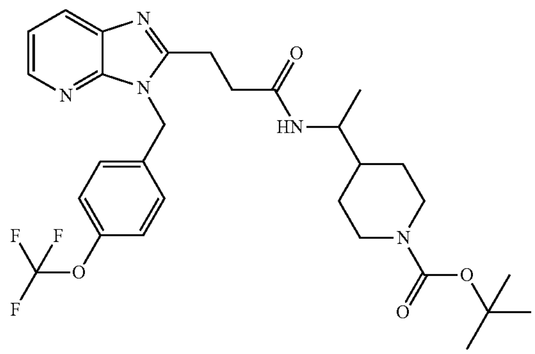 [SMILES: CC(NC(=O)CCc1nc2cccnc2n1Cc1ccc(OC(F)(F)F)cc1)C1CCN(C(=O)OC(C)(C)C)CC1] | 4-(1-{3-[3-(4-Trifluoromethoxy-benzyl)-3H-imidazo[4,5-b]pyridin-2-yl]-propionylamino}-ethyl)-piperidine-1-carboxylic acid tert-butyl ester |
| 44 | 12 nM | 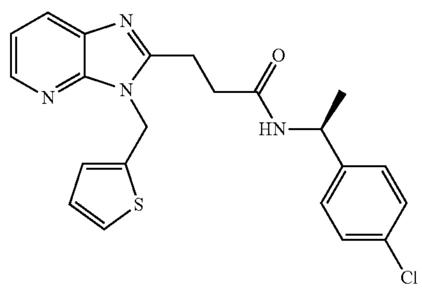 [SMILES: C[C@H](NC(=O)CCc1nc2cccnc2n1Cc1cccs1)c1ccc(Cl)cc1] | N-[(S)-1-(4-Chloro-phenyl)-ethyl]-3-(3-thiophen-2-ylmethyl-3H-imidazo[4,5-b]pyridin-2-yl)-propionamide |
| 45 | 17 nM | 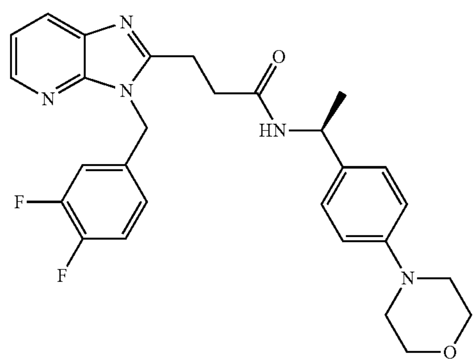 [SMILES: C[C@H](NC(=O)CCc1nc2cccnc2n1Cc1ccc(F)c(F)c1)c1ccc(N2CCOCC2)cc1] | 3-[3-(3,4-Difluoro-benzyl)-3H-imidazo[4,5-b]pyridin-2-yl]-N-[(S)-1-(4-morpholin-4-yl-phenyl)-ethyl]-propionamide |
| 46 | 18 nM | 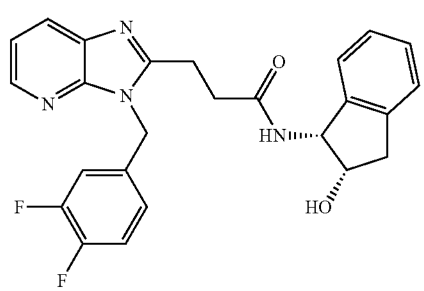 [SMILES: O=C(CCc1nc2cccnc2n1Cc1ccc(F)c(F)c1)N[C@@H]1c2ccccc2C[C@@H]1O] | 3-[3-(3,4-Difluoro-benzyl)-3H-imidazo[4,5-b]pyridin-2-yl]-N-((1R,2S)-2-hydroxy-indan-1-yl)-propionamide |

TABLE 1-continued

ATX activity (Quanta Red assay)

| Example | Activity | Structure | Name |
|---|---|---|---|
| 47 | 19 nM | 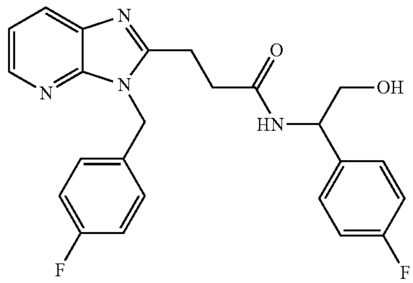 [SMILES: O=C(CCc1nc2cccnc2n1Cc1ccc(F)cc1)NC(CO)c1ccc(F)cc1] | 3-[3-(4-Fluoro-benzyl)-3H-imidazo[4,5-b]pyridin-2-yl]-N-[1-(4-fluoro-phenyl)-2-hydroxy-ethyl]-propionamide |
| 48 | 19 nM | 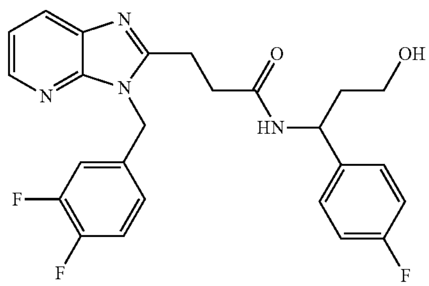 [SMILES: O=C(CCc1nc2cccnc2n1Cc1ccc(F)c(F)c1)NC(CCO)c1ccc(F)cc1] | 3-[3-(3,4-Difluoro-benzyl)-3H-imidazo[4,5-b]pyridin-2-yl]-N-[1-(4-fluoro-phenyl)-3-hydroxy-propyl]-propionamide |
| 49 | 21 nM | 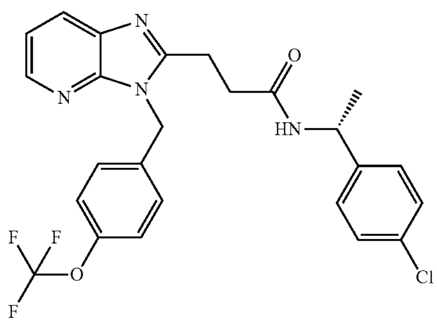 [SMILES: C[C@@H](NC(=O)CCc1nc2cccnc2n1Cc1ccc(OC(F)(F)F)cc1)c1ccc(Cl)cc1] | N-[(R)-1-(4-Chloro-phenyl)-ethyl]-3-[3-(4-trifluoromethoxy-benzyl)-3H-imidazo[4,5-b]pyridin-2-yl]-propionamide |
| 50 | 22 nM | 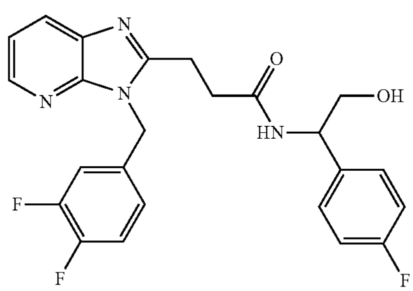 [SMILES: O=C(CCc1nc2cccnc2n1Cc1ccc(F)c(F)c1)NC(CO)c1ccc(F)cc1] | 3-[3-(3,4-Difluoro-benzyl)-3H-imidazo[4,5-b]pyridin-2-yl]-N-[1-(4-fluoro-phenyl)-2-hydroxy-ethyl]-propionamide |
| 51 | 22 nM | 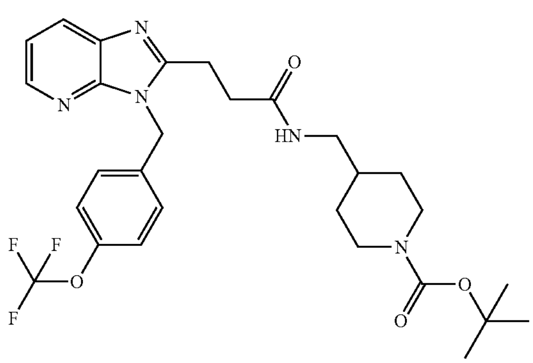 | 4-({3-[3-(4-Trifluoromethoxy-benzyl)-3H-imidazo[4,5-b]pyridin-2-yl]-propionylamino}-methyl)-piperidine-1-carboxylic acid tert-butyl ester |

TABLE 1-continued

ATX activity (Quanta Red assay)

| Example | Activity | Structure | Name |
|---|---|---|---|
| 52 | 29 nM | 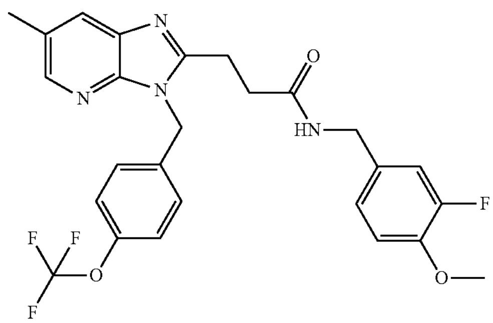 [SMILES: COc1ccc(CNC(=O)CCc2nc3cc(C)cnc3n2Cc2ccc(OC(F)(F)F)cc2)cc1F] | N-(3-Fluoro-4-methoxy-benzyl)-3-[6-methyl-3-(4-trifluoromethoxy-benzyl)-3H-imidazo[4,5-b]pyridin-2-yl]-propionamide |
| 53 | 38 nM | 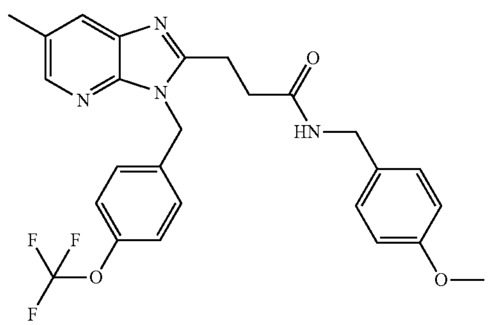 | N-(4-Methoxy-benzyl)-3-[6-methyl-3-(4-trifluoromethoxy-benzyl)-3H-imidazo[4,5-b]pyridin-2-yl]-propionamide |
| 54 | 40 nM | 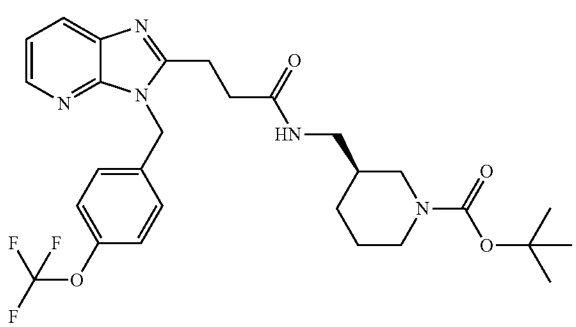 [SMILES: CC(C)(C)OC(=O)N1CCC[C@@H](CNC(=O)CCc2nc3cccnc3n2Cc2ccc(OC(F)(F)F)cc2)C1] | (S)-3-({3-[3-(4-Trifluoromethoxy-benzyl)-3H-imidazo[4,5-b]pyridin-2-yl]-propionylamino}-methyl)-piperidine-1-carboxylic acid tert-butyl ester |
| 55 | 40 nM | 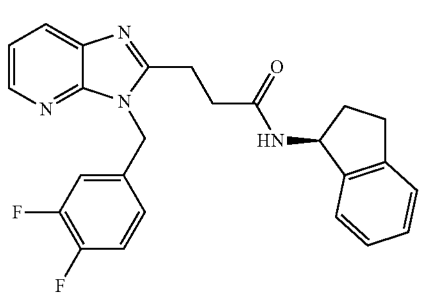 [SMILES: O=C(CCc1nc2cccnc2n1Cc1ccc(F)c(F)c1)N[C@H]1CCc2ccccc21] | 3-[3-(3,4-Difluoro-benzyl)-3H-imidazo[4,5-b]pyridin-2-yl]-N-(S)-indan-1-yl-propionamide |

TABLE 1-continued

ATX activity (Quanta Red assay)

| Example | Activity | Structure | Name |
|---|---|---|---|
| 56 | 45 nM | 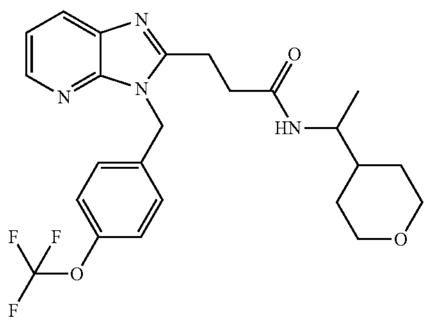 [SMILES: CC(NC(=O)CCc1nc2cccnc2n1Cc1ccc(OC(F)(F)F)cc1)C1CCOCC1] | N-[1-(Tetrahydro-pyran-4-yl)-ethyl]-3-[3-(4-trifluoromethoxy-benzyl)-3H-imidazo[4,5-b]pyridin-2-yl]-propionamide |
| 57 | 58 nM | 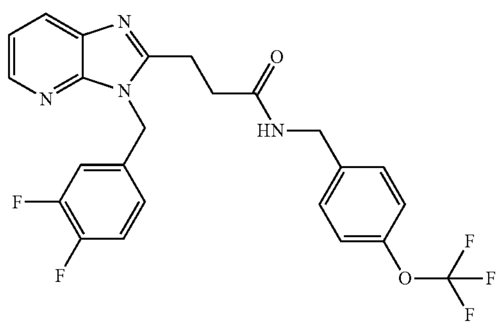 [SMILES: O=C(CCc1nc2cccnc2n1Cc1ccc(F)c(F)c1)NCc1ccc(OC(F)(F)F)cc1] | 3-[3-(3,4-Difluoro-benzyl)-3H-imidazo[4,5-b]pyridin-2-yl]-N-(4-trifluoromethoxy-benzyl)-propionamide |
| 58 | 61 nM | 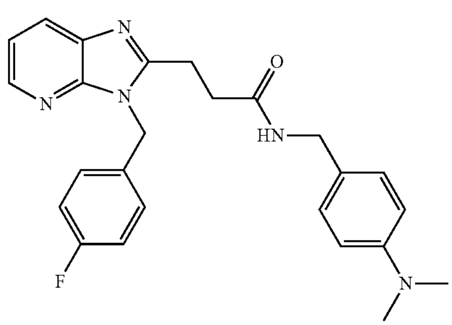 [SMILES: CN(C)c1ccc(CNC(=O)CCc2nc3cccnc3n2Cc2ccc(F)cc2)cc1] | N-(4-Dimethylamino-benzyl)-3-[3-(4-fluoro-benzyl)-3H-imidazo[4,5-b]pyridin-2-yl]-propionamide |
| 59 | 63 nM | 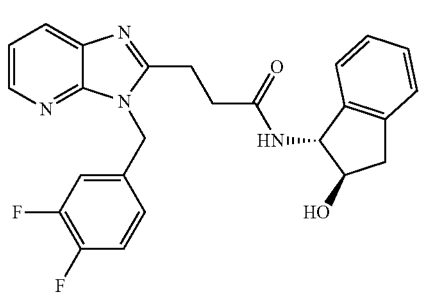 [SMILES: O=C(CCc1nc2cccnc2n1Cc1ccc(F)c(F)c1)N[C@@H]1c2ccccc2C[C@H]1O] | 3-[3-(3,4-Difluoro-benzyl)-3H-imidazo[4,5-b]pyridin-2-yl]-N-((1R,2R)-2-hydroxy-indan-1-yl)-propionamide |

TABLE 1-continued

ATX activity (Quanta Red assay)

| Example | Activity | Structure | Name |
|---|---|---|---|
| 60 | 89 nM | 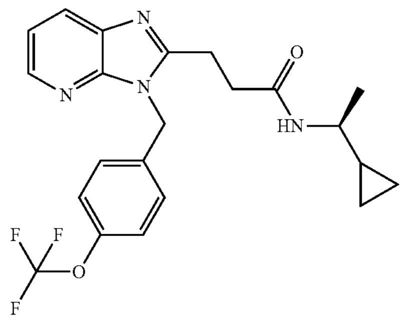 [SMILES: C[C@H](NC(=O)CCc1nc2cccnc2n1Cc1ccc(OC(F)(F)F)cc1)C1CC1] | N-((S)-1-Cyclopropyl-ethyl)-3-[3-(4-trifluoromethoxy-benzyl)-3H-imidazo[4,5-b]pyridin-2-yl]-propionamide |
| 61 | 100 nM | 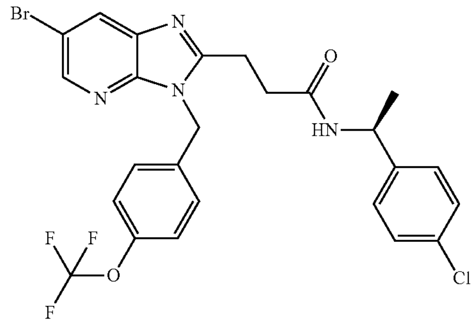 [SMILES: C[C@H](NC(=O)CCc1nc2cc(Br)cnc2n1Cc1ccc(OC(F)(F)F)cc1)c1ccc(Cl)cc1] | 3-[6-Bromo-3-(4-fluoro-benzyl)-3H-imidazo[4,5-b]pyridin-2-yl]-N-[(S)-1-(4-chloro-propionimide)] |
| 62 | 125 nM | 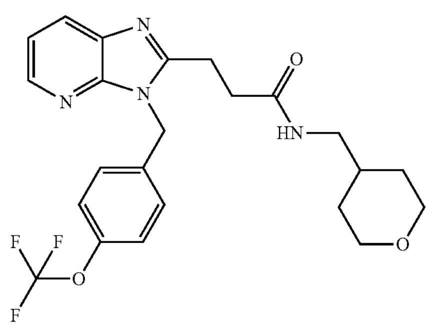 [SMILES: O=C(CCc1nc2cccnc2n1Cc1ccc(OC(F)(F)F)cc1)NCC1CCOCC1] | N-(Tetrahydro-pyran-4-ylmethyl)-3-[3-(4-trifluoromethoxy-benzyl)-3H-imidazo[4,5-b]pyridin-2-yl]-propionamide |
| 63 | 139 nM | 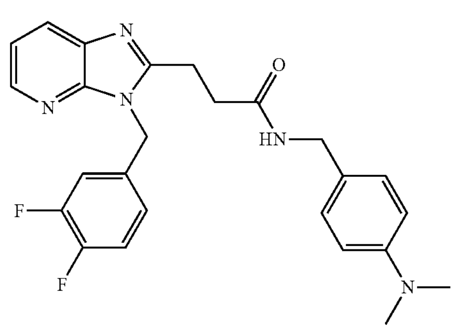 [SMILES: CN(C)c1ccc(CNC(=O)CCc2nc3cccnc3n2Cc2ccc(F)c(F)c2)cc1] | 3-[3-(3,4-Difluoro-benzyl)-3H-imidazo[4,5-b]pyridin-2-yl]-N-(4-dimethylamino-benzyl)-propionamide |

TABLE 1-continued

ATX activity (Quanta Red assay)

| Example | Activity | Structure | Name |
|---|---|---|---|
| 64 | 144 nM | 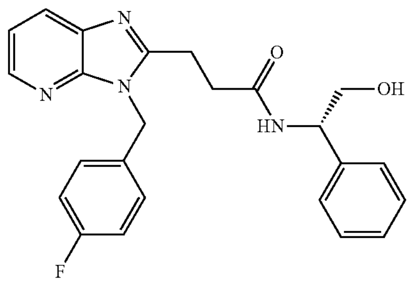 [SMILES: O=C(CCc1nc2cccnc2n1Cc1ccc(F)cc1)N[C@H](CO)c1ccccc1] | 3-[3-(4-Fluoro-benzyl)-3H-imidazo[4,5-b]pyridin-2-yl]-N-((S)-2-hydroxy-1-phenyl-ethyl)-propionamide |
| 65 | 155 nM | 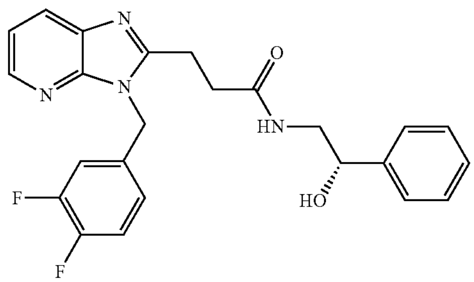 [SMILES: O=C(CCc1nc2cccnc2n1Cc1ccc(F)c(F)c1)NC[C@@H](O)c1ccccc1] | 3-[3-(3,4-Difluoro-benzyl)-3H-imidazo[4,5-b]pyridin-2-yl]-N-((S)-2-hydroxy-2-phenyl-ethyl)-propionamide |
| 66 | 162 nM | 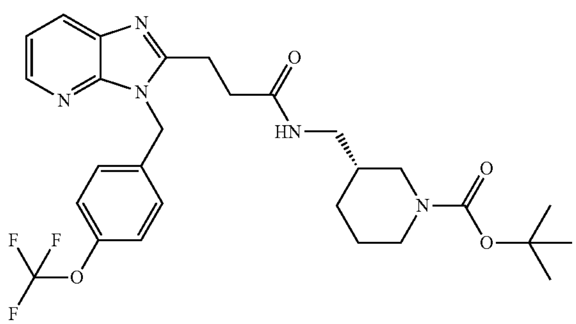 [SMILES: CC(C)(C)OC(=O)N1CCC[C@H](CNC(=O)CCc2nc3cccnc3n2Cc2ccc(OC(F)(F)F)cc2)C1] | (R)-3-({3-[3-(4-Trifluoromethoxy-benzyl)-3H-imidazo[4,5-b]pyridin-2-yl]-propionylamino}-methyl)-piperidine-1-carboxylic acid tert-butyl ester |
| 67 | 169 nM | 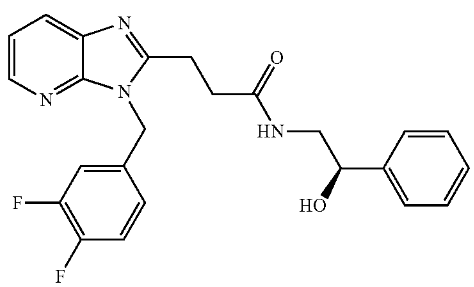 [SMILES: O=C(CCc1nc2cccnc2n1Cc1ccc(F)c(F)c1)NC[C@H](O)c1ccccc1] | 3-[3-(3,4-Difluoro-benzyl)-3H-imidazo[4,5-b]pyridin-2-yl]-N-((R)-2-hydroxy-2-phenyl-ethyl)-propionamide |
| 68 | 212 nM | 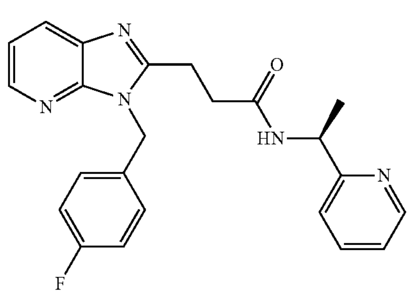 [SMILES: C[C@H](NC(=O)CCc1nc2cccnc2n1Cc1ccc(F)cc1)c1ccccn1] | 3-[3-(4-Fluoro-benzyl)-3H-imidazo[4,5-b]pyridin-2-yl]-N-((S)-1-pyridin-2-yl-ethyl)-propionamide |

TABLE 1-continued

ATX activity (Quanta Red assay)

| Example | Activity | Structure | Name |
|---|---|---|---|
| 69 | 214 nM | 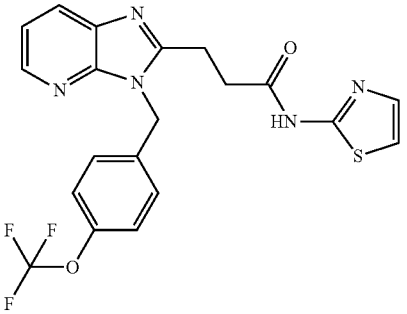 [SMILES: O=C(CCc1nc2cccnc2n1Cc1ccc(OC(F)(F)F)cc1)Nc1nccs1] | N-Thiazol-2-yl-3-[3-(4-trifluoromethoxy-benzyl)-3H-imidazo[4,5-b]pyridin-2-yl]-propionamide |
| 70 | 242 nM | 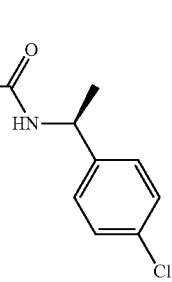 | 3-[6-Bromo-3-(4-fluoro-benzyl)-3H-imidazo[4,5-b]pyridin-2-yl]-N-[(S)-1-(4-chloro-propionimide)] |
| 71 | 243 nM | 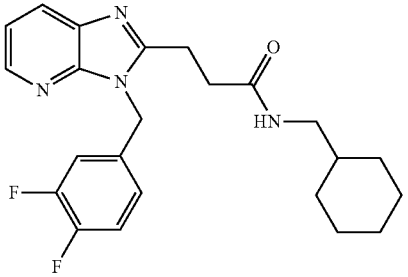 [SMILES: O=C(CCc1nc2cccnc2n1Cc1ccc(F)c(F)c1)NCC1CCCCC1] | N-Cyclohexylmethyl-3-[3-(3,4-difluoro-benzyl)-3H-imidazo[4,5-b]pyridin-2-yl]-propionamide |
| 72 | 247 nM | 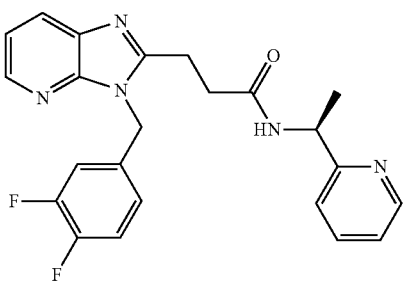 [SMILES: C[C@H](NC(=O)CCc1nc2cccnc2n1Cc1ccc(F)c(F)c1)c1ccccn1] | 3-[3-(3,4-Difluoro-benzyl)-3H-imidazo[4,5-b]pyridin-2-yl]-N-((S)-1-pyridin-2-yl-ethyl)-propionamide |
| 73 | 267 nM | 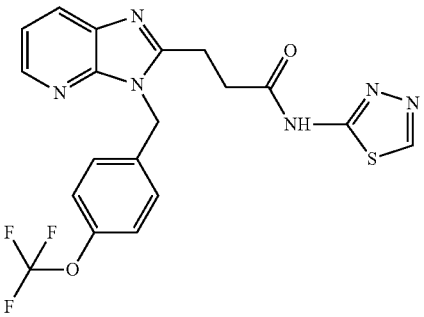 [SMILES: O=C(CCc1nc2cccnc2n1Cc1ccc(OC(F)(F)F)cc1)Nc1nncs1] | N-[1,3,4]Thiadiazol-2-yl-3-[3-(4-trifluoromethoxy-benzyl)-3H-imidazo[4,5-b]pyridin-2-yl]-propionamide |

TABLE 1-continued

ATX activity (Quanta Red assay)

| Example | Activity | Structure | Name |
|---|---|---|---|
| 74 | 339 nM | 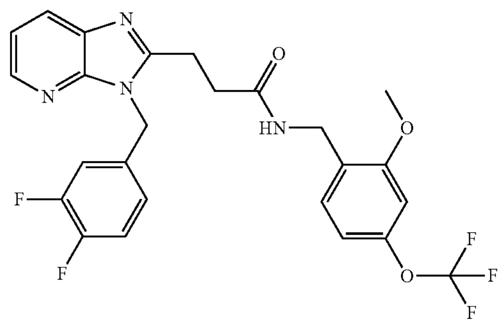 [SMILES: COc1cc(OC(F)(F)F)ccc1CNC(=O)CCc1nc2cccnc2n1Cc1ccc(F)c(F)c1] | 3-[3-(3,4-Difluoro-benzyl)-3H-imidazo[4,5-b]pyridin-2-yl]-N-(2-methoxy-4-trifluoromethoxy-benzyl)-propionamide |
| 75 | 424 nM | 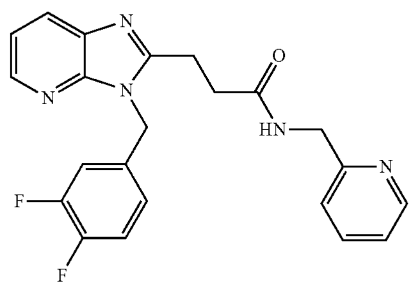 [SMILES: O=C(CCc1nc2cccnc2n1Cc1ccc(F)c(F)c1)NCc1ccccn1] | 3-[3-(3,4-Difluoro-benzyl)-3H-imidazo[4,5-b]pyridin-2-yl]-N-pyridin-2-ylmethyl-propionamide |
| 76 | 500 nM | 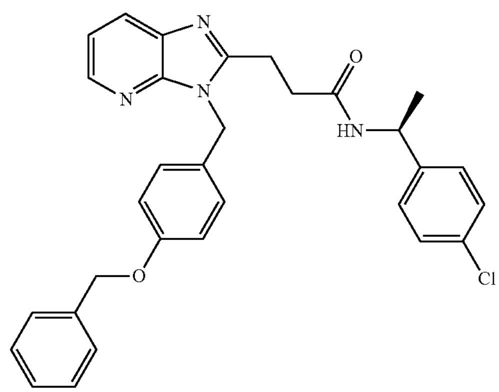 [SMILES: C[C@H](NC(=O)CCc1nc2cccnc2n1Cc1ccc(OCc2ccccc2)cc1)c1ccc(Cl)cc1] | 3-[3-(4-Benzyloxy-benzyl)-3H-imidazo[4,5-b]pyridin-2-yl]-N-[(S)-1-(4-chloro-phenyl)-ethyl]-propionamide |
| 77 | 714 nM | 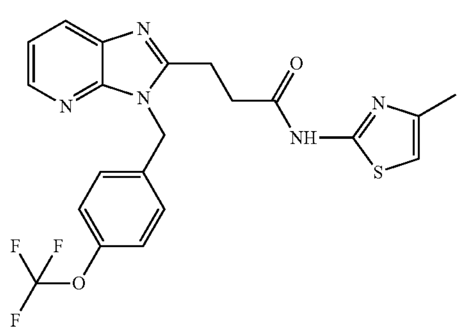 [SMILES: Cc1csc(NC(=O)CCc2nc3cccnc3n2Cc2ccc(OC(F)(F)F)cc2)n1] | N-(4-Methyl-thiazol-2-yl)-3-[3-(4-trifluoromethoxy-benzyl)-3H-imidazo[4,5-b]pyridin-2-yl]-propionamide |

TABLE 1-continued

ATX activity (Quanta Red assay)

| Example | Activity | Structure | Name |
|---|---|---|---|
| 78 | 800 nM | 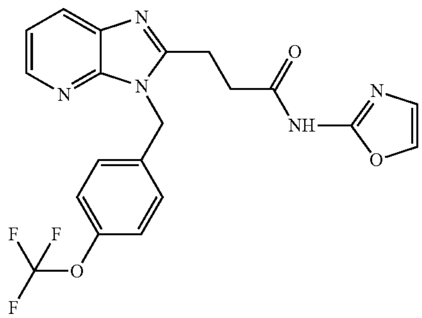 [SMILES: O=C(CCc1nc2cccnc2n1Cc1ccc(OC(F)(F)F)cc1)Nc1ncco1] | N-Oxazol-2-yl-3-[3-(4-trifluoromethoxy-benzyl)-3H-imidazo[4,5-b]pyridin-2-yl]-propionamide |
| 79 | 94 nM | 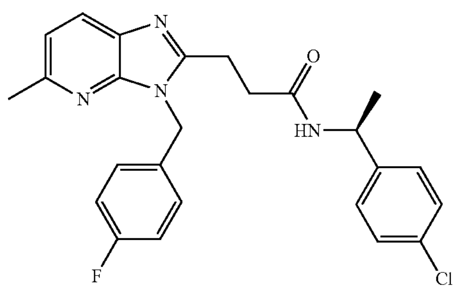 [SMILES: Cc1ccc2nc(CCC(=O)N[C@@H](C)c3ccc(Cl)cc3)n(Cc3ccc(F)cc3)c2n1] | N-[(S)-1-(4-Chloro-phenyl)-ethyl]-3-[3-(4-fluoro-benzyl)-5-methyl-3H-imidazo[4,5-b]pyridin-2-yl]-propionamide |
| 80 | 844 nM | 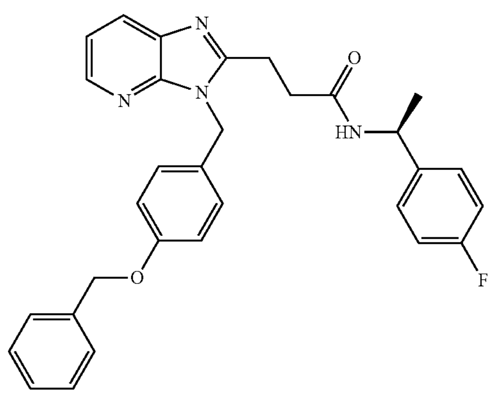 [SMILES: C[C@H](NC(=O)CCc1nc2cccnc2n1Cc1ccc(OCc2ccccc2)cc1)c1ccc(F)cc1] | 3-[3-(4-Benzyloxy-benzyl)-3H-imidazo[4,5-b]pyridin-2-yl-N-[(S)-1-(4-fluoro-phenyl)-ethyl]-propionamide |
| 81 | 1482 nM | 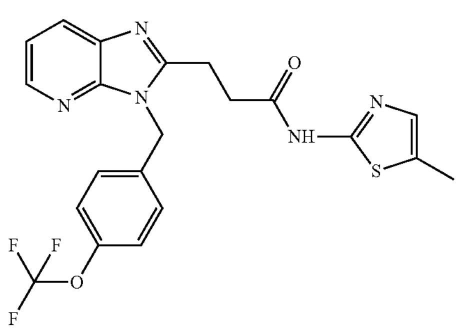 [SMILES: Cc1cnc(NC(=O)CCc2nc3cccnc3n2Cc2ccc(OC(F)(F)F)cc2)s1] | N-(5-Methyl-thiazol-2-yl)-3-[3-(4-trifluoromethoxy-benzyl)-3H-imidazo[4,5-b]pyridin-2-yl]-propionamide |

TABLE 1-continued

ATX activity (Quanta Red assay)

| Example | Activity | Structure | Name |
|---|---|---|---|
| 82 | 987 nM | 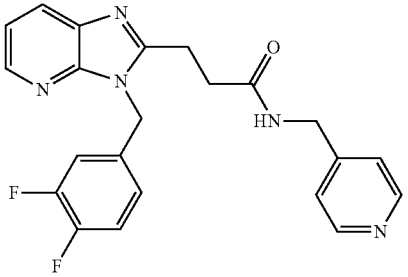 [SMILES: O=C(CCc1nc2cccnc2n1Cc1ccc(F)c(F)c1)NCc1ccncc1] | 3-[3-(3,4-Difluoro-benzyl)-3H-imidazo[4,5-b]pyridin-2-yl]-N-pyridin-4-ylmethyl-propionamide |
| 83 | 2 nM | 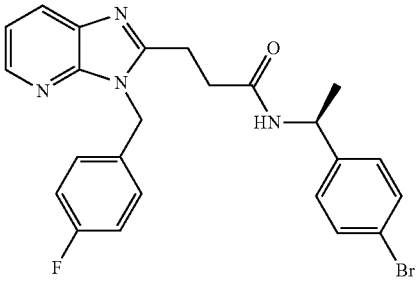 [SMILES: C[C@H](NC(=O)CCc1nc2cccnc2n1Cc1ccc(F)cc1)c1ccc(Br)cc1] | N-[(S)-1-(4-Bromo-phenyl)-ethyl]-3-[3-(4-fluoro-benzyl)-3H-imidazo[4,5-b]pyridin-2-yl]-propionamide |
| 84 | 3 nM | 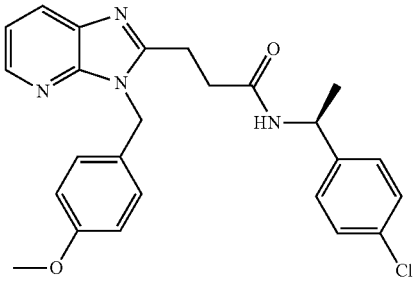 [SMILES: COc1ccc(Cn2c(CCC(=O)N[C@@H](C)c3ccc(Cl)cc3)nc3cccnc32)cc1] | N-[(S)-1-(4-Chloro-phenyl)-ethyl]-3-[3-(4-methoxy-benzyl)-3H-imidazo[4,5-b]pyridin-2-yl]-propionamide |
| 85 | 4 nM | 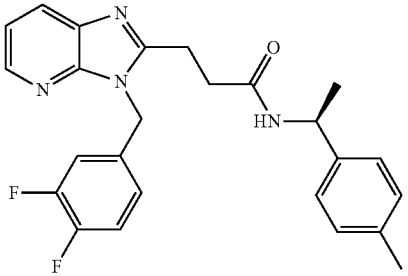 [SMILES: Cc1ccc([C@H](C)NC(=O)CCc2nc3cccnc3n2Cc2ccc(F)c(F)c2)cc1] | 3-[3-(3,4-Difluoro-benzyl)-3H-imidazo[4,5-b]pyridin-2-yl]-N-((S)-1-p-tolyl-ethyl)-propionamide |
| 86 | 5 nM | 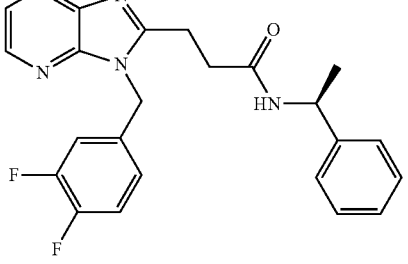 | 3-[3-(3,4-Difluoro-benzyl)-3H-imidazo[4,5-b]pyridin-2-yl]-N-((S)-1-phenyl-ethyl)-propionamide |

TABLE 1-continued

ATX activity (Quanta Red assay)

| Example | Activity | Structure | Name |
|---|---|---|---|
| 87 | 6 nM | 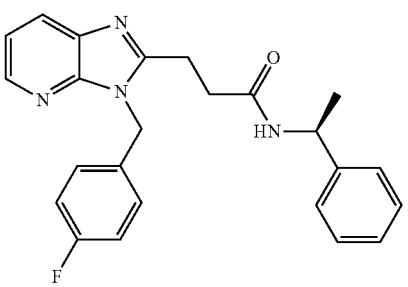 | 3-[3-(4-Fluoro-benzyl)-3H-imidazo[4,5-b]pyridin-2-yl]-N-((S)-1-phenyl-ethyl)-propionamide |
| 88 | 6 nM | 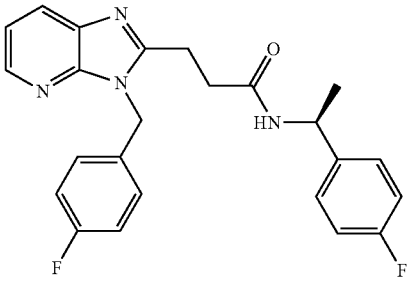 [SMILES: C[C@H](NC(=O)CCc1nc2cccnc2n1Cc1ccc(F)cc1)c1ccc(F)cc1] | 3-[3-(4-Fluoro-benzyl)-3H-imidazo[4,5-b]pyridin-2-yl]-N-[(S)-1-(4-fluoro-phenyl)-ethyl]-propionamide |
| 89 | 8 nM | 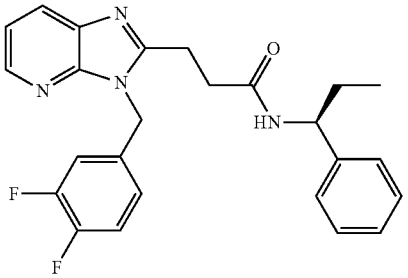 [SMILES: CC[C@H](NC(=O)CCc1nc2cccnc2n1Cc1ccc(F)c(F)c1)c1ccccc1] | 3-[3-(3,4-Difluoro-benzyl)-3H-imidazo[4,5-b]pyridin-2-yl]-N-((S)-1-phenyl-propyl)-propionamide |
| 90 | 9 nM | 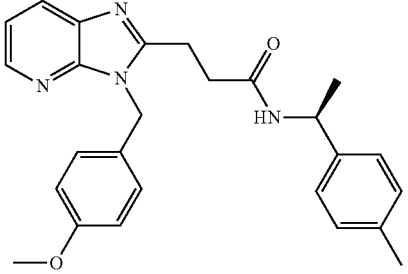 [SMILES: COc1ccc(Cn2c(CCC(=O)N[C@@H](C)c3ccc(C)cc3)nc3cccnc32)cc1] | 3-[3-(4-Methoxy-benzyl)-3H-imidazo[4,5-b]pyridin-2-yl]-N-((S)-1-p-tolyl-ethyl)-propionamide |
| 91 | 14 nM | 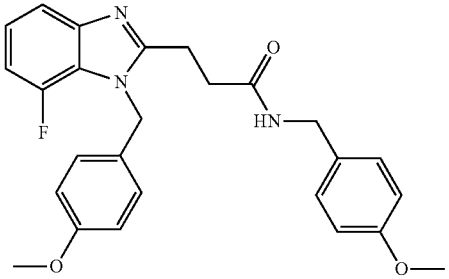 [SMILES: COc1ccc(CNC(=O)CCc2nc3cccc(F)c3n2Cc2ccc(OC)cc2)cc1] | 3-[7-Fluoro-1-(4-methoxy-benzyl)-1H-benzoimidazol-2-yl]-N-(4-methoxy-benzyl)-propionamide |

TABLE 1-continued

ATX activity (Quanta Red assay)

| Example | Activity | Structure | Name |
|---|---|---|---|
| 92 | 17 nM | 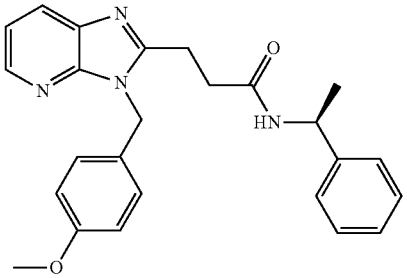 [SMILES: COc1ccc(Cn2c(CCC(=O)N[C@@H](C)c3ccccc3)nc3cccnc32)cc1] | 3-[3-(4-Methoxy-benzyl)-3H-imidazo[4,5-b]pyridin-2-yl]-N-((S)-1-phenyl-ethyl)-propionamide |
| 93 | 15 nM | 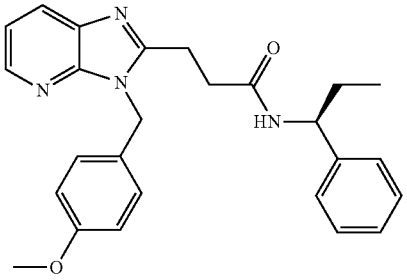 [SMILES: CC[C@H](NC(=O)CCc1nc2cccnc2n1Cc1ccc(OC)cc1)c1ccccc1] | 3-[3-(4-Methoxy-benzyl)-3H-imidazo[4,5-b]pyridin-2-yl]-N-((S)-1-phenyl-propyl)-propionamide |
| 94 | 25 nM | 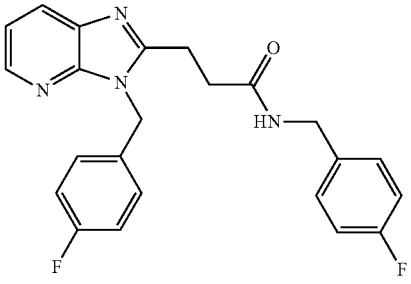 [SMILES: O=C(CCc1nc2cccnc2n1Cc1ccc(F)cc1)NCc1ccc(F)cc1] | N-(4-Fluoro-benzyl)-3-[3-(4-fluoro-benzyl)-3H-imidazo[4,5-b]pyridin-2-yl]-propionamide |
| 95 | 26 nM | 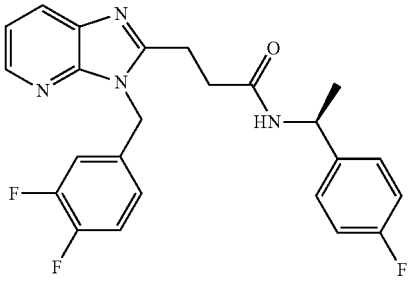 [SMILES: C[C@H](NC(=O)CCc1nc2cccnc2n1Cc1ccc(F)c(F)c1)c1ccc(F)cc1] | 3-[3-(3,4-Difluoro-benzyl)-3H-imidazo[4,5-b]pyridin-2-yl-N-[(S)-1-(4-fluoro-phenyl)-ethyl]-propionamide |
| 96 | 22 nM | 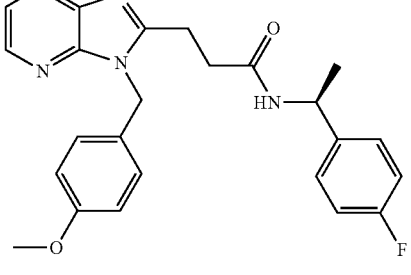 | N-[(S)-1-(4-Fluoro-phenyl)-ethyl]-3-[3-(4-methoxy-benzyl)-3H-imidazo[4,5-b]pyridin-2-yl]-propionamide |

TABLE 1-continued

ATX activity (Quanta Red assay)

| Example | Activity | Structure | Name |
|---|---|---|---|
| 97 | 40 nM | 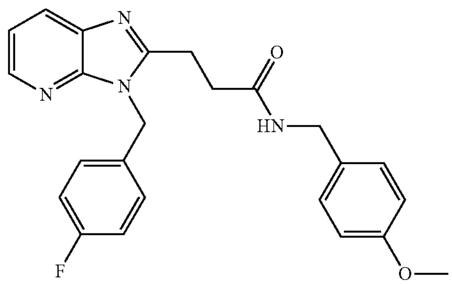 | 3-[3-(4-Fluoro-benzyl)-3H-imidazo[4,5-b]pyridin-2-yl]-N-(4-methoxy-benzyl)-propionamide |
| 98 | 45 nM | 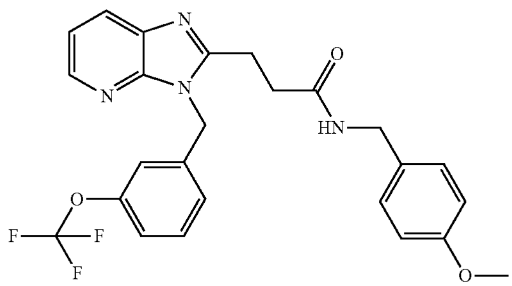 [SMILES: COc1ccc(CNC(=O)CCc2nc3cccnc3n2Cc2cccc(OC(F)(F)F)c2)cc1] | N-(4-Methoxy-benzyl)-3-[3-(3-trifluoromethoxy-benzyl)-3H-imidazo[4,5-b]pyridin-2-yl]-propionamide |
| 99 | 48 nM | 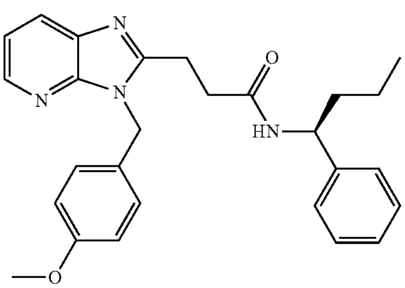 [SMILES: CCC[C@H](NC(=O)CCc1nc2cccnc2n1Cc1ccc(OC)cc1)c1ccccc1] | 3-[3-(4-Methoxy-benzyl)-3H-imidazo[4,5-b]pyridin-2-yl]-N-((S)-1-methyl-1-phenyl-butyl)-propionamide |
| 100 | 50 nM | 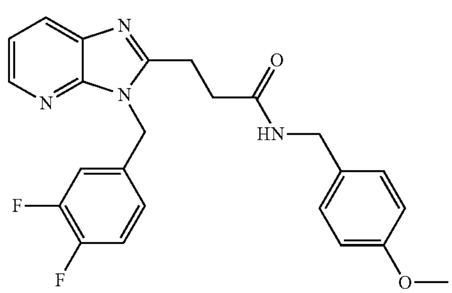 [SMILES: COc1ccc(CNC(=O)CCc2nc3cccnc3n2Cc2ccc(F)c(F)c2)cc1] | 3-[3-(3,4-Difluoro-benzyl)-3H-imidazo[4,5-b]pyridin-2-yl]-N-(4-methoxy-benzyl)-propionamide |
| 101 | 55 nM | 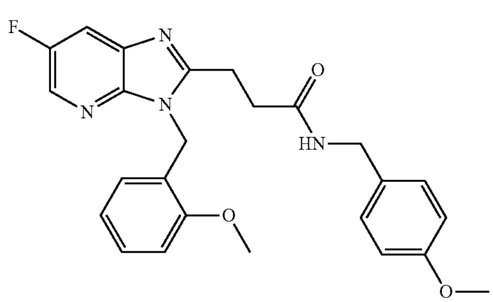 [SMILES: COc1ccc(CNC(=O)CCc2nc3cc(F)cnc3n2Cc2ccccc2OC)cc1] | 3-[6-Fluoro-3-(2-methoxy-benzyl)-3H-imidazo[4,5-b]pyridin-2-yl]-N-(4-methoxy-benzyl)-propionamide |

TABLE 1-continued

ATX activity (Quanta Red assay)

| Example | Activity | Structure | Name |
|---|---|---|---|
| 102 | 568 nM | 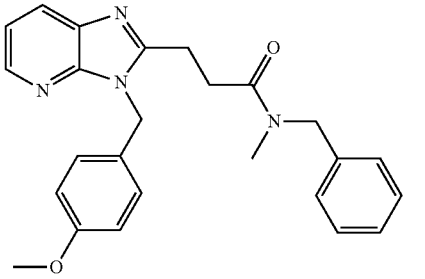 [SMILES: COc1ccc(Cn2c(CCC(=O)N(C)Cc3ccccc3)nc3cccnc32)cc1] | 3-[3-(4-Methoxy-benzyl)-3H-imidazo[4,5-b]pyridin-2-yl]-N-(3-methyl-benzyl)-propionamide |
| 103 | 57 nM | 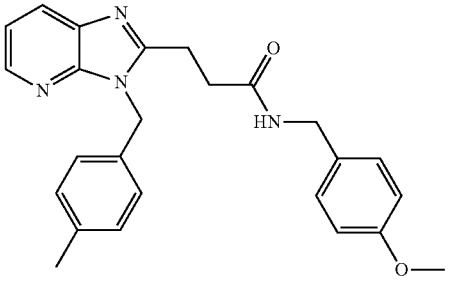 [SMILES: COc1ccc(CNC(=O)CCc2nc3cccnc3n2Cc2ccc(C)cc2)cc1] | N-(4-Methoxy-benzyl)-3-[3-(4-methyl-benzyl)-3H-imidazo[4,5-b]pyridin-2-yl]-propionamide |
| 104 | 69 nM | 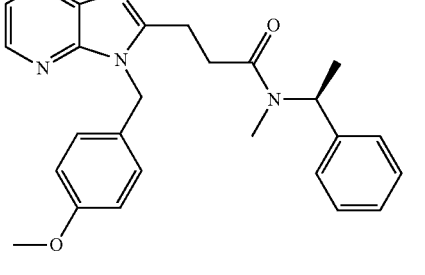 | 3-[3-(4-Methoxy-benzyl)-3H-imidazo[4,5-b]pyridin-2-yl-N-methyl-N-((S)-1-phenyl-ethyl)-propionamide |
| 105 | 88 nM | 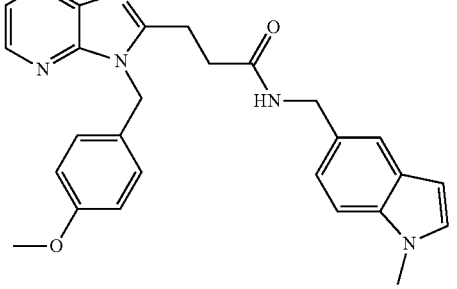 | 3-[3-(4-Methoxy-benzyl)-3H-imidazo[4,5-b]pyridin-2-yl]-N-(1-methyl-1H-indol-5-ylmethyl)-propionamide |
| 106 | 98 nM | 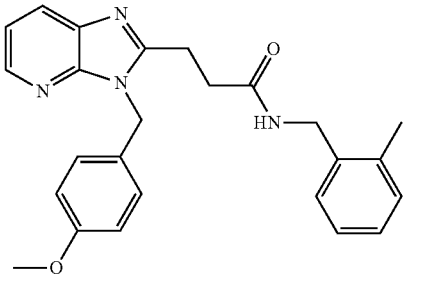 [SMILES: COc1ccc(Cn2c(CCC(=O)NCc3ccccc3C)nc3cccnc32)cc1] | 3-[3-(4-Methoxy-benzyl)-3H-imidazo[4,5-b]pyridin-2-yl]-N-(2-methyl-benzyl)-propionamide |

TABLE 1-continued

ATX activity (Quanta Red assay)

| Example | Activity | Structure | Name |
|---|---|---|---|
| 107 | 102 nM | 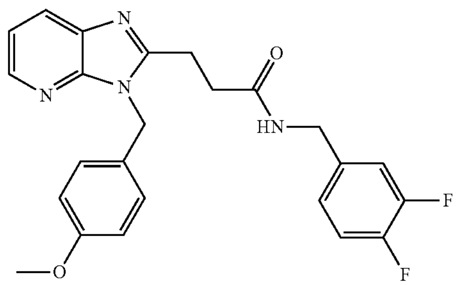 [SMILES: COc1ccc(Cn2c(CCC(=O)NCc3ccc(F)c(F)c3)nc3cccnc32)cc1] | N-(3,4-Difluoro-benzyl)-3-[3-(4-methoxy-benzyl)-3H-imidazo[4,5-b]pyridin-2-yl]-propionamide |
| 108 | 180 nM | 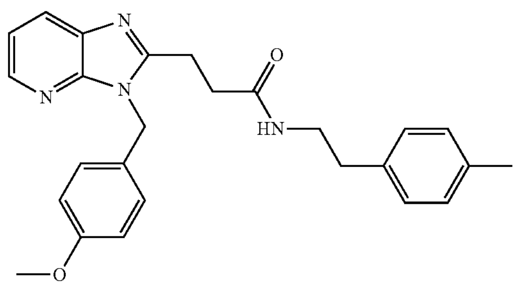 [SMILES: COc1ccc(Cn2c(CCC(=O)NCCc3ccc(C)cc3)nc3cccnc32)cc1] | 3-[3-(4-Methoxy-benzyl)-3H-imidazo[4,5-b]pyridin-2-yl]-N-(2-p-tolyl-ethyl)-propionamide |
| 109 | 185 nM | 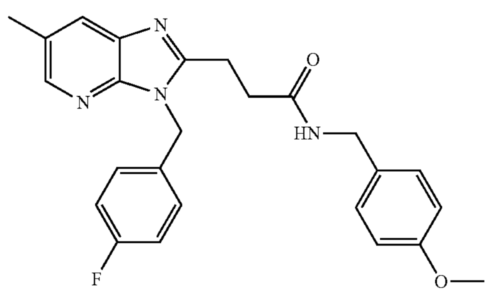 | 3-[3-(4-Fluoro-benzyl)-6-methyl-3H-imidazo[4,5-b]pyridin-2-yl]-N-(4-methoxy-benzyl)-propionamide |
| 110 | 262 nM | 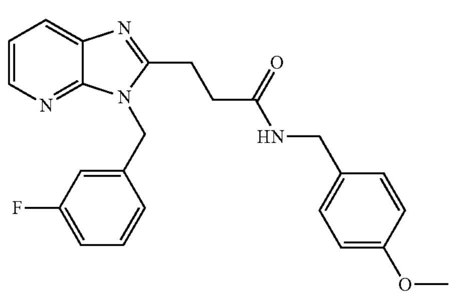 | 3-[3-(3-Fluoro-benzyl)-3H-imidazo[4,5-b]pyridin-2-yl]-N-(4-methoxy-benzyl)-propionamide |
| 111 | 406 nM | 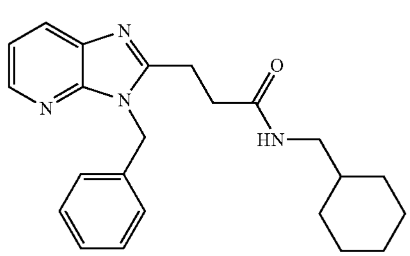 [SMILES: O=C(CCc1nc2cccnc2n1Cc1ccccc1)NCC1CCCCC1] | 3-(3-Benzyl-3H-imidazo[4,5-b]pyridin-2-yl)-N-cyclohexylmethyl-propionamide |

TABLE 1-continued

ATX activity (Quanta Red assay)

| Example | Activity | Structure | Name |
|---|---|---|---|
| 112 | 1060 nM | 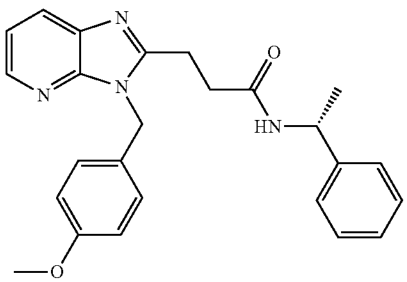 [SMILES: COc1ccc(Cn2c(CCC(=O)N[C@H](C)c3ccccc3)nc3cccnc32)cc1] | 3-[3-(4-Methoxy-benzyl)-3H-imidazo[4,5-b]pyridin-2-yl]-N-((R)-1-phenyl-ethyl)-propionamide |
| 113 | 1503 nM | 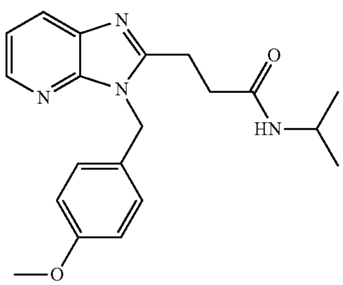 [SMILES: COc1ccc(Cn2c(CCC(=O)NC(C)C)nc3cccnc32)cc1] | N-Isopropyl-3-[3-(4-methoxy-benzyl)-3H-imidazo[4,5-b]pyridin-2-yl]-propionamide |
| 114 | 301 nM | 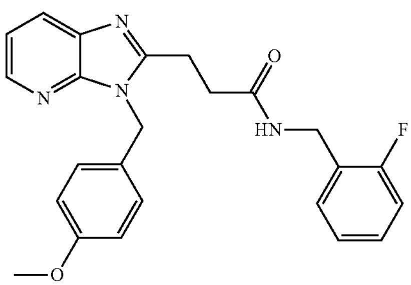 [SMILES: COc1ccc(Cn2c(CCC(=O)NCc3ccccc3F)nc3cccnc32)cc1] | N-(2-Fluoro-benzyl)-3-[3-(4-methoxy-benzyl)-3H-imidazo[4,5-b]pyridin-2-yl]-propionamide |
| 115 | 650 nM | 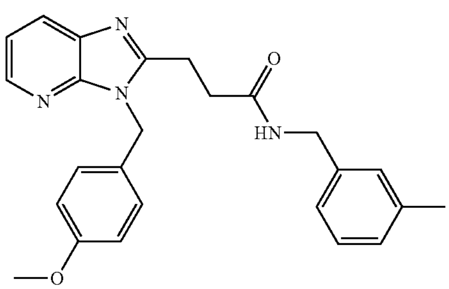 [SMILES: COc1ccc(Cn2c(CCC(=O)NCc3cccc(C)c3)nc3cccnc32)cc1] | 3-[3-(4-Methoxy-benzyl)-3H-imidazo[4,5-b]pyridin-2-yl]-N-(3-methyl-benzyl)-propionamide |
| 116 | 778 nM | 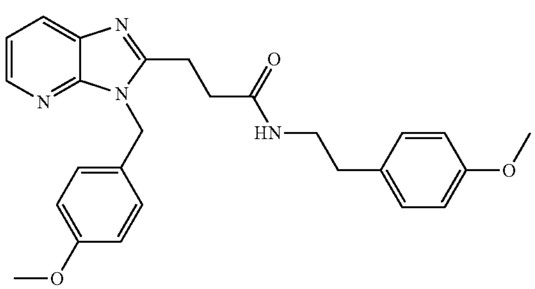 [SMILES: COc1ccc(CCNC(=O)CCc2nc3cccnc3n2Cc2ccc(OC)cc2)cc1] | 3-[3-(4-Methoxy-benzyl)-3H-imidazo[4,5-b]pyridin-2-yl]-N-[2-(4-methoxy-phenyl)-ethyl]-propionamide |

TABLE 1-continued

ATX activity (Quanta Red assay)

| Example | Activity | Structure | Name |
|---|---|---|---|
| 117 | 373 nM | 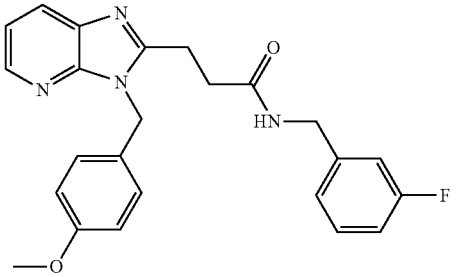 [SMILES: COc1ccc(Cn2c(CCC(=O)NCc3cccc(F)c3)nc3cccnc32)cc1] | N-(3-Fluoro-benzyl)-3-[3-(4-methoxy-benzyl)-3H-imidazo[4,5-b]pyridin-2-yl]-propionamide |
| 118 | 726 nM | 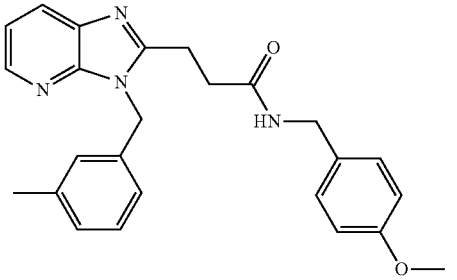 [SMILES: COc1ccc(CNC(=O)CCc2nc3cccnc3n2Cc2cccc(C)c2)cc1] | N-(4-Methoxy-benzyl)-3-[3-(3-methyl-benzyl)-3H-imidazo[4,5-b]pyridin-2-yl]-propionamide |
| 119 | 631 nM | 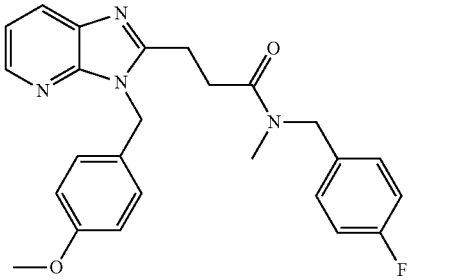 [SMILES: COc1ccc(Cn2c(CCC(=O)N(C)Cc3ccc(F)cc3)nc3cccnc32)cc1] | N-(4-Fluoro-benzyl)-3-[3-(4-methoxy-benzyl)-3H-imidazo[4,5-b]pyridin-2-yl]-N-methyl-propionamide |
| 120 | 292 nM | 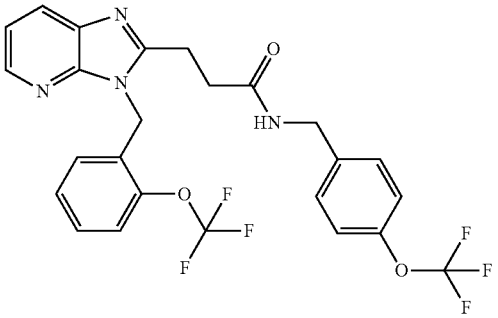 [SMILES: O=C(CCc1nc2cccnc2n1Cc1ccccc1OC(F)(F)F)NCc1ccc(OC(F)(F)F)cc1] | N-(4-Trifluoromethoxy-benzyl)-3-[3-(2-trifluoromethoxy-benzyl)-3H-imidazo[4,5-b]pyridin-2-yl]-propionamide |
| 121 | 269 nM | 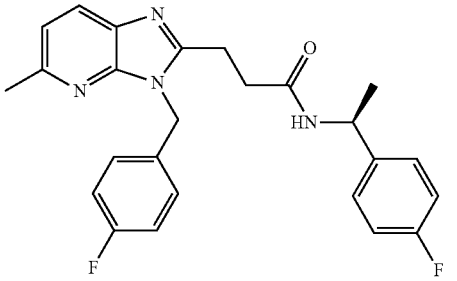 [SMILES: Cc1ccc2nc(CCC(=O)N[C@@H](C)c3ccc(F)cc3)n(Cc3ccc(F)cc3)c2n1] | 3-[3-(4-Fluoro-benzyl)-5-methyl-3H-imidazo[4,5-b]pyridin-2-yl]-N-[(S)-1-(4-fluoro-phenyl)-ethyl]-propionamide |

TABLE 1-continued

ATX activity (Quanta Red assay)

| Example | Activity | Structure | Name |
|---|---|---|---|
| 122 | 3 nM | 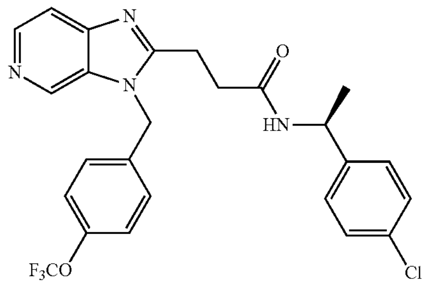 [SMILES: C[C@H](NC(=O)CCc1nc2ccncc2n1Cc1ccc(OC(F)(F)F)cc1)c1ccc(Cl)cc1] | N-[(S)-1-(4-Chloro-phenyl)-ethyl]-3-[3-(4-trifluoromethoxy-benzyl)-3H-imidazo[4,5-c]pyridin-2-yl]-propionamide |
| 123 | 3 nM | 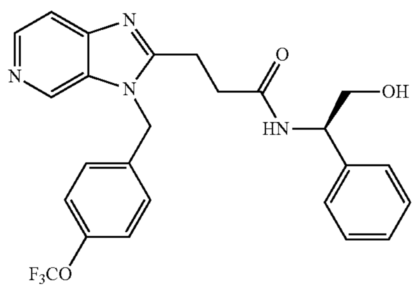 [SMILES: O=C(CCc1nc2ccncc2n1Cc1ccc(OC(F)(F)F)cc1)N[C@@H](CO)c1ccccc1] | N-((R)-2-Hydroxy-1-phenyl-ethyl)-3-[3-(4-trifluoromethoxy-benzyl)-3H-imidazo[4,5-c]pyridin-2-yl]-propionamide |
| 124 | 8 nM | 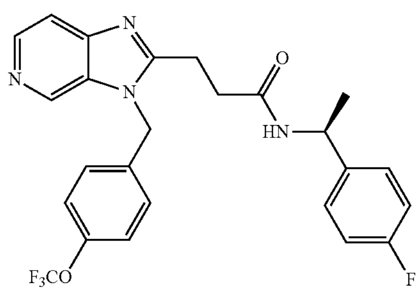 | N-[(S)-1-(4-Fluoro-phenyl)-ethyl]-3-[3-(4-trifluoromethoxy-benzyl)-3H-imidazo[4,5-c]pyridin-2-yl]-propionamide |
| 125 | 9 nM | 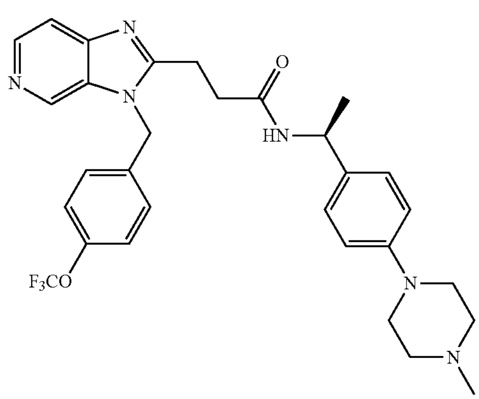 [SMILES: C[C@H](NC(=O)CCc1nc2ccncc2n1Cc1ccc(OC(F)(F)F)cc1)c1ccc(N2CCN(C)CC2)cc1] | N-{(S)-1-[4-(4-Methyl-piperazin-1-yl)-phenyl]-ethyl}-3-[3-(4-trifluoromethoxy-benzyl)-3H-imidazo[4,5-c]pyridin-2-yl]-propionamide |

TABLE 1-continued

ATX activity (Quanta Red assay)

| Example | Activity | Structure | Name |
|---|---|---|---|
| 126 | 11 nM | 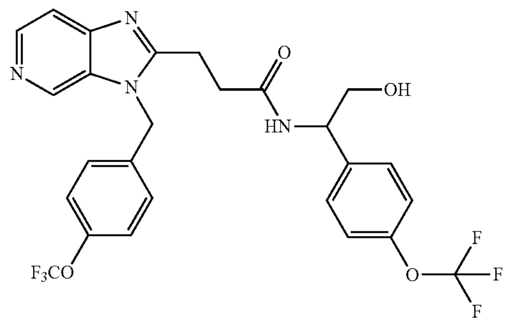 [SMILES: O=C(CCc1nc2ccncc2n1Cc1ccc(OC(F)(F)F)cc1)NC(CO)c1ccc(OC(F)(F)F)cc1] | N-[2-Hydroxy-1-(4-trifluoromethoxy-phenyl)-ethyl]-3-[3-(4-trifluoromethoxy-benzyl)-3H-imidazo[4,5-c]pyridin-2-yl]-propionamide |
| 127 | 14 nM | 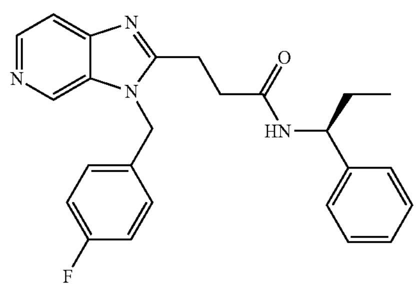 [SMILES: CC[C@H](NC(=O)CCc1nc2ccncc2n1Cc1ccc(F)cc1)c1ccccc1] | 3-[3-(4-Fluoro-benzyl)-3H-imidazo[4,5-c]pyridin-2-yl]-N-((S)-1-phenyl-propyl)-propionamide |
| 128 | 17 nM | 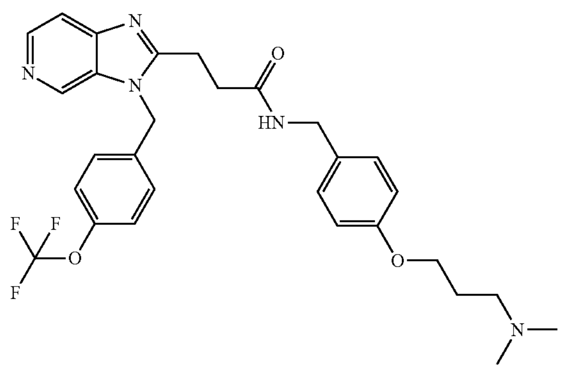 [SMILES: CN(C)CCCOc1ccc(CNC(=O)CCc2nc3ccncc3n2Cc2ccc(OC(F)(F)F)cc2)cc1] | N-[4-(3-Dimethylamino-propoxy)-benzyl]-3-[3-(4-trifluoromethoxy-benzyl)-3H-imidazo[4,5-c]pyridin-2-yl]-propionamide |
| 129 | 20 nM | 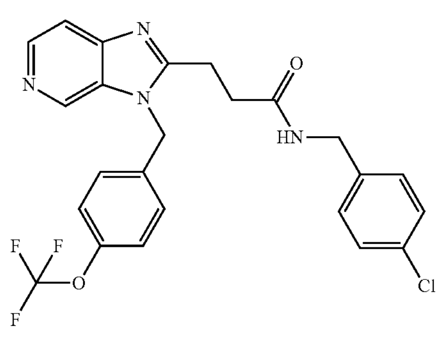 [SMILES: O=C(CCc1nc2ccncc2n1Cc1ccc(OC(F)(F)F)cc1)NCc1ccc(Cl)cc1] | N-(4-Chloro-benzyl)-3-[3-(4-trifluoromethoxy-benzyl)-3H-imidazo[4,5-c]pyridin-2-yl]-propionamide |

TABLE 1-continued

ATX activity (Quanta Red assay)

| Example | Activity | Structure | Name |
|---|---|---|---|
| 130 | 21 nM | 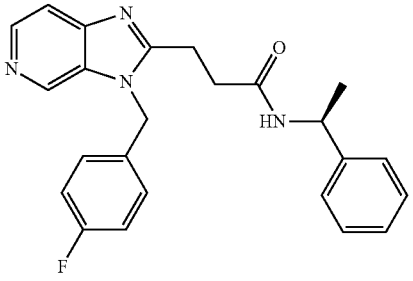 [SMILES: C[C@H](NC(=O)CCc1nc2ccncc2n1Cc1ccc(F)cc1)c1ccccc1] | 3-[3-(4-Fluoro-benzyl)-3H-imidazo[4,5-c]pyridin-2-yl]-N-((S)-1-phenyl-ethyl)-propionamide |
| 131 | 23 nM | 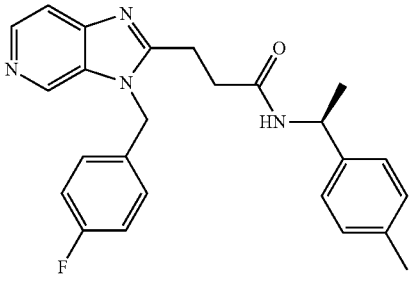 [SMILES: Cc1ccc([C@H](C)NC(=O)CCc2nc3ccncc3n2Cc2ccc(F)cc2)cc1] | 3-[3-(4-Fluoro-benzyl)-3H-imidazo[4,5-c]pyridin-2-yl]-N-((S)-1-p-tolyl-ethyl)-propionamide |
| 132 | 52 nM | 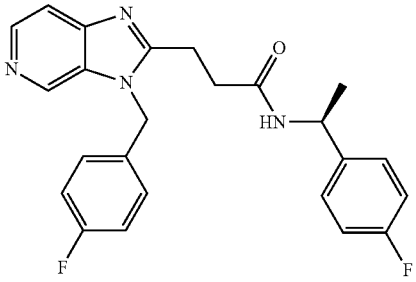 [SMILES: C[C@H](NC(=O)CCc1nc2ccncc2n1Cc1ccc(F)cc1)c1ccc(F)cc1] | 3-[3-(4-Fluoro-benzyl)-3H-imidazo[4,5-c]pyridin-2-yl]-N-[(S)-1-(4-fluoro-phenyl)-ethyl]-propionamide |
| 133 | 52 nM | 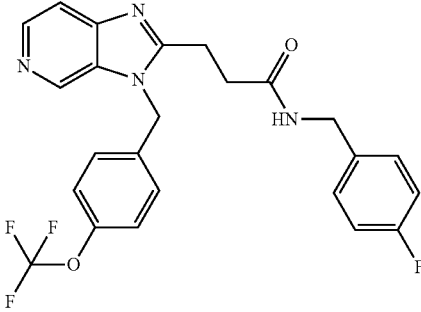 | N-(4-Fluoro-benzyl)-3-[3-(4-trifluoromethoxy-benzyl)-3H-imidazo[4,5-c]pyridin-2-yl]-propionamide |
| 134 | 133 nM | 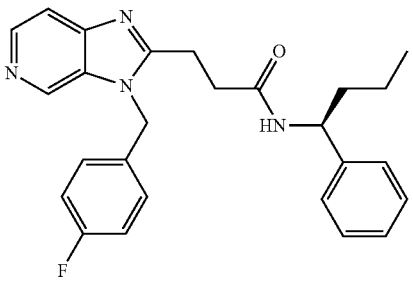 [SMILES: CCC[C@H](NC(=O)CCc1nc2ccncc2n1Cc1ccc(F)cc1)c1ccccc1] | 3-[3-(4-Fluoro-benzyl)-3H-imidazo[4,5-c]pyridin-2-yl]-N-((S)-1-phenyl-butyl)-propionamide |

TABLE 1-continued

ATX activity (Quanta Red assay)

| Example | Activity | Structure | Name |
|---|---|---|---|
| 135 | 1568 nM | 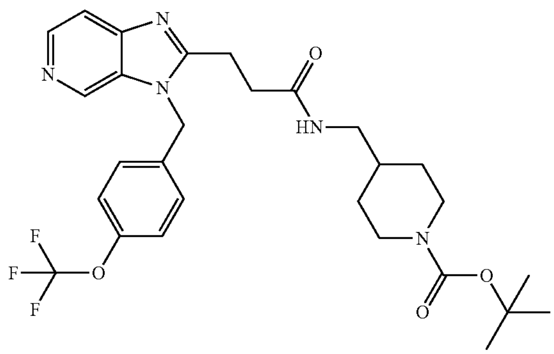 [SMILES: CC(C)(C)OC(=O)N1CCC(CNC(=O)CCc2nc3ccncc3n2Cc2ccc(OC(F)(F)F)cc2)CC1] | 4-({3-[3-(4-Trifluoromethoxy-benzyl)-3H-imidazo[4,5-c]pyridin-2-yl]-propionylamino}-methyl)-piperidine-1-carboxylic acid tert-butyl ester |
| 136 | 115 nM | 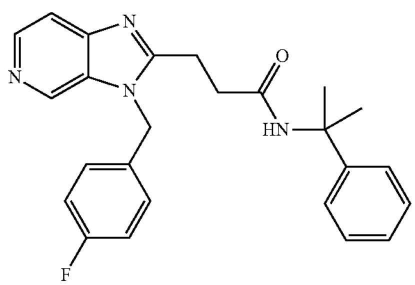 [SMILES: CC(C)(NC(=O)CCc1nc2ccncc2n1Cc1ccc(F)cc1)c1ccccc1] | 3-[3-(4-Fluoro-benzyl)-3H-imidazo[4,5-c]pyridin-2-yl]-N-(1-methyl-1-phenyl-ethyl)-propionamide |
| 137 | 10 nM | 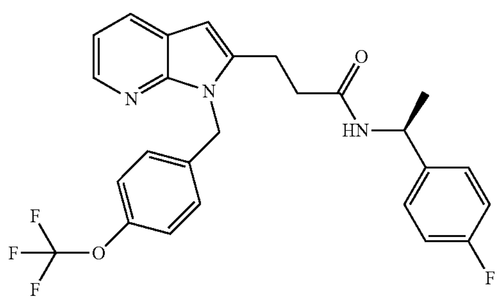 [SMILES: C[C@H](NC(=O)CCc1cc2cccnc2n1Cc1ccc(OC(F)(F)F)cc1)c1ccc(F)cc1] | N-[(S)-1-(4-Fluoro-phenyl)-ethyl]-3-[1-(4-trifluoromethoxy-benzyl)-1H-pyrrolo[2,3-b]pyridin-2-yl]-propionamide |
| 138 | 10 nM | 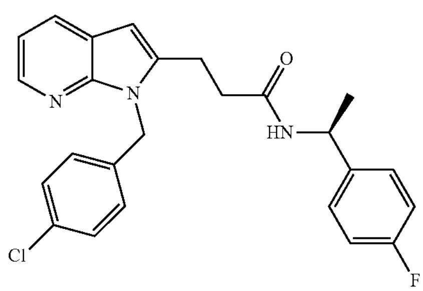 [SMILES: C[C@H](NC(=O)CCc1cc2cccnc2n1Cc1ccc(Cl)cc1)c1ccc(F)cc1] | 3-[1-(4-Chloro-benzyl)-1H-pyrrolo[2,3-b]pyridin-2-yl]-N-[(S)-1-(4-fluoro-phenyl)-ethyl]-propionamide |
| 139 | 13 nM | 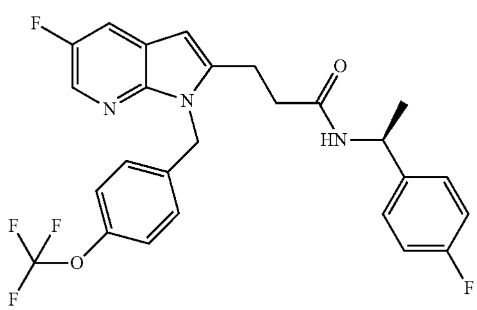 [SMILES: C[C@H](NC(=O)CCc1cc2cc(F)cnc2n1Cc1ccc(OC(F)(F)F)cc1)c1ccc(F)cc1] | N-[(S)-1-(4-Fluoro-phenyl)-ethyl]-3-[5-fluoro-1-(4-trifluoromethoxy-benzyl)-1H-pyrrolo[2,3-b]pyridin-2-yl]-propionamide |

TABLE 1-continued

ATX activity (Quanta Red assay)

| Example | Activity | Structure | Name |
|---|---|---|---|
| 140 | 13 nM | 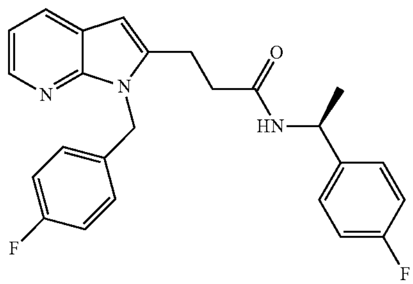 [SMILES: C[C@H](NC(=O)CCc1cc2cccnc2n1Cc1ccc(F)cc1)c1ccc(F)cc1] | 3-[1-(4-Fluoro-benzyl)-1H-pyrrolo[2,3-b]pyridin-2-yl]-N-[(S)-1-(4-fluoro-phenyl)-ethyl]-propionamide |
| 141 | 14 nM | 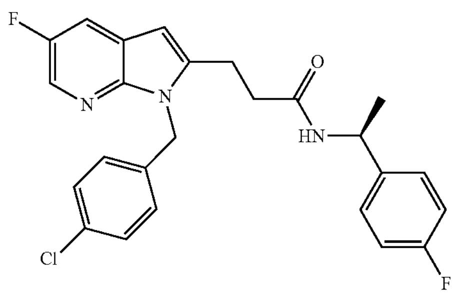 [SMILES: C[C@H](NC(=O)CCc1cc2cc(F)cnc2n1Cc1ccc(Cl)cc1)c1ccc(F)cc1] | 3-[1-(4-Chloro-benzyl)-5-fluoro-1H-pyrrolo[2,3-b]pyridin-2-yl]-N-[(S)-1-(4-fluoro-phenyl)-ethyl]-propionamide |
| 142 | 1 nM | 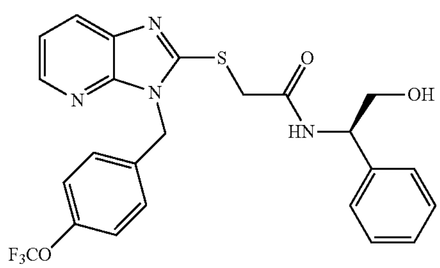 [SMILES: O=C(CSc1nc2cccnc2n1Cc1ccc(OC(F)(F)F)cc1)N[C@@H](CO)c1ccccc1] | N-((R)-2-Hydroxy-1-phenyl-ethyl)-2-[3-(4-trifluoromethoxy-benzyl)-3H-imidazo[4,5-b]pyridin-2-ylsulfanyl]-acetamide |
| 143 | 1 nM | 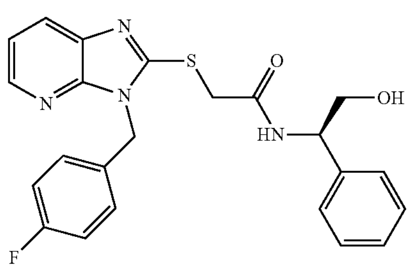 [SMILES: O=C(CSc1nc2cccnc2n1Cc1ccc(F)cc1)N[C@@H](CO)c1ccccc1] | 2-[3-(4-Fluoro-benzyl)-3H-imidazo[4,5-b]pyridin-2-ylsulfanyl]-N-((R)-2-hydroxy-1-phenyl-ethyl)-acetamide |
| 144 | 2 nM | 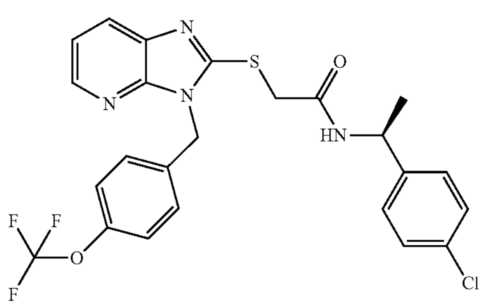 [SMILES: C[C@H](NC(=O)CSc1nc2cccnc2n1Cc1ccc(OC(F)(F)F)cc1)c1ccc(Cl)cc1] | N-[(S)-1-(4-Chloro-phenyl)-ethyl]-2-[3-(4-trifluoromethoxy-benzyl)-3H-imidazo[4,5-b]pyridin-2-ylsulfanyl]-acetamide |

TABLE 1-continued

ATX activity (Quanta Red assay)

| Example | Activity | Structure | Name |
|---|---|---|---|
| 145 | 2 nM | 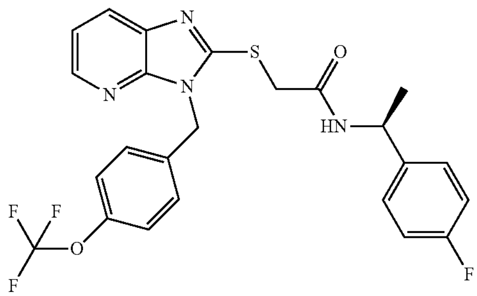 [SMILES: C[C@H](NC(=O)CSc1nc2cccnc2n1Cc1ccc(OC(F)(F)F)cc1)c1ccc(F)cc1] | N-[(S)-1-(4-Fluoro-phenyl)-ethyl]-2-[3-(4-trifluoromethoxy-benzyl)-3H-imidazo[4,5-b]pyridin-2-ylsulfanyl]-acetamide |
| 146 | 3 nM | 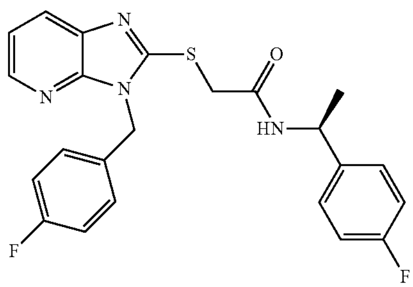 | 2-[3-(4-Fluoro-benzyl)-3H-imidazo[4,5-b]pyridin-2-ylsulfanyl]-N-[(S)-1-(4-fluoro-phenyl)-ethyl]-acetamide |
| 147 | 3 nM | 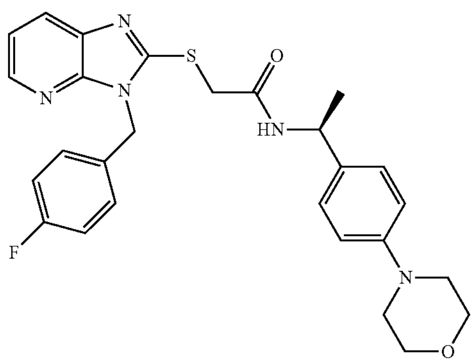 [SMILES: C[C@H](NC(=O)CSc1nc2cccnc2n1Cc1ccc(F)cc1)c1ccc(N2CCOCC2)cc1] | 2-[3-(4-Fluoro-benzyl)-3H-imidazo[4,5-b]pyridin-2-ylsulfanyl]-N-[(S)-1-(4-morpholin-4-yl-phenyl)-ethyl]-acetamide |
| 148 | 10 nM | 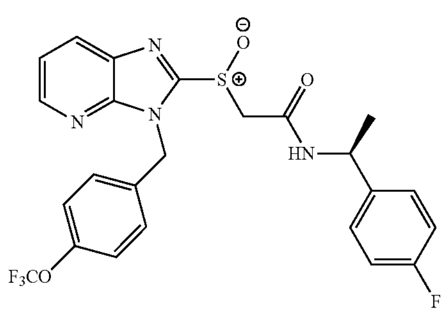 [SMILES: C[C@H](NC(=O)C[S+]([O-])c1nc2cccnc2n1Cc1ccc(OC(F)(F)F)cc1)c1ccc(F)cc1] | N-[(S)-1-(4-Fluoro-phenyl)-ethyl]-2-[3-(4-trifluoromethoxy-benzyl)-3H-imidazo[4,5-b]pyridine-2-sulfinyl]-acetamide (diastereomer 1) |

TABLE 1-continued

| Example | Activity | Structure | Name |
|---|---|---|---|
| 149 | 178 nM | 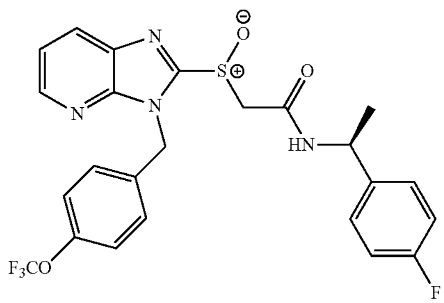 [SMILES: C[C@H](NC(=O)C[S+]([O-])c1nc2cccnc2n1Cc1ccc(OC(F)(F)F)cc1)c1ccc(F)cc1] | N-[(S)-1-(4-Fluoro-phenyl)-ethyl]-2-[3-(4-trifluoromethoxy-benzyl)-3H-imidazo[4,5-b]pyridine-2-sulfinyl]-acetamide (diastereomer 2) |
| 150 | 2884 nM | 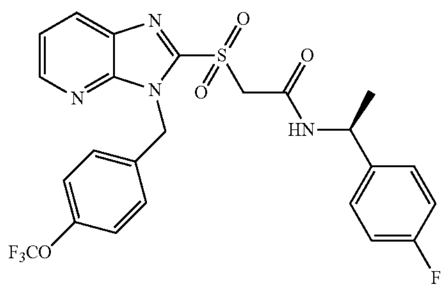 [SMILES: C[C@H](NC(=O)CS(=O)(=O)c1nc2cccnc2n1Cc1ccc(OC(F)(F)F)cc1)c1ccc(F)cc1] | N-[(S)-1-(4-Fluoro-phenyl)-ethyl]-2-[3-(4-trifluoromethoxy-benzyl)-3H-imidazo[4,5-b]pyridine-2-sulfonyl]-acetamide |
| 151 | 3 nM | 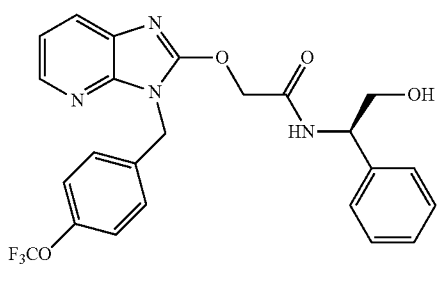 | N-((R)-2-Hydroxy-1-phenyl-ethyl)-2-[3-(4-trifluoromethoxy-benzyl)-3H-imidazo[4,5-b]pyridin-2-yloxy]-acetamide |
| 152 | 5 nM | 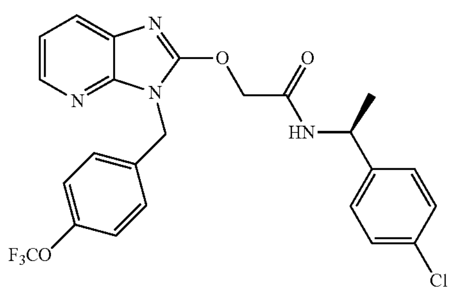 [SMILES: C[C@H](NC(=O)COc1nc2cccnc2n1Cc1ccc(OC(F)(F)F)cc1)c1ccc(Cl)cc1] | N-[(S)-1-(4-Chloro-phenyl)-ethyl]-2-[3-(4-trifluoromethoxy-benzyl)-3H-imidazo[4,5-b]pyridin-2-yloxy]-acetamide |
| 153 | 39 nM | 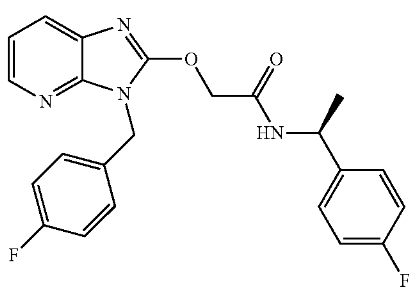 [SMILES: C[C@H](NC(=O)COc1nc2cccnc2n1Cc1ccc(F)cc1)c1ccc(F)cc1] | 2-[3-(4-Fluoro-benzyl)-3H-imidazo[4,5-b]pyridin-2-yloxy]-N-[(S)-1-(4-fluoro-phenyl)-ethyl]-acetamide |

TABLE 1-continued

ATX activity (Quanta Red assay)

| Example | Activity | Structure | Name |
|---|---|---|---|
| 154 | 11 nM | 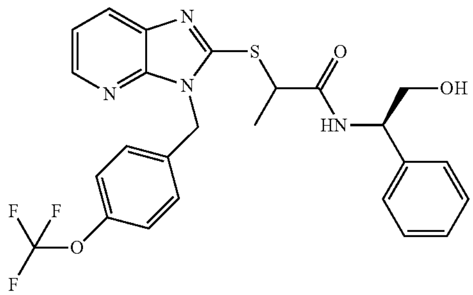 [SMILES: CC(Sc1nc2cccnc2n1Cc1ccc(OC(F)(F)F)cc1)C(=O)N[C@@H](CO)c1ccccc1] | N-((R)-2-Hydroxy-1-phenyl-ethyl)-2-[3-(4-trifluoromethoxy-benzyl)-3H-imidazo[4,5-b]pyridin-2-ylsulfanyl]-propionamide |
| 155 | 254 nM | 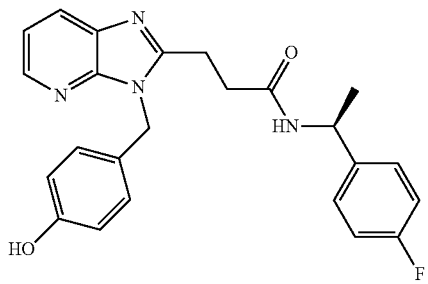 [SMILES: C[C@H](NC(=O)CCc1nc2cccnc2n1Cc1ccc(O)cc1)c1ccc(F)cc1] | N-[(S)-1-(4-Fluoro-phenyl)-ethyl]-3-[3-(4-hydroxy-benzyl)-3H-imidazo[4,5-b]pyridin-2-yl]-propionamide |
| 156 | 704 nM | 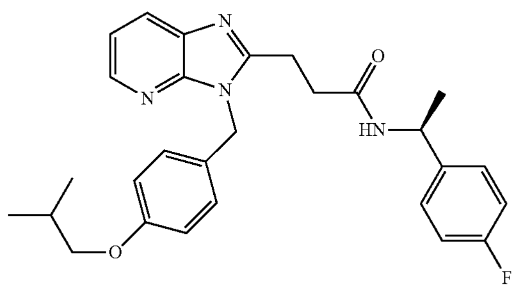 [SMILES: CC(C)COc1ccc(Cn2c(CCC(=O)N[C@@H](C)c3ccc(F)cc3)nc3cccnc32)cc1] | N-[(S)-1-(4-Fluoro-phenyl)-ethyl]-3-[3-(4-isobutoxy-benzyl)-3H-imidazo[4,5-b]pyridin-2-yl]-propionamide |
| 157 | 10 nM | 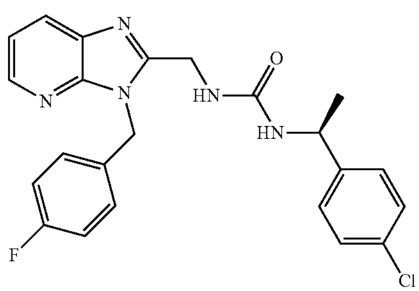 [SMILES: C[C@H](NC(=O)NCc1nc2cccnc2n1Cc1ccc(F)cc1)c1ccc(Cl)cc1] | 1-[(S)-1-(4-Chloro-phenyl)-ethyl]-3-[3-(4-fluoro-benzyl)-3H-imidazo[4,5-b]pyridin-2-ylmethyl]-urea |
| 158 | 17 nM | 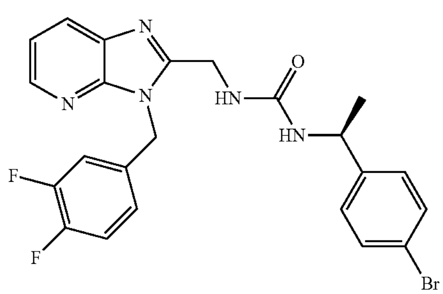 [SMILES: C[C@H](NC(=O)NCc1nc2cccnc2n1Cc1ccc(F)c(F)c1)c1ccc(Br)cc1] | 1-[(S)-1-(4-Bromo-phenyl)-ethyl]-3-[3-(3,4-difluoro-benzyl)-3H-imidazo[4,5-b]pyridin-2-ylmethyl]-urea |

TABLE 1-continued

ATX activity (Quanta Red assay)

| Example | Activity | Structure | Name |
|---|---|---|---|
| 159 | 42 nM | 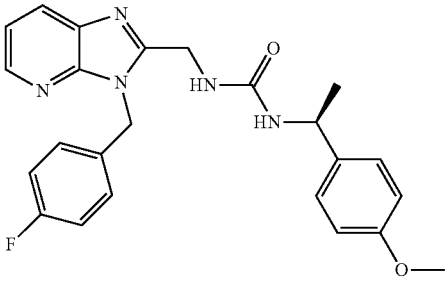 [SMILES: COc1ccc([C@H](C)NC(=O)NCc2nc3cccnc3n2Cc2ccc(F)cc2)cc1] | 1-[3-(4-Fluoro-benzyl)-3H-imidazo[4,5-b]pyridin-2-ylmethyl]-3-[(S)-1-(4-methoxy-phenyl)-ethyl]-urea |
| 160 | 80 nM | 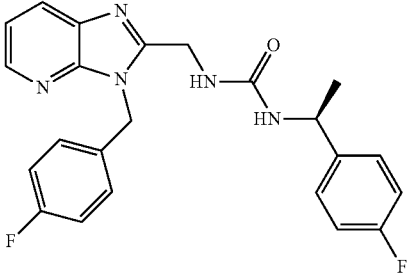 [SMILES: C[C@H](NC(=O)NCc1nc2cccnc2n1Cc1ccc(F)cc1)c1ccc(F)cc1] | 1-[3-(4-Fluoro-benzyl)-3H-imidazo[4,5-b]pyridin-2-ylmethyl]-3-[(S)-1-(4-fluoro-phenyl)-ethyl]-urea |
| 161 | 115 nM | 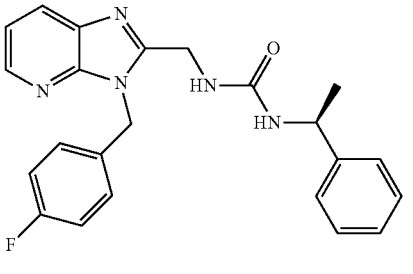 [SMILES: C[C@H](NC(=O)NCc1nc2cccnc2n1Cc1ccc(F)cc1)c1ccccc1] | 1-[3-(4-Fluoro-benzyl)-3H-imidazo[4,5-b]pyridin-2-ylmethyl]-3-((S)-1-phenyl-ethyl)-urea |
| 162 | 209 nM | 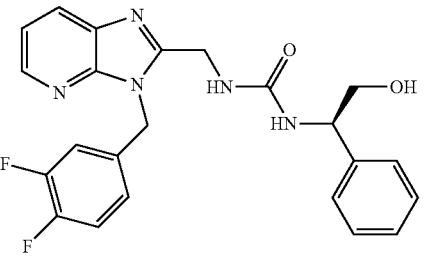 [SMILES: O=C(NCc1nc2cccnc2n1Cc1ccc(F)c(F)c1)N[C@@H](CO)c1ccccc1] | 1-[3-(3,4-Difluoro-benzyl)-3H-imidazo[4,5-b]pyridin-2-ylmethyl]-3-((R)-2-hydroxy-1-phenyl-ethyl)-urea |
| 163 | 309 nM | 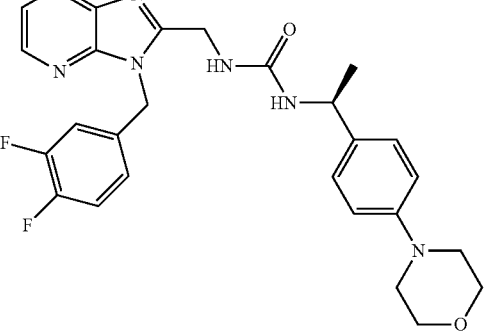 | 1-[3-(3,4-Difluoro-benzyl)-3H-imidazo[4,5-b]pyridin-2-ylmethyl]-3-[(S)-1-(4-morpholin-4-yl-phenyl)-ethyl]-urea |

TABLE 1-continued

ATX activity (Quanta Red assay)

| Example | Activity | Structure | Name |
|---|---|---|---|
| 164 | 957 nM | 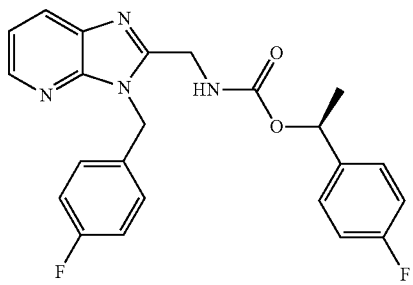 [SMILES: C[C@H](OC(=O)NCc1nc2cccnc2n1Cc1ccc(F)cc1)c1ccc(F)cc1] | [3-(4-Fluoro-benzyl)-3H-imidazo[4,5-b]pyridin-2-ylmethyl]-carbamic acid (S)-1-(4-fluoro-phenyl)-ethyl ester |
| 165 | 514 nM | 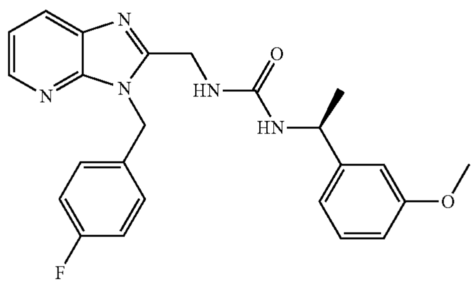 [SMILES: COc1cccc([C@H](C)NC(=O)NCc2nc3cccnc3n2Cc2ccc(F)cc2)c1] | 1-[3-(4-Fluoro-benzyl)-3H-imidazo[4,5-b]pyridin-2-ylmethyl]-3-[(S)-1-(3-methoxy-phenyl)-ethyl]-urea |
| 166 | 336 nM | 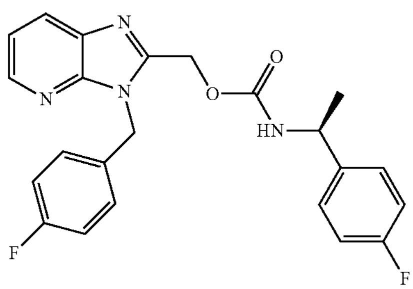 | [(S)-1-(4-Fluoro-phenyl)-ethyl-carbamic acid 3-(4-fluoro-benzyl)-3H-imidazo[4,5-b]pyridin-2-ylmethyl ester |
| 167 | 1 nM | 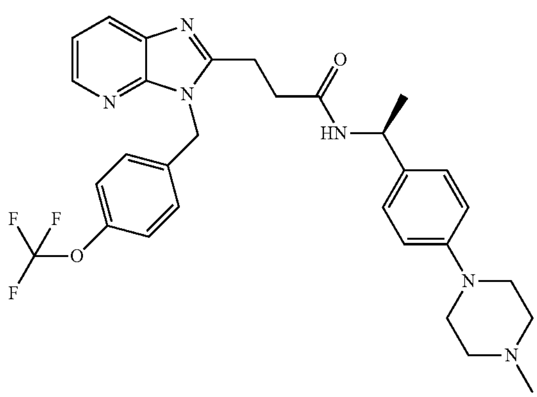 [SMILES: C[C@H](NC(=O)CCc1nc2cccnc2n1Cc1ccc(OC(F)(F)F)cc1)c1ccc(N2CCN(C)CC2)cc1] | N-{(S)-1-[4-(4-Methyl-piperazin-1-yl)-phenyl]-ethyl}-3-[3-(4-trifluoromethoxy-benzyl)-3H-imidazo[4,5-b]pyridin-2-yl]-propionamide |

TABLE 1-continued

ATX activity (Quanta Red assay)

| Example | Activity | Structure | Name |
|---|---|---|---|
| 168 | 1 nM | 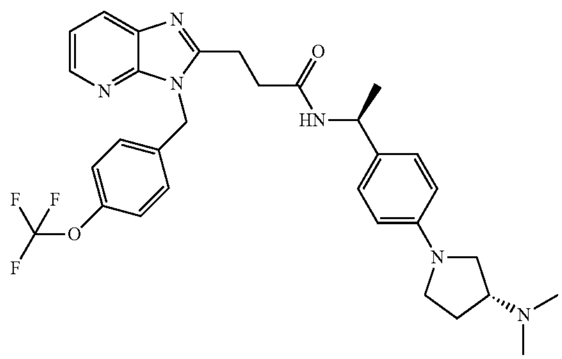 [SMILES: C[C@H](NC(=O)CCc1nc2cccnc2n1Cc1ccc(OC(F)(F)F)cc1)c1ccc(N2CC[C@@H](N(C)C)C2)cc1] | N-{(S)-1-[4-((R)-3-Dimethylamino-pyrrolidin-1-yl)-phenyl]-ethyl}-3-[3-(4-trifluoromethoxy-benzyl)-3H-imidazo[4,5-b]pyridin-2-yl]-propionamide |
| 169 | 1 nM | 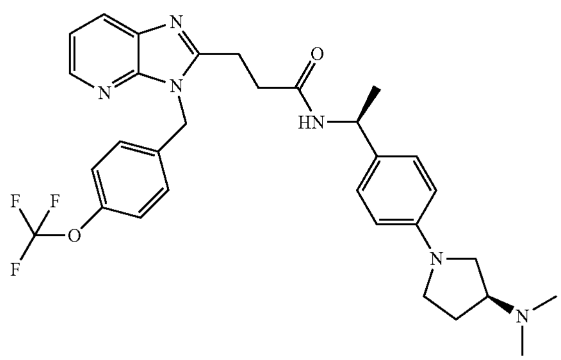 [SMILES: C[C@H](NC(=O)CCc1nc2cccnc2n1Cc1ccc(OC(F)(F)F)cc1)c1ccc(N2CC[C@H](N(C)C)C2)cc1] | N-{(S)-1-[4-((S)-3-Dimethylamino-pyrrolidin-1-yl)-phenyl]-ethyl}-3-[3-(4-trifluoromethoxy-benzyl)-3H-imidazo[4,5-b]pyridin-2-yl]-propionamide |
| 170 | 2 nM | 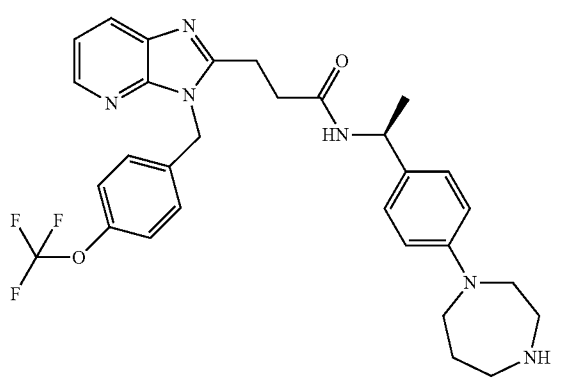 [SMILES: C[C@H](NC(=O)CCc1nc2cccnc2n1Cc1ccc(OC(F)(F)F)cc1)c1ccc(N2CCCNCC2)cc1] | N-[(S)-1-(4-[1,4]Diazepan-1-yl-phenyl)-ethyl]-3-[3-(4-trifluoromethoxy-benzyl)-3H-imidazo[4,5-b]pyridin-2-yl]-propionamide |
| 171 | 2 nM | 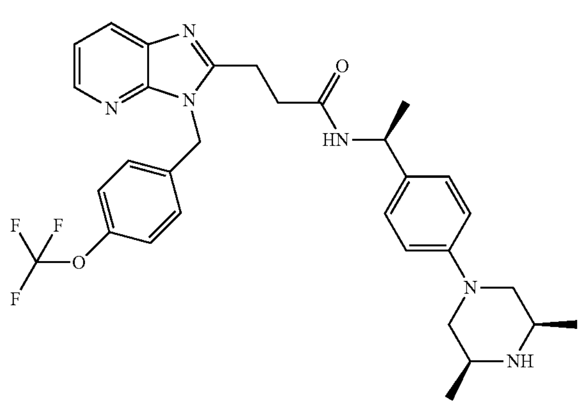 [SMILES: C[C@@H]1CN(c2ccc([C@H](C)NC(=O)CCc3nc4cccnc4n3Cc3ccc(OC(F)(F)F)cc3)cc2)C[C@H](C)N1] | N-{(S)-1-[4-((cis)-3,5-Dimethyl-piperazin-1-yl)-phenyl]-ethyl}-3-[3-(4-trifluoromethoxy-benzyl)-3H-imidazo[4,5-b]pyridin-2-yl]-propionamide |

TABLE 1-continued

ATX activity (Quanta Red assay)

| Example | Activity | Structure | Name |
|---|---|---|---|
| 172 | 2 nM | 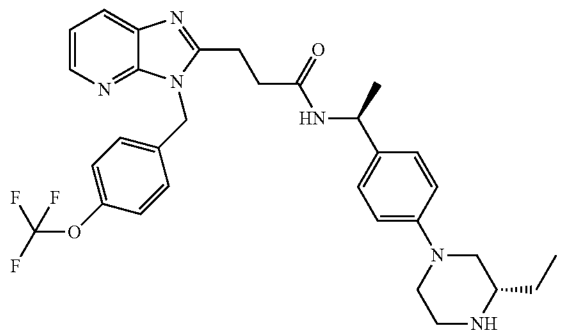 [SMILES: CC[C@H]1CN(c2ccc([C@H](C)NC(=O)CCc3nc4cccnc4n3Cc3ccc(OC(F)(F)F)cc3)cc2)CCN1] | N-{(S)-1-[4-((S)-3-Ethyl-piperazin-1-yl)-phenyl]-ethyl}-3-[3-(4-trifluoromethoxy-benzyl)-3H-imidazo[4,5-b]pyridin-2-yl]-propionamide |
| 173 | 3 nM | 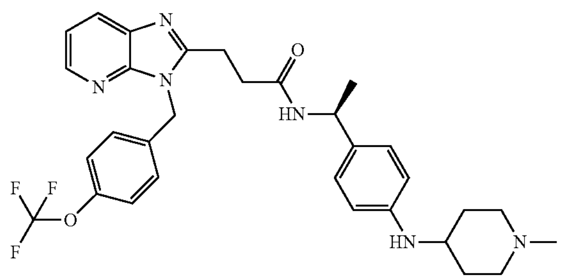 [SMILES: C[C@H](NC(=O)CCc1nc2cccnc2n1Cc1ccc(OC(F)(F)F)cc1)c1ccc(NC2CCN(C)CC2)cc1] | N-{(S)-1-[4-(1-Methyl-piperidin-4-ylamino)-phenyl]-ethyl}-3-[3-(4-trifluoromethoxy-benzyl)-3H-imidazo[4,5-b]pyridin-2-yl]-propionamide |
| 174 | 2 nM | 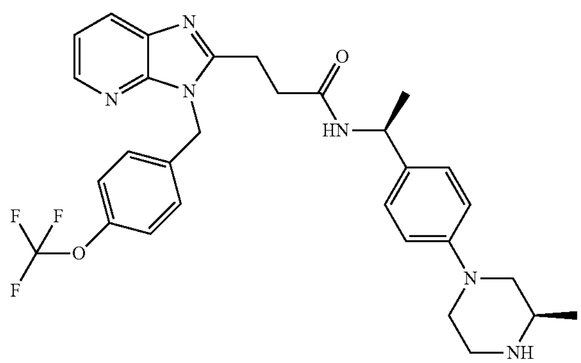 [SMILES: C[C@@H]1CN(c2ccc([C@H](C)NC(=O)CCc3nc4cccnc4n3Cc3ccc(OC(F)(F)F)cc3)cc2)CCN1] | N-{(S)-1-[4-((R)-3-Methyl-piperazin-1-yl)-phenyl]-ethyl}-3-[3-(4-trifluoromethoxy-benzyl)-3H-imidazo[4,5-b]pyridin-2-yl]-propionamide |
| 175 | 3 nM | 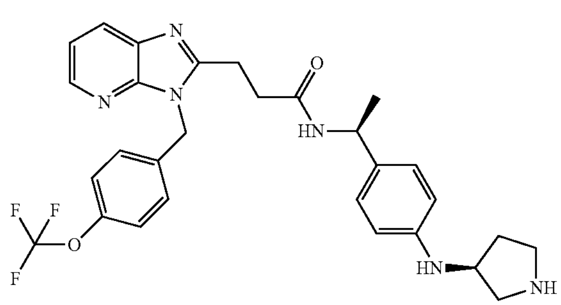 [SMILES: C[C@H](NC(=O)CCc1nc2cccnc2n1Cc1ccc(OC(F)(F)F)cc1)c1ccc(N[C@H]2CCNC2)cc1] | N-{(S)-1-[4-((S)-Pyrrolidin-3-ylamino)-phenyl]-ethyl}-3-[3-(4-trifluoromethoxy-benzyl)-3H-imidazo[4,5-b]pyridin-2-yl]-propionamide |

TABLE 1-continued

ATX activity (Quanta Red assay)

| Example | Activity | Structure | Name |
|---|---|---|---|
| 176 | 3 nM | 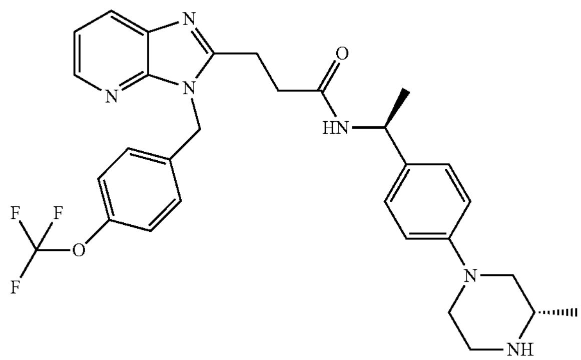 [SMILES: C[C@H](NC(=O)CCc1nc2cccnc2n1Cc1ccc(OC(F)(F)F)cc1)c1ccc(N2CCN[C@@H](C)C2)cc1] | N-{(S)-1-[4-((S)-3-Methyl-piperazin-1-yl)-phenyl]-ethyl}-3-[3-(4-trifluoromethoxy-benzyl)-3H-imidazo[4,5-b]pyridin-2-yl]-propionamide |
| 177 | 3 nM | 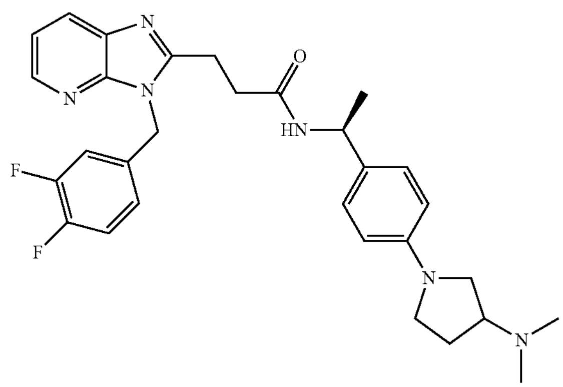 [SMILES: C[C@H](NC(=O)CCc1nc2cccnc2n1Cc1ccc(F)c(F)c1)c1ccc(N2CCC(N(C)C)C2)cc1] | 3-[3-(3,4-Difluoro-benzyl)-3H-imidazo[4,5-b]pyridin-2-yl]-N-{(S)-1-[4-(3-dimethylamino-pyrrolidin-1-ylmethyl)-phenyl]-ethyl}-propionamide |
| 178 | 3 nM | 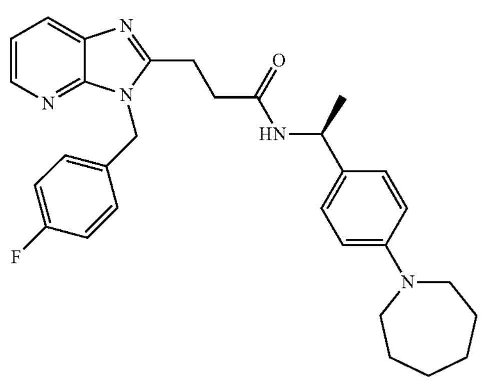 [SMILES: C[C@H](NC(=O)CCc1nc2cccnc2n1Cc1ccc(F)cc1)c1ccc(N2CCCCCC2)cc1] | N-[(S)-1-(4-Azepan-1-yl-phenyl)-ethyl]-3-[3-(4-fluoro-benzyl)-3H-imidazo[4,5-b]pyridin-2-yl]-propionamide |
| 179 | 5 nM | 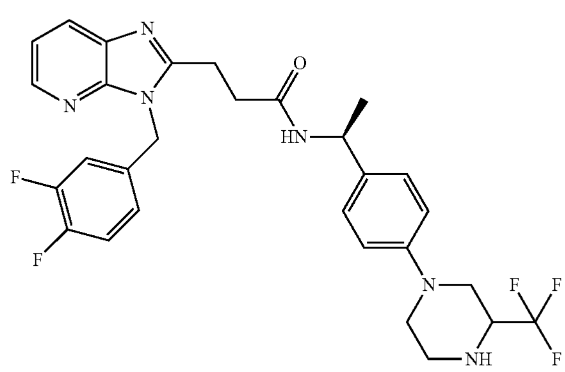 [SMILES: C[C@H](NC(=O)CCc1nc2cccnc2n1Cc1ccc(F)c(F)c1)c1ccc(N2CCNC(C(F)(F)F)C2)cc1] | 3-[3-(3,4-Difluoro-benzyl)-3H-imidazo[4,5-b]pyridin-2-yl]-N-{(S)-1-[4-(3-trifluoromethyl-piperazin-1-yl)-phenyl]-ethyl}-propionamide |

TABLE 1-continued

ATX activity (Quanta Red assay)

| Example | Activity | Structure | Name |
|---|---|---|---|
| 180 | 6 nM | 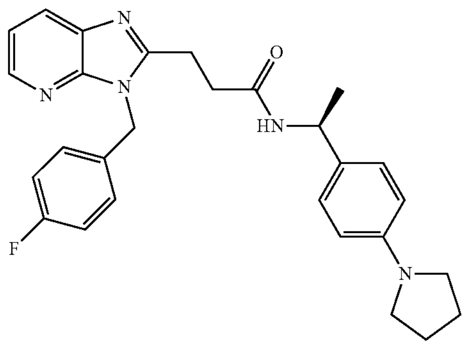 [SMILES: C[C@H](NC(=O)CCc1nc2cccnc2n1Cc1ccc(F)cc1)c1ccc(N2CCCC2)cc1] | 3-[3-(4-Fluoro-benzyl)-3H-imidazo[4,5-b]pyridin-2-yl]-N-[(S)-1-(4-pyrrolidin-1-yl-phenyl)-ethyl]-propionamide |
| 181 | 7 nM | 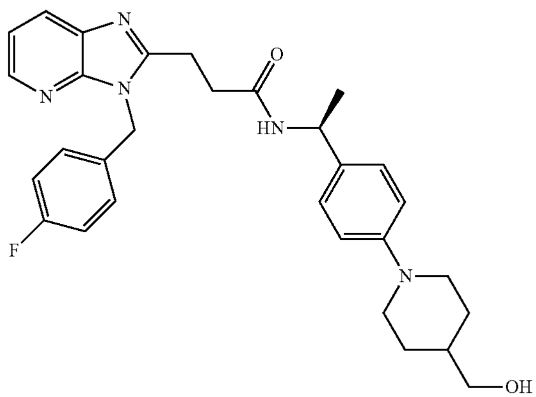 [SMILES: C[C@H](NC(=O)CCc1nc2cccnc2n1Cc1ccc(F)cc1)c1ccc(N2CCC(CO)CC2)cc1] | 3-[3-(4-Fluoro-benzyl)-3H-imidazo[4,5-b]pyridin-2-yl]-N-{(S)-1-[4-(4-hydroxymethyl-piperidin-1-yl)-phenyl]-ethyl}-propionamide |
| 182 | 8 nM | 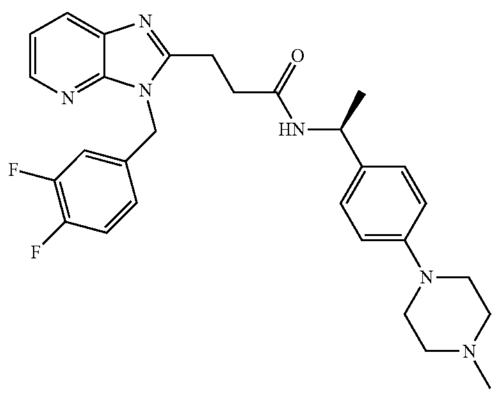 [SMILES: C[C@H](NC(=O)CCc1nc2cccnc2n1Cc1ccc(F)c(F)c1)c1ccc(N2CCN(C)CC2)cc1] | 3-[3-(3,4-Difluoro-benzyl)-3H-imidazo[4,5-b]pyridin-2-yl]-N-{(S)-1-[4-(4-methyl-piperazin-1-ylmethyl)-phenyl]-ethyl}-propionamide |
| 183 | 10 nM | 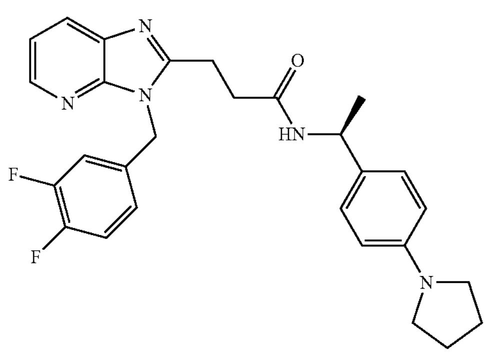 [SMILES: C[C@H](NC(=O)CCc1nc2cccnc2n1Cc1ccc(F)c(F)c1)c1ccc(N2CCCC2)cc1] | 3-[3-(3,4-Difluoro-benzyl)-3H-imidazo[4,5-b]pyridin-2-yl]-N-[(S)-1-(4-pyrrolidin-1-yl-phenyl)-ethyl]-propionamide |

TABLE 1-continued

ATX activity (Quanta Red assay)

| Example | Activity | Structure | Name |
|---|---|---|---|
| 184 | 12 nM | 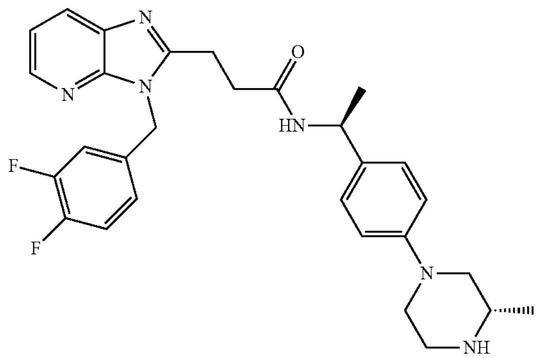 [SMILES: C[C@H](NC(=O)CCc1nc2cccnc2n1Cc1ccc(F)c(F)c1)c1ccc(N2CCN[C@@H](C)C2)cc1] | 3-[3-(3,4-Difluoro-benzyl)-3H-imidazo[4,5-b]pyridin-2-yl]-N-{(S)-1-[4-((S)-3-methyl-piperazin-1-yl)-phenyl]-ethyl}-propionamide |
| 185 | 13 nM | 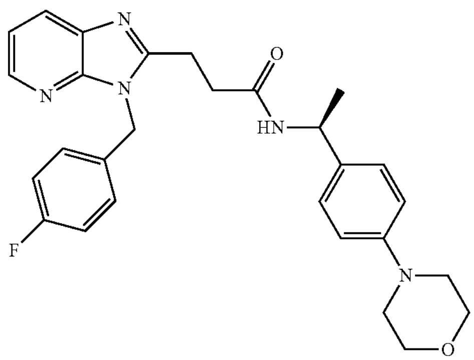 [SMILES: C[C@H](NC(=O)CCc1nc2cccnc2n1Cc1ccc(F)cc1)c1ccc(N2CCOCC2)cc1] | 3-[3-(4-Fluoro-benzyl)-3H-imidazo[4,5-b]pyridin-2-yl]-N-[(S)-1-(4-morpholin-4-yl-phenyl)-ethyl]-propionamide |
| 186 | 13 nM | 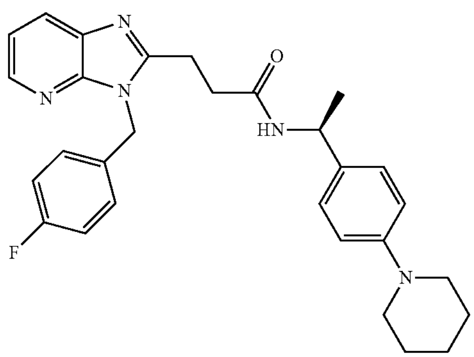 [SMILES: C[C@H](NC(=O)CCc1nc2cccnc2n1Cc1ccc(F)cc1)c1ccc(N2CCCCC2)cc1] | 3-[3-(4-Fluoro-benzyl)-3H-imidazo[4,5-b]pyridin-2-yl]-N-[(S)-1-(4-piperidin-1-yl-phenyl)-ethyl]-propionamide |
| 187 | 15 nM | 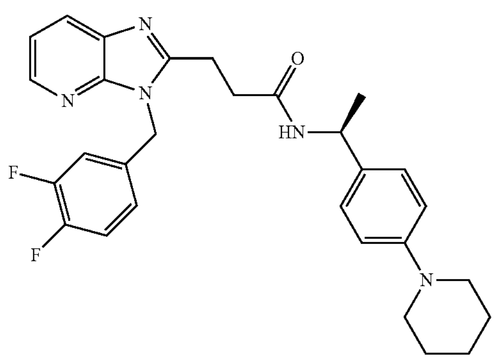 [SMILES: C[C@H](NC(=O)CCc1nc2cccnc2n1Cc1ccc(F)c(F)c1)c1ccc(N2CCCCC2)cc1] | 3-[3-(3,4-Difluoro-benzyl)-3H-imidazo[4,5-b]pyridin-2-yl-N-[(S)-1-(4-piperidin-1-yl-phenyl)-ethyl]-propionamide |

TABLE 1-continued

ATX activity (Quanta Red assay)

| Example | Activity | Structure | Name |
|---|---|---|---|
| 188 | 15 nM | 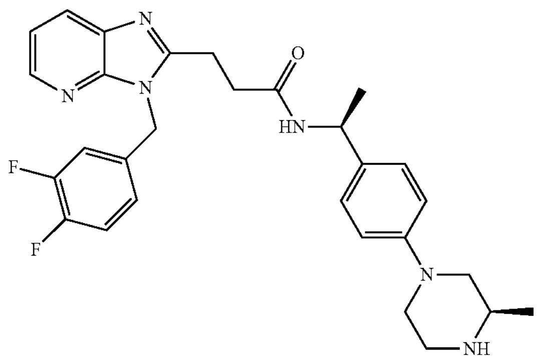 [SMILES: C[C@@H]1CN(c2ccc([C@H](C)NC(=O)CCc3nc4cccnc4n3Cc3ccc(F)c(F)c3)cc2)CCN1] | 3-[3-(3,4-Difluoro-benzyl)-3H-imidazo[4,5-b]pyridin-2-yl]-N-{(S)-1-[4-((R)-3-methyl-piperazin-1-yl)-phenyl]-ethyl}-propionamide |
| 189 | 16 nM | 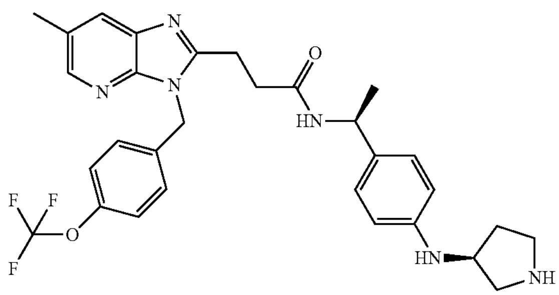 [SMILES: Cc1cnc2c(c1)nc(CCC(=O)N[C@@H](C)c1ccc(N[C@H]3CCNC3)cc1)n2Cc1ccc(OC(F)(F)F)cc1] | 3-[6-Methyl-3-(4-trifluoromethoxy-benzyl)-3H-imidazo[4,5-b]pyridin-2-yl]-N-{(S)-1-[4-((S)-pyrrolidin-3-ylamino)-phenyl]-ethyl}-propionamide |
| 190 | 20 nM | 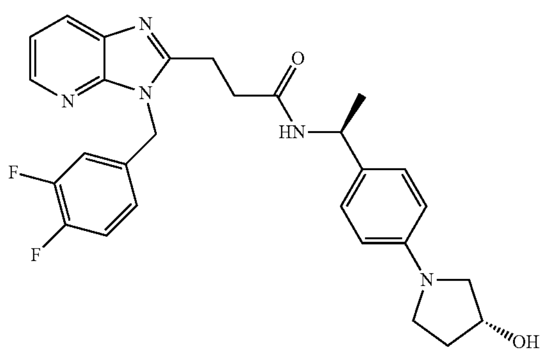 [SMILES: C[C@H](NC(=O)CCc1nc2cccnc2n1Cc1ccc(F)c(F)c1)c1ccc(N2CC[C@@H](O)C2)cc1] | 3-[3-(3,4-Difluoro-benzyl)-3H-imidazo[4,5-b]pyridin-2-yl]-N-{(S)-1-[4-((R)-3-hydroxy-pyrrolidin-1-yl)-phenyl]-ethyl}-propionamide |
| 191 | 25 nM | 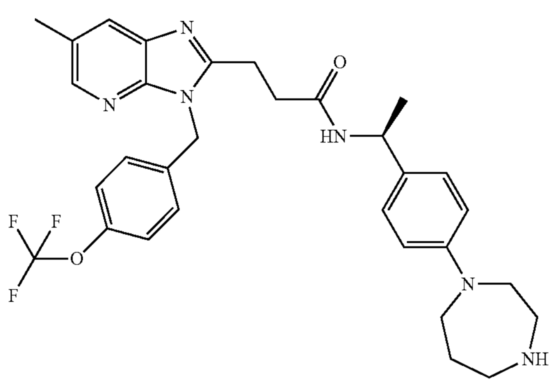 [SMILES: Cc1cnc2c(c1)nc(CCC(=O)N[C@@H](C)c1ccc(N3CCCNCC3)cc1)n2Cc1ccc(OC(F)(F)F)cc1] | N-[(S)-1-(4-[1,4]Diazepan-1-yl-phenyl)-ethyl]-3-[6-methyl-3-(4-trifluoromethoxy-benzyl)-3H-imidazo[4,5-b]pyridin-2-yl]-propionamide |

TABLE 1-continued

ATX activity (Quanta Red assay)

| Example | Activity | Structure | Name |
|---|---|---|---|
| 192 | 56 nM | 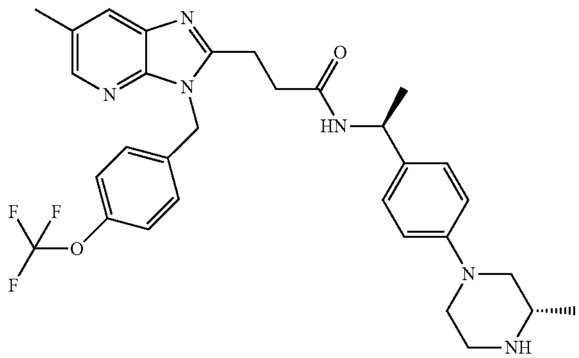 [SMILES: Cc1cnc2c(c1)nc(CCC(=O)N[C@@H](C)c1ccc(N3CCN[C@@H](C)C3)cc1)n2Cc1ccc(OC(F)(F)F)cc1] | N-{(S)-1-[4-((S)-3-Methyl-piperazin-1-yl)-phenyl]-ethyl}-3-[6-methyl-3-(4-trifluoromethoxy-benzyl)-3H-imidazo[4,5-b]pyridin-2-yl]-propionamide |
| 193 | 83 nM | 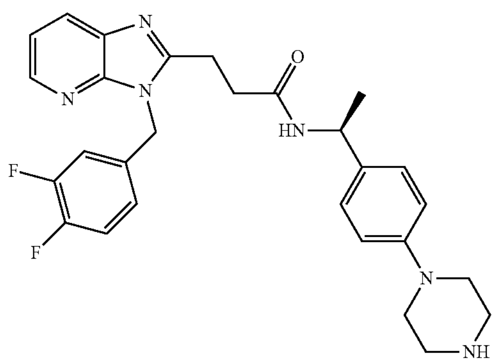 [SMILES: C[C@H](NC(=O)CCc1nc2cccnc2n1Cc1ccc(F)c(F)c1)c1ccc(N2CCNCC2)cc1] | 3-[3-(3,4-Difluoro-benzyl)-3H-imidazo[4,5-b]pyridin-2-yl]-N-[(S)-1-(4-piperazin-1-yl-phenyl)-ethyl]-propionamide |
| 194 | 1 nM | 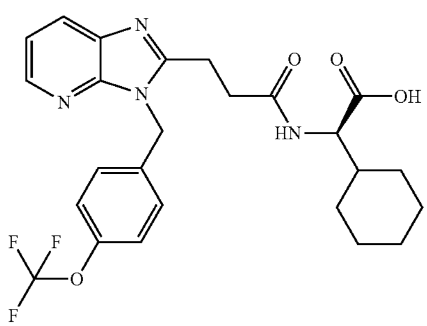 [SMILES: O=C(CCc1nc2cccnc2n1Cc1ccc(OC(F)(F)F)cc1)N[C@@H](C(=O)O)C1CCCCC1] | (R)-Cyclohexyl-{3-[3-(4-trifluoromethoxy-benzyl)-3H-imidazo[4,5-b]pyridin-2-yl]-propionylamino}-acetic acid |
| 195 | 1 nM | 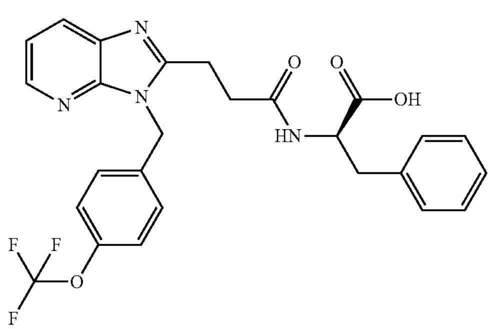 [SMILES: O=C(CCc1nc2cccnc2n1Cc1ccc(OC(F)(F)F)cc1)N[C@H](Cc1ccccc1)C(=O)O] | (R)-3-Phenyl-2-{3-[3-(4-trifluoromethoxy-benzyl)-3H-imidazo[4,5-b]pyridin-2-yl]-propionylamino}-propionic acid |

TABLE 1-continued

ATX activity (Quanta Red assay)

| Example | Activity | Structure | Name |
|---|---|---|---|
| 196 | 2 nM | 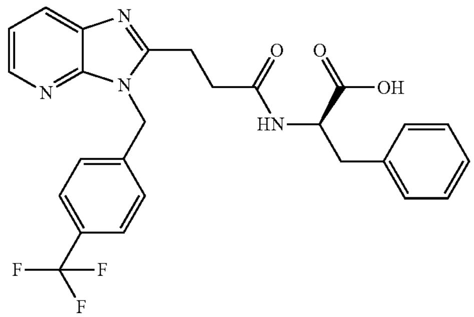 [SMILES: O=C(CCc1nc2cccnc2n1Cc1ccc(C(F)(F)F)cc1)N[C@H](Cc1ccccc1)C(=O)O] | (R)-3-Phenyl-2-{3-[3-(4-trifluoromethyl-benzyl)-3H-imidazo[4,5-b]pyridin-2-yl]-propionylamino}-propionic acid |
| 197 | 5 nM | 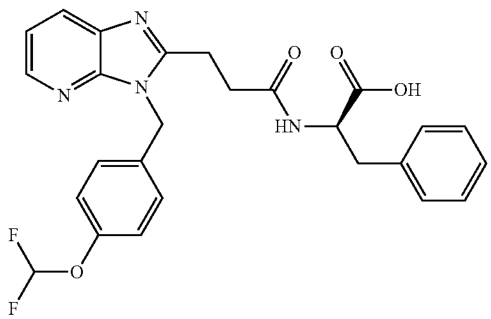 [SMILES: O=C(CCc1nc2cccnc2n1Cc1ccc(OC(F)F)cc1)N[C@H](Cc1ccccc1)C(=O)O] | (R)-2-{3-[3-(4-Difluoromethoxy-benzyl)-3H-imidazo[4,5-b]pyridin-2-yl]-propionylamino}-3-phenyl-propionic acid |
| 198 | 37 nM | 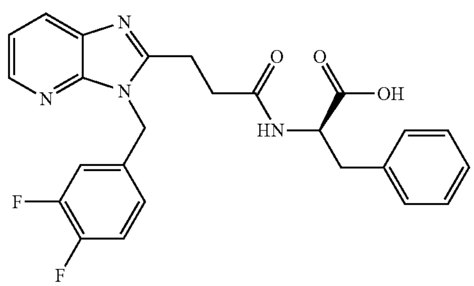 [SMILES: O=C(CCc1nc2cccnc2n1Cc1ccc(F)c(F)c1)N[C@H](Cc1ccccc1)C(=O)O] | (R)-2-{3-[3-(3,4-Difluoro-benzyl)-3H-imidazo[4,5-b]pyridin-2-yl]-propionylamino}-3-phenyl-propionic acid |
| 199 | 71 nM | 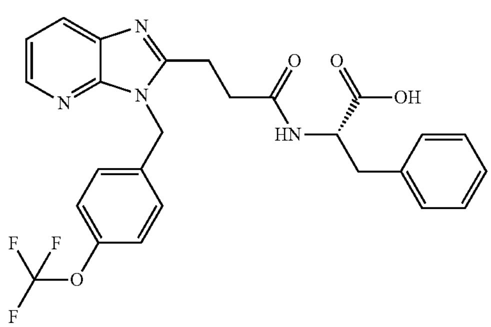 [SMILES: O=C(CCc1nc2cccnc2n1Cc1ccc(OC(F)(F)F)cc1)N[C@@H](Cc1ccccc1)C(=O)O] | (S)-3-Phenyl-2-{3-[3-(4-trifluoromethoxy-benzyl)-3H-imidazo[4,5-b]pyridin-2-yl]-propionylamino}-propionic acid |

TABLE 1-continued

ATX activity (Quanta Red assay)

| Example | Activity | Structure | Name |
|---|---|---|---|
| 200 | 471 nM | 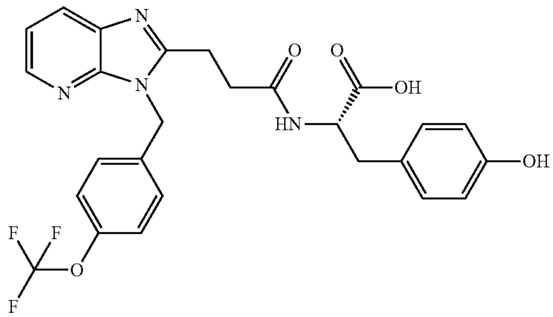 [SMILES: O=C(CCc1nc2cccnc2n1Cc1ccc(OC(F)(F)F)cc1)N[C@@H](Cc1ccc(O)cc1)C(=O)O] | (S)-3-(4-Hydroxy-phenyl)-2-{3-[3-(4-trifluoromethoxy-benzyl)-3H-imidazo[4,5-b]pyridin-2-yl]-propionylamino}-propionic acid |
| 201 | 598 nM | 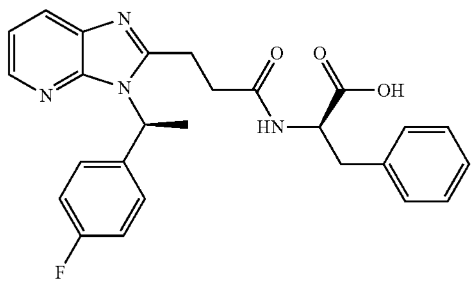 [SMILES: C[C@@H](c1ccc(F)cc1)n1c(CCC(=O)N[C@H](Cc2ccccc2)C(=O)O)nc2cccnc21] | (R)-2-(3-{3-[(S)-1-(4-Fluoro-phenyl)-ethyl]-3H-imidazo[4,5-b]pyridin-2-yl}-propionylamino)-3-phenyl-propionic acid |
| 202 | 819 nM | 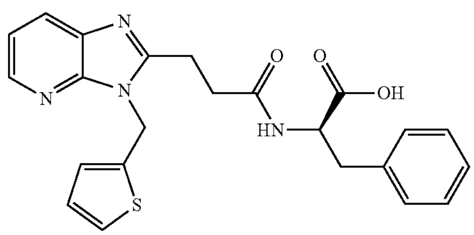 [SMILES: O=C(CCc1nc2cccnc2n1Cc1cccs1)N[C@H](Cc1ccccc1)C(=O)O] | (R)-3-Phenyl-2-[3-(3-thiophen-2-ylmethyl-3H-imidazo[4,5-b]pyridin-2-yl)-propionylamino]-propionic acid |
| 203 | 2 nM | 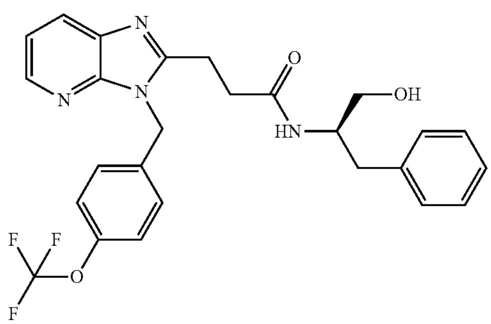 [SMILES: O=C(CCc1nc2cccnc2n1Cc1ccc(OC(F)(F)F)cc1)N[C@@H](CO)Cc1ccccc1] | N-((R)-1-Hydroxymethyl-2-phenyl-ethyl)-3-[3-(4-trifluoromethoxy-benzyl)-3H-imidazo[4,5-b]pyridin-2-yl]-propionamide |
| 204 | 89 nM | 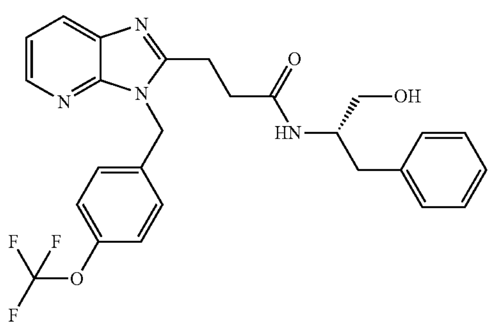 [SMILES: O=C(CCc1nc2cccnc2n1Cc1ccc(OC(F)(F)F)cc1)N[C@H](CO)Cc1ccccc1] | N-((S)-1-Hydroxymethyl-2-phenyl-ethyl)-3-[3-(4-trifluoromethoxy-benzyl)-3H-imidazo[4,5-b]pyridin-2-yl]-propionamide |

TABLE 1-continued

ATX activity (Quanta Red assay)

| Example | Activity | Structure | Name |
|---|---|---|---|
| 205 | 188 nM | 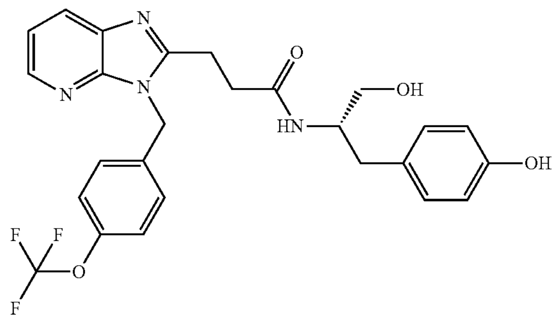 [SMILES: O=C(CCc1nc2cccnc2n1Cc1ccc(OC(F)(F)F)cc1)N[C@H](CO)Cc1ccc(O)cc1] | N-[(S)-1-Hydroxymethyl-2-(4-hydroxy-phenyl)-ethyl]-3-[3-(4-trifluoromethoxy-benzyl)-3H-imidazo[4,5-b]pyridin-2-yl]-propionamide |
| 206 | 3 nM | 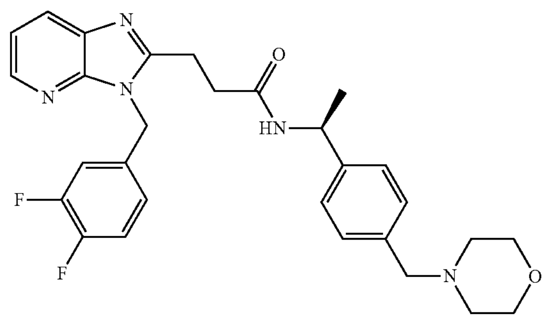 [SMILES: C[C@H](NC(=O)CCc1nc2cccnc2n1Cc1ccc(F)c(F)c1)c1ccc(CN2CCOCC2)cc1] | 3-[3-(3,4-Difluoro-benzyl)-3H-imidazo[4,5-b]pyridin-2-yl]-N-[(S)-1-(4-morpholin-4-ylmethyl-phenyl)-ethyl]-propionamide |
| 207 | 25 nM | 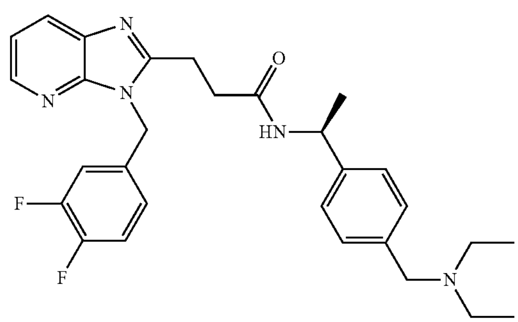 [SMILES: CCN(CC)Cc1ccc([C@H](C)NC(=O)CCc2nc3cccnc3n2Cc2ccc(F)c(F)c2)cc1] | N-[(S)-1-(4-Diethylaminomethyl-phenyl)-ethyl]-3-[3-(3,4-difluoro-benzyl)-3H-imidazo[4,5-b]pyridin-2-yl]-propionamide |
| 208 | 80 nM | 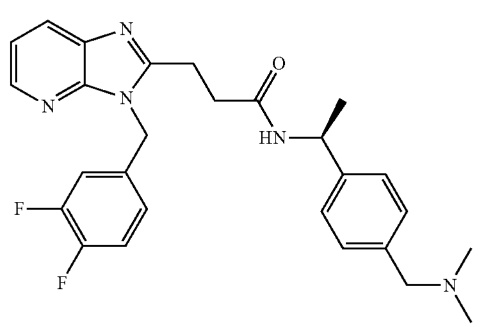 [SMILES: C[C@H](NC(=O)CCc1nc2cccnc2n1Cc1ccc(F)c(F)c1)c1ccc(CN(C)C)cc1] | 3-[3-(3,4-Difluoro-benzyl)-3H-imidazo[4,5-b]pyridin-2-yl]-N-[(S)-1-(4-dimethylaminomethyl-phenyl)-ethyl]-propionamide |

TABLE 1-continued

ATX activity (Quanta Red assay)

| Example | Activity | Structure | Name |
|---|---|---|---|
| 209 | 3 nM | 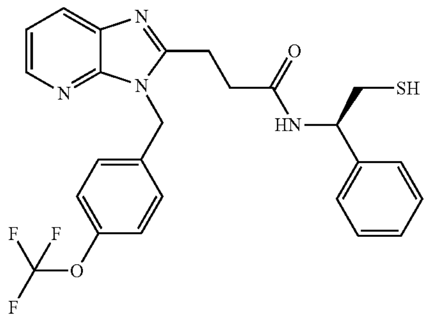 | N-((R)-2-Mercapto-1-phenyl-ethyl)-3-[3-(4-trifluoromethoxy-benzyl)-3H-imidazo[4,5-b]pyridin-2-yl]-propionamide |
| 210 | 3 nM | 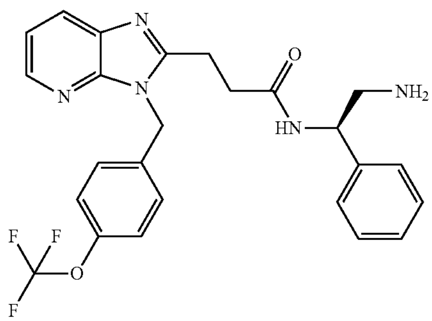 [SMILES: NC[C@H](NC(=O)CCc1nc2cccnc2n1Cc1ccc(OC(F)(F)F)cc1)c1ccccc1] | N-((R)-2-Amino-1-phenyl-ethyl)-3-[3-(4-trifluoromethoxy-benzyl)-3H-imidazo[4,5-b]pyridin-2-yl]-propionamide |
| 211 | 7 nM | 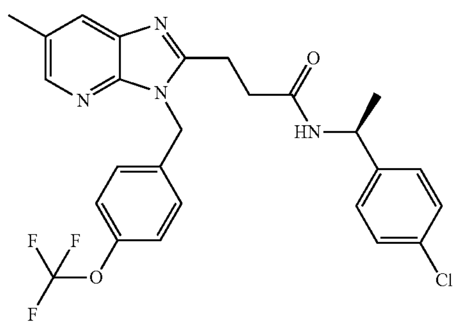 [SMILES: Cc1cnc2c(c1)nc(CCC(=O)N[C@@H](C)c1ccc(Cl)cc1)n2Cc1ccc(OC(F)(F)F)cc1] | N-[(S)-1-(4-Chloro-phenyl)-ethyl]-3-[6-methyl-3-(4-trifluoromethoxy-benzyl)-3H-imidazo[4,5-b]pyridin-2-yl]-propionamide |
| 212 | 7 nM | 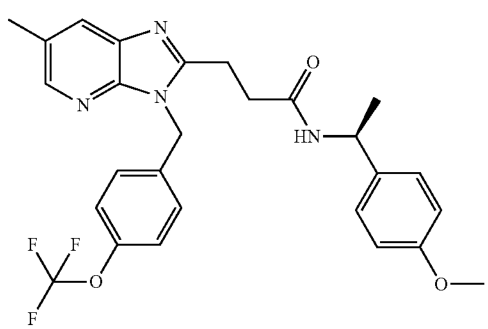 | N-[(S)-1-(4-Methoxy-phenyl)-ethyl]-3-[6-methyl-3-(4-trifluoromethoxy-benzyl)-3H-imidazo[4,5-b]pyridin-2-yl]-propionamide |

TABLE 1-continued

ATX activity (Quanta Red assay)

| Example | Activity | Structure | Name |
|---|---|---|---|
| 213 | 17 nM | 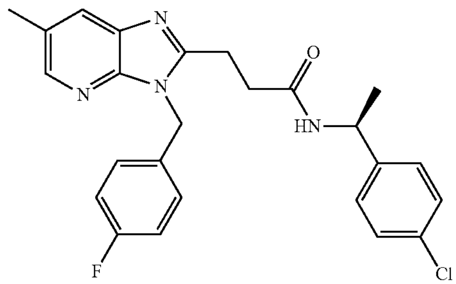 [SMILES: Cc1cnc2c(c1)nc(CCC(=O)N[C@@H](C)c1ccc(Cl)cc1)n2Cc1ccc(F)cc1] | N-[(S)-1-(4-Chloro-phenyl)-ethyl]-3-[3-(4-fluoro-benzyl)-6-methyl-3H-imidazo[4,5-b]pyridin-2-yl]-propionamide |
| 214 | 30 nM | 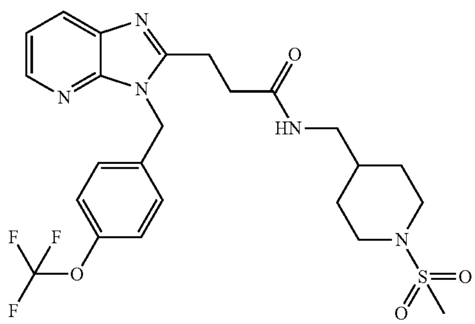 [SMILES: CS(=O)(=O)N1CCC(CNC(=O)CCc2nc3cccnc3n2Cc2ccc(OC(F)(F)F)cc2)CC1] | N-(1-Methanesulfonyl-piperidin-4-ylmethyl)-3-[3-(4-trifluoromethoxy-benzyl)-3H-imidazo[4,5-b]pyridin-2-yl]-propionamide |
| 215 | 81 nM | 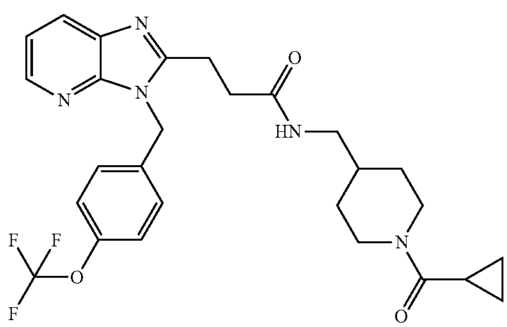 [SMILES: O=C(CCc1nc2cccnc2n1Cc1ccc(OC(F)(F)F)cc1)NCC1CCN(C(=O)C2CC2)CC1] | N-(1-Cyclopropanecarbonyl-piperidin-4-ylmethyl)-3-[3-(4-trifluoromethoxy-benzyl)-3H-imidazo[4,5-b]pyridin-2-yl]-propionamide |
| 216 | 495 nM | 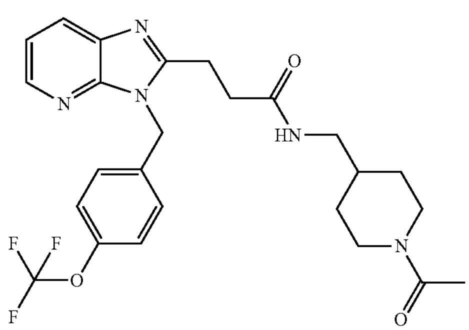 [SMILES: CC(=O)N1CCC(CNC(=O)CCc2nc3cccnc3n2Cc2ccc(OC(F)(F)F)cc2)CC1] | N-(1-Acetyl-piperidin-4-ylmethyl)-3-[3-(4-trifluoromethoxy-benzyl)-3H-imidazo[4,5-b]pyridin-2-yl]-propionamide |

TABLE 2

Additional compounds tested for ATX activity (Quanta Red Assay):

| Example | Activity | Structure | Name |
| --- | --- | --- | --- |
| 217 | 29 nM | 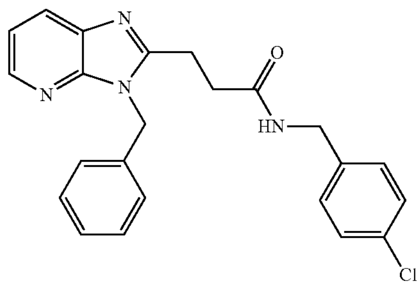 [SMILES: O=C(CCc1nc2cccnc2n1Cc1ccccc1)NCc1ccc(Cl)cc1] | 3-(3-Benzyl-3H-imidazo[4,5-b]pyridin-2-yl)-N-(4-chloro-benzyl)-propionamide |
| 218 | 23 nM | 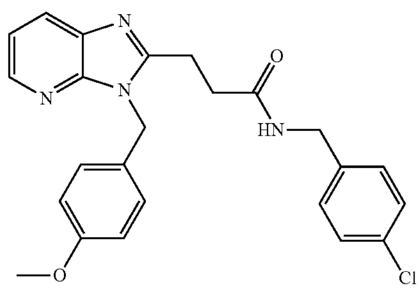 [SMILES: COc1ccc(Cn2c(CCC(=O)NCc3ccc(Cl)cc3)nc3cccnc32)cc1] | N-(4-Chloro-benzyl)-3-[3-(4-methoxy-benzyl)-3H-imidazo[4,5-b]pyridin-2-yl]-propionamide |
| 219 | 89 nM | 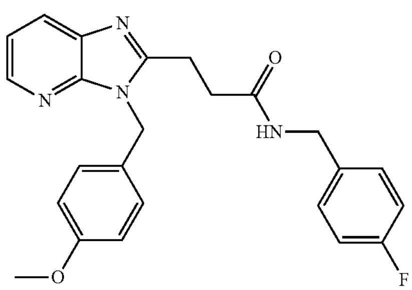 [SMILES: COc1ccc(Cn2c(CCC(=O)NCc3ccc(F)cc3)nc3cccnc32)cc1] | N-(4-Fluoro-benzyl)-3-[3-(4-methoxy-benzyl)-3H-imidazo[4,5-b]pyridin-2-yl]-propionamide |
| 220 | 125 nM | 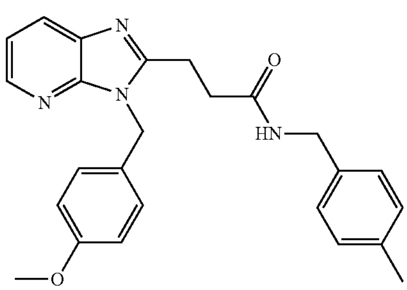 [SMILES: COc1ccc(Cn2c(CCC(=O)NCc3ccc(C)cc3)nc3cccnc32)cc1] | 3-[3-(4-Methoxy-benzyl)-3H-imidazo[4,5-b]pyridin-2-yl]-N-(4-methyl-benzyl)-propionamide |
| 221 | 154 nM | 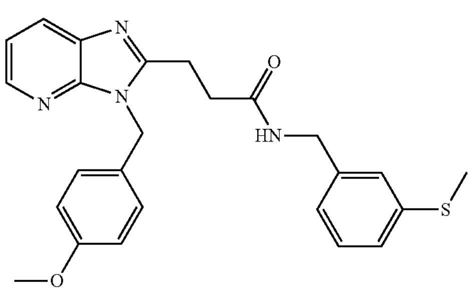 [SMILES: COc1ccc(Cn2c(CCC(=O)NCc3cccc(SC)c3)nc3cccnc32)cc1] | 3-[3-(4-Methoxy-benzyl)-3H-imidazo[4,5-b]pyridin-2-yl]-N-[2-(4-methylsulfanyl-phenyl)-ethyl]-propionamide |

TABLE 2-continued

Additional compounds tested for ATX activity (Quanta Red Assay):

| Example | Activity | Structure | Name |
| --- | --- | --- | --- |
| 222 | 193 nM | 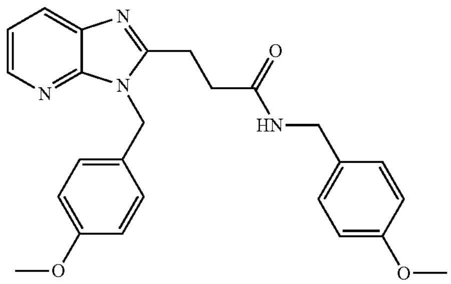 [SMILES: COc1ccc(CNC(=O)CCc2nc3cccnc3n2Cc2ccc(OC)cc2)cc1] | N-(4-Methoxy-benzyl)-3-[3-(4-methoxy-benzyl)-3H-imidazo[4,5-b]pyridin-2-yl]-propionamide |
| 223 | 324 nM | 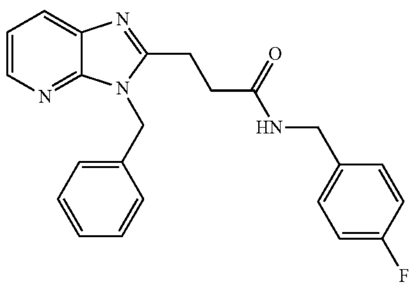 [SMILES: O=C(CCc1nc2cccnc2n1Cc1ccccc1)NCc1ccc(F)cc1] | 3-(3-Benzyl-3H-imidazo[4,5-b]pyridin-2-yl)-N-(4-fluoro-benzyl)-propionamide |
| 224 | 685 nM | 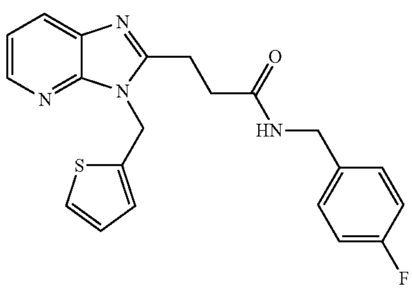 [SMILES: O=C(CCc1nc2cccnc2n1Cc1cccs1)NCc1ccc(F)cc1] | N-(4-Fluoro-benzyl)-3-(3-thiophen-2-ylmethyl-3H-imidazo[4,5-b]pyridin-2-yl)-propionamide |
| 225 | 708 nM | 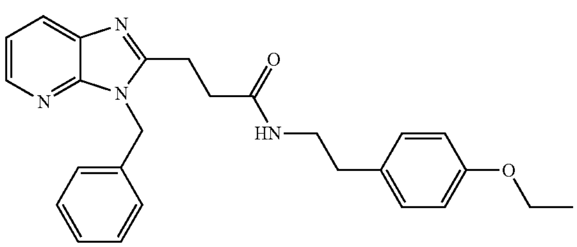 [SMILES: CCOc1ccc(CCNC(=O)CCc2nc3cccnc3n2Cc2ccccc2)cc1] | 3-(3-Benzyl-3H-imidazo[4,5-b]pyridin-2-yl)-N-[2-(4-ethoxy-phenyl)-ethyl]-propionamide |
| 226 | 807 nM | 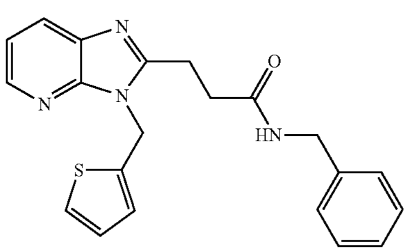 [SMILES: O=C(CCc1nc2cccnc2n1Cc1cccs1)NCc1ccccc1] | N-Benzyl-3-(3-thiophen-2-ylmethyl-3H-imidazo[4,5-b]pyridin-2-yl)-propionamide |

TABLE 2-continued

Additional compounds tested for ATX activity (Quanta Red Assay):

| Example | Activity | Structure | Name |
|---------|----------|-----------|------|
| 227 | 3828 nM | 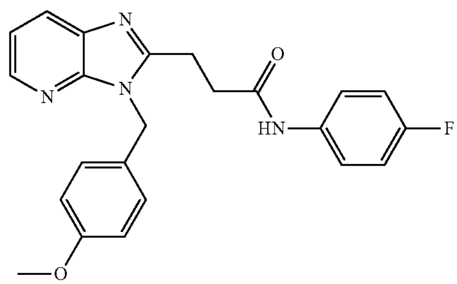 [SMILES: COc1ccc(Cn2c(CCC(=O)Nc3ccc(F)cc3)nc3cccnc32)cc1] | N-(4-Fluoro-phenyl)-3-[3-(4-methoxy-benzyl)-3H-imdidazo[4,5-b]pyridin-2-yl]-propionamide |
| 228 | 8811 nM | 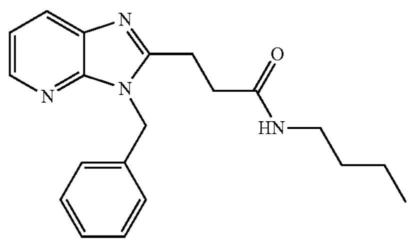 [SMILES: CCCCNC(=O)CCc1nc2cccnc2n1Cc1ccccc1] | 3-(3-Benzyl-3H-imidazo[4,5-b]pyridin-2-yl)-N-butyl-propionamide |
| 229 | 466 nM | 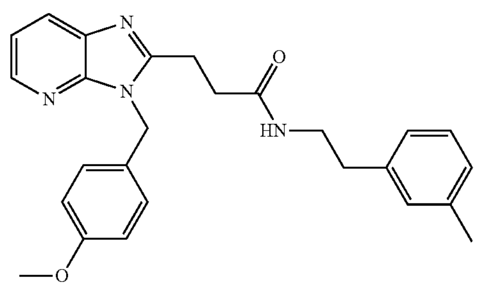 [SMILES: COc1ccc(Cn2c(CCC(=O)NCCc3cccc(C)c3)nc3cccnc32)cc1] | 3-[3-(4-Methoxy-benzyl)-3H-imidazo[4,5-b]pyridin-2-yl]-N-(2-m-tolyl-ethyl)-propionamide |
| 230 | 688 nM | 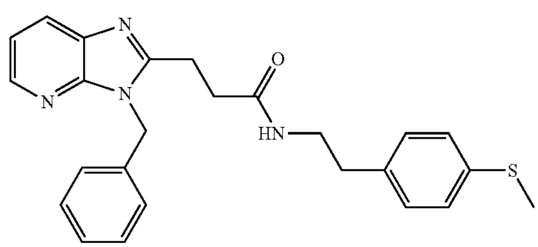 [SMILES: CSc1ccc(CCNC(=O)CCc2nc3cccnc3n2Cc2ccccc2)cc1] | 3-(3-Benzyl-3H-imidazo[4,5-b]pyridin-2-yl)-N-[2-(4-methylsulfanyl-phenyl)-ethyl]-propionamide |
| 231 | 200 nM | 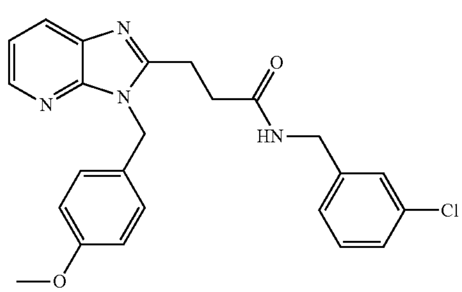 [SMILES: COc1ccc(Cn2c(CCC(=O)NCc3cccc(Cl)c3)nc3cccnc32)cc1] | N-(3-Chloro-benzyl)-3-[3-(4-methoxy-benzyl)-3H-imidazo[4,5-b]pyridin-2-yl]-propionamide |

TABLE 2-continued

Additional compounds tested for ATX activity (Quanta Red Assay):

| Example | Activity | Structure | Name |
|---|---|---|---|
| 232 | 596 nM | (see structure) | 3-(3-Benzyl-3H-imidazo[4,5-b]pyridin-2-yl)-N-(3-chloro-benzyl)-propionamide |
| 233 | 539 nM | | N-[2-(4-Ethoxy-phenyl)-ethyl]-3-[3-(4-methoxy-benzyl)-3H-imidazo[4,5-b]pyridin-2-yl]-propionamide |
| 234 | 720 nM | | N-Benzo[1,3]dioxol-5-ylmethyl-3-[3-(4-methoxy-benzyl)-3H-imidazo[4,5-b]pyridin-2-yl]-propionamide |
| 235 | 627 nM | | 3-(3-Benzyl-3H-imidazo[4,5-b]pyridin-2-yl)-N-(4-methyl-benzyl)-propionamide |

TABLE 3

Commercially available compounds tested for Autotaxin activity (Quanta Red assay)

| Example | Activity | Structure | Name |
|---|---|---|---|
| 236 | 406 nM | | N-Benzyl-3-[3-(4-methoxy-benzyl)-3H-imidazo[4,5-b]pyridin-2-yl]-propionamide |
| 237 | 227 nM | | 3-[3-(4-Methoxy-benzyl)-3H-imidazo-[4,5-b]pyridin-2-yl]-N-phenethyl-propionamide |
| 238 | 473 nM | | 3-(3-Benzyl-3H-imidazo[4,5-b]pyridin-2-yl)-N-(4-methoxy-benzyl)-propionamide |

In Vivo Data

ATX 4T1 Orthotopic, Metastatic Breast Cancer Mouse Model female BALB/c mice 6 weeks of age (Charles River). The test compound (Example F93) was dosed for 15 days (day −1 to day 14)

On day 1 4T1 cells ($10^5$ in 10 μl of PBS) were injected into the fat pad of the $4^{th}$ mammary gland of the mice. Before injection, cells were stored at room temperature for a period that did not exceed 2 hours at which time a new batch of cell suspension was prepared. At day 15 animals were anaesthetised and primary tumours were surgically removed. Primary tumours were weighed, fixed with para-formaldehyde (PFA 4%) for 48 hours, dehydrated for 24 hours in 70% ethanol and embedded in paraffin. Mice were then monitored for an additional 3-week period. At this time they were sacrificed. Re-grown primary tumours were collected, weighed, fixed with PFA, dehydrated with 70% ethanol and embedded in paraffin as described above.

Bone marrow cells from both hind limbs of each animal were flushed with PBS, suspended in RPMI 1640 medium

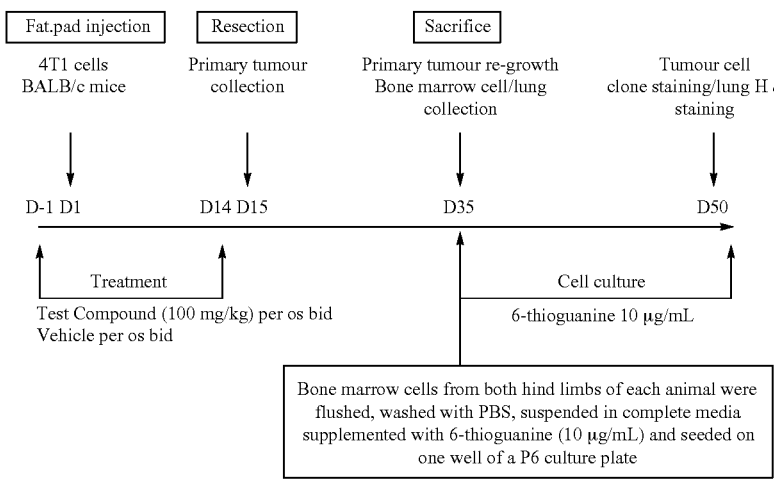

Procedure

On day −1 dosing of the test compound by gavage (100 mg/kg of test compound in 1% methylcellulose solution, twice daily with the second dose 8 hours after the first and assuming a mouse weight of 20 g) was commenced on containing 10% FBS supplemented with 6-thioguanine (10 μg/mL) and seeded on a well of a 6-well culture plate. After a two-week incubation period at 37° C., tumour colonies were stained with crystal violet and counted. The levels of disseminated tumour cells in bone were expressed as the number of colonies per well.

At the time of animal sacrifice, lungs were inflated with PFA prior to removal, then fixed with PFA for 48 hours, dehydrated with ethanol and embedded in paraffin as described above for primary tumour samples. 5 um sections were cut every 50 um through the lungs and the number and total volume of the metastases was determined using the assumption that the metastases were spherical.

Figure 2:
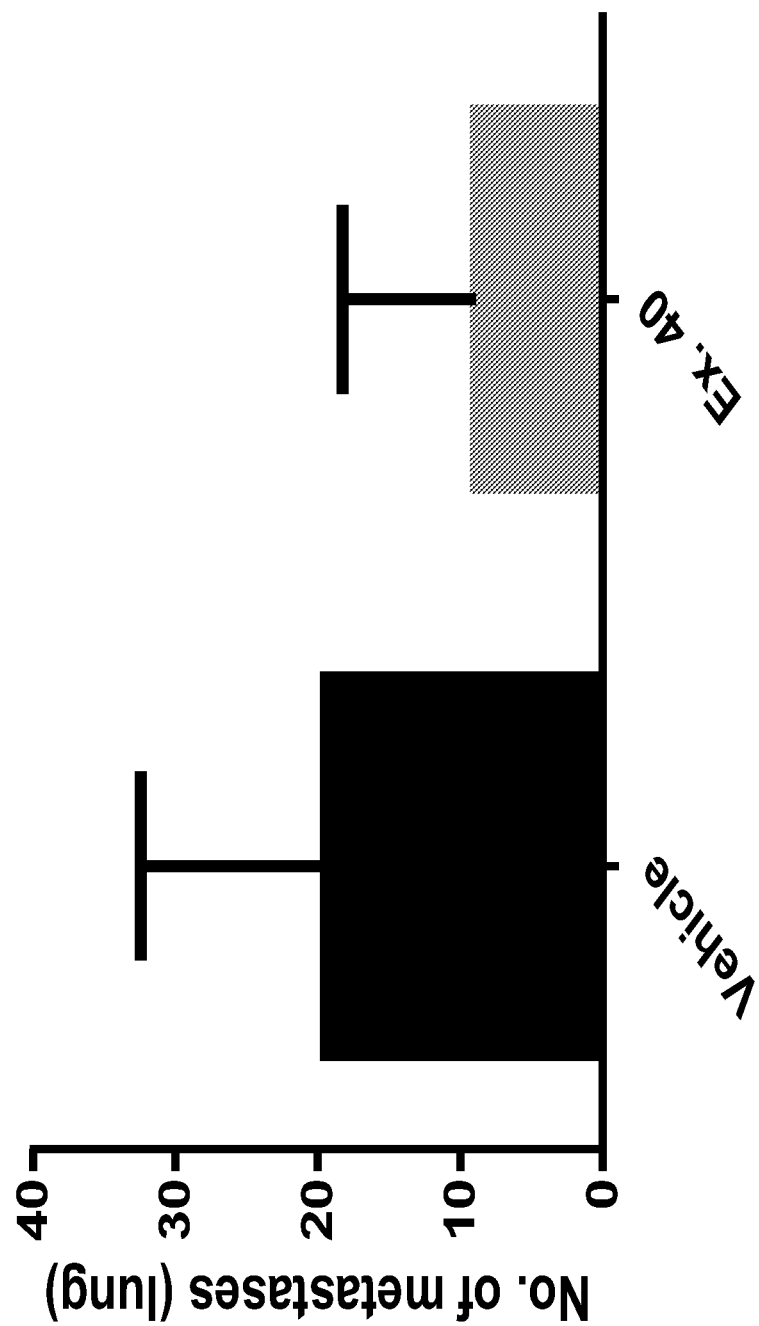
FIG. 2 shows the number of lung metastases achieved through administration of Example 40 compared to the administration of the vehicle, using the 4T1 orthotopic metastatic breast cancer model, described hereinbelow.
Figure 3:
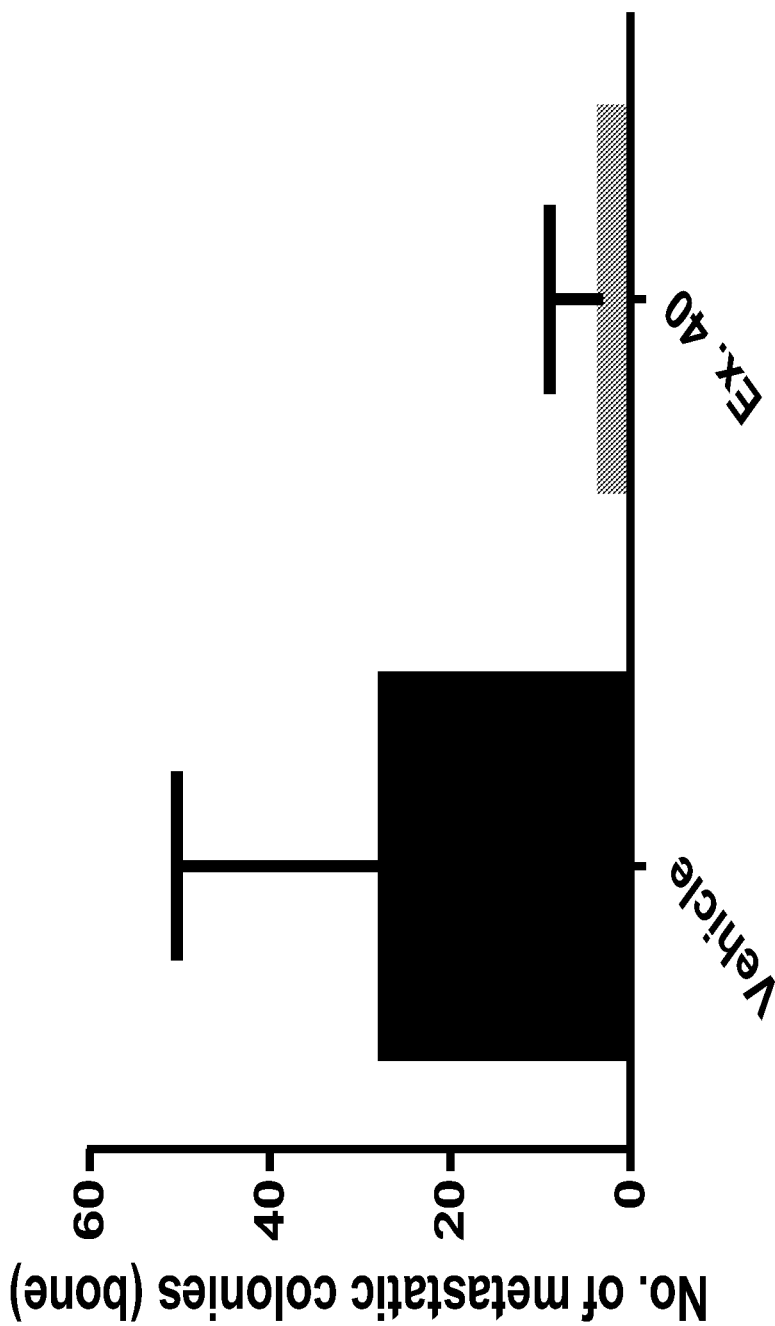
FIG. 3 shows the effect on bone metastatic colony formation in the presence of Example 40 compared to the vehicle, using the 4T1 orthotopic metastatic breast cancer model, described hereinbelow.

The results are summarised in FIGS. 1 to 3. In which:

FIG. 1 shows total volume of lung metastases for Example 40 compared to the vehicle, in the 4T1 orthotopic metastatic breast cancer model.

FIG. 2 shows the number of lung metastases for Example 40 compared to the vehicle, in the 4T1 orthotopic metastatic breast cancer model.

FIG. 3 shows the effect on bone metastatic colony formation in the presence of Example 40 compared to the vehicle, in the 4T1 orthotopic metastatic breast cancer model.

REFERENCES

1) Aznavoorian et al., 1990, "Signal transduction for chemotaxis and haptotaxis by matrix molecules in tumor cells", The Journal of Cell Biology Vol. 110, pp. 1427-1438.
2) Baumforth et al., 2005, "Induction of autotaxin by the Epstein-Barr virus promotes the growth and survival of Hodgkin lymphoma cells", Blood, Vol. 106, pp. 2138-2146.
3) Boucharaba et al., 2004, "Platelet-derived lysophosphatidic acid supports the progression of osteolytic bone metastases in breast cancer", J Clin Invest., 114:1714-25.
4) Boucher et al., 2005, "Potential involvement of adipocyte insulin resistance in obesity-associated up-regulation of adipocyte lysophospholipase D/autotaxin expression", Diabetologia, Vol. 248, pp. 569-577.
5) Choi et al., 2010, "LPA receptors: subtypes and biological actions" Annu Rev Pharmacol Toxicol., 50:157-86.
6) Cui et al., 2007, "Synthesis and biological evaluation of phosphonate derivatives as autotaxin (ATX) inhibitors", Bioorganic & Medicinal Chemistry Letters, Vol. 17, pp. 1634-1640.
7) Cui et al., 2008, "α- and β-Substituted phosphonate analogs of LPA as autotaxin inhibitors", Bioorganic & Medicinal Chemistry Vol. 16, pp. 2212-2225.
8) Ferry et al., 2008, "S32826, A Nanomolar Inhibitor of Autotaxin: Discovery, Synthesis and Applications as a Pharmacological Tool," J. Pharmacol. Exp. Ther. Vol. 327, pp. 809-819.
9) Gajewiak et al., 2008, "Synthesis, Pharmacology, and Cell Biology of sn-2-Aminooxy Analogues of Lysophosphatidic Acid", Org. Lett., Vol. 10, No. 6, pp. 1111-1114.
10) Hausman et al., 2001, "The biology of white adipocyte proliferation", Obes. Rev. Vol. 2, pp. 239-254.
11) Houben A J, Moolenaar W H, 2011, "Autotaxin and LPA receptor signaling in cancer" Cancer Metastasis Rev., 30(3-4):557-65.
12) Inoue et al., 2004, "Initiation of neuropathic pain requires lysophosphatidic acid receptor signalling", Nat. Med. Vol. 10, pp. 712-718.
13) Inoue et al., 2008, "Autotaxin, a synthetic enzyme of lysophosphatidic acid (LPA), mediates the induction of nerve-injured neuropathic pain", Molecular Pain Vol. 4, p. 6.
14) Jiang et al., 2007, "Substituted Phosphonate Analogues of Lysophosphatidic Acid (LPA) Selectively Inhibit Production and Action of LPA", Chem. Med. Chem., Vol. 2, pp. 679-690.
15) Kanda et al., 2008, "Autotaxin, an ectoenzyme that produces lysophosphatidic acid, promotes the entry of lymphocytes into secondary lymphoid organs", Nat. Immunol., Vol. 9, pp. 415-423.
16) Kremer et al., 2012, "Serum autotaxin is increased in pruritus of cholestasis, but not of other origin, and Responds to therapeutic interventions" Hepatology, Vol 56, pp 1391-1400.
17) Knowlden S, Georas S N., 2014, "The autotaxin-LPA axis emerges as a novel regulator of lymphocyte homing and inflammation", J Immunol. 192(3):851-7
18) Leblanc R and Peyruchaud O., 2014, "New insights into the autotaxin/LPA axis in cancer development and metastasis" Exp Cell Res
19) Lin et al., 2009, "The absence of $LPA_2$ attenuates tumor formation in an experimental model of colitis-associated cancer", Gastroenterology, Vol. 136, No. 5, pp. 1711-1720.
20) Liu et al., 2009, "Expression of Autotaxin and Lysophosphatidic Acid Receptors Increases Mammary Tumorigenesis, Invasion, and Metastases", Cancer Cell, Vol. 15, No. 6, pp. 539-550, published 2 Jun. 2009.
21) Marshall et al., 2012, "Effect of inhibition of the lysophosphatidic acid receptor 1 on metastasis and metastatic dormancy in breast cancer", J Natl Cancer Inst., 104:1306-19
22) Masuda et al., 2008, "Serum autotaxin measurement in haematological malignancies: a promising marker for follicular lymphoma", Br. J. Haematol., Vol. 143, pp. 60-70.
23) Meyer zu Heringdorf et al., 2007, "Lysophospholipid receptors: signalling, pharmacology and regulation by lysophospholipid metabolism", Biochim. Biophys. Acta, Vol. 1768, pp. 923-940.
24) Moolenaar W H, et al., 2013, "Autotaxin in embryonic development", Biochim Biophys Acta., 2013; 1831:13-9
25) Murakami et al., 2008, "Identification of the orphan GPCR, P2Y10 receptor as the sphingosine-1-phosphate and lysophosphatidic acid receptor" Biochemical and Biophysical Research Communications, Vol. 371, pp. 707-712.
26) Nakamura et al., 2007, "Serum lysophospholipase D/autotaxin may be a new nutritional assessment marker: study on prostate cancer patients", Ann. Clin. Biochem. Vol. 44, pp. 549-556.
27) Nakao et al., 2014, "Serum autotaxin levels correlate with pruritus in patients with atopic dermatitis", Journal of Investigative Dermatology 134, 1745-1747; doi: 10.1038/jid.2014.24; published online 6 Feb. 2014
28) Nakasaki et al., 2008, "Involvement of the Lysophosphatidic Acid-Generating Enzyme Autotaxin in Lymphocyte-Endothelial Cell Interactions", Am. J. Pathol., Vol. 173, pp. 1566-1576.
29) Nishimura et al., 2014, "ENPP2 contributes to adipose tissue expansion and insulin resistance in diet-induced obesity", Diabetes, 63(12):4154-64
30) Pamuklar et al., 2009, "Autotaxin/lysopholipase D and lysophosphatidic acid regulate murine hemostasis and thrombosis," J. Biol. Chem. e-publication 12 Jan. 2009.
31) Pradere et al., 2007, "LPA1 receptor activation promotes renal interstitial fibrosis", J. Am. Soc. Nephrol. Vol. 18, pp. 3110-3118.
32) Reynolds G., "The autotaxin-lysophosphatidate axis plays a key role in the pathogenesis of Hepatitis C virus-associated Hepatocellular carcinoma", Oral Presentation at the European Congress of Pathology 2014, London.

33) Siess et al., 1999, "Lysophosphatidic acid mediates the rapid activation of platelets and endothelial cells by mildly oxidized low density lipoprotein and accumulates in human atherosclerotic lesions", *Proc. Natl. Acad. Sci. USA*, Vol. 96, pp. 6931-6936.
34) Saga et al., 2014, "A Novel Highly Potent Autotaxin/ENPP2 Inhibitor Produces Prolonged Decreases in Plasma Lysophosphatidic Acid Formation In Vivo and Regulates Urethral Tension", *PLoS* ONE 9(4): e93230. doi:10.1371/journal.pone.0093230
35) Siess et al., 2004, "Thrombogenic and atherogenic activities of lysophosphatidic acid" *Cell Biochem.*, Vol. 92, pp. 1086-1094.
36) Tabata et al., 2007, "The orphan GPCR GPR87 was deorphanized and shown to be a lysophosphatidic acid receptor", *Biochem. Biophys. Res. Commun.* Vol. 363, pp. 861-866.
37) Tager et al., 2008, "The lysophosphatidic acid receptor LPA1 links pulmonary fibrosis to lung injury by mediating fibroblast recruitment and vascular leak", *Nat. Med.* Vol. 14, pp. 45-54.
38) Taghavi et al., 2008, "In vitro genetic screen identifies a cooperative role for LPA signaling and c-Myc in cell transformation", *Oncogene*, Vol. 27, pp. 6806-6816.
39) Tigyi, 2001, "Physiological responses to lysophosphatidic acid and related glycerophospholipids", *Prostaglandins*, Vol. 64, pp. 47-62.
40) van Meeteren et al., 2005, "Inhibition of autotaxin by lysophosphatidic acid and sphingosine 1-phosphate", *J. Biol. Chem.*, Vol. 280, pp. 21155-21161.
41) Van Meeteren et al., 2007, "Regulation and biological activities of the autotaxin-LPA axis", *Prog. Lipid Res.* Vol. 46, pp. 145-160.
42) Watanabe et al., 2007, "Both plasma lysophosphatidic acid and serum autotaxin levels are increased in chronic hepatitis C", *J Clin Gastroenterol.* July; 41(6):616-23
43) Wu et al., 2010, "Autotaxin expression and its connection with the TNF-alpha-NF-kappaB axis inhuman hepatocellular carcinoma" *Molecular Cancer*, 9:71
44) Zhang et al. (2012), "Autotaxin through lysophosphatidic acid stimulates polarization, motility, and transendothelial migration of naive T cells", *J Immunol.*, 89:3914-24
45) Zhang et al., 2009, "Dual Activity Lysophosphatidic Acid Receptor Pan—Antagonist/Autotaxin Inhibitor Reduces Breast Cancer Cell Migration In vitro and Causes Tumor Regression In vivo", *Cancer Res.*, Vol. 69, No. 13, pp. 5441-5449.
46) Zhao et al., 2007, "Distinctive gene expression of prostatic stromal cells cultured from diseased versus normal tissues.", *J. Cell Physiol.*, Vol. 210, pp. 111-121.

The invention claimed is:

1. A compound which is:
N—[(S)-1-(4-chloro-phenyl)-ethyl]-3-[3-(4-trifluoromethoxy-benzyl)-3H-imidazo[4,5-b]pyridin-2-yl]-propionamide,

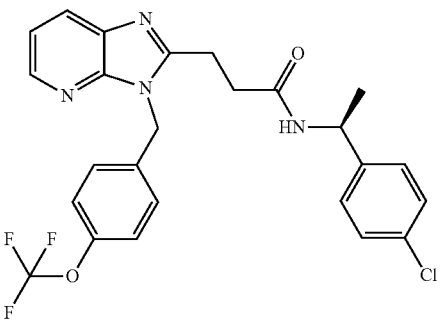 [SMILES: C[C@H](NC(=O)CCc1nc2cccnc2n1Cc1ccc(OC(F)(F)F)cc1)c1ccc(Cl)cc1]

or a pharmaceutically acceptable salt or solvate thereof.

2. A pharmaceutical composition comprising a compound according to claim 1, or a pharmaceutically acceptable salt or solvate thereof, in admixture with a pharmaceutically acceptable diluent or carrier.

* * * * *